US008357688B2

(12) United States Patent
Kaizawa et al.

(10) Patent No.: US 8,357,688 B2
(45) Date of Patent: Jan. 22, 2013

(54) SUBSTITUTED IMIDAZO[1,5-A]QUINOXALIN-4(5H)-ONES AS PDE9 INHIBITORS

(75) Inventors: Hiroyuki Kaizawa, Tokyo (JP); Mari Sugita, Tokyo (JP); Hidenori Azami, Tokyo (JP); Ryushi Seo, Tokyo (JP); Takaho Nomura, Tokyo (JP); Satoshi Yamamoto, Tokyo (JP); Hirofumi Yamamoto, Tokyo (JP); Kazuyuki Tsuchiya, Tokyo (JP); Hideki Kubota, Tokyo (JP); Kazunori Kamijo, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/254,368

(22) PCT Filed: Mar. 4, 2010

(86) PCT No.: PCT/JP2010/053586
§ 371 (c)(1),
(2), (4) Date: Sep. 1, 2011

(87) PCT Pub. No.: WO2010/101230
PCT Pub. Date: Sep. 10, 2010

(65) Prior Publication Data
US 2011/0319385 A1 Dec. 29, 2011

(30) Foreign Application Priority Data
Mar. 5, 2009 (JP) ................................ 2009-052577

(51) Int. Cl.
*A61K 31/495* (2006.01)
(52) U.S. Cl. ........ 514/250; 544/346; 546/112; 546/122; 548/469; 549/356
(58) Field of Classification Search .................. 514/250; 544/346; 546/113, 122; 548/469; 549/356
See application file for complete search history.

(56) References Cited

U.S. PATENT DOCUMENTS

| 5,559,106 A | 9/1996 | Jacobsen et al. |
| 2003/0195205 A1 | 10/2003 | DeNinno et al. |
| 2009/0203703 A1 | 8/2009 | Gotanda et al. |
| 2009/0318478 A1 | 12/2009 | Asagarasu et al. |

FOREIGN PATENT DOCUMENTS

| CA | 2671980 | * | 6/2008 |
| JP | 08 507536 | | 8/1996 |
| JP | 2005 511575 | | 4/2005 |
| WO | 93 12113 | | 6/1993 |
| WO | 93 17025 | | 9/1993 |
| WO | 96 08492 | | 3/1996 |
| WO | 96 08493 | | 3/1996 |
| WO | 99 09845 | | 3/1999 |
| WO | 94 21639 | | 9/2004 |
| WO | 2006 135080 | | 12/2006 |
| WO | 2008 018306 | | 2/2008 |
| WO | 2008 072778 | | 6/2008 |
| WO | 2008 072779 | | 6/2008 |

OTHER PUBLICATIONS

Thiyagarajan, M., et al., "α-Adrenoceptor Antagonists in the Treatment of Benign Prostate Hyperplasia," Pharmacology, vol. 65, pp. 119-128, (2002).
Shah, P.J.R., et al., "Distigmine Bromide and Post-Prostatectomy Voiding," British Journal of Urology, vol. 55, pp. 229-232, (1983).
Finkbeiner, A.E., "Is Bethanechol Chloride Clinically Effective in Promoting Bladder Emptying? A Literature Review," The Journal of Urology, vol. 134, pp. 443-449, (Sep. 1985).
Bloch, W., et al., "Distribution of Nitric Oxide Synthase Implies a Regulation of Circulation, Smooth Muscle Tone, and Secretory Function in the Human Prostate by Nitric Oxide," The Prostate, vol. 33, pp. 1-8, (1997).
Toprakçi, M., et al., "Age-associated changes in nitric oxide metabolites nitrite and nitrate," Int J Clin Lab Res., vol. 30, pp. 83-85, (2000).
Fisher, D.A., et al., "Isolation and Characterization of PDE9A, a Novel Human cGMP-specific Phosphodiesterase," The Journal of Biological Chemistry, vol. 273, No. 25, pp. 15559-15564, (Jun. 19, 1998).
Rentero, C., et al., "Indentification and distribution of different mRNA variants produced by differential splicing in the human phosphodiesterase 9A gene," Biochemical and Biophysical Research Communications, vol. 301, pp. 686-692, (2003).
International Search Report issued May 18, 2010 in PCT/JP10/053586 filed Mar. 4, 2010.

* cited by examiner

*Primary Examiner* — Douglas M Willis
(74) *Attorney, Agent, or Firm* — Oblon, Spivak, McClelland, Maier & Neustadt, L.L.P.

(57) ABSTRACT

Substituted imidazo[1,5-a]quinoxalin-4(5H)-ones are useful as PDE9 inhibitors.

9 Claims, No Drawings

SUBSTITUTED IMIDAZO[1,5-A]QUINOXALIN-4(5H)-ONES AS PDE9 INHIBITORS

CROSS REFERENCES TO RELATED APPLICATIONS

This application is a 371 of International Patent Application No. PCT/JP2010/053586, filed on Mar. 4, 2010, and claims priority to Japanese Patent Application No. 2009-052577, filed on Mar. 5, 2009.

BACKGROUND OF THE INVENTION

1. Field of the Invention

The present invention relates to a quinoxaline compound which is useful as an active ingredient for a pharmaceutical composition, in particular, a pharmaceutical composition for treating storage dysfunction, voiding dysfunction, and bladder/urethral diseases, and the like.

2. Discussion of the Background

The most important roles of voiding function are urine storage and voiding, which are regulated by a coordinated action of the bladder and the urethra. That is, during urine storage, the bladder smooth muscle is relaxed and the urethra sphincter is contracted, whereby a state in which urethral resistance is high is maintained, and urinary continence is also maintained. On the other hand, during voiding, the bladder smooth muscle is contracted, and the urethra smooth muscle is relaxed, and contraction of the external urethral sphincter is also inhibited. Examples of voiding dysfunction include a storage dysfunction such as overactive bladder and the like in which urine cannot be retained during urine storage and voiding in which urine cannot be drained sufficiently due to increase in the urethral resistance and decrease in the bladder contractile force. These two disorders may be expressed simultaneously.

In treatment of a storage dysfunction such as overactive bladder and the like, anticholinergic agents have been used frequently. However, these agents cannot provide a sufficient therapeutic effect, and further, side effects based on the anticholinergic action (dry mouth, gastrointestinal symptoms, eye symptoms, as arrhythmias, or the like) appear, and accordingly, administration of the agents should be often interrupted. Further, the anticholinergic agents reduce the bladder contractile force, and are therefore contraindicated for urinary frequency/incontinence accompanying urethral obstruction such as benign prostatic hyperplasia and the like.

Voiding dysfunction is caused by an increase in urethral resistance during voiding or a decrease in the bladder contractile force. As a disease causing an increase in urethral resistance, voiding dysfunction accompanying benign prostatic hyperplasia is well known, which is characterized by urethral obstruction due to nodular hypertrophy of the prostate tissues. An α1 receptor antagonist has now been used for the purpose of treating voiding dysfunction accompanying benign prostatic hyperplasia (see, for example, Non-Patent Document 1). Other causes of the increase in urethral resistance include functional obstructions such as urethra relaxation failure during voiding or detrusor-external urethral sphincter dyssynergia and the like due to neurological disorders such as diabetes, aging, bone-marrow damage, pelvic surgery, and the like. With patients with these diseases, there exist many cases in which the α1 receptor antagonist is ineffective. On the other hand, a decrease in the bladder contractile force during voiding, referred to as underactive bladder, acontractile bladder, neurogenic bladder, or the like, also causes voiding dysfunction. Known factors for decreasing the bladder contractile force include aging, neurological diseases such as diabetes, Parkinson's disease, multiple sclerosis, and the like, bone marrow damage, and neurological disorders due to pelvic surgery. Examples of an agent for treating a decrease in the bladder contractile force during voiding include bethanechol chloride which is a muscarinic receptor agonist and distigmine bromide which is a cholinesterase inhibitor. Both of these drugs have side effects, and thus, their satisfactoriness is low (see, for example, Non-Patent Documents 2 and 3). In voiding dysfunction caused by an increase in the urethral resistance or a decrease in the bladder contractile force as described above, residual urine after voiding is observed. Increased residual urine may cause a decrease in effective bladder capacity, and thus, cause overactive bladder symptoms such as urinary frequency and the like, or severe symptoms, called hydronephrosis, in some cases, and in this regard, there is a demand for a therapeutic agent which is more effective than a current therapeutic agent.

It is known that a relaxation system due to nitric oxide (NO) is present in the smooth muscle, and NO produced in the nerve terminals or locally activates soluble guanylate cyclase present in the smooth muscle cells. The activated guanylate cyclase increases cyclic guanosine monophosphate (cGMP) in the cells. On the other hand, the cGMP is degraded into 5'-GMP by phosphodiesterase (PDE) which is an enzyme degrading the cGMP. An increase in the intracellular cGMP concentration is considered to contribute significantly to the smooth muscle relaxation. Therefore, the decrease of the NO-cGMP system causes relaxation failure of the smooth muscle. For example, in patients showing urethral obstruction in benign prostatic hyperplasia or in the elderly as described above, it is reported that NO production is significantly decreased (Non-Patent Documents 4 and 5).

As a subtype of PDE which specifically degrades cGMP, PDE5, PDE6, and PDE9 are known, and among these, PDE9 has a higher substrate affinity than PDE5 and PDE6 (Non-Patent Document 6). Further, from the viewpoint that in the distribution of expression in various tissues, PDE9 is observed at its highest expression in the human prostate (Non-Patent Document 7), it plays an important role in smooth muscle relaxation in lower urethra smooth muscle and a PDE9 inhibitor enhances the relaxation of the urethra via cGMP in the tissue. Therefore, it is considered that the PDE9 inhibitor exhibits an effect against voiding dysfunction due to an increase in the urethral resistance. Since the PDE9 inhibitor decreases the urethral resistance, an effect against voiding dysfunction in which the bladder contractile forces are decreased can be expected. In addition, the decrease in residual urine due to improvement of the voiding dysfunction will lead to improvement of overactive bladder symptoms such as urinary frequency or avoidance of renal disorders. Therefore, it is considered that the PDE9 inhibitor is useful as an agent for preventing and/or treating storage dysfunction, voiding dysfunction, and bladder/urethral diseases.

For example, as a compound having a PDE5- and/or PDE9-inhibiting action(s), in Patent Documents 1 and 2, there are disclosed compounds represented by the following formulae (A) and (B), respectively, but there is no specific disclosure of the compounds of the present invention. In addition, in Patent Documents 3 and 4, there are disclosed a thienopyrimidine derivative and a quinazoline derivative as compounds having a PDE5- and/or PDE9-inhibiting action(s), respectively.

Furthermore, in Patent Documents 5 to 10, there are disclosed compounds represented by the following formulae (C) to (H), but there is no specific disclosure of the compounds of the present invention. In addition, there is no description that the compound has a PDE9-inhibiting action.

[Chem. 1]

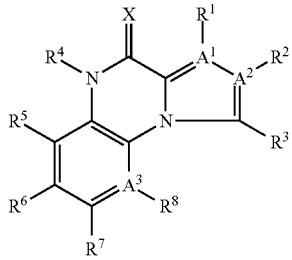

(A)

[Chem. 2]

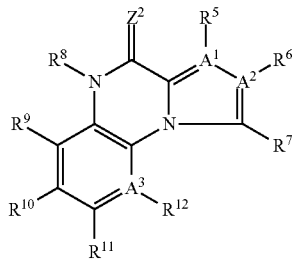

(B)

[Chem. 3]

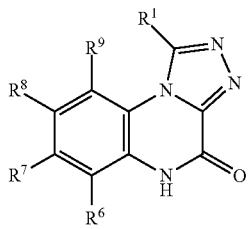

(C)

[Chem. 4]

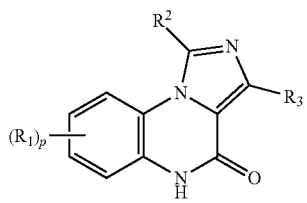

(D)

[Chem. 5]

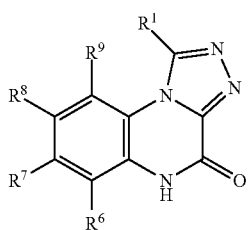

(E)

[Chem. 6]

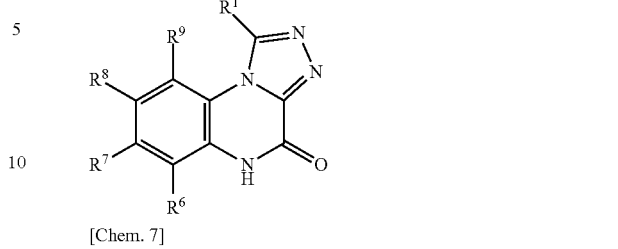

(F)

[Chem. 7]

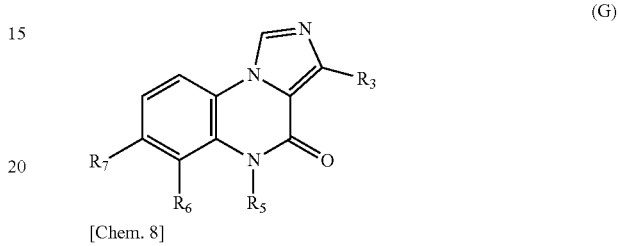

(G)

[Chem. 8]

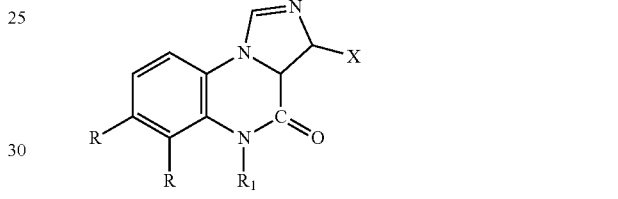

(H)

(For the symbols in the formulae, refer to each of the corresponding patent publications)

3. Related Art

Patent Document

Patent Document 1: Pamphlet of International Publication WO 2008/072779

Patent Document 2: Pamphlet of International Publication WO 2008/072778

Patent Document 3: Pamphlet of International Publication WO 2006/135080

Patent Document 4: Pamphlet of International Publication WO 2008/018306

Patent Document 5: Pamphlet of International Publication WO 94/21639

Patent Document 6: Pamphlet of International Publication WO 99/09845

Patent Document 7: Pamphlet of International Publication WO 96/08492

Patent Document 8: Pamphlet of International Publication WO 96/08493

Patent Document 9: Pamphlet of International Publication WO 93/17025

Patent Document 10: Pamphlet of International Publication WO 93/12113

Non-Patent Document

Non-Patent Document 1: Thiyagarajan, M., Pharmacology, 65: pp. 119-128 (2002)

Non-Patent Document 2: Shah, P. J. R., et al., Br. J. Urol., 55: pp. 229-232 (1983)

Non-Patent Document 3: Finkbeiner, A. E., J. Urol., 134: pp. 443-449 (1985)

Non-Patent Document 4: Bloch, W., et al., Prostate, 33: pp. 1-8 (1997)

Non-Patent Document 5: Toprakqi, M., et al., Int. J. Clin. Lab. Res., 30: pp. 83-85 (2000)

Non-Patent Document 6: Fisher, D. A., et al., J. Biol. Chem., 273: pp. 15559-15564 (1998)

Non-Patent Document 7: Rentero, C., et al., Biochem. Biophys. Res. Commun., 301: pp. 686-692 (2003)

SUMMARY OF THE INVENTION

The present inventors have conducted investigations in order to provide a compound which has a PDE9-inhibiting action and is useful as an active ingredient for an agent for treating and/or preventing storage dysfunction, voiding dysfunction, and bladder/urethral diseases, and the like.

The present inventors have extensively investigated a compound which has a PDE9-inhibiting action, and as a result, they have found that a compound of the formula (I) is useful as a compound having a PDE9-inhibiting action, thereby completing the present invention.

That is, the present invention relates to a compound of the formula (I) or a salt thereof:

[Chem. 9]

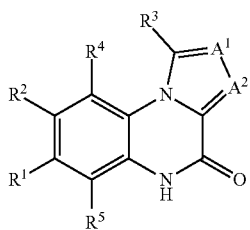

(I)

[wherein
one of $A^1$ and $A^2$ is N and the other is $CR^6$ or N,
one of $R^1$ and $R^2$ is hydrogen, halogen, or lower alkyl, —O-lower alkyl, or cycloalkyl, each of which may be substituted, and the other is a group of the formula (II),

[Chem. 10]

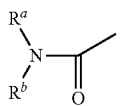

(II)

$R^3$ is lower alkyl, cycloalkyl, cycloalkenyl, aryl, heteroaryl, or a saturated hetero ring, each of which may be substituted, $R^4$ and $R^5$ are the same or different, and each is hydrogen or lower alkyl, $R^6$ is hydrogen or lower alkyl, $R^a$ and $R^b$ are the same or different, and each is hydrogen, or lower alkyl, cycloalkyl, aryl, or a hetero ring, each of which may be substituted, or $R^a$ and $R^b$ are combined with the adjacent nitrogen atom to form a monocyclic nitrogen-containing hetero ring or a polycyclic nitrogen-containing hetero ring, each of which may be substituted.

(provided that
1-cyclohexyl-8-methoxy-N,N-dimethyl-4-oxo-4,5-dihydro [1,2,4]triazolo[4,3-a]quinoxaline-8-carboxamide,
1-cyclohexyl-8-ethoxy-N,N-dimethyl-4-oxo-4,5-dihydro[1, 2,4]triazolo[4,3-a]quinoxaline-8-carboxamide,
8-chloro-1-cyclohexyl-N,N-dimethyl-4-oxo-4,5-dihydro[1, 2,4]triazolo[4,3-a]quinoxaline-8-carboxamide,
8-chloro-1-cyclohexyl-N-(2-methoxyethyl)-N-methyl-4-oxo-4,5-dihydro[1,2,4]triazolo[4,3-a]quinoxaline-8-carboxamide,
1-cyclohexyl-N-methyl-4-oxo-4,5-dihydro[1,2,4]triazolo[4, 3-a]quinoxaline-8-carboxamide,
1-cyclohexyl-N,N-dimethyl-4-oxo-4,5-dihydro[1,2,4]triazolo[4,3-a]quinoxaline-8-carboxamide,
1-cyclohexyl-N-ethyl-N-methyl-4-oxo-4,5-dihydro[1,2,4] triazolo[4,3-a]quinoxaline-8-carboxamide,
1-cyclohexyl-N-(2-methoxyethyl)-4-oxo-4,5-dihydro[1,2,4] triazolo[4,3-a]quinoxaline-8-carboxamide,
1-cyclohexyl-N-(2-methoxyethyl)-N-methyl-4-oxo-4,5-dihydro[1,2,4]triazolo[4,3-a]quinoxaline-8-carboxamide,
1-(1-cyclohexyl-4-oxo-4,5-dihydro[1,2,4]triazolo[4,3-a] quinoxaline-8-yl)carbonyl-4-methylpiperazine,
1-(1-cyclohexyl-4-oxo-4,5-dihydro[1,2,4]triazolo[4,3-a] quinoxaline-8-yl)carbonyl-4-(2-hydroxyethyl)piperidine, and
7-carbamoyl-(2-carboxyethyl)-8-trifluoromethyl[1,2,4]triazolo[4,3-a]quinoxalin-4(5H)-one are excluded; and
when $A^1$ is N and $A^2$ is CH, in the group of the formula (II), which is one of $R^1$ and $R^2$, $R^a$ and $R^b$ are combined with the adjacent nitrogen atom to form a monocyclic nitrogen-containing hetero ring or a polycyclic nitrogen-containing hetero ring, in which the monocyclic nitrogen-containing hetero ring has at least one substituent selected from aryl which may be substituted, a hetero ring which may be substituted, lower alkylene-(aryl which may be substituted), lower alkylene-(a hetero ring which may be substituted), —O-(aryl which may be substituted), —CO-(aryl which may be substituted), and cycloalkyl, and may further have another substituent, and the polycyclic nitrogen-containing hetero ring may have a substituent)].

Furthermore, unless specifically described otherwise, in the case where the symbols in any of the formulas in the present specification are also used in other formulas, the same symbols denote the same meanings.

Furthermore, the present invention relates to a pharmaceutical composition for treating storage dysfunction, voiding dysfunction, and bladder/urethral diseases, and the like, which includes a compound of the formula (I) or a salt thereof, that is, an agent for treating storage dysfunction, voiding dysfunction, and bladder/urethral diseases, and the like, which includes a compound of the formula (I) or a salt thereof.

The present invention further relates to use of the compound of the formula (I) or a salt thereof for preparation of a pharmaceutical composition for treating storage dysfunction, voiding dysfunction, and bladder/urethral diseases, and the like, and a method for treating storage dysfunction, voiding dysfunction, and bladder/urethral diseases, and the like, which includes administering to a patient an effective amount of the compound of the formula (I) or a salt thereof.

The compound of the formula (I) or a salt thereof has a PDE9-inhibiting action, and can be used as a prophylactic and/or therapeutic agent for treating diseases related to degradation of cGMP by PDE9, for example, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, or urethra calculus.

DETAILED DESCRIPTION OF THE PREFERRED EMBODIMENTS

The "lower alkyl" is straight or branched chain alkyl having 1 to 6 carbon atoms (hereinafter simply referred to as $C_{1-6}$), for example, methyl, ethyl, n-propyl, isopropyl, n-butyl, isobutyl, sec-butyl, tert-butyl, n-pentyl, n-hexyl, or the like, and in another embodiment, $C_{1-4}$ alkyl, in a further embodiment, methyl, ethyl, n-propyl, isopropyl, n-butyl, sec-butyl, or tert-butyl.

The "lower alkylene" is to straight or branched $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene, or the like.

The "halogen" means F, Cl, Br, or I.

The "halogeno-lower alkyl" is $C_{1-6}$ alkyl substituted with one or more halogen atoms, in another embodiment, lower alkyl substituted with 1 to 5 halogen atoms, and in a further embodiment, trifluoromethyl.

The "cycloalkyl" is a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like, in another embodiment, $C_{3-8}$ cycloalkyl, in a further embodiment, $C_{3-6}$ cycloalkyl, in a further embodiment, cyclobutyl, cyclopentyl, or cyclohexyl, and in a further embodiment, cyclopropyl.

The "cycloalkenyl" is a $C_{3-10}$ unsaturated hydrocarbon ring group, have a bridge. It is, for example, cyclohexenyl or the like.

The "aryl" is a $C_{6-14}$ monocyclic to tricyclic aromatic hydrocarbon ring group, and examples thereof include $C_{5-8}$ cycloalkene and a ring group condensed at a site of a double bond thereof. It is, for example, phenyl, naphthyl, 5-tetrahydronaphthyl, 1-tetrahydronaphthyl, 4-indenyl, 1-fluorenyl, or the like, and in another embodiment, phenyl or 1-tetrahydronaphthyl.

The "hetero ring" means a ring group containing i) a monocyclic 3- to 8-membered, and in another embodiment, 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by condensation with one or two rings in which the monocyclic hetero ring is selected from the group consisting of a monocyclic hetero ring, a benzene ring, $C_{5-8}$ cycloalkane, and $C_{5-8}$ cycloalkene, and it includes a spiro ring group. The ring atom, sulfur or nitrogen, may be oxidized to form an oxide or a dioxide.

Examples of the "hetero ring" include the following embodiments:

(1) Monocyclic saturated hetero ring (a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like; and (e) those containing 1 to 2 oxygen atoms, for example, oxiranyl, oxetanyl, dioxolanyl, tetrahydrofuranyl, tetrahydropyranyl, 1,4-dioxanyl, and the like;

(2) Monocyclic unsaturated hetero ring group (a) those containing 1 to 4 nitrogen atoms, for example, pyrrolyl, imidazolyl, pyrazolyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, dihydrodithionyl, and the like;

(d) those containing 1 to 2 sulfur atoms and 1 to 2 oxygen atoms, for example, dihydroxathiopyranyl and the like; and (e) those containing 1 to 2 oxygen atoms, for example, furyl, pyranyl, oxepinyl dioxolyl, and the like;

(3) Condensed polycyclic saturated hetero ring group (a) those containing 1 to 5 nitrogen atoms, for example, quinuclidinyl, azabicyclo[2.2.1]heptyl, diazabicyclo[2.2.1]heptyl, azabicyclo[3.2.1]octyl, diazabicyclo[3.2.1]octyl, diazabicyclo[3.3.1]nonyl, and the like;

(b) those containing 1 to 4 nitrogen atoms and 1 to 3 sulfur atoms and/or 1 to 3 oxygen atoms, for example, trithiadiazaindenyl, dioxoloimidazolidinyl, 2-oxa-5-azabicyclo[2.2.1]heptyl, and the like; and (c) those containing 1 to 3 sulfur atoms and/or 1 to 3 oxygen atoms, for example, 2,6-dioxabicyclo[3.2.2]octo-7-yl and the like;

(4) Condensed polycyclic unsaturated hetero ring group (a) those containing 1 to 5 nitrogen atoms, for example, indolyl, isoindolyl, indolinyl (2,3-dihydroindolyl), isoindolinyl (1,3-dihydroisoindolyl), indolidinyl, benzoimidazolyl, dihydrobenzoimidazolyl, tetrahydrobenzoimidazolyl, dihydropyrrolopyridyl, dihydropyrrolopyrimidinyl, quinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, tetrahydronaphthyridinyl, tetrahydropyridopyrimidinyl, tetrahydropyrazolopyridyl, tetrahydropyrrolopyrazinyl, tetrahydroimidazopyrazinyl, tetrahydrobenzoazepinyl, tetrahydropyridonaphthyridinyl, tetrahydropyridoindolyl, hexahydropyridoindolyl, tetrahydropyrrolopyridyl, tetrahydroimidazopyridyl, tetrahydrocarbolinyl, tetrahydrotriazolopyrazinyl, and the like;

(b) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxazinyl, dihydropyridoxazinyl, benzoxadiazolyl, benzoisothiazolyl, benzoisoxazolyl, tetrahydrothienopyridyl, tetrahydroxazolopyridyl, tetrahydrothiazolopyridyl, tetrahydroisoquixazolopyridyl, and the like;

(c) those containing 1 to 3 sulfur atoms, for example, benzothienyl, benzodithiopyranyl, dibenzothienyl, and the like;

(d) those containing 1 to 3 sulfur atoms and 1 to 3 oxygen atoms, for example, benzoxathiopyranyl, phenoxazinyl, and the like;

(e) those containing 1 to 3 oxygen atoms, for example, benzodioxolyl, benzofuranyl, dihydrobenzofuranyl, isobenzofuranyl, chromanyl, chromenyl, dibenzofuranyl, methylenedioxyphenyl, ethylenedioxyphenyl, and the like; and (5) Spiro ring group (a) those containing only a saturated bond, for example, azaspiro[4,4]nonyl, azaspiro[4,5]decyl, diazaspiro[4,5]decyl, triazaspiro[4,5]decyl, azaspiro[5,5]undecyl, diazaspiro[5,5]undecyl, and the like; and (b) those containing an unsaturated bond, for example, 3H-spiro[2-benzofuran-1,4'-piperidyl], spiro[1-benzofuran-3,4'-piperidyl], 2,3-dihydrospiro[indene-1,4'-piperidyl], 3,4-dihydro-2H-spiro[naphthalene-1,3'-piperidyl], 1,2-dihydrospiro[indole-3,4'-piperidyl], and the like.

In another embodiment, the "hetero ring" is pyridyl, thiazolyl, pyrrolidinyl, piperidyl, or morpholinyl.

The "saturated hetero ring" means a group described in (1) Monocyclic saturated hetero ring and (3) Condensed polycyclic saturated hetero ring of the "hetero ring" above. The ring atom, sulfur or nitrogen, may be oxidized to form an oxide or a dioxide. In another embodiment, the saturated hetero ring is a monocyclic saturated hetero ring, and in another embodiment, oxetanyl, tetrahydrofuranyl, tetrahydropyranyl, or tetrahydrothiopyranyl.

The "monocyclic nitrogen-containing hetero ring" means a monocyclic saturated hetero ring or monocyclic unsaturated hetero ring which contains at least one nitrogen atom and may further contain a heteroatom selected from oxygen and sulfur, as the group described in (1) (a), (1) (b), (2) (a), (2) (b), or the like of the "hetero ring" above, which is a group having a binding arm to a nitrogen atom. The ring atom, sulfur or nitrogen, may be oxidized to form an oxide or a dioxide. In another embodiment, the monocyclic nitrogen-containing hetero ring is azetidinyl, pyrrolidinyl, piperidyl, piperazinyl, morpholinyl, thiomorpholinyl, azepanyl, or diazepanyl, in a further embodiment, pyrrolidinyl, and in a further embodiment, morpholinyl.

The "polycyclic nitrogen-containing hetero ring" means a bi- to tricyclic condensed polycyclic saturated hetero ring or a bi- to tricyclic condensed polycyclic unsaturated hetero ring, which contains at least one nitrogen atom and may further contain a heteroatom selected from oxygen and sulfur, as the group described in (3) (a), (3) (b), (4) (a), (4) (b), or the like of the "hetero ring" above, which is a group having a binding arm to a nitrogen atom. Further, the polycyclic nitrogen-containing hetero ring includes the groups having at least one nitrogen atom among the (5) spiro rings of the "hetero ring" above. The ring atom, sulfur or nitrogen, may be oxidized to form an oxide or a dioxide. In another embodiment, the polycyclic nitrogen-containing hetero ring is indolinyl, isoindolinyl, dihydropyrrolopyridyl, dihydropyrrolopyrimidinyl, tetrahydroquinolyl, tetrahydroisoquinolyl, dihydrobenzoxazinyl, dihydropyridoxazinyl, tetrahydronaphthyridinyl, tetrahydropyridopyrimidinyl, tetrahydrothienopyridyl, tetrahydroxazolopyridyl, tetrahydropyrazolopyridyl, tetrahydropyrrolopyrazinyl, tetrahydroimidazopyrazinyl, tetrahydrothiazolopyridyl, tetrahydrobenzoazepinyl, tetrahydropyridonaphthyridinyl, hexahydropyridoindolyl, tetrahydroisoquixazolopyridyl, tetrahydropyrrolopyridyl, tetrahydroimidazopyridyl, tetrahydropyridoindolyl, tetrahydrotriazolopyrazinyl, diazabicyclo[2.2.1]heptyl, diazabicyclo[3.2.1]octyl, 3H-spiro[2-benzofuran-1,4'-piperidyl], 2,3-dihydrospiro[indene-1,4'-piperidyl], in a further embodiment, indolinyl, isoindolinyl, dihydropyrrolopyridyl, tetrahydroisoquinolyl, tetrahydronaphthyridinyl, tetrahydrothienopyridyl, or tetrahydrobenzoazepinyl.

The "monocyclic sulfur-containing saturated hetero ring" means a monocyclic saturated hetero ring group which contains at least one sulfur atom and may further contain an oxygen atom, as the group described in (1) (c) and (1) (d) of the "hetero ring" above. The ring atom, sulfur or nitrogen, may be oxidized to form an oxide or a dioxide. In another embodiment, the monocyclic sulfur-containing saturated hetero ring is thienyl, thiepinyl, dihydrodithiopyranyl, dihydrodithionyl, dihydroxathiopyranyl, or tetrahydrothiopyranyl.

The "heteroaryl" means one having an aromatic property, among the groups described in (2), (4), and (5) (b) of the "hetero ring" above. In another embodiment, the heteroaryl is monocyclic heteroaryl, in another embodiment, thienyl, furyl, thiazolyl, oxazolyl, pyrazolyl, or pyridyl, and in a further embodiment, thienyl.

The "protected carboxy" group may include the following groups.

(1) Ester group. Specific examples thereof include —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, and the like, and in another embodiment, —CO—O-lower alkyl, and —CO—O-benzyl.

(2) Carbamoyl group. Specific examples thereof include —CO—NH$_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-CO$_2$H, and the like, and in another embodiment, —CO—NH$_2$, —CO—NH-lower alkyl, and —CO—N(lower alkyl)$_2$.

In the present specification, the expression "which may be substituted" represents "which is not substituted" or "which is substituted with 1 to 5 substituents". Further, if it has a plurality of substituents, the substituents may be the same as or different from each other.

Examples of the substituent for "lower alkyl, —O-lower alkyl, or cycloalkyl, each of which may be substituted" in $R^1$ and $R^2$ include —OH, —O-lower alkyl, —NH$_2$, —NH-lower alkyl, —N(lower alkyl)$_2$, and a monocyclic nitrogen-containing hetero ring which may be substituted with lower alkyl. The substituent for the "lower alkyl which may be substituted" is, in another embodiment, —O-lower alkyl. The substituent for the "—O-lower alkyl which may be substituted" is, in another embodiment, —OH, —N(lower alkyl)$_2$, or pyrrolidinyl which may be substituted with lower alkyl.

Examples of the substituent for the "lower alkyl, cycloalkyl, cycloalkenyl, aryl, heteroaryl, or a saturated hetero ring, each of which may be substituted" in $R^3$ include halogen, lower alkyl, cycloalkyl, —OH, oxo (═O), —O-lower alkyl, —COOH, protected carboxy, and a monocyclic sulfur-containing saturated hetero ring.

Examples of the substituent for the "lower alkyl which may be substituted" include, in another embodiment, any of a combination of cycloalkyl and a combination of halogen, —OH and oxo (═O), and in a further embodiment, a monocyclic sulfur-containing saturated hetero ring. Examples of the substituent for the "cycloalkyl which may be substituted" include, in another embodiment, halogen, lower alkyl, —OH, oxo (═O), —O-lower alkyl, —COOH, and protected carboxy, in a further embodiment, halogen, —OH, and oxo (═O), and in a further embodiment, —OH, oxo (═O), —COOH, and —CO—NH$_2$. Examples of the substituent for the "cycloalkenyl which may be substituted" include, in another embodiment, oxo (═O), —COOH, and protected carboxy. Examples of the substituent for the "aryl which may be substituted" include halogen, lower alkyl, —O-lower alkyl, and —OH. Examples of the substituent for the "heteroaryl which may be substituted" include, in another embodiment, lower alkyl. Examples of the substituent for the "saturated hetero ring which may be substituted" include, in another embodiment, halogen, lower alkyl, —OH, oxo (=O), —O-lower alkyl, —COOH, protected carboxy, and in a further embodiment, lower alkyl.

Examples of the substituent for the "lower alkyl, cycloalkyl, aryl, or a hetero ring, each of which may be substituted" in $R^a$ and $R^b$ include halogen; —OH; —O-lower alkyl; halogeno-lower alkyl; —NH$_2$; —NH-lower alkyl; —N(lower alkyl)$_2$; aryl which may be substituted with a group selected from a group $G_1$; a hetero ring which may be substituted with a group selected from a group $G_2$; —O-(aryl which may be substituted with a group selected from a group $G_1$); —O-(a hetero ring which may be substituted with a group selected from a group $G_2$); lower alkylene-(aryl which may be substituted with a group selected from a group $G_1$); lower alkylene-(a hetero ring which may be substituted with a group selected from a group $G_2$); —O-lower alkylene-(aryl which may be substituted with a group selected from a group $G_1$); and —O-lower alkylene-(a hetero ring which may be substituted with a group selected from a group $G_2$).

Examples of the substituent for the "lower alkyl which may be substituted" include, in another embodiment, —OH; —O-lower alkyl; —NH$_2$; —NH-lower alkyl; —N(lower alkyl)$_2$; aryl which may be substituted with a group selected from a group $G_1$; a hetero ring which may be substituted with a group selected from a group $G_2$; —O-aryl; and —O-hetero ring, and in a further embodiment, —OH; —O-lower alkyl; —N(lower alkyl)$_2$; aryl which may be substituted with a group selected from a group $G_1$; a hetero ring which may be substituted with a group selected from a group $G_2$; and —O-aryl. Examples of the substituent for the "cycloalkyl which may be substituted" include, in another embodiment, lower alkyl. Examples of the substituent for the "aryl which may be substituted" include, in another embodiment, halogen; —O-lower alkyl; aryl which may be substituted with a group selected from a group $G_1$; a hetero ring which may be substituted with a group selected from a group $G_2$; —O-lower alkylene-aryl; and —O-lower alkylene-hetero ring, and in a further embodiment, halogen; —O-lower alkyl; and —O-lower alkylene-aryl. Examples of the substituent for the "a hetero ring which may be substituted" include, in another embodiment, lower alkyl; aryl which may be substituted with a group selected from a group $G_1$; a hetero ring which may be substituted with a group selected from a group $G_2$; lower alkylene-aryl; and lower alkylene-hetero ring, and in a further embodiment, lower alkyl and lower alkylene-aryl.

Examples of the substituent for the "monocyclic nitrogen-containing hetero ring or polycyclic nitrogen-containing hetero ring, each of which may be substituted", formed by $R^a$ and $R^b$ which are each combined with the adjacent nitrogen atom, include halogen; —OH; oxo (=O); —O-lower alkyl; cyano; nitro; halogeno-lower alkyl; cycloalkyl; aryl which may be substituted with a group selected from a group $G_1$; a hetero ring which may be substituted with a group selected from a group $G_2$; lower alkylene-SO$_2$—NR$^7$R$^8$; lower alkylene-(aryl which may be substituted with a group selected from a group $G_1$); lower alkylene-(a hetero ring which may be substituted with a group selected from a group $G_2$); lower alkyl which may be substituted with —OH, —O-lower alkyl, or cyano; —COOH; protected carboxy; —NH—SO$_2$—R$^9$; —SO$_2$—NR$^7$R$^8$; cycloalkyl; —O-(aryl which may be substituted with a group selected from a group $G_1$); and —CO-(aryl which may be substituted with a group selected from a group $G_1$).

Here, $R^7$ and $R^8$ are the same or different, and each is hydrogen or lower alkyl, and $R^9$ is lower alkyl, or aryl which may be substituted with lower alkyl.

Examples of the substituent for the "monocyclic nitrogen-containing hetero ring which may be substituted" include, in another embodiment, —OH; oxo (=O); —O-lower alkyl; aryl which may be substituted with a group selected from a group $G_1$; a hetero ring which may be substituted with a group selected from a group $G_2$; lower alkylene-(aryl which may be substituted with a group selected from a group $G_1$); lower alkylene-hetero ring; lower alkyl which may be substituted with —OH, —O-lower alkyl, or cyano; cycloalkyl; —O-aryl; and —CO-aryl, and in a further embodiment, —OH; oxo (=O); lower alkyl; aryl which may be substituted with a group selected from a group $G_1$; hetero ring; lower alkylene-(aryl which may be substituted with a group selected from a group $G_1$); lower alkylene-hetero ring; —O-aryl; and —CO-aryl. Examples of the substituent for the "polycyclic nitrogen-containing hetero ring which may be substituted" include, in another embodiment, halogen; —OH; oxo (=O); —O-lower alkyl; cyano; nitro; halogeno-lower alkyl; cycloalkyl; aryl which may be substituted with a group selected from a group $G_1$; a hetero ring which may be substituted with a group selected from a group $G_2$; lower alkylene-(aryl which may be substituted with a group selected from a group $G_1$); lower alkylene-SO$_2$—NR$^7$R$^8$; lower alkylene-hetero ring; lower alkyl which may be substituted with —OH, —O-lower alkyl, cyano, or cycloalkyl; —COOH; protected carboxy; —NH—SO$_2$—R$^9$; —SO$_2$—NR$^7$R$^8$; and a monocyclic nitrogen-containing hetero ring, in a further embodiment, halogen; —OH; oxo (=O); —O-lower alkyl; cyano; nitro; halogeno-lower alkyl; cycloalkyl; aryl which may be substituted with a group selected from a group $G_1$; hetero ring; lower alkylene-hetero ring; lower alkyl which may be substituted with —OH, —O-lower alkyl, or cyano; —COOH; protected carboxy; —NH—SO$_2$—R$^9$; —SO$^2$—NR$^7$R$^8$; and a monocyclic nitrogen-containing hetero ring, in a further embodiment, halogen, lower alkyl which may be substituted with —OH, —O-lower alkyl, cycloalkyl, cyano, halogeno-lower alkyl, or a monocyclic nitrogen-containing hetero ring, and in a further embodiment, halogen, lower alkyl which may be substituted with —OH, —O-lower alkyl, or cyano.

The group $G_1$ is halogen, lower alkyl, halogeno-lower alkyl, —OH, —O-lower alkyl, —O-lower alkylene-aryl, —O-lower alkylene-hetero ring, —O-halogeno-lower alkyl, aryl, or a hetero ring, in another embodiment, halogen, lower alkyl, halogeno-lower alkyl, —OH, —O-lower alkylene-aryl, —O-lower alkylene-hetero ring, or —O-halogeno-lower alkyl, and in a further embodiment, halogen, aryl, —O-lower alkyl, or —O-lower alkylene-hetero ring.

The group $G_2$ is halogen, lower alkyl, halogeno-lower alkyl, —OH, —O-lower alkyl, —O-lower alkylene-aryl, —O-lower alkylene-hetero ring, —O-halogeno-lower alkyl, aryl, or hetero ring, and in another embodiment, lower alkyl.

Certain embodiments of the present invention are presented below.

(1) The compound, wherein $A^1$ and $A^2$ are both N, in another embodiment, one is N and the other is CR$^6$, and in a further embodiment, $A^1$ is N and $A^2$ is CR$^6$.

(2) The compound, wherein (2-i) $R^1$ is hydrogen or lower alkyl and $R^2$ is a group of the formula (II), or (2-ii) $R^1$ is a group of the formula (II) and $R^2$ is hydrogen, halogen, or lower alkyl, —O-lower alkyl, or cycloalkyl, each of which may be substituted.

(3) The compound, wherein (4-i) $R^1$ is lower alkyl and $R^2$ is a group of the formula (II), or (4-ii) $R^1$ is a group of the formula (II) and $R^2$ is (a) halogen, (b) cycloalkyl, or (c) lower alkyl or —O-lower alkyl, which may be substituted with a substituent selected from —OH, —O-lower alkyl, —NH$_2$, —NH-lower alkyl, —N(lower alkyl)$_2$, and a monocyclic nitrogen-containing hetero ring which may be substituted with lower alkyl.

(4) The compound, wherein $R^1$ is a group of the formula (II) and $R^2$ is (a) halogen, (b) cycloalkyl, or (c) lower alkyl or —O-lower alkyl, which may be substituted with a substituent selected from —OH, —O-lower alkyl, —NH$_2$, —NH-lower alkyl, —N(lower alkyl)$_2$, and a monocyclic nitrogen-containing hetero ring which may be substituted with lower alkyl.

(5) The compound, wherein $R^1$ is a group of the formula (II) and $R^2$ is halogen, cyclopropyl, or lower alkyl which may be substituted with —O-lower alkyl.

(6) The compound, wherein $R^1$ is a group of the formula (II) and $R^2$ is (10-i) halogen, (10-ii) cyclopropyl, (10-iii) lower alkyl which may be substituted with —O-lower alkyl, or (10-iv)-O-lower alkyl which may be substituted with —OH, —N(lower alkyl)$_2$, or pyrrolidinyl which may be substituted with, lower alkyl, (7) The compound, wherein $R^3$ is lower alkyl which may be substituted, in another embodiment, cycloalkyl which may be substituted, in a further embodiment, cycloalkenyl which may be substituted, in a further embodiment, aryl which may be substituted, in a further embodiment, heteroaryl which may be substituted, and in a further embodiment, a saturated hetero ring which may be substituted.

(8) The compound, wherein $R^3$ is (5-i) lower alkyl which is substituted with cycloalkyl and which may be substituted with 1 to 3 substituents selected from —OH, oxo (=O), and halogen, (5-ii) lower alkyl which may be substituted with a monocyclic sulfur-containing saturated hetero ring, or (5-iii) cycloalkyl or a monocyclic saturated hetero ring which may be substituted with 1 or 2 substituents selected from halogen, lower alkyl, —OH, oxo (=O), —O-lower alkyl, —COOH and protected carboxy.

(9) The compound, wherein $R^3$ is (7-i) lower alkyl which is substituted with cyclopropyl and which may be substituted with 1 to 3 substituents selected from —OH, oxo (=O), and halogen, (7-ii) cycloalkyl which may be substituted with 1 or 2 substituents selected from —OH and halogen, (7-iii) tetrahydrofuranyl, or (7-iv) tetrahydropyranyl which may be substituted with lower alkyl.

(10) The compound, wherein $R^3$ is (a) cyclopentyl or cyclohexyl which may be substituted with —OH, —COOH, or —CO—NH$_2$, or (b) tetrahydrofuranyl or tetrahydropyranyl.

(11) The compound, wherein $R^4$ is hydrogen, and in another embodiment, lower alkyl.

(12) The compound, wherein $R^5$ is hydrogen, and in another embodiment, lower alkyl.

(13) The compound, wherein $R^6$ is hydrogen, and in another embodiment, lower alkyl.

(14) The compound, wherein $R^a$ is hydrogen, lower alkyl which may be substituted, or cycloalkyl which may be substituted, in another embodiment, aryl which may be substituted, and in a further embodiment, a hetero ring which may be substituted.

(15) The compound, wherein $R^b$ is hydrogen, lower alkyl which may be substituted, or cycloalkyl which may be substituted, in another embodiment, aryl which may be substituted, and in a further embodiment, a hetero ring which may be substituted.

(16) The compound, wherein $R^a$ and $R^b$ are combined with the adjacent nitrogen atom to form a monocyclic nitrogen-containing hetero ring which may be substituted.

(17) The compound, wherein $R^a$ and $R^b$ are combined with the adjacent nitrogen atom to form a monocyclic nitrogen-containing hetero ring, in which the monocyclic nitrogen-containing hetero ring has at least one group selected from aryl which may be substituted, a hetero ring which may be substituted, lower alkylene-(aryl which may be substituted), lower alkylene-(a hetero ring which may be substituted), —O-(aryl which may be substituted), —CO-(aryl which may be substituted), and cycloalkyl, and may have other substituent(s).

(18) The compound, wherein $R^a$ and $R^b$ are combined with the adjacent nitrogen atom to form a polycyclic nitrogen-containing hetero ring which may be substituted.

(19) The compound, wherein $R^a$ and $R^b$ are combined with the adjacent nitrogen atom to form, a bicyclic nitrogen-containing hetero ring which may be substituted, and in another embodiment, a bicyclic nitrogen-containing hetero ring having a spiro bond.

(20) The compound, wherein $R^a$ and $R^b$ are combined with the adjacent nitrogen atom to form a tricyclic nitrogen-containing hetero ring which may be substituted, and in another embodiment, a tricyclic nitrogen-containing hetero ring having a spiro bond.

(21) The compound, wherein $R^a$ and $R^b$ are combined with the adjacent nitrogen atom to form a polycyclic nitrogen-containing hetero ring, which may be substituted with 1 to 3 substituents selected from halogen, lower alkyl which may be substituted with —OH, —O-lower alkyl, cycloalkyl, cyano, halogeno-lower alkyl, and a monocyclic nitrogen-containing hetero ring.

(22) The compound, wherein $R^a$ and $R^b$ are combined with the adjacent nitrogen atom to form indolinyl, isoindolinyl, dihydropyrrolopyridyl, tetrahydroisoquinolyl, or tetrahydronaphthyridinyl, which may be substituted with 1 to 3 substituents selected from 1 to 3 substituents selected from halogen, lower alkyl which may be substituted with —OH, —O-lower alkyl, and cyano.

(23) The compound, which is a combination of two or more groups of the groups described in (1) to (22) above.

Specific examples of the (23) include the following combinations.

(24) The compound, wherein $A^1$ is N, and (2-i) $R^1$ is hydrogen or lower alkyl and $R^2$ is a group of the formula (II), or (2-ii) $R^1$ is a group of the formula (II) and $R^2$ is hydrogen, halogen, or lower alkyl, —O-lower alkyl, or cycloalkyl, each of which may be substituted.

(25) The compound, wherein $A^1$ is N, and (3-i) $A^2$ is N, and $R^a$ and $R^b$ are combined with the adjacent nitrogen atom to form a monocyclic nitrogen-containing hetero ring or a polycyclic nitrogen-containing hetero ring, each of which may be substituted, or (3-ii) $A^2$ is $CR^6$, and $R^a$ and $R^b$ are combined with the adjacent nitrogen atom to form a polycyclic nitrogen-containing hetero ring which may be substituted.

(26) The compound as in (25), wherein (4-i) $R^1$ is lower alkyl and $R^2$ is a group of the formula (II), or (4-ii) $R^1$ is a group of the formula (II), and $R^2$ is (a) halogen, (b) cycloalkyl, or (c) lower alkyl or —O-lower alkyl, which may be substituted with a substituent selected from —OH, —O-lower alkyl, —NH$_2$, —NH-lower alkyl, —N(lower alkyl)$_2$, and a monocyclic nitrogen-containing hetero ring which may be substituted with lower alkyl, $R^4$, $R^5$ and $R^6$ are hydrogen, and $R^a$ and $R^b$ are combined with the adjacent nitrogen atom to form a polycyclic nitrogen-containing hetero ring which may be substituted.

(27) The compound as in (26), wherein $R^1$ is a group of the formula (II), $R^2$ is (a) halogen, (b) cycloalkyl, or (c) lower alkyl or —O-lower alkyl, which may be substituted with a substituent selected from —OH, —O-lower alkyl, —NH$_2$, —NH-lower alkyl, —N(lower alkyl)$_2$, and a monocyclic nitrogen-containing hetero ring which may be substituted with lower alkyl, and $R_3$ is (5-i) lower alkyl which is substituted with cycloalkyl and which may be substituted with 1 to 3 substituents selected from —OH, oxo (=O), and halogen, (5-ii) lower alkyl which may be substituted with a monocyclic sulfur-containing saturated hetero ring, or (5-iii) cycloalkyl or a monocyclic saturated hetero ring which may be substituted with 1 or 2 substituents selected from halogen, lower alkyl, —OH, oxo (=O), —O-lower alkyl, —COOH, and protected carboxy, R$^a$ and R$^b$ are combined with the adjacent nitrogen atom to form a polycyclic nitrogen-containing hetero ring, which may be substituted with 1 to 3 substituents selected from halogen, lower alkyl which may be substituted with —OH, —O-lower alkyl, cycloalkyl, cyano, halogeno-lower alkyl, and a monocyclic nitrogen-containing hetero ring.

(28) The compound as in (27), wherein A$^2$ is N.

(29) The compound as in (27), wherein A$^2$ is CR$^6$.

(30) The compound as in (28), wherein R$^2$ is halogen, cyclopropyl, or lower alkyl which may be substituted with —O-lower alkyl, R$^3$ is (7-i) lower alkyl which is substituted with cyclopropyl and which may be substituted with 1 to 3 substituents selected from —OH, oxo (=O), and halogen, (7-ii) cycloalkyl which may be substituted with 1 or 2 substituents selected from —OH and halogen, (7-iii) tetrahydrofuranyl, or (7-iv) tetrahydropyranyl which may be substituted with lower alkyl, and the polycyclic nitrogen-containing hetero ring which may be substituted, formed when R$^a$ and R$^b$ are combined with the adjacent nitrogen atom, is indolinyl, isoindolinyl, dihydropyrrolopyridyl, tetrahydroisoquinolyl, or tetrahydronaphthyridinyl, which may be substituted with 1 to 3 substituents selected from halogen, lower alkyl which may be substituted with —OH, —O-lower alkyl, and cyano.

(31) The compound as in (29), wherein R$^2$ is (10-i) halogen, (10-ii) cyclopropyl, (10-iii) lower alkyl which may be substituted with —O-lower alkyl, or (10-iv) —OH, —N(lower alkyl)$_2$, or pyrrolidinyl which may be substituted with lower alkyl, and —O-lower alkyl which may be substituted, and R$^3$ is (a) cyclopentyl or cyclohexyl which may be substituted with —OH, —COOH or —CO—NH$_2$, or (b) tetrahydrofuranyl or tetrahydropyranyl, and the polycyclic nitrogen-containing hetero ring which may be substituted, formed when R$^a$ and R$^b$ are combined with the adjacent nitrogen atom, is indolinyl, isoindolinyl, dihydropyrrolopyridyl, tetrahydroisoquinolyl, or tetrahydronaphthyridinyl, which may be substituted with 1 to 3 substituents selected from halogen, lower alkyl which may be substituted with —OH, —O-lower alkyl, and cyano.

(32) The compound, wherein A$^1$ is N, A$^2$ is CH, and R$^1$ is a group of the formula (II), R$^2$ is hydrogen, lower alkyl, —O-lower alkyl, halogen, or cycloalkyl, R$^4$ and R$^5$ is hydrogen, and R$^a$ and R$^b$ are combined with the adjacent nitrogen atom to form a bicyclic nitrogen-containing hetero ring which may be substituted or a tricyclic nitrogen-containing hetero ring which may be substituted.

(33) The compound, wherein A$^1$ is N, A$^2$ is N, R$^1$ is a group of the formula (II), R$^2$ is hydrogen, lower alkyl, —O-lower alkyl, halogen, or cycloalkyl, R$^4$ and R$^5$ are hydrogen, and R$^a$ and R$^b$ are combined with the adjacent nitrogen atom to form a bicyclic nitrogen-containing hetero ring which may be substituted or a tricyclic nitrogen-containing hetero ring which may be substituted.

Examples of the specific compounds included in the present invention include:

1-(3-chloro-4-hydroxyphenyl)-8-methyl-7-[(1-pyridin-4-yl-3,4-dihydroisoquinolin-2(1H)-yl)carbonyl][1,2,4]triazolo[4,3-a]quinoxalin-4(5H)-one, methyl 2-{[8-methyl-4-oxo-1-(tetrahydro-2H-pyran-4-yl)-4,5-dihydroimidazo[1,5-a]quinoxaline-7-yl]carbonyl}-1,2,3,4-tetrahydroisoquinoline-8-carboxylate, N,N-dimethyl-1-{[8-methyl-4-oxo-1-(tetrahydro-2H-pyran-4-yl)-4,5-dihydroimidazo[1,5-a]quinoxaline-7-yl]carbonyl}indoline-5-sulfonamide, 1-cyclopentyl-7-(2,3-dihydro-1H-indol-1-ylcarbonyl)-8-methylimidazo[1,5-a]quinoxalin-4(5H)-one, 7-(8,9-dihydropyrido[2,3-b]-1,6-naphthyridin-7(6H)-ylcarbonyl)-8-methyl-1-(tetrahydro-2H-pyran-4-yl)imidazo[1,5-a]quinoxalin-4(5H)-one, 7-(6,7-dihydrothieno[3,2-c]pyridine-5(4H)-ylcarbonyl)-8-methyl-1-(tetrahydro-2H-pyran-4-yl)imidazo[1,5-a]quinoxalin-4(5H)-one, 7-(1,3-dihydro-2H-isoindol-2-ylcarbonyl)-8-methyl-1-(tetrahydro-2H-pyran-4-yl)[1,2,4]triazolo[4,3-a]quinoxalin-4(5H)-one, 7-(1,3-dihydro-2H-isoindol-2-ylcarbonyl)-8-methyl-1-(tetrahydro-2H-pyran-4-yl)imidazo[1,5-a]quinoxalin-4(5H)-one, 7-[(5-chloro-3,4-dihydroisoquinolin-2(1H)-yl)carbonyl]-1-(4-hydroxyphenyl)[1,2,4]triazolo[4,3-a]quinoxalin-4(5H)-one, and N-(3-chlorobenzyl)-N-methyl-4-oxo-1-propyl-4,5-dihydro[1,2,4]triazolo[4,3-a]quinoxaline-7-carboxamide.

Other embodiments as examples of the specific compounds included in the present invention include:

7-(1,3-dihydro-2H-isoindol-2-ylcarbonyl)-8-methyl-1-(tetrahydro-2H-pyran-4-yl)[1,2,4]triazolo[4,3-a]quinoxalin-4(5H)-one, 7-[(5-chloro-3,4-dihydroisoquinolin-2(1H)-yl)carbonyl]-1-cyclopentyl-8-methyl[1,2,4]triazolo[4,3-a]quinoxalin-4(5H)-one, 7-[(5-bromo-2,3-dihydro-1H-pyrrolo[2,3-b]pyridin-1-yl)carbonyl]-8-methyl-1-(tetrahydrofuran-3-yl)[1,2,4]triazolo[4,3-a]quinoxalin-4(5H)-one, 7-[(6-chloro-5-fluoro-2,3-dihydro-1H-indol-1-yl)carbonyl]-1-cyclopentyl-8-methyl[1,2,4]triazolo[4,3-a]quinoxalin-4(5H)-one, 1-(4,4-difluorocyclohexyl)-7-[(5-fluoro-2,3-dihydro-1H-indol-1-yl)carbonyl]-8-methyl[1,2,4]triazolo[4,3-a]quinoxalin-4(5H)-one, 7-[(5-chloro-2,3-dihydro-1H-indol-1-yl)carbonyl]-8-methyl-1-(tetrahydro-2H-pyran-3-yl)[1,2,4]triazolo[4,3-a]quinoxalin-4(5H)-one, 1-cyclopentyl-7-[(5,6-difluoro-2,3-dihydro-1H-indol-1-yl)carbonyl)-8-methyl[1,2,4]triazolo[4,3-a]quinoxalin-4(5H)-one, 7-[(5-chloro-6-fluoro-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5-bromo-2,3-dihydro-1H-pyrrolo[2,3-b]pyridin-1-yl)carbonyl]-8-methyl-1-(tetrahydro-2H-pyran-4-yl)[1,2,4]triazolo[4,3-a]quinoxalin-4(5H)-one, 7-[(5-fluoro-2,3-dihydro-1H-indol-1-yl)carbonyl]-8-methyl-1-(4-methyltetrahydro-2H-pyran-4-yl)[1,2,4]triazolo[4,3-a]quinoxalin-4(5H)-one, 7-[(5-chloro-6-fluoro-2,3-dihydro-1H-indol-1-yl)carbonyl]-1-cyclopentyl-8-methyl[1,2,4]triazolo[4,3-a]quinoxalin-4(5H)-one, 7-(1,3-dihydro-2H-isoindol-2-ylcarbonyl)-8-methoxy-1-(tetrahydro-2H-pyran-4-yl)[1,2,4]triazolo[4,3-a]quinoxalin-4(5H)-one, 7-[(5-bromo-2,3-dihydro-1H-pyrrolo[2,3-b]pyridin-1-yl)carbonyl]-1-(3,3-difluorocyclobutyl)-8-methyl[1,2,4]triazolo[4,3-a]quinoxalin-4(5H)-one, 7-[(5-chloro-2,3-dihydro-1H-indol-1-yl)carbonyl]-8-(methoxymethyl)-1-(tetrahydro-2H-pyran-4-yl)[1,2,4]triazolo[4,3-a]quinoxalin-4(5H)-one, 7-[(5-fluoro-2,3-dihydro-1H-pyrrolo[2,3-b]pyridin-1-yl)carbonyl]-8-methyl-1-(tetrahydro-2H-pyran-4-yl)[1,2,4]triazolo[4,3-a]quinoxalin-4(5H)-one, 7-[(5-chloro-2,3-dihydro-1H-indol-1-yl)carbonyl]-1-(cis-4-hydroxycyclohexyl)-8-methyl[1,2,4]triazolo[4,3-a]quinoxalin-4(5H)-one, 7-[(5-chloro-2,3-dihydro-1H-indol-1-yl)carbonyl]-1-[cyclopropyl(hydroxy)methyl]-8-methyl[1,2,4]triazolo[4,3-a]quinoxalin-4(5H)-one, 7-[(5-chloro-2,3-dihydro-1H-indol-1-yl)carbonyl]-1-[cyclopropyl(fluoro)methyl]-8-methyl[1,2,4]triazolo[4,3-a]quinoxalin-4(5H)-one, 7-[(5-chloro-3,3-dimethyl-2,3-dihydro-1H-indol-1-yl)carbonyl]-8-methyl-1-(tetrahydro-2H-pyran-4-yl)[1,2,4]triazolo[4,3-a]quinoxalin-4(5H)-one, 7-[(5,6-difluoro-2,3-dihydro-1H-indol-1-yl)carbonyl]-8-(methoxymethyl)-1-(tetrahydro-2H-pyran-4-yl)[1,2,4]triazolo[4,3-a]quinoxalin-4(5H)-one, 7-[(5-chloro-2,3-dihydro-1H-indol-1-yl)carbonyl]-1-(cyclopropylmethyl)-8-(methoxymethyl)[1,2,4]triazolo[4,3-a]quinoxalin-4(5H)-one, or salts thereof.

Other embodiments as examples of the specific compounds included in the present invention include:

7-(1,3-dihydro-2H-isoindol-2-ylcarbonyl)-8-methyl-1-(tetrahydro-2H-pyran-4-yl)imidazo[1,5-a]quinoxalin-4(5H)-one, 7-[(5-chloro-1,3-dihydro-2H-isoindol-2-yl)carbonyl]-8-methyl-1-(tetrahydro-2H-pyran-4-yl)imidazo[1,5-a]quinoxalin-4(5H)-one, 7-[(5-chloro-2,3-dihydro-1H-indol-1-yl)carbonyl]-8-methyl-1-(tetrahydro-2H-pyran-4-yl)imidazo[1,5-a]quinoxalin-4(5H)-one, 7-[(5-fluoro-2,3-dihydro-1H-indol-1-yl)carbonyl]-8-methyl-1-(tetrahydro-2H-pyran-4-yl)imidazo[1,5-a]quinoxalin-4(5H)-one, 1-cyclohexyl-7-{[3-(hydroxymethyl)-3,4-dihydroisoquinolin-2(1H)-yl]carbonyl}-8-methoxyimidazo[1,5-a]quinoxalin-4(5H)-one, 7-[(5-fluoro-2,3-dihydro-1H-indol-1-yl)carbonyl]-8-methyl-1-(tetrahydro-2H-pyran-3-yl)imidazo[1,5-a]quinoxalin-4(5H)-one, 7-[(5-chloro-2,3-dihydro-1H-indol-1-yl)carbonyl]-8-cyclopropyl-1-(tetrahydro-2H-pyran-4-yl)imidazo[1,5-a]quinoxalin-4(5H)-one, 8-methoxy-7-[(5-methoxy-2,3-dihydro-1H-pyrrolo[2,3-c]pyridin-1-yl)carbonyl]-1-(tetrahydro-2H-pyran-4-yl)imidazo[1,5-a]quinoxalin-4(5H)-one, 8-chloro-7-(2,3-dihydro-1H-pyrrolo[2,3-b]pyridin-1-ylcarbonyl)-1-(tetrahydro-2H-pyran-4-yl)imidazo[1,5-a]quinoxalin-4(5H)-one, 7-[(5-chloro-6-fluoro-2,3-dihydro-1H-indol-1-yl)carbonyl]-8-methyl-1-(tetrahydro-2H-pyran-4-yl)imidazo[1,5-a]quinoxalin-4(5H)-one, 7-[(5-chloro-2,3-dihydro-1H-indol-1-yl)carbonyl]-8-(methoxymethyl)-1-(tetrahydro-2H-pyran-4-yl)imidazo[1,5-a]quinoxalin-4(5H)-one, 8-[2-(dimethylamino)ethoxy]-7-[(5-fluoro-2,3-dihydro-1H-indol-1-yl)carbonyl]-1-(tetrahydro-2H-pyran-4-yl)imidazo[1,5-a]quinoxalin-4(5H)-one, 7-[(5-bromo-2,3-dihydro-1H-pyrrolo[2,3-b]pyridin-1-yl)carbonyl]-8-(methoxymethyl)-1-(tetrahydro-2H-pyran-4-yl)imidazo[1,5-a]quinoxalin-4(5H)-one, 7-[(5-chloro-2,3-dihydro-1H-indol-1-yl)carbonyl]-8-(2-hydroxyethoxy)-1-(tetrahydro-2H-pyran-4-yl)imidazo[1,5-a]quinoxalin-4(5H)-one, 7-[(5-chloro-2,3-dihydro-1H-indol-1-yl)carbonyl]-1-(cis-4-hydroxycyclohexyl)-8-methylimidazo[1,5-a]quinoxalin-4(5H)-one, 7-[(5-methoxy-2,3-dihydro-1H-pyrrolo[2,3-c]pyridin-1-yl)carbonyl]-8-(methoxymethyl)-1-(tetrahydro-2H-pyran-4-yl)imidazo[1,5-a]quinoxalin-4(5H)-one, 7-[(5-chloro-2,3-dihydro-1H-indol-1-yl)carbonyl]-1-[cis-2-hydroxycyclopentyl]-8-methylimidazo[1,5-a]quinoxalin-4(5H)-one, 7-[(5-fluoro-2,3-dihydro-1H-pyrrolo[2,3-b]pyridin-1-yl)carbonyl]-8-methyl-1-(tetrahydro-2H-pyran-4-yl)imidazo[1,5-a]quinoxalin-4(5H)-one, 7-(7,8-dihydro-1,6-naphthyridin-6(5H)-ylcarbonyl)-8-(methoxymethyl)-1-(tetrahydro-2H-pyran-4-yl)imidazo[1,5-a]quinoxalin-4(5H)-one, 7-[(5-chloro-3,3-dimethyl-2,3-dihydro-1H-indol-1-yl)carbonyl]-8-methyl-1-(tetrahydro-2H-pyran-4-yl)imidazo[1,5-a]quinoxalin-4(5H)-one, trans-4-{7-[(5-chloro-2,3-dihydro-1H-indol-1-yl)carbonyl]-8-methyl-4-oxo-4,5-dihydroimidazo[1,5-a]quinoxalin-1-yl}cyclohexanecarboxamide, or salts thereof.

The compound of the formula (I) may exist in the form of tautomers or geometrical isomers depending on the kind of substituents. In the present specification, the compound of the formula (I) shall be described in only one form of isomer, yet the present invention includes such an isomer, isolated forms of the isomers, or a mixture thereof.

In addition, the compound of the formula (I) may have asymmetric carbon atoms or axial asymmetry in some cases, and correspondingly, it may exist in the form of optical isomers. The present invention includes both an isolated form of the optical isomers of the compound of the formula (I) or a mixture thereof.

Furthermore, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituent thereof and by applying various known synthesis methods. During the preparation, protecting the relevant functional group with a suitable protective group or replacing the relevant functional group with a group that can be easily converted into the functional group at the stage from starting material to an intermediate may be effective depending on the type of the functional group in production technology in some cases. The protective group for such a functional group may include, for example, the protective groups described in "Greene's Protective Groups in Organic Synthesis (4th Ed, 2006)" written by P. G. M. Wuts and T. W. Greene, and one of these should only be selected and used as necessary depending on reaction conditions. In this kind of method, a desired compound can be obtained by introducing the protective group, by carrying out a reaction and by eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

additive (for example, 1-hydroxybenzotriazole). It may be advantageous in some cases for the smooth progress of the reaction to carry out the reaction in the presence of an organic base such as triethylamine, N,N-diisopropylethylamine, N-methylmorpholine, and the like, or an inorganic base such as potassium carbonate, sodium carbonate, potassium hydroxide, sodium hydroxide, and the like. Further, use of a microwave reactor (Biotage AB) may allow the smooth progress of the reaction in some cases. Depending on the case, an isocyanate-carrying polystyrene resin, for example, PS-Isocyanate (Biotage AB, Sweden) and the like can also be used in order to remove an excess amount of amine after completion of the reaction, and also, a quaternary ammonium salt-carrying polystyrene resin, for example, MP-Carbonate (Biotage AB, Sweden) and the like can also be used in order to remove an excess amount of the additives after completion of the reaction.

Moreover, a method in which a carboxylic acid (1a) is converted to its a reactive derivative and then reacted with amine (1b) can also be used. Here, examples of the reactive derivative of the carboxylic acid include acid halides that can be obtained by the reaction of a halogenating agent such as phosphorus oxychloride, thionyl chloride, and the like, mixed

[Chem. 11]

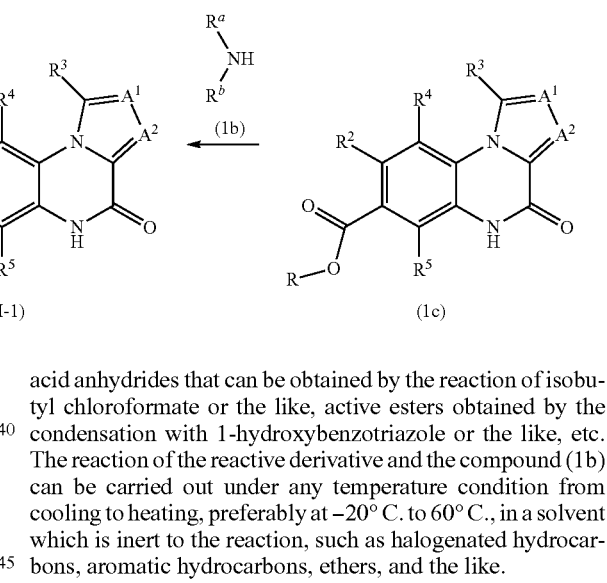

(wherein $A^1$, $A^2$, $R^a$, $R^b$, $R^2$, $R^3$, $R^4$, and $R^5$ represent the same meanings as defined above. R represents lower alkyl. The same shall apply hereinafter.)

The compound (I-1) of the present invention can be obtained by the reaction of a compound (1a) with a compound (1b).

In this reaction, the compound (1a) and the compound (1b) in equivalent amounts, or with either thereof in an excess amount are used, and a mixture thereof is stirred under any temperature condition from cooling to heating, preferably at −20° C. to 120° C., usually for 0.1 hours to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, N,N-dimethylformamide, dimethylsulfoxide, ethyl acetate, acetonitrile, or water and a mixture thereof. Examples of the condensing agent include 1-(3-dimethylaminopropyl)-3-ethylcarbodiimide, 1,3-dicyclohexylcarbodiimide, O-(7-azabenzotriazol-1-yl)-N,N,N',N'-tetramethyluronium hexafluorophosphate, O-(benzotriazol-1-yl)-N,N,N',N'-tetramethyluronium tetrafluoroborate (TBTU), bromo (tripyrrolidin-1-yl)phosphonium hexafluorophosphate, 1,1'-carbonyldiimidazole, diphenylphosphoryl azide, and phosphorous oxychloride, but are not limited to these, and a condensing agent-carrying polystyrene resin, for example, PS-Carbodiimide (Biotage AB, Sweden) can also be used. It may be preferable for the reaction in some cases to use an acid anhydrides that can be obtained by the reaction of isobutyl chloroformate or the like, active esters obtained by the condensation with 1-hydroxybenzotriazole or the like, etc. The reaction of the reactive derivative and the compound (1b) can be carried out under any temperature condition from cooling to heating, preferably at −20° C. to 60° C., in a solvent which is inert to the reaction, such as halogenated hydrocarbons, aromatic hydrocarbons, ethers, and the like.

In addition, a method may be used in which an aluminum amide reagent obtained by reacting an ester (1c) with trimethylaluminum and amine (1b) is allowed to undergo a reaction. For this operation, reference may be made to the methods described in "Organic Functional Group Preparations", written by S. R. Sandler and W. Karo, 2nd edition, Vol. 1, Academic Press Inc., 1991, and "Courses in Experimental Chemistry (5th edition)", edited by The Chemical Society of Japan, Vol. 16 (2005) (Maruzen).

In addition, some of the compounds represented by the formula (I) can also be produced from the compound according to the present invention produced as described above by appropriately combining processes usually used by those skilled in the art, such as known alkylation, acylation, substitution, oxidation, reduction, hydrolysis, deprotection, halogenation, and the like (see, for example, "Courses in Experimental Chemistry" (5th Edition), edited by The Chemical Society of Japan, (2005) (Maruzen)). Furthermore, a process which can be usually used by those skilled in the art can also be used for intermediates for preparation (Starting Material Synthesis 1)

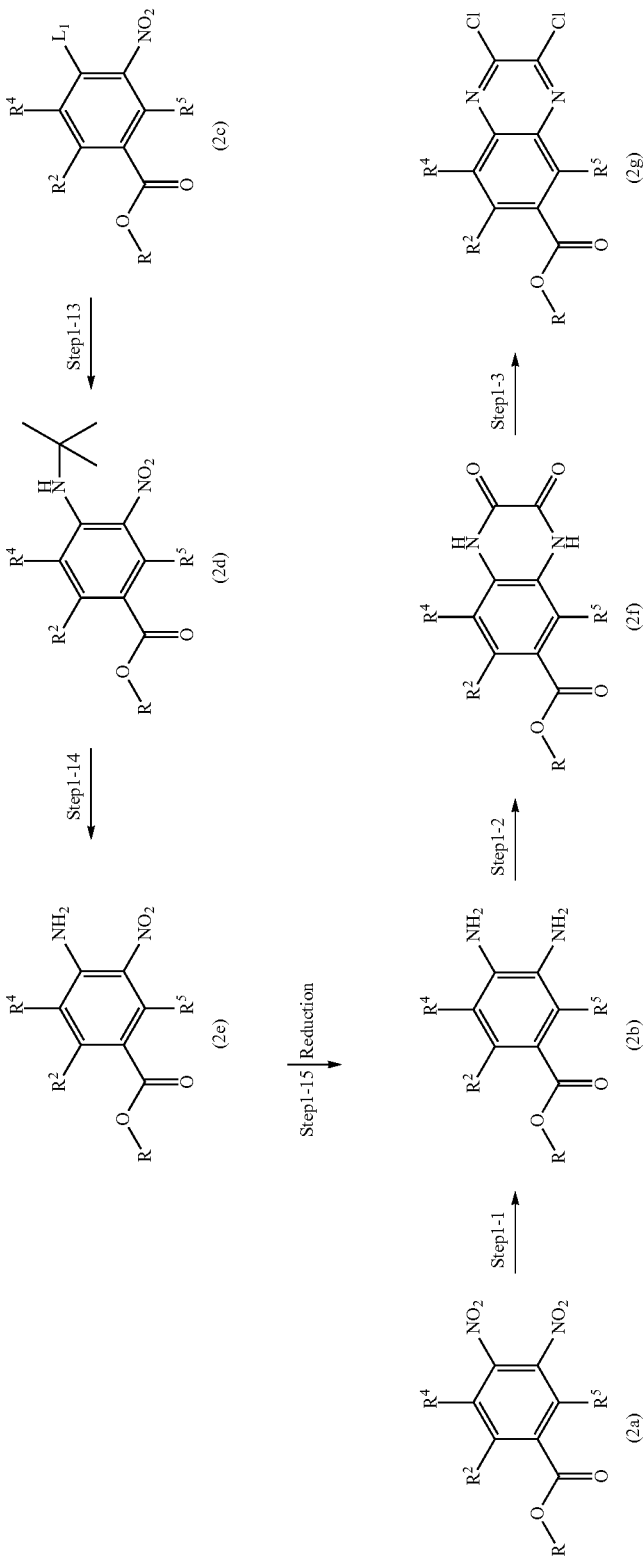

-continued
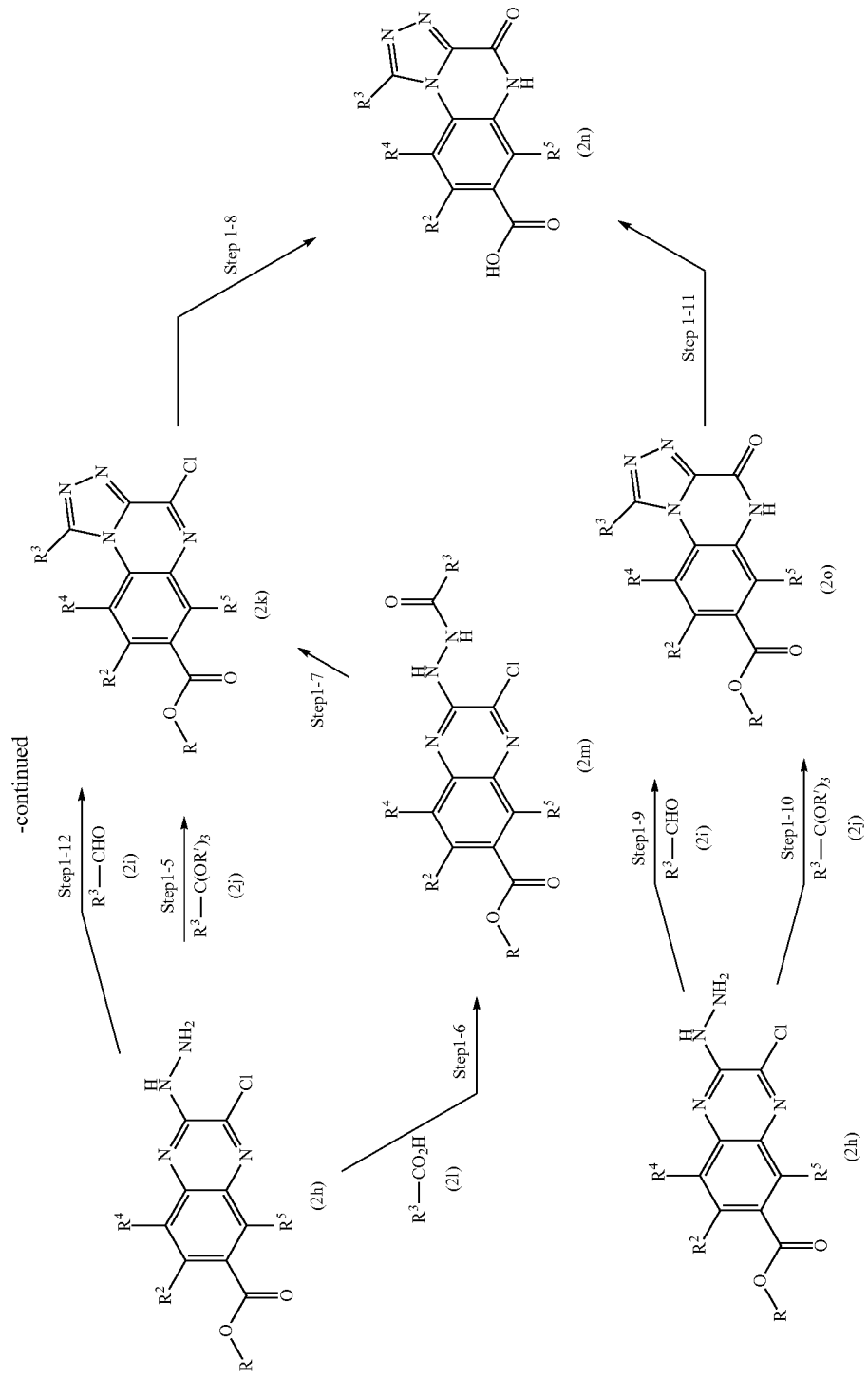

(wherein $L_1$ means a leaving group and R' means lower alkyl. The same shall apply hereinafter).

The step represented by Step 1-1 is a reaction for obtaining a compound (2b) by a hydrogenation reaction of a compound (2a). In this reaction, the compound (2a) is stirred in the presence of a metal catalyst, usually for 1 hour to 5 days, in a solvent inert to the reaction, under a hydrogen atmosphere. This reaction is usually carried out in a range of normal pressure to 90 bar and under any temperature condition from cooling to heating, preferably at normal pressure and room temperature. Examples of the solvent used herein are not particularly limited, but include alcohols such as methanol, ethanol, 2-propanol, and the like, ethers such as diethyl ether, tetrahydrofuran, dioxane, dimethoxyethane, and the like, water, ethyl acetate, N,N-dimethylformamide, dimethylsulfoxide, and a mixture thereof. As the metal catalyst, palladium catalysts such as palladium carbon, palladium black, palladium hydroxide, and the like, platinum catalysts such as a platinum plate, platinum oxide, and the like, nickel catalysts such as reduced nickel, Raney nickel, and the like, rhodium catalysts such as tetrakistriphenylphosphine chlororhodium, and the like, or iron catalysts such as reduced iron and the like are preferably used. Instead of hydrogen gas, formic acid or ammonium formate in equivalent amounts, or with either thereof in an excess amount can be used as a hydrogen source, relative to the compound (2a). This step further includes a reaction for obtaining a compound (2b) by a reduction reaction of a compound (2a). In this reaction, the compound (2a) is stirred in the presence of an iron catalyst such as reduced iron, activated iron carbonate (III), and the like, usually for 0.5 hours to 5 days, in a solvent inert to the reaction. This reaction is usually carried out under any temperature condition from cooling to heating, preferably at 0° C. to 100° C. For this step, reference may be made to the methods described in "Reductions in Organic Chemistry, $2^{nd}$ Ed. (ACS Monograph: 188)" written by M. Hudlicky, ACS, 1996, "Courses in Experimental Chemistry" ($4^{th}$ Edition), edited by The Chemical Society of Japan, Vol. 26 (1992) (Maruzen), and the like.

The step represented by Step 1-13 is a reaction for obtaining a compound (2d) by the reaction of compound (2c) and tert-butylamine. In this reaction, the compound (2c) and tert-butylamine in equivalent amounts, or with either thereof in an excess amount are used, and a mixture thereof is stirred under any temperature condition from cooling to heating and refluxing, preferably at 0° C. to 80° C., usually for 0.1 hours to 5 days, in a solvent which is inert to the reaction. The solvent as used herein is not particularly limited, but examples thereof include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, N,N-dimethylacetamide, dimethylsulfoxide, ethyl acetate, acetonitrile, N-ethylpiperidone, and a mixture thereof. It may be advantageous in some cases for the smooth progress of the reaction to carry out the reaction in the presence of an organic base such as triethylamine, N,N-diisopropylethylamine, pyridine, N-methylmorpholine, and the like, or an inorganic base such as sodium hydroxide, potassium carbonate, sodium carbonate, potassium hydroxide, and the like. For this step, reference may be made to the methods described in "Organic Functional Group Preparations", written by S. R. Sandler and W. Karo, $2^{nd}$ edition, Vol. 1, Academic Press Inc., 1991, "Courses in Experimental Chemistry ($5^{th}$ edition)", edited by The Chemical Society of Japan, Vol. 14 (2005) (Maruzen), and the like.

The step represented by Step 1-14 is a reaction for obtaining a compound (2e) by a dealkylation reaction of the compound (2d). Here, the dealkylation reaction can be carried out with reference to the method described in "Greene's Protective Groups in Organic Synthesis ($4^{th}$ edition, 2006)".

The step represented by Step 1-15 is a reaction for obtaining a compound (2b) by a hydrogenation reaction or reduction reaction of the compound (2e), for which the method used in Step 1-1 can be incorporated.

The step represented by Step 1-2 is a reaction for obtaining a compound (2f) by a cyclization reaction of the compound (2b) with diethyl oxalate (($COOEt)_2$) or oxalic acid. For this step, reference may be made to the methods described in J. Med. Chem., 38 (19): pp. 3720-3740 (1995), the specification of US Patent Application Publication No. 2004/192698, and the like.

The step represented by Step 1-3 is a reaction for obtaining a compound (2g) by chlorination of the compound (2f). In this reaction, a chlorinating agent is used in equivalent amounts, or with either thereof in an excess amount, relative to the compound (2f), and a mixture thereof is stirred under any temperature condition from cooling to heating and refluxing, preferably at room temperature to under heating and refluxing, usually for 0.1 hours to 5 days, in a solvent which is inert to the reaction or without a solvent. The solvent as used herein is not particularly limited, but examples thereof include aromatic hydrocarbons such as benzene, toluene, xylene, and the like, ethers such as tetrahydrofuran, dioxane, dimethoxyethane, and the like, halogenated hydrocarbons such as 1,2-dichloroethane, chloroform, and the like, acetonitrile, and a mixture thereof. It may be advantageous in some cases for the smooth progress of the reaction to carry out the reaction in the presence of N,N-dimethylformamide or N,N-diethylaniline, and the like. Examples of the chlorinating agent include phosphoryl chloride, phosphorous pentachloride, and thionyl chloride.

The step represented by Step 1-4 is a reaction for obtaining a compound (2h) by the reaction of the compound (2g) with hydrazine monohydrate, for which the method used in Step 1-13 can be incorporated.

Each of the steps represented by Step 1-5 and Step 1-10 is a reaction for obtaining a compound (2k) or a compound (2o) by a cyclization reaction, or a cyclization reaction and hydrolysis of the compound (2h) or the compound (2j). In this reaction, the compound (2j) is used in an equivalent amount or an excess amount, relative to the compound (2h), and a mixture thereof is stirred under any temperature condition from cooling to heating and refluxing, preferably at room temperature to under heating and refluxing, usually for 0.1 hours to 5 days, in a solvent which is inert to the reaction or without a solvent. For this step, reference may be made to the method described in J. Med. Chem., 33 (8): pp. 2240-2254 (1990).

The step represented by Step 1-6 is a reaction for obtaining a compound (2m) by the reaction of the compound (2h) with the compound (2l), for which the method used in (Production Process 1) can be incorporated.

The step represented by Step 1-7 is a reaction for obtaining a compound (2k) by the reaction of the compound (2m) with thionyl chloride, for which the method used in (Step 1-3) can be incorporated.

Each of the steps represented by Step 1-8 and Step 1-11 is a reaction for obtaining a compound (2n) by a hydrolysis reaction of the compound (2k) or the compound (2o). Here, the hydrolysis reaction can be carried out with reference to the method described in "Greene's Protective Groups in Organic Synthesis ($4^{th}$ edition, 2006)".

Each of the steps represented by Step 1-9 and Step 1-12 is a reaction for obtaining a compound (2k) or a compound (2o) by the reaction of the compound (2h) with the compound (21). In this reaction, the compound (2h) and the compound (21) in equivalent amounts, or with either thereof in an excess amount are used, and a mixture thereof is stirred under any temperature condition from room temperature to heating and refluxing, usually for 1 to 5 days, in a solvent which is inert to the reaction or without a solvent, in the presence of an oxidant. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as t diethyl ether, tetrahydrofuran, dioxane, dimethoxyethane, and the like, N,N-dimethylformamide, dimethylsulfoxide, acetic acid, ethylene glycol, ethyl acetate, acetonitrile, water, hydrochloric acid, and a mixture thereof. Examples of the oxidant include copper acetate, copper chloride, bromine, chloranil, 2,3-dichloro-5, 6-dicyano-p-benzoquinone, and the like. In this reaction, each of imine formation by dehydration, cyclization using an oxidant, and hydrolysis can be carried out stepwise. For this step, reference may be made to the method described in Indian J. Chem., 38B: pp. 45-51, 1371-1373 (1999).

(Starting Material Synthesis 2)

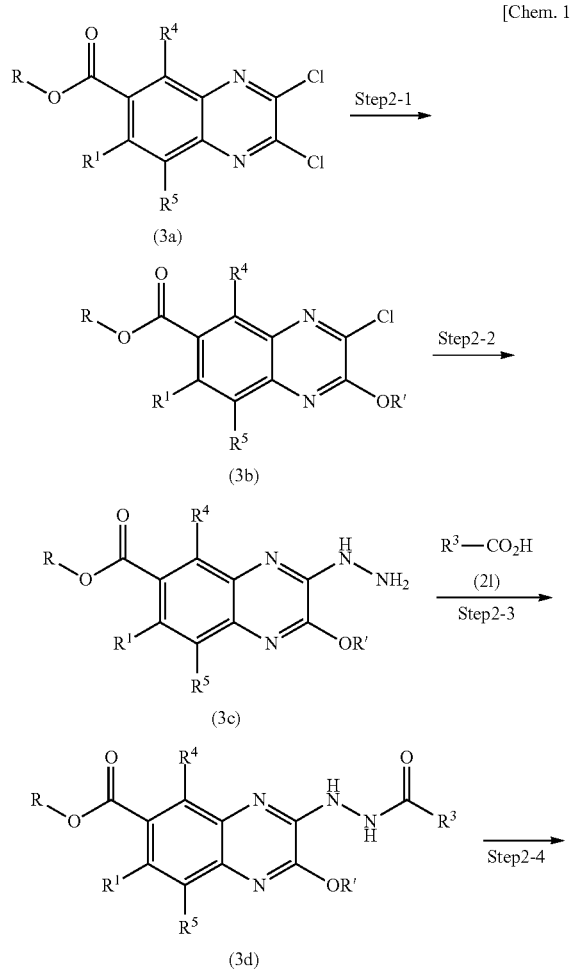

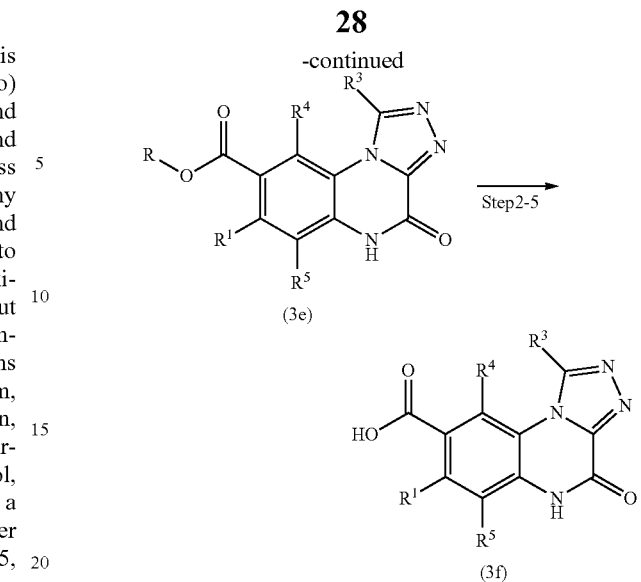

(wherein $R^1$ represents the meaning as defined above).

The step represented by Step 2-1 is a reaction for obtaining a compound (3b) by the reaction of a compound (3a) with alkoxide. In this reaction, the compound (3a) and sodium methoxide in equivalent amounts, or with either thereof in an excess amount are used, and a mixture thereof is stirred under any temperature condition from cooling to heating and refluxing, usually for 0.1 hours to 5 days, in a solvent which is inert to the reaction or without a solvent. It may be advantageous in some cases for the smooth progress of the reaction to carry out the reaction in the presence of a copper catalyst such as copper (I) halide and the like, a phase transfer catalyst, or a crown ether. Examples of the chlorinating agent include phosphoryl chloride, phosphorous pentachloride, and thionyl chloride. For this step, reference may be made to the method described in "Courses in Experimental Chemistry ($5^{th}$ edition)", edited by The Chemical Society of Japan, Vol. 14 (2005) (Maruzen), and the like.

The step represented by Step 2-2 is a reaction for obtaining a compound (3c) by the reaction of the compound (3b) with hydrazine monohydrate, for which the method used in Step 1-4 of (Starting Material Synthesis 1) can be incorporated.

The step represented by Step 2-3 is a reaction for obtaining a compound (3d) by the reaction of the compound (3c) with the compound (21), for which the method used in (Production Process 1) can be incorporated.

The step represented by Step 2-4 is a reaction for obtaining a compound (3e) by the reaction of the compound (3d) with thionyl chloride, for which the method used in Step 1-3 of (Starting Material Synthesis 1) can be incorporated. In this reaction, each step of a cyclization reaction and a dealkylation reaction using thionyl chloride can be carried out stepwise. Here, the dealkylation can be carried out with reference to the method described in "Greene's Protective Groups in Organic Synthesis ($4^{th}$ edition, 2006)".

The step represented by Step 2-5 is a reaction for obtaining a compound (3f) by a hydrolysis reaction of the compound (3e), for which the method used in Step 1-11 of (Starting Material Synthesis 1) can be incorporated.

(Starting Material Synthesis 3)

[Chem. 14]

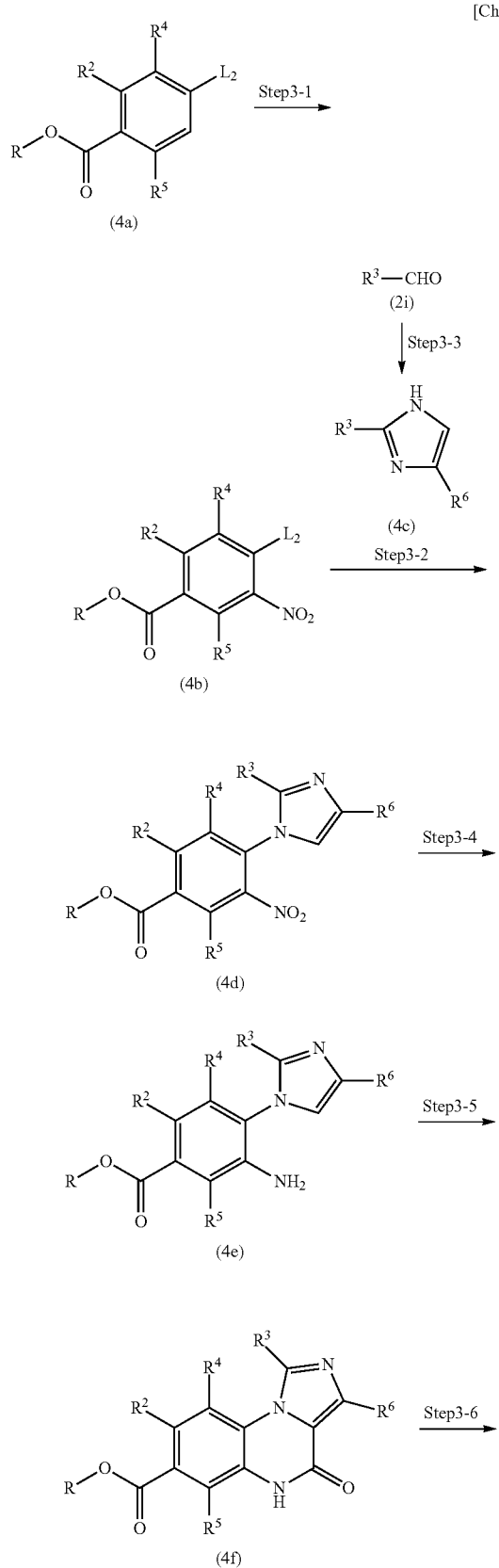

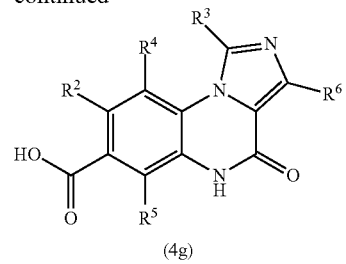

(wherein $R^6$ represents the meaning as defined above. $L_2$ represents a leaving group).

Step 3-1 is a step for obtaining a compound (4b) by a nitration reaction of the compound (4a), and examples of the nitrating agent include nitric acid, a mixture (mixed acid) of nitric acid and sulfuric acid, a mixture of a metal nitrate such as lithium nitrate, sodium nitrate, potassium nitrate, and the like and sulfuric acid, nitronium salts such as nitronium tetrafluoroborate and the like, acetyl nitrate, and the like. For this step, reference may be made to the method described in "Courses in Experimental Chemistry ($5^{th}$ edition)", edited by The Chemical Society of Japan, Vol. 14 (2005) (Maruzen), and the like.

Step 3-2 is a step for obtaining a compound (4d) by the reaction of the compound (4b) and the compound (4c), for which the method used in Step 1-4 of (Starting Material Synthesis 1) can be incorporated. Here, examples of the leaving group include halogen, a methanesulfonyloxy group, a p-toluenesulfonyloxy group, and the like.

Step 3-3 is a step for obtaining a compound (4c) by a cyclization reaction of the compound (21), which can be carried out in the presence of glyoxal, or dichloroacetaldehyde and aqueous ammonia. For this step, reference may be made to the method described in Angew. Chem. Int. Ed. Engl., 22 (7): pp. 560-561 (1983).

Step 3-4 is a step for obtaining a compound (4e) by the hydrogenation reaction or the reduction reaction of the compound (4d), for which the method used in Step 1-1 of (Starting Material Synthesis 1) can be incorporated.

Step 3-5 is a step for obtaining a compound (4f) by a cyclization reaction of the compound (4e) with 1,1'-carbonyldiimidazole or triphosgene. For this step, reference may be made to the method described in J. Med. Chem., 34 (9): pp. 2671-2677 (1991).

Step 3-6 is a step for obtaining a compound (4g) by the hydrolysis reaction of the compound (4f), for which the method used in Step 1-11 of (Starting Material Synthesis 1) can be incorporated.

(Starting Material Synthesis 4)

[Chem. 15]

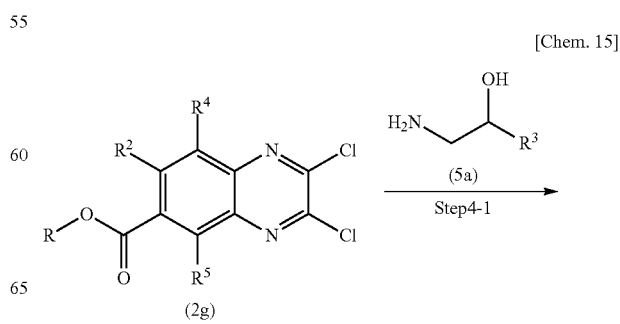

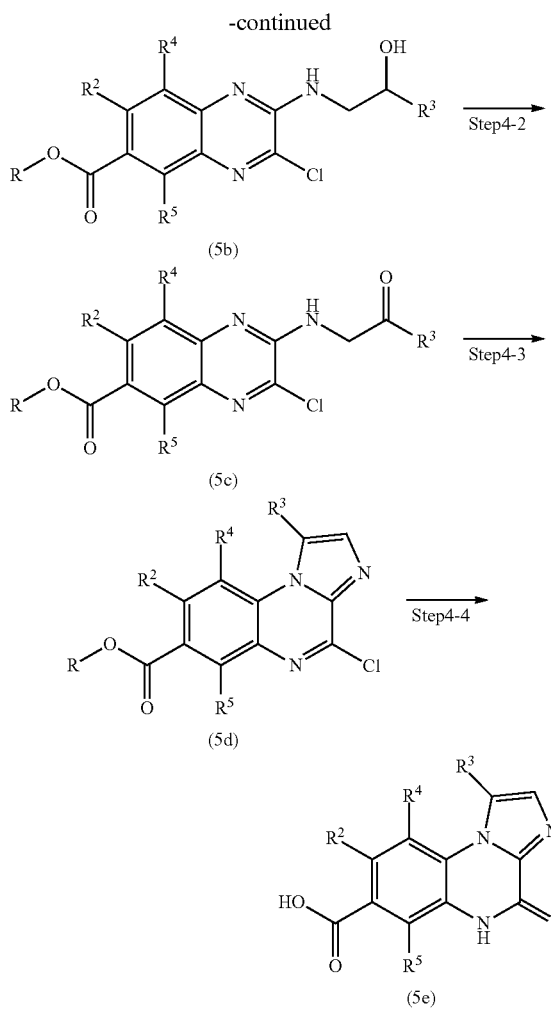

The step represented by Step 4-1 is a step for obtaining a compound (5b) by the reaction of the compound (2g) with the compound (5a), for which the method used in Step 1-4 of (Starting Material Synthesis 1) can be incorporated.

The step represented by Step 4-2 is a step for obtaining a compound (5c) by an oxidation reaction of the compound (5b). In this reaction, an oxidant is used in an equivalent amount or in an excess amount, relative to the compound (5b), and a mixture thereof is stirred under any temperature condition from cooling to heating and refluxing, preferably from cooling to room temperature usually for 0.1 hours to 5 days, in a solvent which is inert to the reaction. Examples of the oxidant include dimethylsulfoxide and the like, activated with Dess-Martin periodinane, oxalyl chloride, or the like. For this step, reference may be made to the method described in "Courses in Experimental Chemistry (5$^{th}$ edition)", edited by The Chemical Society of Japan, Vol. 15 (2005) (Maruzen), and the like.

The step represented by Step 4-3 is a step for obtaining a compound (5d) by a cyclization reaction of the compound (5c). In this reaction, a mixture of trifluoroacetic acid anhydride and trifluoroacetic acid is used in an equivalent amount or in an excess amount, relative to the compound (5c), and a mixture thereof is stirred under any temperature condition from cooling to heating and refluxing, preferably from cooling to room temperature usually for 0.1 hours to 5 days, in a solvent which is inert to the reaction.

For the steps of Step 4-1, Step 4-2, and Step 4-3, reference may be made to the method described in J. Med. Chem., 40 (13): pp. 2053-2063 (1997).

The step represented by Step 4-4 is a step for obtaining a compound (5e) by a hydrolysis reaction of the compound (5d), for which the method used in Step 1-8 of (Starting Material Synthesis 1) can be incorporated.

The compounds of the formula (I) can be isolated and purified as their free compounds, salts, hydrates, solvates, or polymorphic crystal substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting material.

The pharmacological activity of the compound of the formula (I) was confirmed by the tests shown below.

TEST EXAMPLE 1

PDE9-Inhibiting Activity (1) Acquisition of PDE9

The PDE9 used in the present experiment was expressed/purified by the method as in, for example, Guipponi et al., and Fisher et., al. (Fisher, D. A., et al., J. Biol. Chem., 273: pp. 15559-15564 (1998), Guipponi, M., et al., Hum. Genet., 103: pp. 386-392 (1998)).

(2) Evaluation of PDE9-Inhibiting Activity

The PDE9-inhibiting activity was measured by the following method. That is, to a buffer solution containing tris(hydroxymethyl)aminomethane-hydrochloric acid (40 mM, pH 8.0), magnesium chloride (5 mM), and 2-mercaptoethanol (4 mM) were added cGMP (1 μM) and $^3$H-cGMP (0.33 μCi/ml) to give a substrate buffer solution. A test substance solution and an enzyme solution which had been adjusted to an optimal concentration were added thereto to perform a reaction at 30° C. The enzyme reaction was stopped by the addition of Scintillation Proximity Assay (SPA) Beads (GE Healthcare, UK) containing 5 mM 3-isobutyl-1-methylxanthine (IBMX). For the enzyme activity, the amount of 5'-GMP, which is a reaction degradation product bound to SPA beads, was measured with a TopCount microplate reader (Hewlett Packard, USA).

The inhibitory rate was calculated by taking the radioactivity of the control containing no test substance as (A), taking the radioactivity of the blank containing no enzyme as (B), and taking the radioactivity of the test substance as (C), and using the following equation.

Inhibitory rate=$100-\{(C)-(B)/(A)-(B)\}\times 100(\%)$

In addition, the IC$_{50}$ value was calculated as a compound concentration which inhibits the results obtained by 50% by a Logistic regression method.

(3) Other evaluation of PDE-Inhibiting activity

For the PDE1, a recombinant enzyme was purchased (BPS Bioscience Inc., USA). The PDE2 was expressed/purified by a method of Yang et., al. (Yang, Q., et al., Biochem. Biophys. Res. Commun., 205: pp. 1850-1858 (1994)), and the PDE4 was expressed/purified by a method of Nemoz et., al. (Nemoz, G., et al., FEBS Lett., 384: pp. 97-102 (1996)). The PDE3, PDE5, and PDE6 were isolated from rabbit myocardium, rabbit prostate, and rat retina. That is, desired tissues were selected from each of the animals, and chipped in a buffer solution containing bis(2-hydroxyethyl)iminotris(hydroxymethyl)aminomethane (20 mM), dithioerythritol (5 mM), glycol ether diamine teteraacetic acid (2 mM), and sodium acetate (50 mM). Then, the cells were crushed using an ultrasonic cell crusher. Each cell-crushed solution was ultracentrifuged (1,000,000×g, 4° C., 60 minutes), and then, the supernatant was added to a Q Sepharose column. By the concentration gradient of a buffer solution containing 0.05 to 1.2 M sodium acetate, sodium chloride (140 mM), potassium chloride (5 mM), glucose (5 mM), and 2[4-(2-hydroxyethyl)-1-piperazinyl]ethane sulfonic acid (10 mM), elution was performed by ion exchange to obtain a fraction as a source of enzymes. For each of the eluate fractions, PDE subtypes were identified by enzymatic properties and selective inhibitor susceptibility.

For the PDE enzyme activity, the degradability for cAMP or cGMP was measured by the amount of 5'-AMP or 5'-GMP, which is a reaction degradation product bound to SPA beads, by the method as in PDE9 above.

For the compound of the formula (I), the PDE9-inhibiting activity action was confirmed by the test method above. For example, the following Example compounds exhibited the following PDE9-inhibiting activity actions ($IC_{50}$ values: nM).

Example 3 (6.7), Example 4 (19), Example 5 (2.3), Example 11 (3.1), Example 13 (22), Example 27 (18), Example 35 (12), Example 68 (3.5), Example 71 (9.2), Example 76 (2.5), Example 77 (1.0), Example 80 (2.6), Example 91 (20), Example 93 (15), Example 103 (11), Example 134 (950), Example 220 (18), Example 248 (5.8), Example 263 (0.9), Example 277 (16), Example 279 (10), Example 281 (1.6), Example 289 (3.9), Example 290 (1.0), Example 291 (2.8), Example 300 (0.8), Example 306 (4.2), Example 309 (4.1), Example 312 (20), Example 318 (5.9), Example 320 (1.0), Example 322 (29), Example 324 (1.7), Example 326 (1.2), Example 330 (1.2), Example 333 (2.9), Example 338 (28), Example 343 (13), Example 344 (7.7), Example 346 (27), Example 347 (3.3), Example 350 (9.2), Example 352 (12), Example 356 (1.5), Example 359 (5.4), Example 516 (0.8), Example 517 (0.9), Example 519 (6.8), Example 522 (3.6), Example 528 (0.9).

Furthermore, among the compounds of the formula (I), some of the compounds, wherein $A^1$ is N, $R^1$ is a group of the formula (II), $R^4$ to $R^6$ are hydrogen, and $R^a$ and $R^b$ are combined with the adjacent nitrogen atom to form a polycyclic nitrogen-containing hetero ring which may be substituted, in particular, lots of the Example compounds included in the afore-mentioned embodiments (27) to (31) of the present invention were confirmed to have a selective PDE9-inhibiting activity. The selective PDE9-inhibiting activity refers to a further potent inhibiting activity than the inhibiting activity, particularly on PDE1, PDE3, and PDE6, it is, for example, a case where the $IC_{50}$ value (nM) is 1/10 or less, as compared with any of PDE1, PDE3, and PDE6, preferably a case where the $IC_{50}$ value (nM) is 1/50 or less, as compared with 1, 2, or all of PDE1, PDE3, and PDE6, and more preferably a case where the $IC_{50}$ value (nM) is 1/100 or less, as compared with 1, 2, or all of PDE1, PDE3, and PDE6.

TEST EXAMPLE 2

Evaluation of PDE9-Inhibiting Activity in Cells

A CRE-luc gene in which a luciferase (luc) gene was linked to the PDE9 gene and the cyclic AMP response element (CRE) gene in the HEK293 cell was transiently introduced to prepare a PDE9 and CRE-luc co-expressing cell. The next day, a 0.5 mM IBMX and a test substance solution were added to the cells and cultured at 37° C. for 6 hours, and then the culture supernatant was removed. 0.2% Triton X-100-containing phosphate buffer solution was added thereto to crush the cells. The PDE9-inhibiting activity in the cell was evaluated by adding the cell solution obtained by crushing the cells and measuring the luciferase activity in a fluorescence/illuminant plate reader.

As a result, it was confirmed that there are some compounds exhibiting the effective activity among the compounds of the present invention.

TEST EXAMPLE 3

Action in Simultaneous Measurement Model for Rat Bladder Contraction/Urethra Relaxation Responses Simultaneous measurement of the bladder contraction and urethra relaxation responses using a rat was carried out with a partial modification of a method in Wibberley et al., (Wibberley, A., et al., Br. J. Pharmacol., 136: pp. 399-414 (2002)). That is, a female Sprague-Dawley (SD) rat (Charles River Laboratories Japan, Inc.) was anesthetized with urethane, and the bladder was exposed by a midline incision in the lower abdomen. A double lumen cannula (a cannula having a dual structure by PE190 and PE50) from the bladder apex was inserted into the bladder, and the bladder apex and the cannula were fixed by sutures at a point where the tip reached the proximal urethra. While infusing physiological saline into the urethra through the outer cannula, the urethral inner pressure was measured by a pressure transducer through the inner cannula with a saline solution infused into the urethra through the outer cannula. On the other hand, a single cannula (PE50) was inserted into the bladder from the bladder apex and placed therein. The inner pressure of the bladder was measured through this cannula. After a postoperative stabilization period had passed, physiological saline was infused into the bladder through the cannula of the bladder apex to cause a bladder contraction reaction response, and thus cause an action accompanying the bladder contraction reflex. The test substance was administered intravenously or intraduodenally.

As a result, it was confirmed that there are some compounds exhibiting the effective activity among the compounds of the present invention.

TEST EXAMPLE 4

Action in Rat Drug-Induced Voiding Dysfunction Model

A male SD rat (Japan SLC, Inc.) was aroused in a Ballman cage under anesthesia with diethyl ether after placing a cannula in the bladder and the jugular vein. After a postoperative stabilization period had passed, physiological saline was infused into the bladder to cause voiding. Infusion of the physiological saline and was stopped immediately after voiding, and the amount of the drained urine was measured using a pan balance placed under a Ballman cage. After completion of voiding, the residual urine was collected by gravity through a cannula placed in the bladder, and the weight was measured. Further, the inner pressure of the bladder was measured by a pressure transducer through the bladder cannula. Voiding dysfunction was caused by intravenous administration of one or a combination of an anticholinergic agent, an α1 receptor agonist, and an NO production inhibitor, and the voiding dynamics were observed after the drug administration. The test substance was administered intravenously or orally.

As a result, it was confirmed that there are some compounds exhibiting the effective activity among the compounds of the present invention.

As a result of the test above, it was confirmed that the compound of the formula (I) has a PDE9-inhibiting action and it was also confirmed that there are effective compounds in the animal models. Accordingly, the compound can be used for treatment or the like, for diseases related to degradation of cGMP by PDE9, for example, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, and urethra calculus.

In addition, among the compounds of the formula (I), some compounds, wherein $A^1$ is N, $R^1$ is a group of the formula (II), $R^4$ to $R^6$ are hydrogen, and $R^a$ and $R^b$ are combined with the adjacent nitrogen atom to form a polycyclic nitrogen-containing hetero ring which may be substituted has a selective PDE9-inhibiting activity, and as a result, the side effects derived from the action of other PDE subtypes can be avoided, whereby the compounds can be excellent therapeutic agents having higher safety. For example, cardiovascular risk derived from the PDE3 inhibitory action or the risk of blindness derived from the PDE6 inhibitory action can be avoided (A. M. Laties Drug Safety 2009; 32, 1-18/J. B. Shipley et al., Am. J. Med. Sci., 1996; 311, 286-291/T. M. Vinogradova et al., Circ. Res., 2008; 102, 761-769).

A pharmaceutical composition containing one or two or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration injections, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or more active ingredient(s) are mixed with at least one inactive excipient, such as lactose, mannitol, glucose, hydroxypropyl cellulose, microcrystalline cellulose, starch, polyvinyl pyrrolidone, and/or magnesium aluminometasilicate. In a conventional method, the composition may contain inactive additives, such as a lubricant such as magnesium stearate, a disintegrating agent such as sodium carboxymethyl starch and the like, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include propylene glycol, polyethylene glycol, plant oils such as olive oil, alcohols such as ethanol, polysorbate 80 (Japanese Pharmacopeia), and the like. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, patches, sprays, lotions, eye drops, eye ointments, and the like. The agents contain generally used ointment bases, lotion bases, aqueous or non-aqueous liquid preparations, suspensions, emulsions, and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, hydrofluoroalkane, carbon dioxide, and the like, or other forms.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various therapeutic or prophylactic agents for the diseases for which the compound of the formula (I) is considered to be effective. The combined preparation may be administered simultaneously, or separately and continuously, or at a desired time interval. The preparations to be co-administered may be a blend, or may be prepared individually.

EXAMPLES

Hereinbelow, the preparation methods for the compound of the formula (I) will be described in more detail with reference to Examples. Further, the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

The following abbreviations may be used in some cases in the Examples, Preparation Examples, and Tables below. tert-: Tertiary, Pr: Preparation Example No., Ex: Example No., No: Compound No., Structure: Structural formula, Syn: Preparation method (the numeral shows that the Example compound was prepared in the same manner as a compound having its number as the Example No. "Pr-3" or the like shows that the Example compound was prepared in the same manner as a compound of Preparation Example 3 or the like), Data: Physicochemical data, ESI+: m/z values in mass spectroscopy (Ionization ESI, representing (M+H)$^+$ unless otherwise specified), ESI−: m/z values in mass spectroscopy (Ionization ESI, representing (M−H)$^-$ unless otherwise specified), EI+: m/z values in mass spectroscopy (Ionization EI, representing (M)$^+$ unless otherwise specified), FAB+: m/z values in mass spectroscopy (Ionization FAB, representing (M+H)$^+$ unless otherwise specified), FAB−: m/z values in mass spectroscopy (Ionization FAB, representing (M−H)$^-$ unless otherwise specified), APCI+: m/z values in mass spectroscopy (Ionization APCI, representing (M+H)$^+$ unless otherwise specified), APCI/ESI+: m/z values in mass spectroscopy (Ionization APCI and ESI simultaneously performed, representing (M+H)$^+$ unless otherwise specified), APCI/ESI−: m/z values in mass spectroscopy (Ionization APCI and ESI simultaneously performed, representing (M−H)$^-$ unless otherwise specified), mp: Melting point, dec.: decomposition, NMR: δ (ppm) of peak in $^1$H NMR, s: singlet (spectrum), d: doublet (spectrum), t: triplet (spectrum), q: quartet (spectrum), sex: sextet (spectrum), br: broad line (spectrum) (example: br and s). Further, HCl in the structure represents hydrochloride (the numeral prefixed to HCl denotes a molar ratio), Rac represents racemic mixture, and (+)- and (−)- represents (+) and (−) configurations of the enantiomers, respectively.

Preparation Example 1

700 mg of methyl 3-chloro-2-hydrazinoquinoxaline-6-carboxylate was suspended in 3.7 mL of trimethyl orthobutyrate, followed by heating and refluxing for 2 hours. The suspension was ice-cooled, and the solid was collected by filtration and washed with cold ethyl acetate. The obtained solid was washed with hot ethyl acetate to obtain 612 mg of methyl 4-chloro-1-propyl[1,2,4]triazolo[4,3-a]quinoxaline-7-carboxylate.

Preparation Example 2

To 2.97 g of methyl 4-chloro-1-propyl[1,2,4]triazolo[4,3-a]quinoxaline-7-carboxylate was added 70 mL of 6 M hydrochloric acid, followed by heating and refluxing for 5 hours. After air-cooling, the precipitated solid was collected by filtration, and washed with water and ethyl acetate. The obtained solid was washed with hot acetonitrile to obtain 2.05 g of 4-oxo-1-propyl-4,5-dihydro[1,2,4]triazolo[4,3-a]quinoxaline-7-carboxylic acid as a pale yellow solid.

Preparation Example 3

To a mixed liquid of 1.70 g of methyl 4-chloro-8-methyl-1-(tetrahydro-2H-thiopyran-4-ylmethyl)[1,2,4]triazolo[4,3-a]quinoxaline-7-carboxylate, 18.0 mL of tetrahydrofuran, and 18.0 mL of methanol was added 9.20 mL of a 3 M aqueous sodium hydroxide solution, followed by stirring at 60° C. overnight. 3 M hydrochloric acid was added thereto to adjust the pH to about 3, and the precipitated solid was collected by filtration and dried under reduced pressure to obtain 1.20 g of 8-methyl-4-oxo-1-(tetrahydro-2H-thiopyran-4-ylmethyl)-4,5-dihydro[1,2,4]triazolo[4,3-a]quinoxaline-7-carboxylic acid as a yellow solid.

Preparation Example 4

To a mixture of 100 mg of methyl 3-chloro-2-hydrazinoquinoxaline-6-carboxylate, 57 mg of tetrahydro-2H-pyran-4-carboxylic acid, 0.16 mL of diisopropylethylamine, and 1.0 mL of N,N-dimethylformamide was added 203 mg of bromo(tripyrrolidin-1-yl)phosphonium hexafluorophosphate, followed by stirring at room temperature overnight. To the reaction mixture was added water, followed by extraction with ethyl acetate. The organic layer was washed with saturated brine and dried over anhydrous magnesium sulfate, and then the solvent was evaporated under reduced pressure. The obtained residue was purified by silica gel column chromatography (chloroform/methanol) to obtain 144 mg of methyl 3-chloro-2-[2-(tetrahydro-2H-pyran-4-ylcarbonyl)hydrazino]quinoxaline-6-carboxylate.

Preparation Example 5

To a mixture of 1.20 g of methyl 3-chloro-2-[2-(tetrahydro-2H-pyran-4-ylcarbonyl)hydrazino]quinoxaline-6-carboxylate and 36 mL of acetonitrile was added 0.5 mL of thionyl chloride, followed by stirring at 90° C. for 4.5 hours. The solvent was evaporated under reduced pressure, to the obtained residue was added water, and the solid was collected by filtration and dried under reduced pressure to obtain 1.13 g of methyl 4-chloro-1-(tetrahydro-2H-pyran-4-yl)[1,2,4]triazolo[4,3-a]quinoxaline-7-carboxylate.

Preparation Example 6

A mixture of 6.00 g of methyl 3-chloro-2-hydrazinoquinoxaline-6-carboxylate, 2.9 mL of 4-methoxybenzaldehyde, and 150 mL of acetic acid was stirred at room temperature for 3 hours. To the reaction mixture was added 4.74 g of copper (II) acetate, followed by stirring at 100° C. for 3 hours. Water was added thereto at room temperature, and the precipitated solid was collected by filtration and dried under reduced pressure. The obtained mixture was purified by silica gel column chromatography (chloroform/methanol) to obtain 5.27 g of methyl 1-(4-methoxyphenyl)-4-oxo-4,5-dihydro[1,2,4]triazolo[4,3-a]quinoxaline-7-carboxylate.

Preparation Example 7

A mixture of 5.3 g of methyl 2-methyl-4,5-dinitrobenzoate, 1.06 g of 10% palladium on carbon (50% wet), 53 mL of ethanol, and 53 mL of dioxane was thoroughly stirred at room temperature under a hydrogen atmosphere. The insoluble materials were filtered and washed sufficiently with methanol. The filtrates were concentrated together, and then dried under reduced pressure to obtain 3.98 g of methyl 4,5-diamino-2-methylbenzoate.

Preparation Example 8

A mixture of 3.98 g of methyl 4,5-diamino-2-methylbenzoate and 40 mL of diethyl oxalate was stirred at 145° C. for 3 hours. After cooling to room temperature, the solid was collected by filtration, washed with diethyl ether, and dried under reduced pressure to obtain 4.75 g of methyl 7-methyl-2,3-dioxo-1,2,3,4-tetrahydroquinoxaline-6-carboxylate.

Preparation Example 9

A mixture of 4.75 g of methyl 7-methyl-2,3-dioxo-1,2,3, 4-tetrahydroquinoxaline-6-carboxylate and 38 mL of phosphoryl chloride was heated and refluxed for 35 hours. The reaction mixture was cooled to room temperature, then concentrated, and azeotroped with toluene. To the obtained residue was added diethyl ether, followed by stirring at room temperature for 0.5 hours. The precipitate was collected by filtration and washed with diethyl ether to obtain 3.23 g of a powder. The filtrate was concentrated and the residue was treated with diethyl ether in the same manner to obtain 2.22 g of a solid. 3.23 g of the powder and 2.22 g of the solid were washed together with diethyl ether to obtain 3.57 g of methyl 2,3-dichloro-7-methylquinoxaline-6-carboxylate.

Preparation Example 10

To a suspension of 3.57 g of methyl 2,3-dichloro-7-methylquinoxaline-6-carboxylate in 214 mL of methanol were added 7.0 mL of pyridine and 2.34 mL of hydrazine monohydrate at 0° C., and then the mixture was stirred at room temperature overnight. The mixture was concentrated until its total amount reached about 100 mL, and water was added thereto, followed by stirring at room temperature for 1 hour. The precipitate was collected by filtration, washed with water and ethanol, and dried under reduced pressure to obtain 2.94 g of methyl 3-chloro-2-hydrazino-7-methylquinoxaline-6-carboxylate.

Preparation Example 11

To a mixture of 9.45 g of methyl 4-fluoro-2-methylbenzoate and 54 mL of concentrated sulfuric acid was added 6.14 g of potassium nitrate under cooling at −10° C. over 10 minutes. After stirring at the same temperature for 4 hours, the reaction mixture was added to 300 mL of ice-cooled water, followed by stirring. The solid was collected by filtration, washed with water, and then dried under reduced pressure to obtain 10.9 g of a mixture of methyl 4-fluoro-2-methyl-5-nitrobenzoate and methyl 4-fluoro-2-methyl-3-nitrobenzoate.

Preparation Example 12

To 2.74 g of a mixture of methyl 4-fluoro-2-methyl-5-nitrobenzoate and methyl 4-fluoro-2-methyl-3-nitrobenzoate, 1.75 g of 2-cyclopentyl-1H-imidazole, and 17.5 mL of acetonitrile, was added 4.9 mL of triethylamine, followed by stirring at 70° C. for 7 hours. To the reaction mixture were added water and ethyl acetate, followed by extraction with ethyl acetate. The organic layer was washed with saturated brine and then dried over anhydrous magnesium sulfate, and then solvent was evaporated under reduced pressure. The obtained residue was purified by silica gel column chromatography (normal hexane/ethyl acetate) to obtain 2.12 g of methyl 4-(2-cyclopentyl-1H-imidazol-1-yl)-2-methyl-5-nitrobenzoate.

Preparation Example 13

A mixture of 1.79 g of methyl 5-amino-4-(2-cyclopentyl-1H-imidazol-1-yl)-2-methylbenzoate, 1.04 g of 1,1'-carbonyldiimidazole, and 18 mL of 1,2-dichlorobenzene was stirred at 190° C. for 3 hours. After air-cooling, the reaction mixture was purified by silica gel column chromatography (chloroform/methanol) to obtain 0.91 g of methyl 1-cyclopentyl-8-methyl-4-oxo-4,5-dihydroimidazo[1,5-a]quinoxaline-7-carboxylate.

Preparation Example 14

To a solution of 2.5 mL of tetrahydrofuran-3-carboxyaldehyde (50% aqueous solution) in 40 mL of ethanol were added dropwise 2.6 mL of a 40% aqueous glyoxal solution and 14 mL of 28% aqueous ammonia in this order under ice-cooling, followed by stirring for 3.5 hours while slowly warming to room temperature. Ethanol was evaporated under reduced pressure, and the aqueous solution of the residue was saturated by the addition of sodium chloride, followed by extraction with chloroform. The organic layer was dried over anhydrous magnesium sulfate and concentrated under reduced pressure. The obtained residue was heated and dissolved in ethyl acetate and then left to stand, and the precipitated solid was collected by filtration to obtain 1.58 g of 2-(tetrahydrofuran-3-yl)-1H-imidazole as a white solid.

Preparation Example 15

2.94 g of methyl 3-chloro-2-hydrazino-7-methylquinoxaline-6-carboxylate was suspended in 14 mL of trimethyl orthobutyrate, followed by heating and refluxing for 2 hours. After ice-cooling, the insoluble materials were filtered and washed with cold ethyl acetate. The filtrate was concentrated, and to the residue were added ethyl acetate, water and a saturated aqueous sodium hydrogen carbonate solution, followed by extraction with chloroform. The organic layer was dried over anhydrous magnesium sulfate, and then the solvent was evaporated under reduced pressure. A mixture of the obtained residue, 1.8 g of sodium acetate, and 29 mL of acetic acid was heated and refluxed for 2 hours. To the mixture was added water under ice-cooling, followed by stirring for 1 hour. The precipitate was collected by filtration, washed with water, and then washed with hot methanol to obtain 2.33 g of methyl 8-methyl-4-oxo-1-propyl-4,5-dihydro[1,2,4]triazolo [4,3-a]quinoxaline-7-carboxylate.

Preparation Example 16

To a mixed liquid of 1.40 g of methyl 3-chloro-2-hydrazino-7-methylquinoxaline-6-carboxylate and 28.0 mL of acetic acid was added 820 mg of tetrahydro-2H-thiopyran-4-ylacetaldehyde, followed by stirring at room temperature for 2 hours. The solvent was evaporated under reduced pressure, and to the residue was added 28.0 mL of N,N-dimethylformamide, followed by replacement with argon. Then, a mixed liquid of 706 mg of copper(II) chloride and 28.0 mL of N,N-dimethylformamide was added thereto, followed by stirring at 50° C. for 20 minutes and at 100° C. for 1 hour. To the reaction liquid were added water and chloroform, followed by extraction with chloroform, the organic layer was washed with 1 M hydrochloric acid, water, a saturated aqueous sodium hydrogen carbonate solution, and saturated brine and, dried over anhydrous magnesium sulfate, and then the solvent was evaporated under reduced pressure. The residue was purified by silica gel column chromatography (chloroform/methanol) to obtain 600 mg of methyl 4-chloro-8-methyl-1-(tetrahydro-2H-thiopyran-4-ylmethyl)[1,2,4]triazolo[4,3-a]quinoxaline-7-carboxylate as a brown solid.

Preparation Example 17

To a mixed liquid of 5.50 g of methyl 4-fluoro-2-(methoxymethyl)-5-nitrobenzoate and 55.0 mL of pyridine was added 7.20 mL of tert-butylamine, followed by stirring at room temperature overnight. The solvent was evaporated under reduced pressure, and to the residue was added water. Then, 1 M hydrochloric acid was added thereto to adjust the pH to about 4, and the precipitated solid was collected by filtration and dried under reduced pressure to obtain 6.82 g of methyl 4-(tert-butylamino)-2-(methoxymethyl)-5-nitrobenzoate as a yellow solid.

Preparation Example 18

To a mixed liquid of 6.80 g of methyl 4-(tert-butylamino)-2-(methoxymethyl)-5-nitrobenzoate and 68.0 mL of methanol was added 37.0 mL of 6 M hydrochloric acid, followed by stirring overnight under the heating and refluxing condition. The solvent was evaporated under reduced pressure, and then 111 mL of methanol and 1.00 mL of concentrated sulfuric acid were added thereto, followed by stirring overnight under the heating and refluxing condition. Ethyl acetate and a saturated aqueous sodium hydrogen carbonate solution were added thereto, followed by extraction with ethyl acetate, the organic layer was washed with saturated brine and then dried over anhydrous magnesium sulfate, and the solvent was evaporated under reduced pressure to obtain 4.73 g of methyl 4-amino-2-(methoxymethyl)-5-nitrobenzoate as a yellow solid.

Preparation Example 19

To a mixed liquid of 4.70 g of methyl 4-amino-2-(methoxymethyl)-5-nitrobenzoate, 750 mg of ammonium chloride, 47.0 mL of tetrahydrofuran, 94.0 mL of methanol, and 14.0 mL of water was added 7.65 g of reduced iron, followed by stirring at 80° C. overnight. After cooling to room temperature, the insoluble materials were filtered through celite and the filtrate was evaporated under reduced pressure to obtain 4.33 g of methyl 4,5-diamino-2-(methoxymethyl)benzoate as a brown solid.

Preparation Example 20

Under cooling in an ice-acetone bath, to a mixed liquid of 10.0 g of methyl 2,3-dichloro-7-methylquinoxaline-6-carboxylate in methanol was added dropwise a mixed liquid of 8.54 g of a 28% sodium methoxide solution in methanol and 80.0 mL of methanol over 6 hours. After stirring at the same temperature for 1 hour, the mixture was warmed to room temperature, followed by stirring for 1 hour. To the reaction mixture were added chloroform and water, followed by extraction with chloroform, and the organic layer was washed with saturated brine and then dried over anhydrous magnesium sulfate. The solvent was evaporated under reduced pressure to obtain 10.1 g of methyl 3-chloro-2-methoxy-7-methylquinoxaline-6-carboxylate as a pale yellow solid.

Preparation Example 21

To a mixed liquid of 4.83 g of methyl 2-methoxy-7-methyl-3-[2-(tetrahydro-2H-pyran-4-ylcarbonyl)hydrazino]quinoxaline-6-carboxylate and 96.6 mL of tetrahydrofuran were added 2 drops of N,N-dimethylformamide and 1.90 mL of thionyl chloride at room temperature, followed by stirring at 70° C. overnight. The reaction liquid was diluted with chloroform and added to ice-water portionwise, followed by stirring for 10 minutes. The obtained solid was collected by filtration and washed with diethyl ether to obtain 1.94 g of methyl 7-methyl-4-oxo-1-(tetrahydro-2H-pyran-4-yl)-4,5-dihydro[1,2,4]triazolo[4,3-a]quinoxaline-8-carboxylate as a pale yellow solid.

Preparation Example 22

To a mixture of 1.00 g of ethyl cis-2-hydroxy-1-cyclopentane carboxylate, 8.00 mL of chloroform, 16.0 mL of normal hexane, and 1.77 mL of 3,4-dichlorobenzyl-2,2,2-trichloroacetimidate was added 0.335 mL of trifluoromethane sulfonic acid at room temperature under a nitrogen atmosphere, followed by stirring for 3 hours. The insoluble materials were removed by filtration, and to the filtrate was added a saturated aqueous sodium hydrogen carbonate solution under ice-cooling to adjust the pH to about 7, followed by extraction with chloroform. The organic layer was dried over anhydrous magnesium sulfate, and then the solvent was evaporated. The obtained residue was purified by silica gel column chromatography (normal hexane/ethyl acetate) to obtain 1.27 g of ethyl cis-2-benzyloxy-1-cyclopentane carboxylate as a colorless oily substance.

Preparation Example 23

To a mixture of 5.18 g of ethyl cis-2-benzyloxy-1-cyclopentane carboxylate and 120 mL of tetrahydrofuran was added 63.0 mL of a 1 M aqueous lithium hydroxide solution, followed by stirring at room temperature for 2 days. The reaction liquid was concentrated under reduced pressure, and then to the residue were added water and 1 M hydrochloric acid to adjust the pH to about 2, followed by stirring at room temperature for 1 hour. The precipitated solid was collected by filtration and dried under reduced pressure. The obtained crude product was purified by silica gel column chromatography (normal hexane/ethyl acetate) to obtain 3.73 g of cis-2-benzyloxy-1-cyclopentanecarboxylic acid as a pale yellow solid.

Preparation Example 24

900 mg of benzyl cyclopropyl(hydroxy)acetate, 9.0 ml of pyridine, and 820 μL of anhydrous acetic acid were added, followed by stirring at room temperature overnight. To the reaction mixture were added water and ethyl acetate, followed by extraction with ethyl acetate. The organic layer was washed with a saturated aqueous sodium hydrogen carbonate solution and saturated brine, and then dried over anhydrous magnesium sulfate, and the solvent was evaporated under reduced pressure to obtain 1.45 g of benzyl acetoxy(cyclopropyl)acetate.

Preparation Example 25

1.40 g of benzyl acetoxy(cyclopropyl)acetate was added to 280 mL of methanol, followed by filtration. The filtrate was subjected to reduction using a continuous hydrogenation reactor (H-Cube (registered trademark); manufactured by ThalesNano) under the condition of CatCart (registered trademark), 10% palladium on carbon (manufactured by ThalesNano), a flow rate of 1.0 ml/min, and a pressure of 4 bar (Full H2 mode). The solvent was evaporated under reduced pressure to obtain 1.16 g of acetoxy(cyclopropyl)acetic acid.

Preparation Example 26

3.38 g of methyl 3-chloro-2-hydrazine-7-methylquinoxaline-6-carboxylate was dissolved in 30.0 mL of dichloromethane, and 7.09 g of bromo(tripyrrolidin-1-yl)phosphonium hexafluorophosphate and 5.30 mL of triethylamine were added thereto under ice-cooling, followed by stirring at room temperature overnight. A saturated aqueous sodium hydrogen carbonate solution was added thereto, followed by stirring at room temperature for 1 hour. The precipitated solid was collected by filtration and dried under reduced pressure to obtain methyl 3-chloro-7-methyl-2-(2-phenylhydrazino)quinoxaline-6-carboxylate. The obtained methyl 3-chloro-7-methyl-2-(2-phenylhydrazino)quinoxaline-6-carboxylate was suspended in 50.0 mL of tetrahydrofuran, and 1.85 mL of thionyl chloride was added thereto at room temperature, followed by heating and refluxing overnight. The reaction liquid was left to stand at room temperature and concentrated under reduced pressure, and the obtained residue was purified by silica gel column chromatography (chloroform/methanol) to obtain 2.06 g of methyl 4-chloro-8-methyl-1-phenyl[1,2,4]triazolo[4,3-a]quinoxaline-7-carboxylate as a brown solid Preparation Example 27

270 mg of methyl 1-(1,4-dioxaspiro[4.5]decan-8-yl)-8-methyl-4-oxo-4,5-dihydroimidazo[1,5-a]quinoxaline-7-carboxylate was added to 10 mL of tetrahydrofuran, and 2 mL of 1 M hydrochloric acid was added thereto under ice-cooling, followed by stirring at room temperature for 3 days. To the reaction mixture were added a saturated aqueous sodium hydrogen carbonate solution to adjust the pH to about 7, followed by extraction with chloroform. The organic layer was washed with saturated brine and then dried over anhydrous magnesium sulfate, and the solvent was evaporated under reduced pressure to obtain 301 mg of methyl 8-methyl-4-oxo-1-(4-oxocyclohexyl)-4,5-dihydroimidazo[1,5-a]quinoxaline-7-carboxylate as a yellow solid.

Preparation Example 28

To a mixture of 3.09 g of 2-(4-{[tert-butyl(dimethyl)silyl]oxy}cyclohexyl)-1H-imidazole and 10.7 mL of acetonitrile was added 2.8 mL of triethylamine, followed by stirring at 70° C. for 4 hours. To the reaction mixture were added water and ethyl acetate, and the organic layer was extracted with ethyl acetate. The organic layer was washed with saturated brine and then dried over anhydrous magnesium sulfate, and the solvent was evaporated under reduced pressure. The obtained residue was purified by silica gel column chromatography (normal hexane/ethyl acetate). Thus, as a low-polarity compound, 1.05 g of a yellow solid having methyl 4-[2-(cis-4-{[tert-butyl(dimethyl)silyl]oxy}cyclohexyl)-1H-imidazol-1-yl]-2-methyl-5-nitrobenzoate as a main product was obtained, while as a high-polarity compound, 0.59 g of a yellow solid having methyl 4-[2-(trans-4-{[tert-butyl(dimethyl)silyl]oxy}cyclohexyl)-1H-imidazol-1-yl]-2-methyl-5-nitrobenzoate as a main product was obtained.

To a solution of 1.05 g of the yellow solid having methyl 4-[2-(cis-4-{[tert-butyl(dimethyl)silyl]oxy}cyclohexyl)-1H-imidazol-1-yl]-2-methyl-5-nitrobenzoate obtained as a low-polarity compound in 15 mL of methanol was added 0.40 g of 10% palladium on carbon (50% wet), followed by stirring overnight under a hydrogen atmosphere. The reaction mixture was filtered through celite and the filtrate was concentrated under reduced pressure. The obtained residue was purified by silica gel column chromatography (normal hexane/ethyl acetate) to obtain 0.62 g of methyl 5-amino-4-[2-(cis-4-{[tert-butyl(dimethyl)silyl]oxy}cyclohexyl)-1H-imidazol-1-yl]-2-methylbenzoate as a yellow oily substance.

The same reaction was carried out using 0.59 g of a yellow solid having methyl 4-[2-(trans-4-{[tert-butyl(dimethyl)silyl]oxy}cyclohexyl)-1H-imidazol-1-yl]-2-methyl-5-nitrobenzoate as a main product to obtain 0.61 g of methyl 5-amino-4-[2-(trans-4-{[tert-butyl(dimethyl)silyl]oxy}cyclohexyl)-1H-imidazol-1-yl]-2-methylbenzoate as yellow oily substance.

A mixture of 0.62 g of methyl 5-amino-4-[2-(cis-4-{[tert-butyl(dimethyl)silyl]oxy}cyclohexyl)-1H-imidazol-1-yl]-2-methylbenzoate as obtained above, 0.46 g of 1,1'-carbonyldiimidazole, and 1.3 mL of 1,2-dichlorobenzene was stirred at 120° C. for 2 hours. After air-cooling, to the reaction mixture were added water and chloroform, followed by extraction with chloroform. The organic layer was washed with saturated brine and then dried over anhydrous magnesium sulfate, and the solvent was evaporated under reduced pressure. The obtained residue was purified by silica gel column chromatography (normal hexane/ethyl acetate) to obtain 0.56 g of methyl 1-(cis-4-{[tert-butyl(dimethyl)silyl]oxy}cyclohexyl)-8-methyl-4-oxo-4,5-dihydroimidazo[1,5-a]quinoxaline-7-carboxylate as a brown solid.

The same reaction was carried out using 0.61 g of methyl 5-amino-4-[2-(trans-4-{[tert-butyl(dimethyl)silyl]oxy}cyclohexyl)-1H-imidazol-1-yl]-2-methylbenzoate to obtained 365 mg of methyl 1-(trans-4-{[tert-butyl(dimethyl)silyl]oxy}cyclohexyl)-8-methyl-4-oxo-4,5-dihydroimidazo[1,5-a]quinoxaline-7-carboxylate as a yellow solid.

Preparation Example 29

To a mixture of 3 g of methyl 4-fluoro-2-methoxy-5-nitrobenzoate, 1.99 g of 2-(tetrahydro-2H-pyran-4-yl)-1H-imidazole, and 15 mL of N-ethylpiperidone was added 3.6 g of potassium carbonate, followed by stirring at 100° C. for 3 hours. To the reaction mixture were added water and ethyl acetate, followed by extraction with ethyl acetate, the organic layer was washed with saturated brine and then dried over anhydrous magnesium sulfate, and the solvent was evaporated under reduced pressure. The obtained residue was purified by silica gel column chromatography (chloroform/methanol) to obtain 4.12 g of methyl 4-[2-tetrahydro-2H-pyran-4-yl)-1H-imidazol-1-yl]-2-methoxy-5-nitrobenzoate.

Preparation Example 30

Under a nitrogen atmosphere, to a mixed liquid of 2.58 g of methyl 2-bromo-4-fluoro-5-nitrobenzoate in 50 mL of toluene and 1 mL of water were added 956 mg of cyclopropylboric acid, 360 mg of tricyclohexyl phosphine, 3.95 g of tripotassium phosphate, and 140 mg of palladium acetate, followed by stirring at 110° C. for 1.5 hours. The mixture was poured into a mixed liquid of water and ethyl acetate, and the insoluble materials were removed by filtration. The aqueous layer was separated, the organic layer was washed with saturated brine and then dried over anhydrous magnesium sulfate, and the solvent was evaporated under reduced pressure. The obtained residue was purified by silica gel column chromatography (normal hexane/ethyl acetate) to obtain 1.38 g of methyl 2-cyclopropyl-4-fluoro-5-nitrobenzoate.

Preparation Example 31

Under an argon atmosphere, to a solution of 3.45 g of 1-bromo-4-fluoro-2-(methoxymethyl)benzene in 20 mL of dimethylsulfoxide were added 353 mg of palladium acetate, 650 mg of 1,3-bis(diphenylphosphino)propane, 4.4 mL of triethylamine, and 10 mL of methanol in this order, and the atmosphere in the reaction container were replaced with carbon monoxide, followed by stirring at 70° C. for 6 hours. The reaction mixture was poured into a mixed liquid of water and ethyl acetate. The aqueous layer was separated, the organic layer was washed with saturated brine and then dried over anhydrous magnesium sulfate, and the solvent was evaporated under reduced pressure. The obtained residue was purified by silica gel column chromatography (normal hexane/ethyl acetate) to obtain 1.75 g of methyl 4-fluoro-2-(methoxymethyl)benzoate.

Preparation Example 32

To a solution of 2 g of methyl 4-fluoro-2-hydroxybenzoate in 60 mL of tetrahydrofuran were added 1.83 g of hydroxyethyl 2-acetate and 3.56 g of tributylphosphine, and then 5.93 g of 1,1'-(azodicarbonyl)dipiperidine was slowly added thereto under ice-cooling, followed by stirring for 20 minutes. The mixture was warmed to room temperature and stirred for 6 hours. The reaction mixture was poured into a mixed liquid of water and ethyl acetate. The aqueous layer was separated, the organic layer was washed with saturated brine and then dried over anhydrous magnesium sulfate, and the solvent was evaporated under reduced pressure. The obtained residue was purified by silica gel column chromatography (normal hexane/ethyl acetate) to obtain 2.4 g of methyl 2-(2-acetoxyethoxy)-4-fluorobenzoate.

Preparation Example 33

To a solution of 2.4 g of methyl 2-(2-acetoxymethoxy)-4-fluorobenzoate in 48 mL of acetonitrile was added 1.36 g of nitronium tetrafluoroborate, followed by stirring at room temperature for 16 hours. The reaction liquid was ice-cooled, and 20 mL of a 5% aqueous sodium thiosulfate solution was added thereto, followed by stirring for approximately 10 minutes. A mixture of 150 mL of water and 300 mL of ethyl acetate was poured into the mixed liquid and the aqueous layer was separated. The organic layer was washed with saturated brine and then dried over anhydrous magnesium sulfate, and the solvent was evaporated under reduced pressure to obtain 1 g of methyl 2-(2-acetoxyethoxy)-4-fluoro-5 nitrobenzoate.

Preparation Example 34

To a mixed liquid of 1.70 g of 2-(tetrahydro-2H-pyran-4-yl)-1H-imidazole and 20.0 mL of N,N-dimethylformamide was added slowly 450 mg of 60% sodium hydride portionwise under ice-cooling, followed by stirring at the same temperature for 10 minutes and then stirring at room temperature for 30 minutes. After ice-cooling again, a mixed liquid of 2.00 g of methyl 4-fluoro-2-methyl-3-nitrobenzoate in 10.0 mL of N,N-dimethylformamide was added thereto, followed by stirring at the same temperature for 10 minutes and then stirring at room temperature overnight. To the reaction liquid were added ethyl acetate and water, followed by extraction with ethyl acetate, the organic layer was washed with water, a saturated aqueous sodium hydrogen carbonate solution, and saturated brine, and dried over anhydrous magnesium sulfate, and then the solvent was evaporated under reduced pressure. The residue was purified by silica gel column chromatography (chloroform/methanol) to obtain 3.13 g of methyl 2-methyl-3-nitro-4-[2-(tetrahydro-2H-pyran-4-yl)-1H-imidazol-1-yl]benzoate as a pale yellow solid.

Preparation Example 35

To a mixed liquid of 1.69 g of methyl 2,3-dichloro-7-methylquinoxaline-6-carboxylate, 2.25 g of 2-amino-1-cyclopentylethanolparatoluenesulfonate, and 33.8 mL of 1,4-dioxane was added 4.27 mL of diisopropylethylamine, followed by stirring at 100° C. overnight. The solvent was evaporated under reduced pressure and the residue was purified by silica gel column chromatography (normal hexane/ethyl acetate) to obtain 2.07 g of methyl 3-chloro-2-[(2-cyclopentyl-2-hydroxyethyl)amino]-7-methylquinoxaline-6-carboxylate as a pale yellow solid.

Preparation Example 36

To a mixed liquid of 520 mg of methyl 3-chloro-2-[(2-cyclopentyl-2-oxoethyl)amino]-7-methylquinoxaline-6-carboxylate and 11.3 mL of chloroform were added 4.00 mL of trifluoroacetic anhydride and 0.11 mL of trifluoroacetic acid, followed by heating and refluxing for 6 hours. Ethyl acetate and a saturated aqueous sodium hydrogen carbonate solution were added thereto, followed by extraction with ethyl acetate, the organic layer was washed with saturated brine and dried over anhydrous magnesium sulfate, and then the solvent was evaporated under reduced pressure. The residue was purified by silica gel column chromatography (chloroform/methanol) to obtain 388 mg of methyl 4-chloro-1-cyclopentyl-8-methylimidazo[1,2-a]quinoxaline-7-carboxylate as a pale yellow solid.

Preparation Example 37

Under a nitrogen atmosphere, to a mixture of ethyl cis-2-{[tert-butyl(dimethyl)silyl]oxy}cyclopentane carboxylate and 50.0 mL of diethyl ether was added dropwise a 1.04 M diisobutylaluminum hydride solution in normal hexane at −78° C., followed by stirring at the same temperature for 2 hours. To the reaction liquid was added methanol to decompose the excess diisobutylaluminum hydride, followed by warming to room temperature. To the reaction liquid was added an aqueous (+)-potassium sodium tartrate solution, followed by extraction with diethyl ether, the organic layer was washed with saturated brine and dried over anhydrous magnesium sulfate, and then the solvent was evaporated. The obtained residue was purified by silica gel column chromatography (normal hexane/ethyl acetate) to obtain 7.20 g of cis-2-{[tert-butyl(dimethyl)silyl]oxy}cyclopentanecarboxyaldehyde as a colorless oily substance.

Preparation Example 38

500 mg of 5-fluoro-1H-pyrrolo[2,3-b]pyridine was added to 100 mL of methanol, followed by filtration. The filtrate was subjected to a reaction using a continuous hydrogenation reactor (H-Cube (registered trademark); manufactured by ThalesNano) under the condition of CatCart (registered trademark), Raney nickel (manufactured by ThalesNano), a flow rate of 0.5 ml/min, and a pressure of 50 bar (Full H2 mode), and the solvent was evaporated under reduced pressure. The obtained residue was purified by silica gel column chromatography (normal hexane/ethyl acetate) to obtain 247 mg of 5-fluoro-2,3-dihydro-1H-pyrrolo[2,3-b]pyridine as a white solid.

Preparation Example 39

To 500 mg of tert-butyl 5-methoxy-2,3-dihydro-1H-pyrrolo[2,3-c]pyridine-1-carboxylate was added 1.5 mL of trifluoroacetic acid, followed by stirring at room temperature for 0.5 hours. The reaction liquid was poured into ice water, and neutralized with a 1 M aqueous sodium hydroxide solution, then chloroform was added thereto, and the aqueous layer was separated. The organic layer was washed with water and saturated brine and dried over anhydrous magnesium sulfate, and then the solvent was evaporated to obtain 262 mg of 5-methoxy-2,3-dihydro-1H-pyrrolo[2,3-c]pyridine as a pale yellow solid.

Preparation Example 40

To a mixture of 1.0 g of trans-4-(hydroxymethyl)cyclohexanecarboxylic acid, 20 mL of N,N-dimethylformamide, 1.32 g of potassium carbonate, and 0.24 g of tetrabutylammonium iodide was added dropwise 0.83 mL of benzyl bromide at room temperature, followed by stirring overnight. The reaction liquid was filtered and then the filtrate was concentrated. To the residue were added ethyl acetate and water, and the aqueous layer was separated. The organic layer was washed with water, a saturated aqueous ammonium chloride solution, a saturated aqueous sodium hydrogen carbonate solution, and saturated brine in this order, and dried over anhydrous sodium sulfate, and then the solvent was evaporated to obtain 1.70 g of benzyl trans-4-(hydroxymethyl)cyclohexane carboxylate.

Under nitrogen air flow, to a solution of 0.73 mL of oxalyl chloride in 13 mL of dichloromethane was added dropwise a mixed liquid of 1.23 mL of dimethylsulfoxide and 14 mL of dichloromethane at −78° C. First, a solution of 1.70 g of the obtained benzyl trans-4-(hydroxymethyl)cyclohexane carboxylate in 20 mL of dichloromethane was added dropwise to the reaction mixture at −78° C. After stirring at −78° C. for 0.5 hours, triethylamine was added thereto at −78° C., followed by stirring at −65° C. for 2 hours. The reaction liquid was warmed to room temperature, dichloromethane and water were added thereto, and the aqueous layer was separated. The organic layer was washed with water, 1 M hydrochloric acid, a saturated aqueous sodium hydrogen carbonate solution, and saturated brine in this order, and dried over anhydrous sodium sulfate, and then the solvent was evaporated to obtain 1.60 g of benzyl trans-4-formylcyclohexanecarboxylate.

To 1.60 g of the obtained benzyl trans-4-formylcyclohexanecarboxylate was added 20 mL of methanol at −15° C. 0.55 g of glyoxal dihydrate was added thereto at −15° C., and 65 mL of a saturated aqueous ammonia solution in ethanol was further added dropwise thereto at −15° C. The mixture was stirred at −15° C. for 3 hours and then warmed to at room temperature, followed by stirring for 1 hour. The reaction liquid was cooled to −20° C., ethyl acetate and water were added thereto, and the aqueous layer was separated. The organic layer was washed with saturated brine and dried over anhydrous sodium sulfate, and then the solvent was evaporated. The residue was triturated with a mixture of normal pentane and ethyl acetate (1:1) to give a powder, followed by collecting by filtration and washing with normal pentane to obtain 1.1 g of benzyl trans-4-(1H-imidazol-2-yl)cyclohexane carboxylate as a white solid.

Preparation Example 41

To 70 mL of a solution of 1-benzyl-4-(pyrrolidin-1-yl)-1,2,3,6-tetrahydropyridine in benzene was added dropwise a solution 13 g of 4-bromoacetyl pyridine bromohydride in 150 mL of benzene at 0° C. over 1 hour, followed by stirring at 0° C. for 1 hour and then at room temperature for 15 hours. To the reaction mixture was added water, followed by extraction with ethyl acetate. The organic layer was dried over anhydrous magnesium sulfate, and then the solvent was evaporated under reduced pressure. The obtained residue was purified by silica gel column chromatography (dichloromethane/methanol), and to the obtained 1.86 g of 1-benzyl-3-[2-oxo-2-(pyridin-4-yl)ethyl]piperidine-4-one were added 20 mL of acetic acid and 605 mg of ammonium acetate, followed by heating and refluxing for 1 hour. The reaction mixture was cooled to room temperature and the pH was adjusted to about 9 with a 10% aqueous sodium hydroxide solution, followed by extraction with ethyl acetate. The organic layer was dried over anhydrous magnesium sulfate, and then the solvent was evaporated under reduced pressure. The obtained residue was purified by silica gel column chromatography (dichloromethane/methanol) to obtain 1.26 g of 5-benzyl-2-(pyridin-4-yl)-4,5,6,7-tetrahydro-1H-pyrrolo[3,2-c]pyridine.

Preparation Example 42

To a solution of 630 mg of 5-chloro-3,3-dimethyl-1,3-dihydro-2H-indole-2-one in 6.30 mL of tetrahydrofuran was added 609 mg of sodium borohydride, followed by stirring for 10 minutes. Then, a solution of 1.63 g of iodine in 3.78 mL of tetrahydrofuran was added dropwise thereto at −10° C. or lower under cooling in an ice-acetone bath, followed by stirring at the same temperature for 30 minutes, then warming to room temperature, and stirring overnight. After diluting with chloroform, a saturated aqueous ammonium chloride solution was added dropwise thereto. The aqueous layer was separated and then the organic layer was washed with a saturated aqueous sodium sulfite solution and a saturated aqueous sodium chloride solution, and dried over anhydrous magnesium sulfate, and then the solvent was evaporated under reduced pressure. The obtained residue was purified by silica gel column chromatography (normal hexane/ethyl acetate) to obtain 480 mg of 5-chloro-3,3-dimethylindoline as a colorless oily substance.

Preparation Example 43

To a mixed liquid of 360 mg of 8-bromo-4-oxo-1-(tetrahydro-2H-pyran-4-yl)-4,5-dihydro[1,2,4]triazolo[4,3-a]quinoxaline-7-carboxylic acid and 10 mL of methanol was added 2 mL of concentrated sulfuric acid, followed by stirring overnight under a refluxing condition. After cooling to room temperature, the pH was adjusted to about 8 by the addition of a saturated aqueous sodium hydrogen carbonate solution, followed by extraction with a mixed liquid of chloroform and isopropanol. The organic layer was washed with saturated brine and dried over anhydrous magnesium sulfate. The solvent was evaporated under reduced pressure to obtain 320 mg of methyl 8-bromo-4-oxo-1-(tetrahydro-2H-pyran-4-yl)-4,5-dihydro[1,2,4]triazolo[4,3-a]quinoxaline-7-carboxylate as an orange solid.

In the same manner as the method of Preparation Example 2, the compounds of Preparation Examples 2-1 to 2-11 were prepared, in the same manner as the method of Preparation Example 3, the compounds of Preparation Examples 3-1 to 3-32 were prepared, in the same manner as the method of Preparation Example 4, the compounds of Preparation Examples 4-1 to 4-20 were prepared, in the same manner as the method of Preparation Example 5, the compounds of Preparation Examples 5-1 to 5-19 were prepared, in the same manner as the method of Preparation Example 6, the compound of Preparation Example 6-1 was prepared, in the same manner as the method of Preparation Example 7, the compounds of Preparation Examples 7-1 to 7-13 were prepared, in the same manner as the method of Preparation Example 8, the compounds of Preparation Examples 8-1 to 8-3 were prepared, in the same manner as the method of Preparation Example 9, the compounds of Preparation Examples 9-1 to 9-3 were prepared, in the same manner as the method of Preparation Example 10, the compounds of Preparation Examples 10-1 to 10-4 were prepared, in the same manner as the method of Preparation Example 11, the compound of Preparation Example 11-1 was prepared, in the same manner as the method of Preparation Example 12, the compounds of Preparation Examples 12-1 to 12-13 were prepared, in the same manner as the method of Preparation Example 13, the compounds of Preparation Examples 13-1 to 13-14 were prepared, in the same manner as the method of Preparation Example 14, the compounds of Preparation Examples 14-1 to 14-5 were prepared, in the same manner as the method of Preparation Example 19, the compounds of Preparation Examples 19-1 to 19-4 were prepared, in the same manner as the method of Preparation Example 26, the compound of Preparation Example 26-1 was prepared, in the same manner as the method of Preparation Example 30, the compounds of Preparation Examples 30-1 to 30-2 were prepared, in the same manner as the method of Preparation Example 32, the compounds of Preparation Examples 32-1 to 32-2 were prepared, in the same manner as the method of Preparation Example 33, the compounds of Preparation Examples 33-1 to 33-2 were prepared, in the same manner as the method of Preparation Example 39, the compounds of Preparation Examples 39-1 to 39-2 were prepared, in the same manner as the method of Example 1, the compounds of Preparation Examples 44-1 to 44-2 were prepared, in the same manner as the method of Example 2, the compound of Preparation Example 45 was prepared, in the same manner as the method of Example 10, the compounds of Preparation Examples 46-1 to 46-2 were prepared, in the same manner as the method of Example 12, the compounds of Preparation Example 47 was prepared, in the same manner as the method of Example 13, and the compounds of Preparation Example 48 was prepared, each of which was prepared using the corresponding starting material. The structures and the physiological data of Preparation Example compounds are shown in Tables below.

Example 1

To a mixture of 150 mg of 4-oxo-1-propyl-4,5-dihydro[1,2,4]triazolo[4,3-a]quinoxaline-7-carboxylic acid, 165 mg of 1-methyl-2-phenyl piperazine dihydrochloride, 0.24 mL of triethylamine, 112 mg of 1-hydroxybenzotriazole, and 2.25 mL of N,N-dimethylformamide was added 158 mg of 1-(3-dimethylaminopropyl)-3-ethylcarbodiimide hydrochloride, followed by stirring at room temperature for 1 day. To the reaction liquid were added a saturated aqueous sodium hydrogen carbonate solution and saturated brine, followed by extraction with chloroform. The organic layer was dried over anhydrous magnesium sulfate and then the solvent was evaporated. The residue was purified by silica gel column chromatography (chloroform/methanol=95/5 to 90/10). The obtained solid was triturated with a mixture of ethanol and diisopropyl ether to give a powder. The precipitate was collected by filtration, washed with diisopropyl ether, and dried under reduced pressure to obtain 197 mg of 7-[(4-methyl-3-phenyl piperazin-1-yl)carbonyl]-1-propyl[1,2,4]triazolo[4,3-a]quinoxalin-4(5H)-one as a white powder.

Example 2

To a mixture of 125 mg of 4-oxo-1-propyl-4,5-dihydro[1,2,4]triazolo[4,3-a]quinoxaline-7-carboxylic acid, 73 mg of 1,2,3,4-tetrahydroisoquinoline, 0.26 mL of diisopropylethylamine, and 3 mL of N,N-dimethylformamide was added 262 mg of O-(7-azabenzotriazol-1-yl)-N,N,N',N'-tetramethyluronium hexafluorophosphate, followed by stirring at room temperature overnight. To the reaction liquid was added water, followed by extraction with ethyl acetate. The organic layer was washed with saturated brine and dried over anhydrous magnesium sulfate, and then the solvent was evaporated. The obtained residue was purified by silica gel column chromatography (chloroform/methanol=99/1 to 95/5). The obtained solid was washed with 2 mL of hot methanol to obtain 159 mg of 7-(3,4-dihydroisoquinolin-2(1H)-ylcarbonyl)-1-propyl[1,2,4]triazolo[4,3-a]quinoxalin-4(5H)-one as a white solid.

Example 3

To a mixture of 90 mg of 1-cyclopentyl-8-methyl-4-oxo-4,5-dihydroimidazo[1,5-a]quinoxaline-7-carboxylic acid, 0.18 mL of diisopropylethylamine, and 5.4 mL of dichloromethane was added 162 mg of bromo(tripyrrolidin-1-yl)phosphonium hexafluorophosphate, followed by stirring at room temperature overnight. To the reaction liquid was added water, followed by extraction with chloroform. The organic layer was washed with saturated brine, and dried over anhydrous magnesium sulfate, and then the solvent was evaporated. The obtained residue was purified by silica gel column chromatography (chloroform/methanol=100/0 to 97/3). The obtained solid was heated and washed with 3 mL of ethyl acetate and 15 mL of normal hexane to obtain 183 mg of 1-cyclopentyl-7-(2,3-dihydro-1H-indol-1-ylcarbonyl)-8-methylimidazo[1,5-a]quinoxalin-4(5H)-one as a white solid.

Example 4

To a mixture of 403 mg of 7-[(5-chloro-3,4-dihydroisoquinolin-2(1H)-yl)carbonyl]-1-(4-methoxyphenyl)[1,2,4]triazolo[4,3-a]quinoxalin-4(5H)-one and 10 mL of dichloromethane was added 2.9 mL of a 1 M boron tribromide solution in dichloromethane, followed by stirring at the same temperature for 16 hours. The reaction liquid was poured into ice-water, followed by stirring for 5 minutes and extracting with chloroform. The organic layer was washed with saturated brine and dried over anhydrous sodium sulfate, and then the solvent was evaporated. The obtained residue was purified by silica gel column chromatography (chloroform/methanol=100/0 to 97/3) and then further purified by preparative HPLC (acetonitrile/0.01% aqueous formic acid solution). The obtained solid was heated and washed with a mixed solvent of 3 mL of methanol and 1 mL of water to obtain 18 mg of 7-[(5-chloro-3,4-dihydroisoquinolin-2(1H)-yl)carbonyl]-1-(4-hydroxyphenyl)[1,2,4]triazolo[4,3-a]quinoxalin-4(5H)-one as a white solid.

Example 5

A mixture of 160 mg of methyl 3-chloro-2-hydrazino-7-methylquinoxaline-6-carboxylate, 103 mg of 3-chloro-4-hydroxybenzaldehyde, and 4 mL of acetic acid was stirred at room temperature for 2 hours, and then to the reaction mixture was added 120 mg of copper(II) acetate, followed by stirring at 100° C. for 3 hours. The reaction mixture was added to 20 mL of water at room temperature, and the precipitated solid was collected by filtration and dried under reduced pressure. To the obtained solid were added 2 mL of water and 2 mL of concentrated hydrochloric acid, followed by stirring at 110° C. for 3.5 hours. The reaction mixture was cooled to 0° C., and the precipitated solid was collected by filtration, washed with water, and then dried under reduced pressure. An amount of 0.5 mL was taken from a mixture of the obtained solid and 6 mL of N,N-dimethylformamide, and a mixture of 12.6 mg of 1-pyridin-4-yl-1,2,3,4-tetrahydroisoquinoline, 14 µL of triethylamine, 6.8 mg of 1-hydroxybenzotriazole, and 0.5 mL of N,N-dimethylformamide was added thereto. Further, 14 mg of 1-(3-dimethylaminopropyl)-3-ethylcarbodiimide hydrochloride was added thereto, followed by stirring at room temperature overnight. To the reaction liquid was added water, followed by extraction with chloroform. The solvent of the organic layer was evaporated, and the obtained residue was purified by preparative HPLC (methanol/0.1% aqueous formic acid solution) to obtain 5.2 mg of 1-(3-chloro-4-hydroxyphenyl)-8-methyl-7-[(1-pyridin-4-yl-3,4-dihydroisoquinolin-2(1H)-yl)carbonyl][1,2,4]triazolo[4,3-a]quinoxalin-4(5H)-one.

Example 6

To a mixture of 8.2 mg of 4-oxo-1-propyl-4,5-dihydro[1,2,4]triazolo[4,3-a]quinoxaline-7-carboxylic acid, 1.6 mg of 3-chloroaniline, 4.1 mg of 1-hydroxybenzotriazole, 8.4 µL of triethylamine, and 1 mL of N,N-dimethylformamide was added 100 mg of PS-Carbodiimide (Biotage AB), followed by stirring at 60° C. overnight. To the reaction mixture were added 50 mg of MP-Carbonate (Biotage AB) and 50 mg of PS-Isocyanate (Biotage AB) at room temperature, followed by stirring for 4 hours. The reaction mixture was filtered and the filtrate was concentrated under reduced pressure. The obtained residue was purified by preparative HPLC (methanol/0.1% aqueous formic acid solution) to obtain 0.87 mg of N-(3-chlorophenyl)-4-oxo-1-propyl-4,5-dihydro[1,2,4]triazolo[4,3-a]quinoxaline-7-carboxamide.

Example 7

Under an argon atmosphere, to a mixture of 320 mg of methyl 8-bromo-4-oxo-1-(tetrahydro-2H-pyran-4-yl)-4,5-dihydro[1,2,4]triazolo[4,3-a]quinoxaline-7-carboxylate, 11.8 mg of palladium acetate, 30.4 mg of tricyclohexyl phosphine, 333 mg of tripotassium phosphate, 6.40 mL of toluene, and 100 µL of water was added 81.0 mg of cyclopropylboric acid, followed by stirring at 110° C. for 2 days. The solvent was evaporated under reduced pressure. To the obtained residue were added water and 1 M hydrochloric acid to adjust the pH to about 3, and then the solvent was evaporated under reduced pressure.

To the residue were added 5.00 mL of methanol, 5.00 mL of tetrahydrofuran, and 5.00 mL of a 1 M aqueous sodium hydroxide solution, followed by stirring at room temperature for 4 hours. The solvent was evaporated under reduced pressure and then 1 M hydrochloric acid was added thereto to adjust the pH to about 3. The precipitated solid was collected by filtration to obtain 95.0 mg of a mixture of 8-cyclopropyl-4-oxo-1-(tetrahydro-2H-pyran-4-yl)-4,5-dihydro[1,2,4]triazolo[4,3-a]quinoxaline-7-carboxylic acid and 8-bromo-4-oxo-1-(tetrahydro-2H-pyran-4-yl)-4,5-dihydro[1,2,4]triazolo[4,3-a]quinoxaline-7-carboxylic acid as a yellow solid.

To a mixed liquid of 95.0 mg of a mixture of 8-cyclopropyl-4-oxo-1-(tetrahydro-2H-pyran-4-yl)-4,5-dihydro[1,2,4]triazolo[4,3-a]quinoxaline-7-carboxylic acid and 8-bromo-4-oxo-1-(tetrahydro-2H-pyran-4-yl)-4,5-dihydro[1,2,4]triazolo[4,3-a]quinoxaline-7-carboxylic acid, 39.0 mg of isoindoline, 190 µL of diisopropylethylamine, and 1.50 mL of N,N-dimethylformamide was added 156 mg of O-(7-azabenzotriazol-1-yl)-N,N,N',N'-tetramethyluronium hexafluorophosphate, followed by stirring at room temperature overnight. To the reaction liquid was added a saturated aqueous sodium hydrogen carbonate solution, followed by extraction with chloroform. The organic layer was washed with saturated brine and then dried over anhydrous magnesium sulfate. The solvent was evaporated under reduced pressure, and the residue was purified by preparative HPLC (methanol/0.1% aqueous formic acid solution) to obtain 24.8 mg of 8-cyclopropyl-7-(1,3-dihydro-2H-isoindol-2-ylcarbonyl)-1-(tetrahydro-2H-pyran-4-yl)[1,2,4]triazolo[4,3-a]quinoxalin-4(5H)-one as a pale brown solid.

Example 8

To a mixed liquid of 150 mg of 7-(1,3-dihydro-2H-isoindol-2-ylcarbonyl)-8-methyl-1-(tetrahydro-2H-thiopyran-4-ylmethyl)[1,2,4]triazolo[4,3-a]quinoxalin-4(5H)-one and 10.0 mL of dichloromethane was added a mixed liquid of 115 mg of 75% methachloroperbenzoic acid and 5.00 mL of dichloromethane under ice-cooling, followed by stirring for 1 hour, warming to room temperature, and then stirring for 2 hours. A saturated aqueous sodium hydrogen carbonate solution was added thereto, followed by extraction with chloroform. The organic layer was washed with saturated brine and dried over anhydrous magnesium sulfate. The solvent was evaporated under reduced pressure and the residue was purified by silica gel column chromatography (chloroform/methanol=100/0 to 90/10). To the obtained solid were added 2.00 mL of methanol and 2.00 mL of a 4 M hydrogen chloride/ethyl acetate solution, followed by stirring for 0.5 hours, and the precipitated solid was collected by filtration and dried under reduced pressure to obtain 75.3 mg of 7-(1,3-dihydro-2H-isoindol-2-ylcarbonyl)-1-[(1,1-dioxidetetrahydro-2H-thiopyran-4-yl)methyl]-8-methyl[1,2,4]triazolo[4,3-a]quinoxalin-4(5H)-one hydrochloride as a colorless solid.

Example 9

To a mixed liquid of 170 mg of 7-(1,3-dihydro-2H-isoindol-2-ylcarbonyl)-8-methyl-1-(tetrahydro-2H-thiopyran-4-ylmethyl)[1,2,4]triazolo[4,3-a]quinoxalin-4(5H)-one and 11.3 mL of dichloromethane was added a mixed liquid of 85.0 mg of 75% meta-chlorobenzoic acid and 5.70 mL of dichloromethane under ice-cooling, followed by stirring for 1 hour, warming to room temperature, and stirring for 2 hours. A saturated aqueous sodium hydrogen carbonate solution was added thereto, followed by extraction with chloroform. The organic layer was washed with saturated brine and dried over anhydrous magnesium sulfate. The solvent was evaporated under reduced pressure and the residue was purified by silica gel column chromatography (chloroform/methanol=100/0 to 90/10) to obtain 26.4 mg of 7-(1,3-dihydro-2H-isoindol-2- ylcarbonyl)-8-methyl-1-[(1-oxidetetrahydro-2H-thiopyran-4-yl)methyl][1,2,4]triazolo[4,3-a]quinoxalin-4(5H)-one as a pale yellow solid.

Example 10

To a mixture of 0.355 g of 1-[cis-2-(benzyloxy)cyclopentyl]-7-(1,3-dihydro-2H-isoindol-2-ylcarbonyl)-8-methyl[1,2,4]triazolo[4,3-a]quinoxalin-4(5H)-one and 50.0 mL of ethanol was added 142 mg of 10% palladium on carbon (50% wet), followed by stirring overnight under a hydrogen atmosphere. The reaction mixture was filtered through celite and the filtrate was concentrated under reduced pressure. The obtained residue was purified by silica gel column chromatography (chloroform/methanol=97/3 to 90/10) to give a powder from 2-propanol, thereby obtaining 114 mg of 7-(1,3-dihydro-2H-isoindol-2-ylcarbonyl)-1-[cis-2-hydroxycyclopentyl]-8-methyl[1,2,4]triazolo[4,3-a]quinoxalin-4(5H)-one as a colorless solid.

Example 11

A mixed solution of 60 mg of 7-[(5-chloro-2,3-dihydro-1H-indol-1-yl)carbonyl]-1-[cyclopropyl(hydroxy)methyl]-8-methyl[1,2,4]triazolo[4,3-a]quinoxalin-4(5H)-one and 3 mL of dichloromethane was cooled to −70° C., and 100 μL of N,N-diethylaminosulfur trifluoride was added thereto, followed by slowly warming to −20° C. over 4 hours. The reaction liquid was returned to room temperature and stirred overnight. To the mixed liquid were added a saturated aqueous sodium hydrogen carbonate solution and chloroform, followed by extraction with chloroform, the organic layer was washed with saturated brine and dried over anhydrous sodium sulfate, and then the solvent was evaporated under reduced pressure. The obtained residue was purified by silica gel column chromatography (chloroform/methanol=100/0 to 97/3). To the obtained solid was added 4 mL of methanol, followed by warming and washing. The precipitate was collected by filtration and dried under reduced pressure to obtain 31 mg of 7-[(5-chloro-2,3-dihydro-1H-indol-1-yl)carbonyl]-1-[cyclopropyl(fluoro)methyl]-8-methyl[1,2,4]triazolo[4,3-a]quinoxalin-4(5H)-one as a white solid.

Example 12

To a mixed solution of 100 mg of 7-[(5-chloro-2,3-dihydro-1H-indol-1-yl)carbonyl]-1-[cyclopropyl(hydroxy)methyl]-8-methyl[1,2,4]triazolo[4,3-a]quinoxalin-4(5H)-one and 5 mL of dichloromethane was added 113 mg of Dess-Martin periodinane under ice-cooling. The mixed reaction liquid was returned to room temperature, followed by stirring for 4 hours. To the mixed reaction liquid were added a saturated aqueous sodium thiosulfate solution and chloroform, followed by stirring for a while, and then extracting with chloroform, and the organic layer was washed with saturated brine and dried over anhydrous sodium sulfate. Then, the solvent was evaporated under reduced pressure. The obtained residue was purified by silica gel column chromatography (chloroform/methanol=100/0 to 97/3). To the obtained solid was added 4 mL of methanol to give a mixed solvent, followed by warming and washing. The precipitate was collected by filtration and dried under reduced pressure to obtain 36 mg of 7-[(5-chloro-2,3-dihydro-1H-indol-1-yl)carbonyl]-1-(cyclopropylcarbonyl)-8-methyl[1,2,4]triazolo[4,3-a]quinoxalin-4(5H)-one as a skin-colored solid.

Example 13

To a mixture of 150 mg of 1-(4,4-difluorocyclohexyl)-8-methyl-4-oxo-4,5-dihydro[1,2,4]triazolo[4,3-a]quinoxaline-7-carboxylic acid, 62.5 mg of 5-fluoroindoline, 0.25 mL of diisopropylethylamine, and 3 mL of N,N-dimethylformamide was added 146 mg of TBTU, followed by stirring at room temperature overnight. To the reaction liquid were added water and a saturated aqueous sodium hydrogen carbonate solution, followed by extraction with chloroform. The organic layer was washed with saturated brine and dried over anhydrous magnesium sulfate, and then the solvent was evaporated. The obtained residue was purified by silica gel column chromatography (chloroform/methanol=100/0 to 95/5). The obtained solid was washed with a mixed solution of hot diethyl ether and normal hexane to obtain 108 mg of 1-(4,4-difluorocyclohexyl)-7-[(5-fluoro-2,3-dihydro-1H-indol-1-yl)carbonyl]-8-methyl[1,2,4]triazolo[4,3-a]quinoxalin-4(5H)-one.

To a mixture of 106 mg of 1-(4,4-difluorocyclohexyl)-7-[(5-fluoro-2,3-dihydro-1H-indol-1-yl)carbonyl]-8-methyl[1,2,4]triazolo[4,3-a]quinoxalin-4(5H)-one, 1 mL of methanol, and 1 mL of tetrahydrofuran was added 55 μL of 4 M hydrogen chloride/ethyl acetate, followed by stirring at room temperature for 1 hour. The reaction solution was concentrated under reduced pressure. The obtained residue was triturated with a mixture of ethyl acetate, diethyl ether, and normal hexane to give a powder, and the suspension was stirred for 30 minutes. The solid was collected by filtration and dried under reduced pressure to obtain 97 mg of 1-(4,4-difluorocyclohexyl)-7-[(5-fluoro-2,3-dihydro-1H-indol-1-yl)carbonyl]-8-methyl[1,2,4]triazolo[4,3-a]quinoxalin-4(5H)-one hydrochloride as a pale yellow solid.

Example 14

100 mg of 7-(1,3-dihydro-2H-isoindol-2-ylcarbonyl)-8-methyl-1-(tetrahydro-2H-pyran-3-yl)imidazo[1,5-a]quinoxalin-4(5H)-one was purified by preparative HPLC (acetonitrile/water=35/65) using CHIRALCEL (registered trademark) OJ-RH semi-preparative column, particle diameter 5 μm, inner diameter 20 mm, and column length 150 mm (Daicel Chemical Industries, Ltd.). As a high-polarity compound, 34 mg of (−)-7-(1,3-dihydro-2H-isoindol-2-ylcarbonyl)-8-methyl-1-(tetrahydro-2H-pyran-3-yl)imidazo[1,5-a]quinoxalin-4(5H)-one was obtained and as a low-polarity compound, 37 mg of (+)-7-(1,3-dihydro-2H-isoindol-2-ylcarbonyl)-8-methyl-1-(tetrahydro-2H-pyran-3-yl)imidazo[1,5-a]quinoxalin-4(5H)-one was obtained.

To a mixture of 34 mg of (−)-7-(1,3-dihydro-2H-isoindol-2-ylcarbonyl)-8-methyl-1-(tetrahydro-2H-pyran-3-yl)imidazo[1,5-a]quinoxalin-4(5H)-one, 1 mL of methanol, and 2 mL of tetrahydrofuran was added 30 μL of 4 M hydrogen chloride/ethyl acetate, followed by stirring at room temperature for 1 hour. The reaction solution was concentrated under reduced pressure. The obtained residue was triturated with 1 mL of ethyl acetate to give a powder, and the suspension was stirred for 30 minutes. The solid was collected by filtration, washed with ethyl acetate, and then dried under reduced pressure to obtain 34 mg (>99% ee) of (−)-7-(1,3-dihydro-2H-isoindol-2-ylcarbonyl)-8-methyl-1-(tetrahydro-2H-pyran-3-yl)imidazo[1,5-a]quinoxalin-4(5H)-one hydrochloride as a white solid.

To a mixture of 37 mg of (+)-7-(1,3-dihydro-2H-isoindol-2-ylcarbonyl)-8-methyl-1-(tetrahydro-2H-pyran-3-yl)imidazo[1,5-a]quinoxalin-4(5H)-one in 1 mL of methanol and 2 mL of tetrahydrofuran was added 32 μL of 4 M hydrogen chloride/ethyl acetate, followed by stirring at room temperature for 1 hour. The precipitated solid was collected by filtration, washed with ethyl acetate, and then dried under reduced pressure to obtain 24 mg (>99% ee) of (+)-7-(1,3-dihydro- 2H-isoindol-2-ylcarbonyl)-8-methyl-1-(tetrahydro-2H-pyran-3-yl)imidazo[1,5-a]quinoxalin-4(5H)-one hydrochloride as a white solid.

Example 15

To a mixture of 560 mg of 1-[cis-2-{[tert-butyl(dimethyl)silyl]oxy}cyclopentyl]-7-(1,3-dihydro-2H-isoindol-2-ylcarbonyl)-8-methylimidazo[1,5-a]quinoxalin-4(5H)-one and 20.0 mL of methanol was added 0.2 mL of concentrated hydrochloric acid, followed by stirring at room temperature overnight. The reaction liquid was concentrated under reduced pressure, and then, the residue was dissolved in water. A saturated aqueous sodium hydrogen carbonate solution was added thereto to adjust the pH to about 5, followed by extraction with a mixed solvent of chloroform/methanol=4/1, the organic layer was dried over anhydrous magnesium sulfate, and then the solvent was evaporated. The obtained residue was purified by silica gel column chromatography (chloroform/methanol=97/3-90/10) to give a powder from 2-propanol, thereby obtaining 333 mg of 7-(1,3-dihydro-2H-isoindol-2-ylcarbonyl)-1-[cis-2-hydroxycyclopentyl]-8-methylimidazo[1,5-a]quinoxalin-4(5H)-one as a colorless solid.

Example 16

A mixed solution of 87 mg of 7-[(5-chloro-2,3-dihydro-1H-indol-1-yl)carbonyl]-1-(trans-4-hydroxycyclohexyl)-8-methylimidazo[1,5-a]quinoxalin-4(5H)-one and 2.8 mL of dichloromethane was cooled to −70° C., and 48 μL of N,N-diethylaminosulfur trifluoride was added thereto, followed by stirring at the same temperature for 2 hours. To the mixed reaction liquid were added a saturated aqueous sodium hydrogen carbonate solution and chloroform, followed by extraction with chloroform, and the organic layer was washed with saturated brine and dried over anhydrous sodium sulfate. Then, the solvent was evaporated and the obtained residue was purified by silica gel column chromatography (chloroform/methanol=100/0 to 97/3). To the obtained solid was added 1.5 mL of methanol to give a mixture, and then warmed. A precipitate was collected by filtration and dried under reduced pressure to obtain 7 mg of 7-[(5-chloro-2,3-dihydro-1H-indol-1-yl)carbonyl]-1-(cyclohex-3-en-1-yl)-8-methylimidazo[1,5-a]quinoxalin-4(5H)-one as a white solid.

Example 17

Under a nitrogen atmosphere, to a solution of 132 mg of 5-fluoroindoline in 1 mL of dichloromethane was added 0.68 mL of a 1.8 M trimethylaluminum solution in toluene at 0° C., followed by stirring at room temperature for 2 hours (solution A).

Under a nitrogen air flow, to a solution of 132 mg of methyl 8-(2-acetoxyethoxy)-4-oxo-1-(tetrahydro-2H-pyran-4-yl)-4,5-dihydroimidazo[1,5-a]quinoxaline-7-carboxylate in 3.3 mL of toluene was added the solution A above, followed by stirring at 70° C. for 8 hours. To the reaction mixture was added 0.5 M hydrochloric acid, and a mixture of 10 mL of water and 20 mL of ethyl acetate was poured into the mixed liquid. The pH was adjusted to about 10 with 28% aqueous ammonia, and the insoluble materials were removed by filtration. The aqueous layer was separated, the organic layer was washed with saturated brine and then dried over anhydrous magnesium sulfate, and the solvent was evaporated under reduced pressure. The obtained residue was purified by silica gel column chromatography (chloroform/methanol=100/0 to 90/10). The obtained powder was suspended in a mixed liquid of 0.6 mL of methanol and 0.4 mL of tetrahydrofuran, and 0.3 mL of a 4 M hydrogen chloride/ethyl acetate solution was added thereto, followed by stirring for 30 minutes. The obtained powder was collected by filtration, washed with methanol and then dried under reduced pressure to obtain 44 mg of 7-[(5-fluoro-2,3-dihydro-1H-indol-1-yl)carbonyl]-8-(2-hydroxyethoxy)-1-(tetrahydro-2H-pyran-4-yl)imidazo[1,5-a]quinoxalin-4(5H)-one hydrochloride as a white solid.

Example 18

To 676 mg of benzyl trans-4-{7-[(5-chloro-2,3-dihydro-1H-indol-1-yl)carbonyl]-8-methyl-4-oxo-4,5-dihydroimidazo[1,5-a]quinoxalin-1-yl}cyclohexane carboxylate were added 6.7 mL of methanol and 1.5 mL of a 3 M aqueous sodium hydroxide solution, followed by stirring at room temperature for 16 hours. 1 M hydrochloric acid was added thereto, and the precipitate was collected by filtration and washed with water. The obtained solid was air-dried, suspended in chloroform, collected by filtration, and dried under reduced pressure to obtain 485 mg of trans-4-{7-[(5-chloro-2,3-dihydro-1H-indol-1-yl)carbonyl]-8-methyl-4-oxo-4,5-dihydroimidazo[1,5-a]quinoxalin-1-yl}cyclohexanecarboxylic acid as a white solid.

In the same manner as in the methods of Examples 1 to 18, the compounds of Examples 19 to 531 were prepared. The structures, the physicochemical data, and the preparation methods of the Example compounds are shown in Tables below with No. Examples 1 to 18.

TABLE 1

| Pr | Structure | Data |
|---|---|---|
| 1 | *structure* | APCI+: 305, 307 |
| 2 | *structure* | ESI+: 273 |
| 2-1 | *structure* | ESI−: 313 |

TABLE 1-continued

| Pr | Structure | Data |
|---|---|---|
| 2-2 | 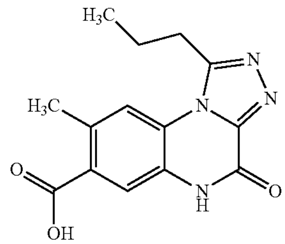 [SMILES: CCCc1nnc2c(=O)[nH]c3cc(C(=O)O)c(C)cc3n12] | ESI+: 287 |
| 2-3 | 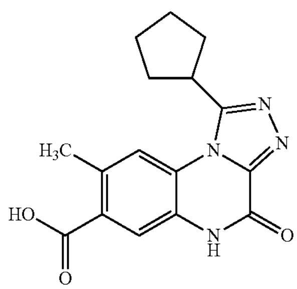 [SMILES: Cc1cc2c(cc1C(=O)O)[nH]c(=O)c1nnc(C3CCCC3)n12] | ESI+: 313 |
| 2-4 | 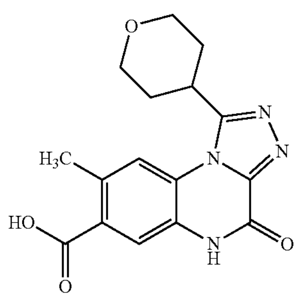 [SMILES: Cc1cc2c(cc1C(=O)O)[nH]c(=O)c1nnc(C3CCOCC3)n12] | ESI−: 327 |

TABLE 2

| Pr | Structure | Data |
|---|---|---|
| 2-5 | 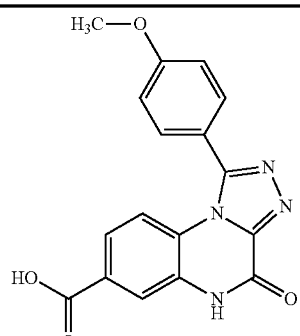 | ESI−: 335 |
| 2-6 | 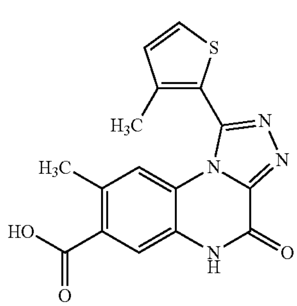 [SMILES: Cc1cc2c(cc1C(=O)O)[nH]c(=O)c1nnc(-c3sccc3C)n12] | ESI+: 341 |

TABLE 2-continued

| Pr | Structure | Data |
|---|---|---|
| 2-7 | 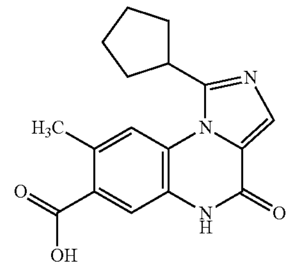 [SMILES: Cc1cc2c(cc1C(=O)O)[nH]c(=O)c1cnc(C3CCCC3)n12] | ESI+: 312 |
| 2-8 | 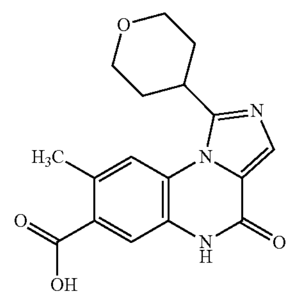 [SMILES: Cc1cc2c(cc1C(=O)O)[nH]c(=O)c1cnc(C3CCOCC3)n12] | ESI−: 326 |
| 2-9 | 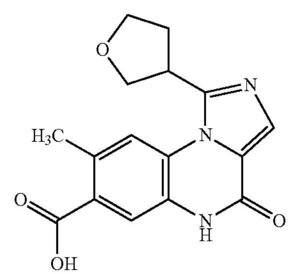 [SMILES: Cc1cc2c(cc1C(=O)O)[nH]c(=O)c1cnc(C3CCOC3)n12] | APCI/ESI+: 314 |
| 2-10 | 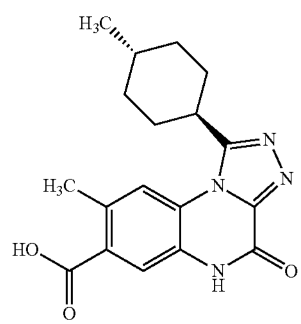 [SMILES: Cc1cc2c(cc1C(=O)O)[nH]c(=O)c1nnc([C@H]3CC[C@H](C)CC3)n12] | ESI+: 341 |

TABLE 3

| Pr | Structure | Data |
|---|---|---|
| 2-11 | 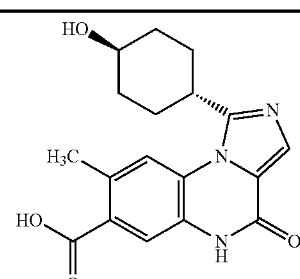 | ESI+: 342 |

TABLE 3-continued

| Pr | Structure | Data |
|---|---|---|
| 3 | 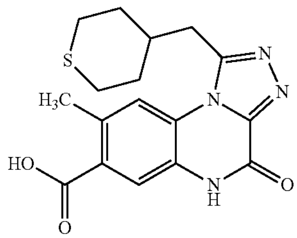 [SMILES: Cc1cc2c(cc1C(=O)O)[nH]c(=O)c1nnc(CC3CCSCC3)n12] | ESI+: 359 |
| 3-1 | 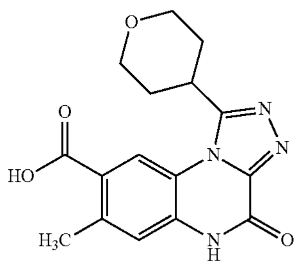 [SMILES: Cc1cc2[nH]c(=O)c3nnc(C4CCOCC4)n3c2cc1C(=O)O] | ESI+: 329 |
| 3-2 | 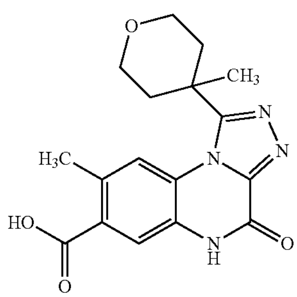 [SMILES: Cc1cc2c(cc1C(=O)O)[nH]c(=O)c1nnc(C3(C)CCOCC3)n12] | ESI+: 343 |
| 3-3 | 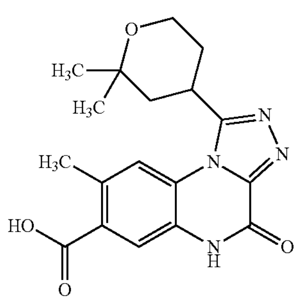 [SMILES: Cc1cc2c(cc1C(=O)O)[nH]c(=O)c1nnc(C3CCOC(C)(C)C3)n12] | ESI+: 357 |
| 3-4 | 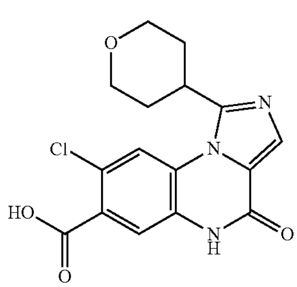 [SMILES: O=C(O)c1cc2[nH]c(=O)c3cnc(C4CCOCC4)n3c2cc1Cl] | ESI+: 348, 350 |

TABLE 4

| Pr | Structure | Data |
|---|---|---|
| 3-5 | 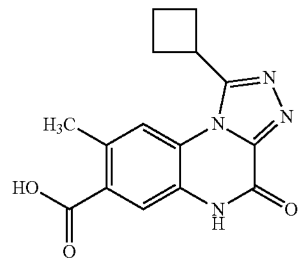 [SMILES: Cc1cc2c(cc1C(=O)O)[nH]c(=O)c1nnc(C3CCC3)n12] | ESI+: 299 |
| 3-6 | 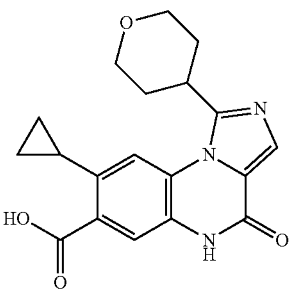 [SMILES: O=C(O)c1cc2[nH]c(=O)c3cnc(C4CCOCC4)n3c2cc1C1CC1] | ESI+: 354 |
| 3-7 | 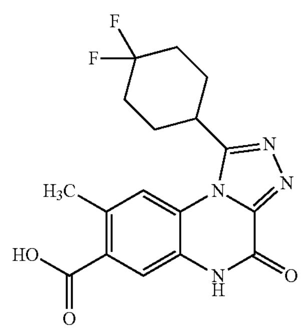 [SMILES: Cc1cc2c(cc1C(=O)O)[nH]c(=O)c1nnc(C3CCC(F)(F)CC3)n12] | ESI+: 363 |
| 3-8 | 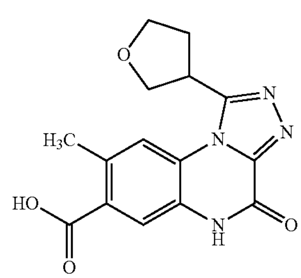 [SMILES: Cc1cc2c(cc1C(=O)O)[nH]c(=O)c1nnc(C3CCOC3)n12] | ESI−: 313 |
| 3-9 | 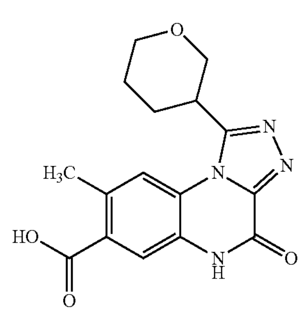 [SMILES: Cc1cc2c(cc1C(=O)O)[nH]c(=O)c1nnc(C3CCCOC3)n12] | ESI+: 329 |

TABLE 5
| Pr | Structure | Data |
|---|---|---|
| 3-10 | 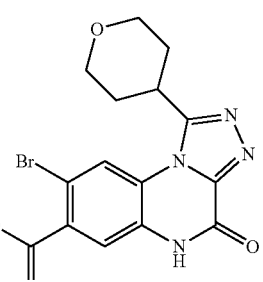 | ESI+: 393, 395 |
| 3-11 | 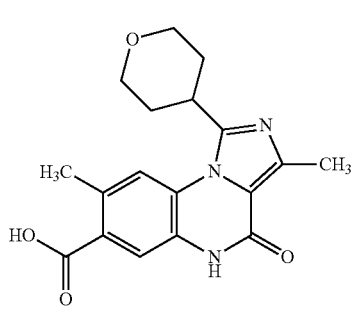 [SMILES: Cc1cc2c(cc1C(=O)O)[nH]c(=O)c1c(C)nc(C3CCOCC3)n12] | ESI+: 342 |
| 3-12 | 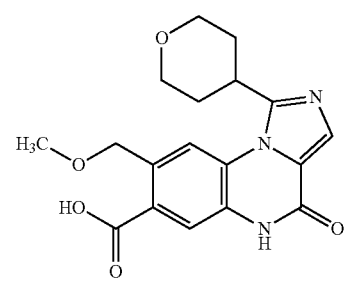 [SMILES: COCc1cc2c(cc1C(=O)O)[nH]c(=O)c1cnc(C3CCOCC3)n12] | ESI+: 358 |
| 3-13 | 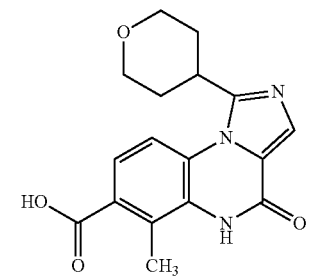 [SMILES: Cc1c(C(=O)O)ccc2c1[nH]c(=O)c1cnc(C3CCOCC3)n12] | ESI+: 328 |
| 3-14 | 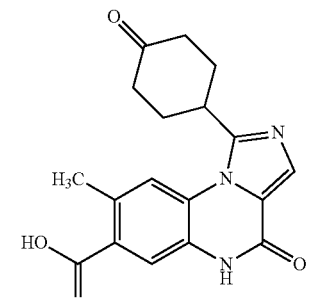 | ESI-: 338 |
TABLE 6
| Pr | Structure | Data |
|---|---|---|
| 3-15 | 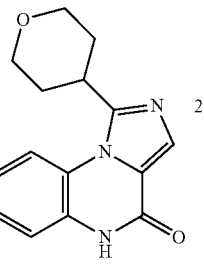 | ESI+: 401 |
| 3-16 | 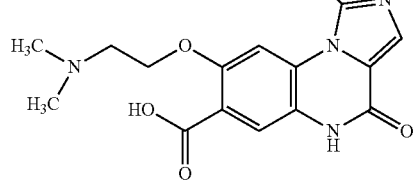 | ESI+: 312 |
| 3-17 | 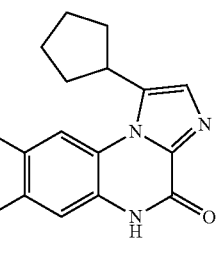 | ESI+: 442 |
| 3-18 | 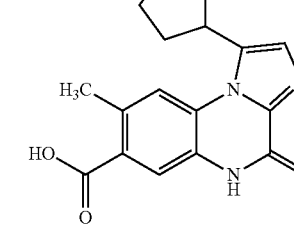 | ESI-: 454 |
| 3-19 | 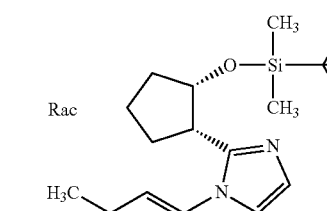 | ESI+: 345 |

TABLE 7

| Pr | Structure | Data |
|---|---|---|
| 3-20 | 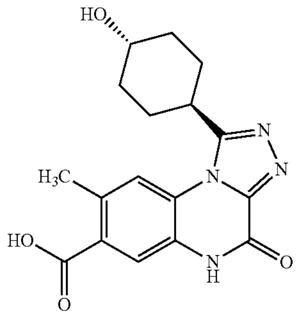 [SMILES: Cc1cc2c(cc1C(=O)O)[nH]c(=O)c1nnc([C@H]3CC[C@H](O)CC3)n12] | ESI+: 343 |
| 3-21 | 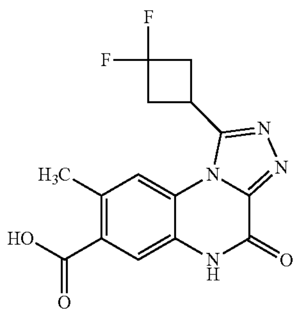 [SMILES: Cc1cc2c(cc1C(=O)O)[nH]c(=O)c1nnc(C3CC(F)(F)C3)n12] | ESI+: 335 |
| 3-22 | 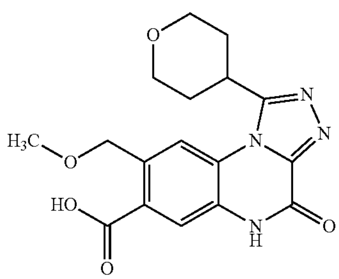 [SMILES: COCc1cc2c(cc1C(=O)O)[nH]c(=O)c1nnc(C3CCOCC3)n12] | ESI+: 359 |
| 3-23 | 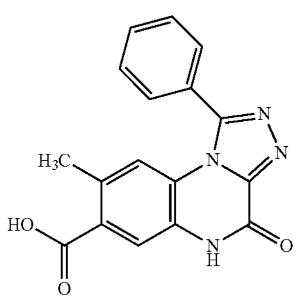 [SMILES: Cc1cc2c(cc1C(=O)O)[nH]c(=O)c1nnc(-c3ccccc3)n12] | ESI+: 321 |
| 3-24 | 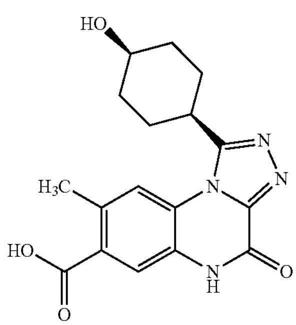 [SMILES: Cc1cc2c(cc1C(=O)O)[nH]c(=O)c1nnc([C@H]3CC[C@@H](O)CC3)n12] | ESI−: 341 |

TABLE 8

| Pr | Structure | Data |
|---|---|---|
| 3-25 | 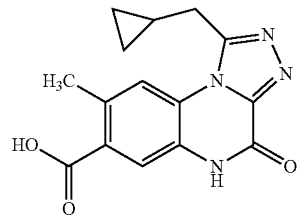 [SMILES: Cc1cc2c(cc1C(=O)O)[nH]c(=O)c1nnc(CC3CC3)n12] | ESI+: 299 |
| 3-26 Rac | | ESI+: 419 |
| 3-27 | 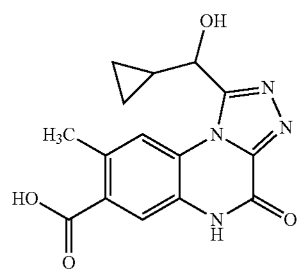 [SMILES: Cc1cc2c(cc1C(=O)O)[nH]c(=O)c1nnc(C(O)C3CC3)n12] | ESI+: 315 |
| 3-28 | 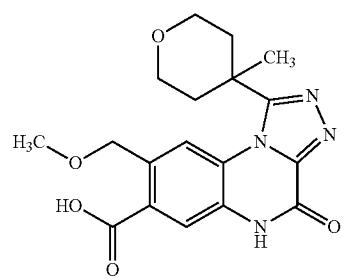 [SMILES: COCc1cc2c(cc1C(=O)O)[nH]c(=O)c1nnc(C3(C)CCOCC3)n12] | ESI+: 373 |
| 3-29 2HCl | | ESI+: 427 |

TABLE 8-continued
| Pr | Structure | Data |
|---|---|---|
| 3-30 | 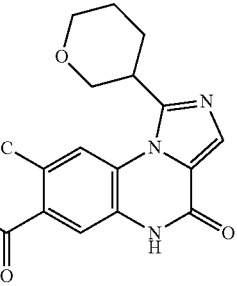 | ESI+: 328 |
TABLE 9
| Pr | Structure | Data |
|---|---|---|
| 3-31 | 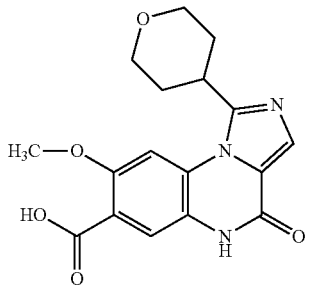 [SMILES: COc1cc2c(cc1C(=O)O)[nH]c(=O)c1cnc(C3CCOCC3)n12] | ESI+: 344 |
| 3-32 | 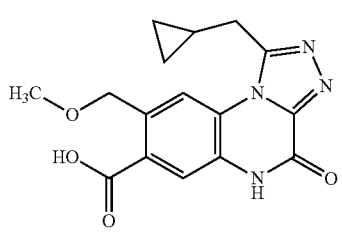 [SMILES: COCc1cc2c(cc1C(=O)O)[nH]c(=O)c1nnc(CC3CC3)n12] | ESI+: 329 |
TABLE 9-continued
| Pr | Structure | Data |
|---|---|---|
| 4 | 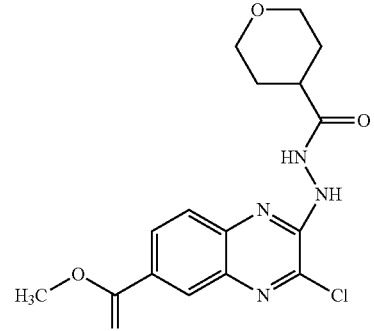 | APCI/ESI+: 365, 367 |
| 4-1 | 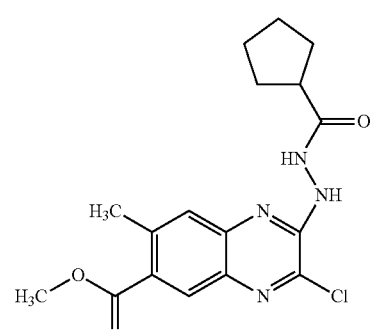 | ESI+: 363, 365 |
| 4-2 | 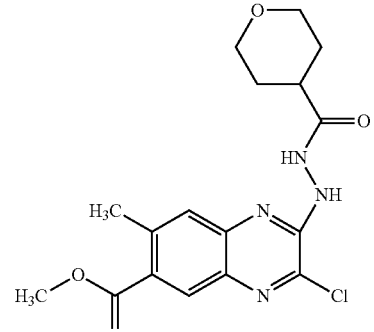 | ESI+: 379, 381 |
TABLE 10
| Pr | Structure | Data |
|---|---|---|
| 4-3 | 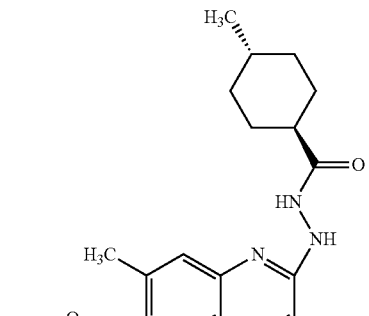 | ESI+: 391, 393 |

TABLE 10-continued

| Pr | Structure | Data |
|---|---|---|
| 4-4 | 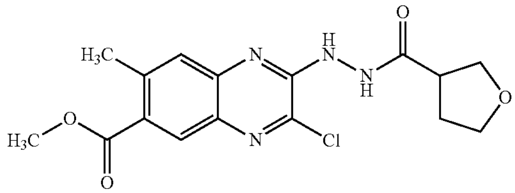 [SMILES: COC(=O)c1cc2nc(Cl)c(NNC(=O)C3CCOC3)nc2cc1C] | ESI+: 365, 367 |
| 4-5 | 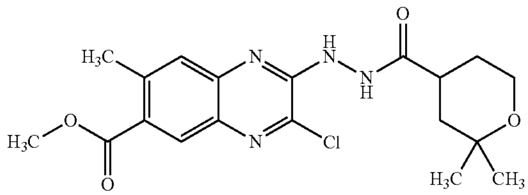 [SMILES: COC(=O)c1cc2nc(Cl)c(NNC(=O)C3CCOC(C)(C)C3)nc2cc1C] | ES1+: 407, 409 |
| 4-6 | 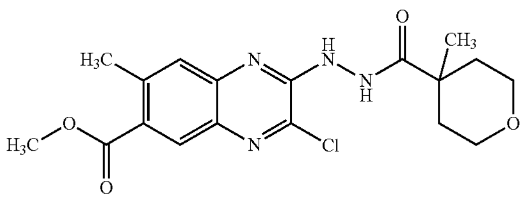 [SMILES: COC(=O)c1cc2nc(Cl)c(NNC(=O)C3(C)CCOCC3)nc2cc1C] | ES1+: 393, 395 |
| 4-7 | 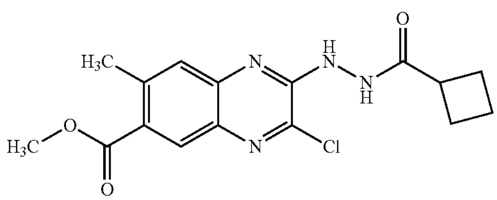 [SMILES: COC(=O)c1cc2nc(Cl)c(NNC(=O)C3CCC3)nc2cc1C] | ESI+: 349, 351 |
| 4-8 | 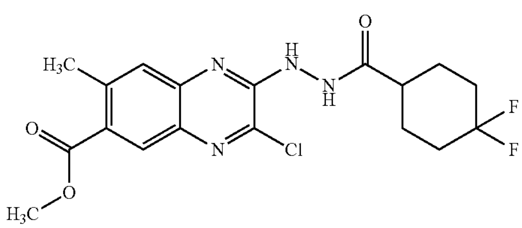 [SMILES: COC(=O)c1cc2nc(Cl)c(NNC(=O)C3CCC(F)(F)CC3)nc2cc1C] | ESI+: 413, 415 |

TABLE 11

| Pr | Structure | Data |
|---|---|---|
| 4-9 | 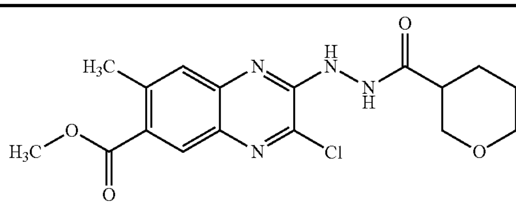 | ESI+: 379, 381 |
| 4-10 | 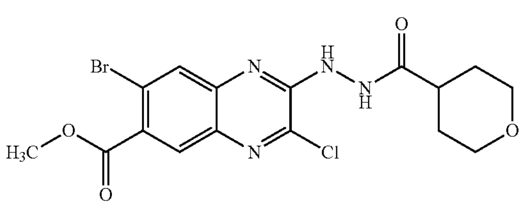 [SMILES: COC(=O)c1cc2nc(Cl)c(NNC(=O)C3CCOCC3)nc2cc1Br] | ESI+: 443, 445 |

TABLE 11-continued
| Pr | Structure | Data |
|---|---|---|
| 4-11 | 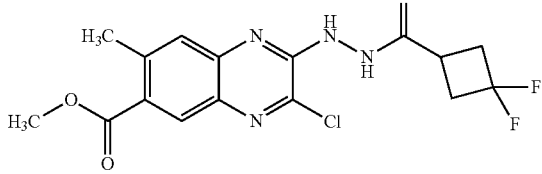 | ESI+: 385, 387 |
| 4-12 | 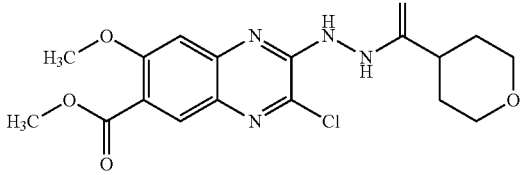 | ESI+: 395, 397 |
| 4-13 | 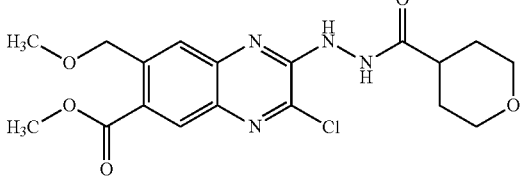 | ESI+: 409, 411 |
| 4-14 | 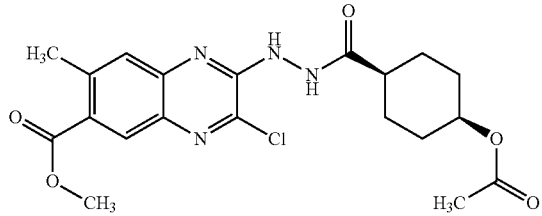 [SMILES: COC(=O)c1cc2nc(Cl)c(NNC(=O)[C@H]3CC[C@@H](OC(C)=O)CC3)nc2cc1C] | ESI+: 435, 437 |
| 4-15 | 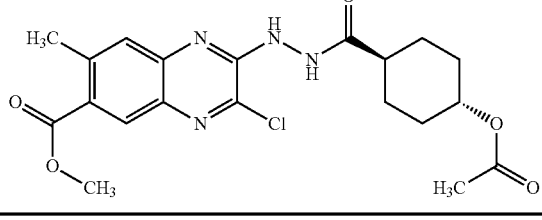 | ESI−: 433, 435 |
TABLE 12
| Pr | Structure | Data |
|---|---|---|
| 4-16 | 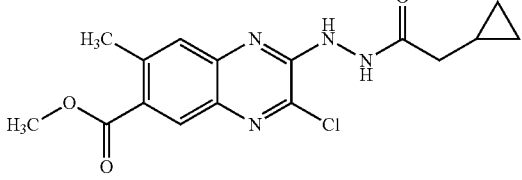 | ESI+: 349, 351 |
| 4-17 | 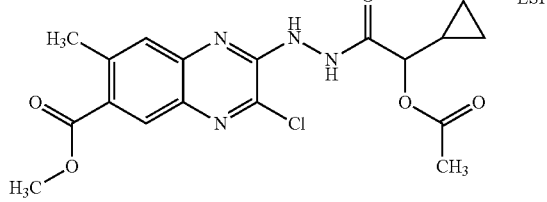 | ESI−: 405, 407 |

TABLE 12-continued

| Pr | Structure | Data |
|---|---|---|
| 4-18 | (methyl 3-methoxy-7-methyl-2-(2-(tetrahydro-2H-pyran-4-carbonyl)hydrazinyl)quinoxaline-6-carboxylate) | ESI+: 375 |
| 4-19 | (methyl 3-chloro-7-(methoxymethyl)-2-(2-(4-methyltetrahydro-2H-pyran-4-carbonyl)hydrazinyl)quinoxaline-6-carboxylate) | ESI+: 423, 425 |
| 4-20 | (methyl 3-chloro-2-(2-(2-cyclopropylacetyl)hydrazinyl)-7-(methoxymethyl)quinoxaline-6-carboxylate) | ESI+: 379, 381 |
| 5 | (methyl 4-chloro-1-(tetrahydro-2H-pyran-4-yl)-[1,2,4]triazolo[4,3-a]quinoxaline-7-carboxylate) | ESI+: 347, 349 |

TABLE 13

| Pr | Structure | Data |
|---|---|---|
| 5-1 | (methyl 4-chloro-1-cyclopentyl-8-methyl-[1,2,4]triazolo[4,3-a]quinoxaline-7-carboxylate) | ESI+: 345, 347 |
| 5-2 | (methyl 4-chloro-8-methyl-1-(tetrahydro-2H-pyran-4-yl)-[1,2,4]triazolo[4,3-a]quinoxaline-7-carboxylate) | ESI+: 361, 363 |

TABLE 13-continued

| Pr | Structure | Data |
|---|---|---|
| 5-3 | (cyclohexyl-methyl substituted triazoloquinoxaline with Cl, CH3, methyl ester) | ESI+: 373, 375 |
| 5-4 | (tetrahydrofuran-3-yl substituted triazoloquinoxaline with Cl, CH3, methyl ester) | ESI+: 347, 349 |
| 5-5 | (2,2-dimethyltetrahydropyran-4-yl substituted triazoloquinoxaline with Cl, CH3, methyl ester) | ESI+: 389, 391 |

TABLE 14

| Pr | Structure | Data |
|---|---|---|
| 5-6 | (4-methyltetrahydropyran-4-yl substituted triazoloquinoxaline with Cl, CH3, methyl ester) | ESI+: 375, 377 |
| 5-7 | (4,4-difluorocyclohexyl substituted triazoloquinoxaline with Cl, CH3, methyl ester) | ESI+: 395, 397 |
| 5-8 | (tetrahydropyran-3-yl substituted triazoloquinoxaline with Cl, CH3, methyl ester) | ESI+: 361, 363 |
| 5-9 | (tetrahydropyran-4-yl substituted triazoloquinoxaline with Cl, OCH3, methyl ester) | ESI+: 377, 379 |
| 5-10 | (3,3-difluorocyclobutyl substituted triazoloquinoxaline with Cl, CH3, methyl ester) | ESI+: 367, 369 |

TABLE 15

| Pr | Structure | Data |
|---|---|---|
| 5-11 | 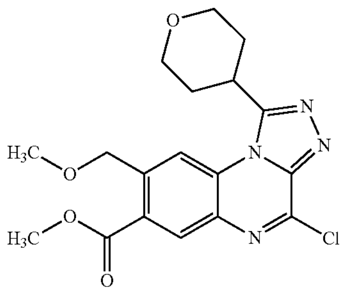 [SMILES: COCc1cc2c(cc1C(=O)OC)nc(Cl)c1nnc(C3CCOCC3)n12] | ESI+: 391, 393 |
| 5-12 | 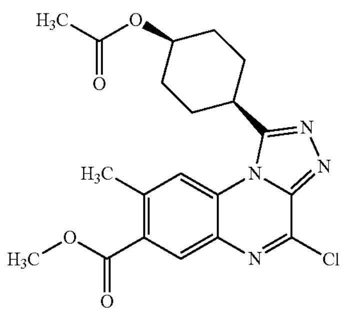 [SMILES: COC(=O)c1cc2nc(Cl)c3nnc([C@H]4CC[C@@H](OC(C)=O)CC4)n3c2cc1C] | ESI+: 417, 419 |
| 5-13 | 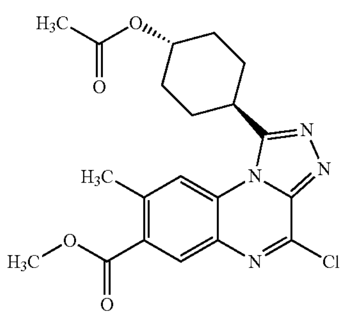 [SMILES: COC(=O)c1cc2nc(Cl)c3nnc([C@H]4CC[C@H](OC(C)=O)CC4)n3c2cc1C] | ESI+: 417, 419 |
| 5-14 | 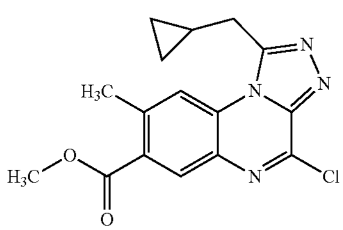 [SMILES: COC(=O)c1cc2nc(Cl)c3nnc(CC4CC4)n3c2cc1C] | ESI+: 331, 333 |
| 5-15 | 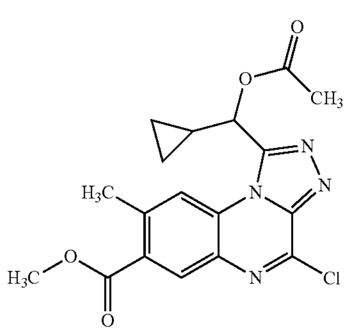 [SMILES: COC(=O)c1cc2nc(Cl)c3nnc(C(OC(C)=O)C4CC4)n3c2cc1C] | ESI+: 389, 391 |

TABLE 16

| Pr | Structure | Data |
|---|---|---|
| 5-16 | 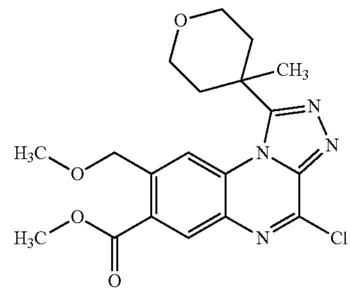 [SMILES: COCc1cc2c(cc1C(=O)OC)nc(Cl)c1nnc(C3(C)CCOCC3)n12] | ESI+: 405, 407 |
| 5-17 | 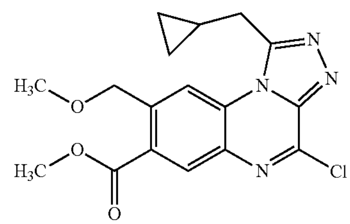 [SMILES: COCc1cc2c(cc1C(=O)OC)nc(Cl)c1nnc(CC3CC3)n12] | ESI+: 361, 363 |
| 5-18 | 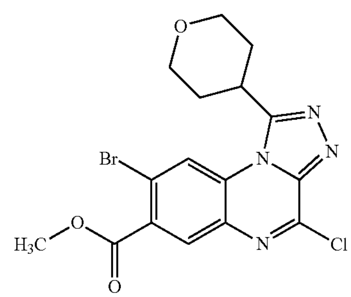 [SMILES: COC(=O)c1cc2nc(Cl)c3nnc(C4CCOCC4)n3c2cc1Br] | ESI+: 425, 427 |
| 5-19 | 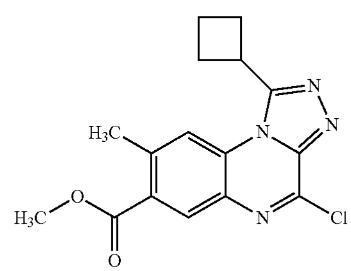 [SMILES: COC(=O)c1cc2nc(Cl)c3nnc(C4CCC4)n3c2cc1C] | ESI+: 331, 333 |
| 6 | 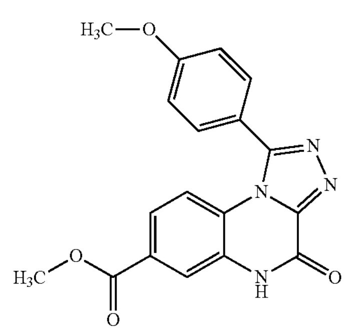 [SMILES: COC(=O)c1ccc2c(c1)[nH]c(=O)c1nnc(-c3ccc(OC)cc3)n12] | ESI+: 351 |

TABLE 16-continued
| Pr | Structure | Data |
|---|---|---|
| 6-1 | 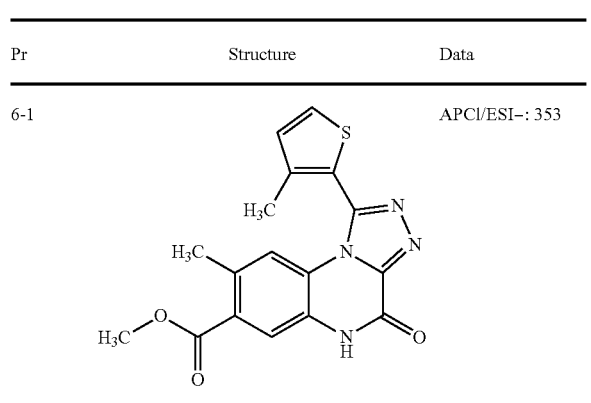 | APCI/ESI−: 353 |
TABLE 17
| Pr | Structure | Data |
|---|---|---|
| 7 | 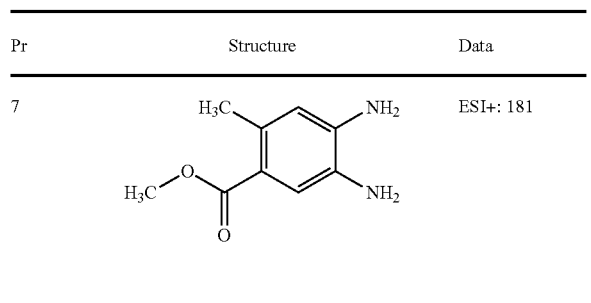 | ESI+: 181 |
| 7-1 | 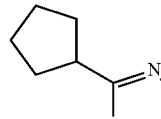 | ESI+: 300 |
| 7-2 | 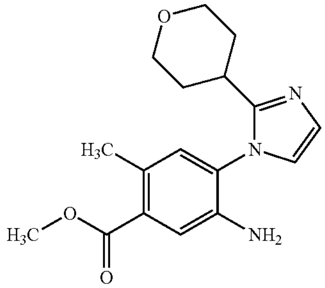 | ESI+: 316 |
| 7-3 | 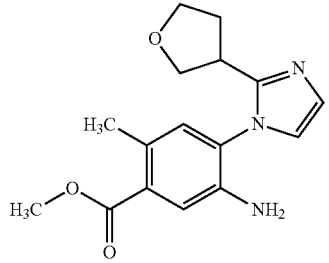 [SMILES: COC(=O)c1cc(N)c(-n2ccnc2C2CCOC2)cc1C] | APCI/ESI+: 302 |
| 7-4 | | ESI+: 316 |
| 7-5 | | APCI+: 330 |
TABLE 18
| Pr | Structure | Data |
|---|---|---|
| 7-6 | 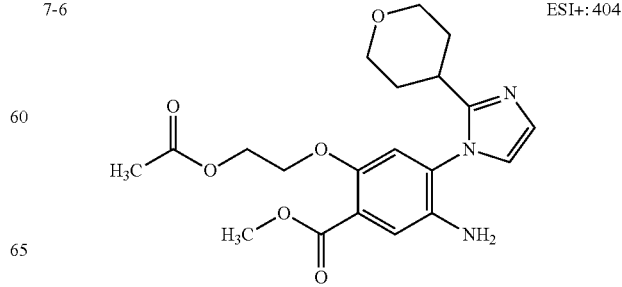 | ESI+: 404 |
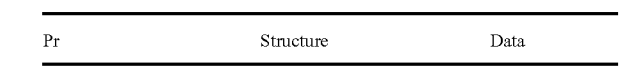

TABLE 18-continued

| Pr | Structure | Data |
|---|---|---|
| 7-7 | (structure) | ESI+: 430 |
| 7-8 | (structure) | ESI+: 415 |

TABLE 18-continued

| Pr | Structure | Data |
|---|---|---|
| 7-9 | (structure) | ESI+: 346 |
| 7-10 | (structure) | ESI+: 332 |

TABLE 19

| Pr | Structure | Data |
|---|---|---|
| 7-11 | (structure) | APCI/ESI+: 389 |
| 7-12 | (structure) | ESI+: 316 |

TABLE 19-continued

| Pr | Structure | Data |
|---|---|---|
| 7-13 | (structure) | ESI+: 372 |
| 8 | (structure) | FAB+: 235 |
| 8-1 | (structure) | NMR-DMSO-d6: 3.32-3.44 (3H, m), 3.82 (3H, s), 4.71 (2H, s), 7.37 (1H, s), 7.70 (1H, s), 11.98 (1H, s), 12.09 (1H, s) |
| 8-2 | (structure) | NMR-DMSO-d6: 3.84 (3H, s), 7.38 (1H, s), 7.61 (1H, s), 12.03 (1H, s), 12.10 (1H, s) |
| 8-3 | (structure) | NMR-DMSO-d6: 3.74-3.80 (6H, m), 6.81 (1H, s), 7.54 (1H, s), 11.84 (1H, s), 12.01 (1H, s) |

TABLE 20

| Pr | Structure | Data |
|---|---|---|
| 9 | (structure) | EI+: 270, 272 |
| 9-1 | (structure) | EI+: 334, 336, 338, 340 |
| 9-2 | (structure) | ESI+: 287, 289 |
| 9-3 | (structure) | ESI+: 301, 303 |

TABLE 20-continued
| Pr | Structure | Data |
|---|---|---|
| 10 | 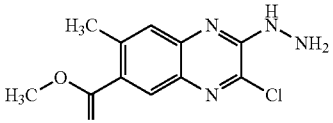 | ESI +: 267, 269 |
| 10-1 | 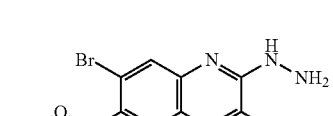 | ESI+: 331, 333, 335 |
| 10-2 | 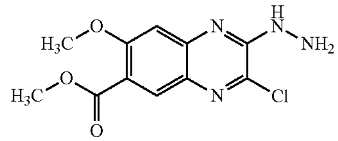 [SMILES: COC(=O)c1cc2nc(Cl)c(NN)nc2cc1OC] | ESI+: 283, 285 |
| 10-3 | 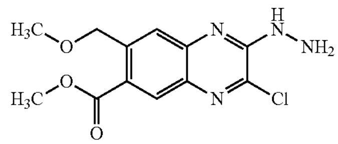 [SMILES: COCc1cc2nc(NN)c(Cl)nc2cc1C(=O)OC] | ESI+: 297, 299 |
| 10-4 | 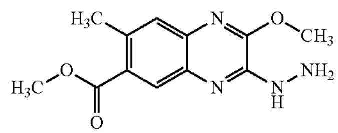 | ESI+: 263 |
TABLE 21
| Pr | Structure | Data |
|---|---|---|
| 11 | 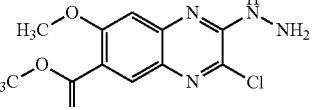 | ESI−: 212 |
| 11-1 | 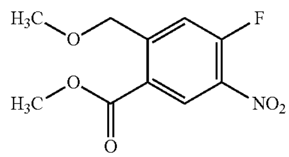 [SMILES: COCc1cc(F)c([N+](=O)[O-])cc1C(=O)OC] | ESI+: 266 (M + Na)+ |
| 12 | 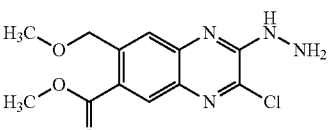 | ESI+: 330 |
| 12-1 | 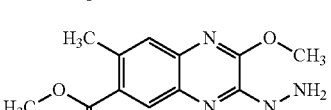 | ESI+: 346 |

TABLE 21-continued

| Pr | Structure | Data |
|---|---|---|
| 12-2 | 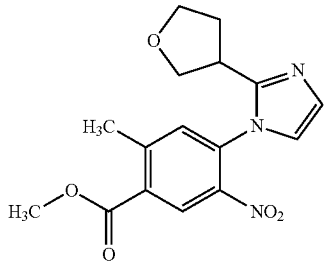 [SMILES: COC(=O)c1cc([N+](=O)[O-])c(-n2ccnc2C2CCOC2)cc1C] | APCI/ESI+: 332 |
| 12-3 | 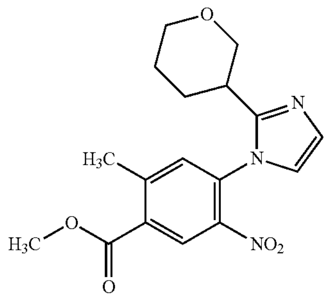 [SMILES: COC(=O)c1cc([N+](=O)[O-])c(-n2ccnc2C2CCCOC2)cc1C] | ESI+: 346 |

TABLE 22

| Pr | Structure | Data |
|---|---|---|
| 12-4 | 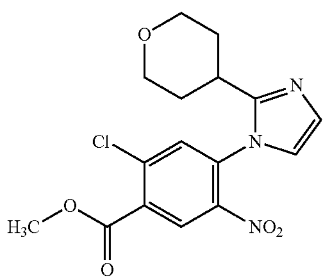 [SMILES: COC(=O)c1cc([N+](=O)[O-])c(-n2ccnc2C2CCOCC2)cc1Cl] | ESI+: 366, 368 |
| 12-5 | 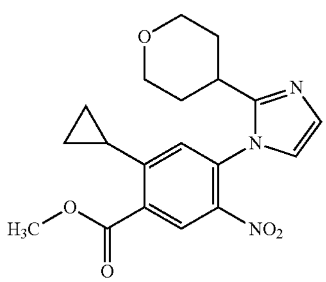 [SMILES: COC(=O)c1cc([N+](=O)[O-])c(-n2ccnc2C2CCOCC2)cc1C1CC1] | ESI+: 372 |
| 12-6 | 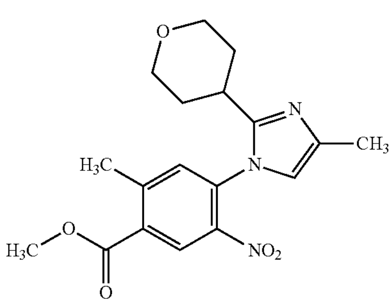 | APCI+: 360 |
| 12-7 | | ESI+: 376 |
| 12-8 | | APCI/ESI+: 419 |

TABLE 23
| Pr | Structure | Data |
|---|---|---|
| 12-9 | 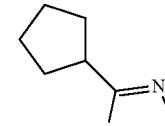 | ESI+: 434 |
| 12-10 | 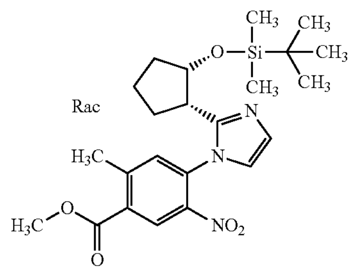 | ESI+: 460 |
| 12-11 | 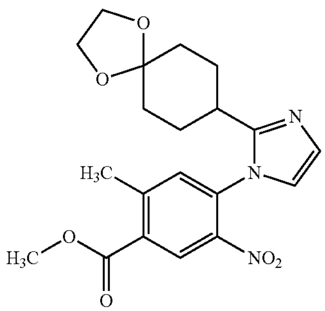 [SMILES: COC(=O)c1cc([N+](=O)[O-])c(-n2ccnc2C2CCC3(CC2)OCCO3)cc1C] | ESI+: 402 |
| 12-12 | 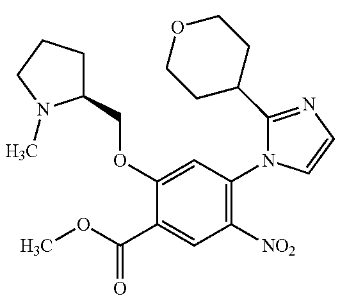 [SMILES: COC(=O)c1cc([N+](=O)[O-])c(-n2ccnc2C2CCOCC2)cc1OC[C@@H]1CCCN1C] | ESI+: 445 |
| 12-13 | 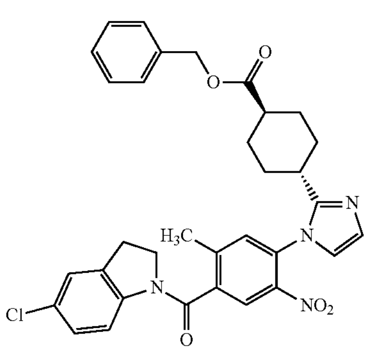 [SMILES: Cc1cc(-n2ccnc2[C@H]2CC[C@H](C(=O)OCc3ccccc3)CC2)c([N+](=O)[O-])cc1C(=O)N1CCc2cc(Cl)ccc21] | ESI+: 599, 601 |
TABLE 24
| Pr | Structure | Data |
|---|---|---|
| 13 | 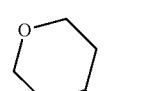 | ESI+: 326 |
| 13-1 | 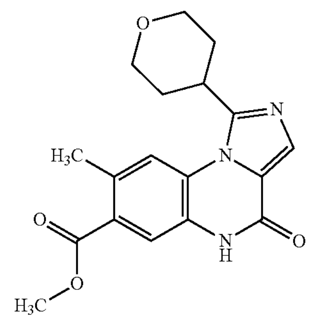 [SMILES: COC(=O)c1cc2[nH]c(=O)c3cnc(C4CCOCC4)n3c2cc1C] | ESI+: 342 |
| 13-2 | 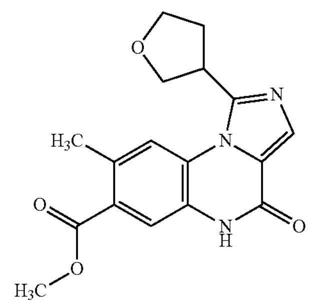 [SMILES: COC(=O)c1cc2[nH]c(=O)c3cnc(C4CCOC4)n3c2cc1C] | APCI/ESI+: 328 |
| 13-3 | 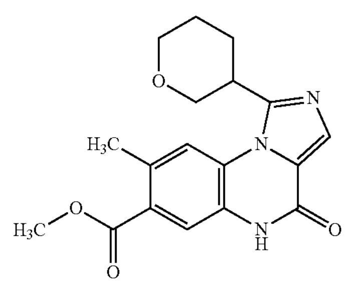 [SMILES: COC(=O)c1cc2[nH]c(=O)c3cnc(C4CCCOC4)n3c2cc1C] | ESI+: 342 |
| 13-4 | 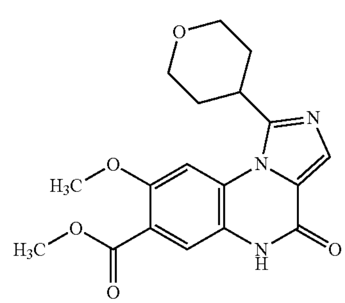 [SMILES: COC(=O)c1cc2[nH]c(=O)c3cnc(C4CCOCC4)n3c2cc1OC] | ESI+: 358 |

TABLE 25
| Pr | Structure | Data |
|---|---|---|
| 13-5 | 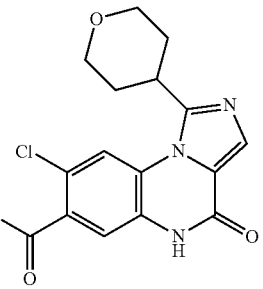 | ESI+: 362, 364 |
| 13-6 | 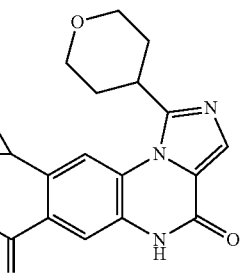 | ESI+: 368 |
| 13-7 | 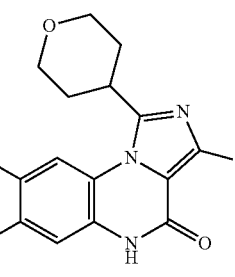 | ESI+: 356 |
| 13-8 | 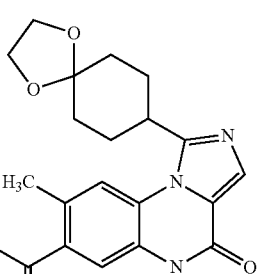 | ESI+: 398 |
| 13-9 | 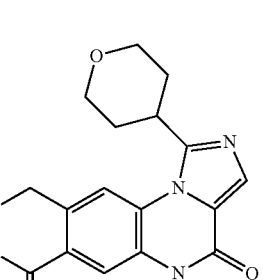 | NMR-DMSO-d6: 1.85-2.10 (4H, m), 3.47 (3H, s), 3.50-3.70 (3H, m), 3.86 (3H, s), 4.00-4.10 (2H, m), 4.80 (2H, s), 7.82 (1H, s), 7.89 (1H, s), 8.20 (1H, s), 11.49 (1H, s) |

TABLE 26

| Pr | Structure | Data |
|---|---|---|
| 13-10 | 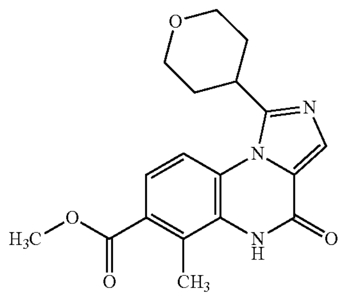 [SMILES: COC(=O)c1ccc2c([nH]c(=O)c3cnc(C4CCOCC4)n32)c1C] | ESI+: 342 |
| 13-11 | 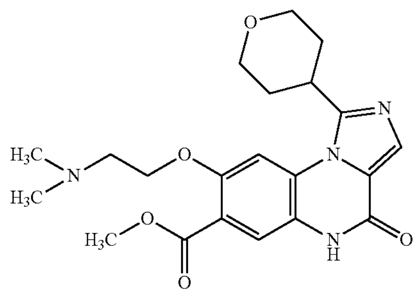 [SMILES: COC(=O)c1cc2[nH]c(=O)c3cnc(C4CCOCC4)n3c2cc1OCCN(C)C] | ESI+: 415 |
| 13-12 | 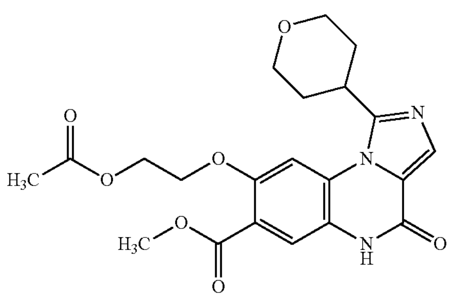 [SMILES: COC(=O)c1cc2[nH]c(=O)c3cnc(C4CCOCC4)n3c2cc1OCCOC(C)=O] | ESI+: 430 |

TABLE 26-continued

| Pr | Structure | Data |
|---|---|---|
| 13-13 | 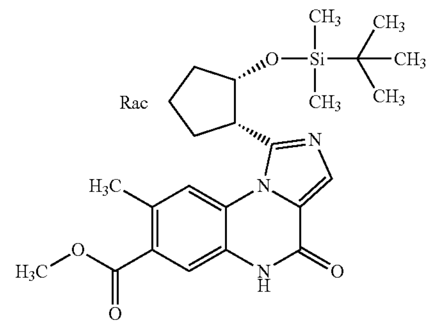 [SMILES: COC(=O)c1cc2[nH]c(=O)c3cnc([C@@H]4CCC[C@@H]4O[Si](C)(C)C(C)(C)C)n3c2cc1C] | ESI+: 456 |
| 13-14 | 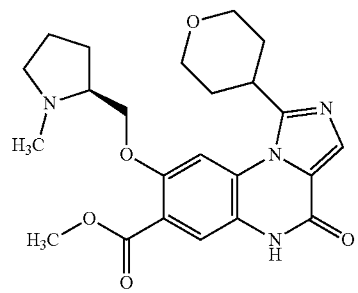 [SMILES: COC(=O)c1cc2[nH]c(=O)c3cnc(C4CCOCC4)n3c2cc1OC[C@@H]1CCCN1C] | ESI+: 441 |
| 14 | 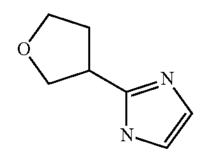 | ESI+: 139 |

TABLE 27

| Pr | Structure | Data |
|---|---|---|
| 14-1 | 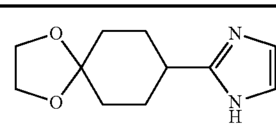 | APCl+: 209 |
| 14-2 | 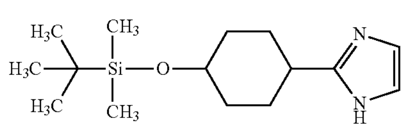 [SMILES: CC(C)(C)[Si](C)(C)OC1CCC(c2ncc[nH]2)CC1] | APCl+: 281 |
| 14-3 | 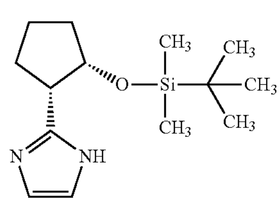 | ESI+: 267 |
| 14-4 | 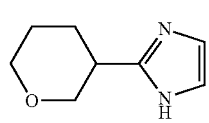 [SMILES: c1c[nH]c(C2CCCOC2)n1] | ESI+: 153 |

TABLE 27-continued

| Pr | Structure | Data |
|---|---|---|
| 14-5 | 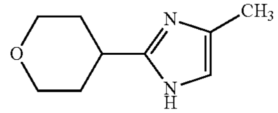 | ESI+: 167 |
| 15 | 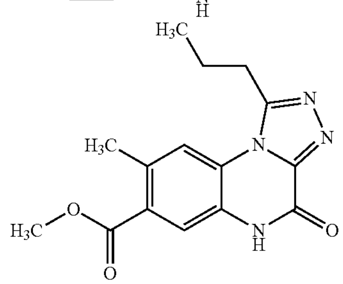 | ESI+: 301 |
| 16 | 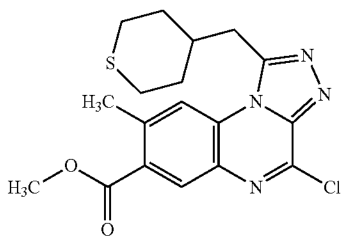 [SMILES: COC(=O)c1cc2nc(Cl)c3nnc(CC4CCSCC4)n3c2cc1C] | NMR-DMSO-d6: 1.46-1.62 (2H, m), 2.04-2.21 (3H, m), 2.56-2.66 (4H, m), 2.77 (3H, s), 3.41-3.51 (2H, m), 3.92 (3H, s), 8.10 (1H, s), 8.38 (1H, s) |
| 17 | 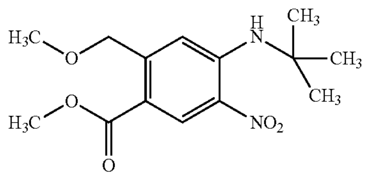 [SMILES: COCc1cc(NC(C)(C)C)c([N+](=O)[O-])cc1C(=O)OC] | ESI+: 297 |

TABLE 28

| Pr | Structure | Data |
|---|---|---|
| 18 | 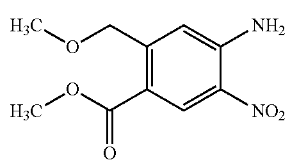 [SMILES: COCc1cc(N)c([N+](=O)[O-])cc1C(=O)OC] | ESI+: 241 |
| 19 | 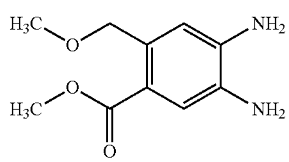 | ESI+: 211 |
| 19-1 | 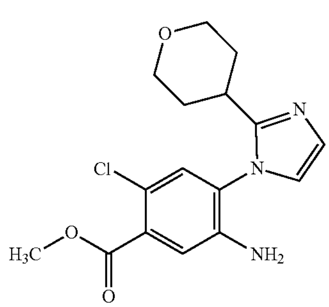 [SMILES: COC(=O)c1cc(N)c(-n2ccnc2C2CCOCC2)cc1Cl] | ESI+: 336, 338 |
| 19-2 | | ESI+: 342 |
| 19-3 | | ESI+: 245, 247 |

TABLE 28-continued

| Pr | Structure | Data |
|---|---|---|
| 19-4 | 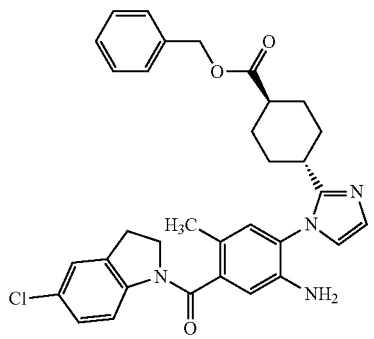 [SMILES: Cc1cc(-n2ccnc2[C@H]2CC[C@H](C(=O)OCc3ccccc3)CC2)c(N)cc1C(=O)N1CCc2cc(Cl)ccc21] | ESI+: 569, 571 |
| 20 | 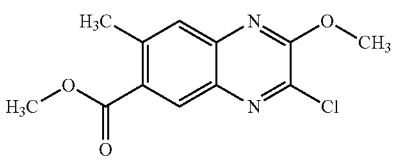 | ESI+: 267, 269 |

TABLE 29

| Pr | Structure | Data |
|---|---|---|
| 21 | 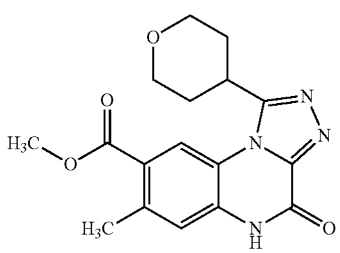 [SMILES: COC(=O)c1cc2c(cc1C)[nH]c(=O)c1nnc(C3CCOCC3)n12] | ESI+: 343 |
| 22 | 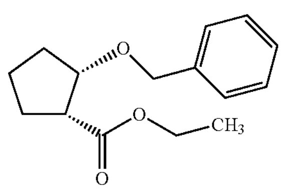 | EI: 248 |
| 23 | 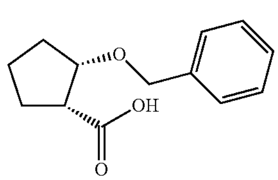 | ESI+: 221 |
| 24 | 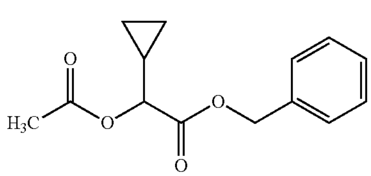 [SMILES: CC(=O)OC(C(=O)OCc1ccccc1)C1CC1] | ESI+: 271 (M + Na)+ |

TABLE 29-continued

| Pr | Structure | Data |
|---|---|---|
| 25 | 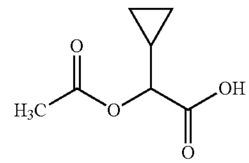 | ESI−: 157 |
| 26 | 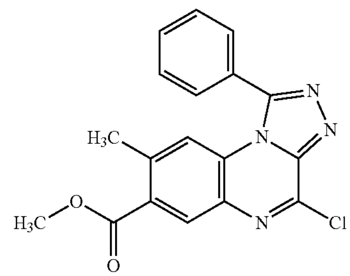 [SMILES: COC(=O)c1cc2nc(Cl)c3nnc(-c4ccccc4)n3c2cc1C] | ESI+: 353, 355 |
| 26-1 | 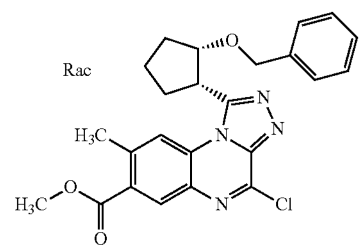 [SMILES: COC(=O)c1cc2nc(Cl)c3nnc([C@@H]4CCC[C@@H]4OCc4ccccc4)n3c2cc1C] | ESI+: 451, 453 |

TABLE 30

| Pr | Structure | Data |
|---|---|---|
| 27 | 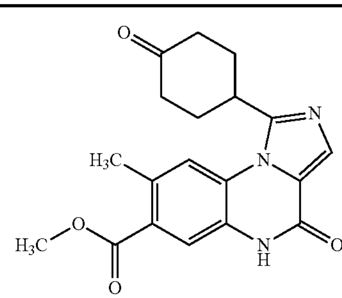 | ESI−: 352 |
| 28(a) | 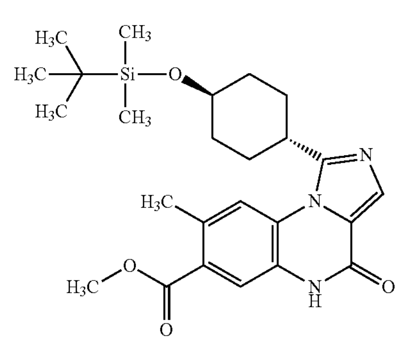 [SMILES: COC(=O)c1cc2[nH]c(=O)c3cnc([C@H]4CC[C@H](O[Si](C)(C)C(C)(C)C)CC4)n3c2cc1C] | ESI+: 470 |

TABLE 30-continued

| Pr | Structure | Data |
|---|---|---|
| 28(b) | (TBS-O-cyclohexyl-imidazo-quinoxalinone with methyl and methyl ester) | ESI+: 470 |
| 29 | (tetrahydropyran-imidazole-methoxy-nitro-methylbenzoate) | ESI+: 362 |️
| 30 | (methyl 2-cyclopropyl-4-fluoro-5-nitrobenzoate) | ESI+: 239 M+ |
| 30-1 | (tert-butyl 4-cyclopropylisoindoline-2-carboxylate) | ESI+: 260 |

TABLE 31

| Pr | Structure | Data |
|---|---|---|
| 30-2 | (tert-butyl 5-cyclopropyl-2,3-dihydro-1H-pyrrolo[2,3-b]pyridine-1-carboxylate) | ESI+: 261 |
| 31 | (methyl 4-fluoro-2-(methoxymethyl)benzoate) | NMR-CDCl3: 3.49 (3H, s), 3.88 (3H, s), 4.85 (2H, s), 6.9-7.05 (1H, m), 7.41 (1H, dd, J = 10, 3 Hz), 8.0 (1H, dd, J = 9, 6 Hz) |
| 32 | (methyl 2-(2-acetoxyethoxy)-4-fluorobenzoate) | ESI+: 279 (M + Na)+ |
| 32-1 | (methyl 2-(2-(dimethylamino)ethoxy)-4-fluorobenzoate) | ESI+: 242 |

TABLE 31-continued

| Pr | Structure | Data |
| --- | --- | --- |
| 32-2 | (structure) | ESI+: 268 |
| 33 | (structure) | APCI/ESI+: 287 |
| 33-1 | (structure) | ESI+: 324 (M + Na)+ |
| 33-2 | (structure) | ESI+: 313 |

TABLE 32

| Pr | Structure | Data |
| --- | --- | --- |
| 34 | (structure) | ESI+: 346 |
| 35 | (structure) | ESI+: 364, 366 |

TABLE 32-continued

| Pr | Structure | Data |
|---|---|---|
| 36 | (structure: 1-cyclopentyl-4-chloro-7-methoxycarbonyl-8-methyl-imidazo[1,2-a]quinoxaline) | ESI+: 344., 346 |
| 37 | Rac (structure: trans-2-((tert-butyldimethylsilyl)oxy)cyclopentane-1-carbaldehyde) | EI: 229 |
| 38 | (structure: 5-fluoro-2,3-dihydro-1H-pyrrolo[2,3-b]pyridine) | ESI+: 139 |
| 39 | (structure: 5-methoxy-2,3-dihydro-1H-pyrrolo[2,3-c]pyridine) | ESI+: 151 |
| 39-1 | (structure: 4-cyclopropyl-2,3-dihydro-1H-isoindole) | ESI+: 160 |

TABLE 33

| Pr | Structure | Data |
|---|---|---|
| 39-2 | (structure: 5-cyclopropyl-2,3-dihydro-1H-pyrrolo[2,3-b]pyridine) | APCl+: 161 |
| 40 | (structure: benzyl trans-4-(1H-imidazol-2-yl)cyclohexane-1-carboxylate) | ESI+: 285 |
| 41 | (structure: 5-benzyl-2-(pyridin-4-yl)-4,5,6,7-tetrahydro-1H-pyrrolo[3,2-c]pyridine) | NMR-CDCl3: 2.77 (2H, d, J = 4.8 Hz), 2.81 (2H, d, J = 4.8 Hz), 3.51 (2H, s), 3.73 (2H, s), 6.45 (1H, d, J = 2.5 Hz), 7.23-7.26 (3H, m), 7.28-7.41 (4H, m), 8.40 (1H, br s), 8.47 (2H, dd, J = 1.6 Hz, 4.6 Hz) |

103
TABLE 33-continued
| Pr | Structure | Data |
|---|---|---|
| 42 | 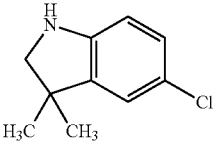 | ESI+: 182, 184 |
| 43 | 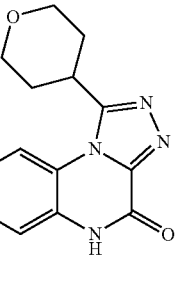 | NMR-DMSO-d6: 1.85-2.12 (4H, m), 3.58-3.71 (2H, m), 3.84-4.06 (6H, m), 7.81 (1H, s), 8.12 (1H, s), 12.20 (1H, br s) |
| 44-1 | 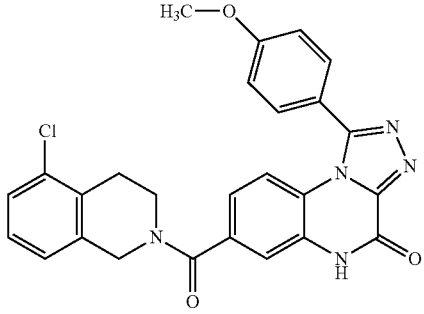 [SMILES: COc1ccc(-c2nnc3c(=O)[nH]c4cc(C(=O)N5CCc6c(Cl)cccc6C5)ccc4n23)cc1] | ESI+: 486, 488 |
TABLE 34
| Pr | Structure | Data |
|---|---|---|
| 44-2 | 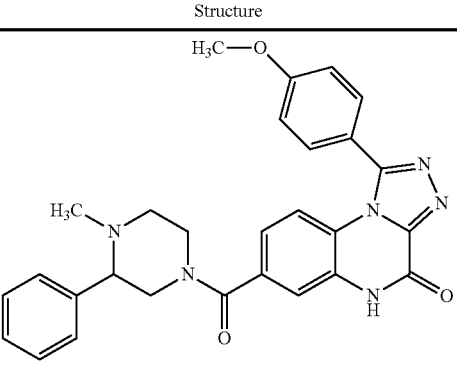 | ESI+: 495 |
| 45 Rac | 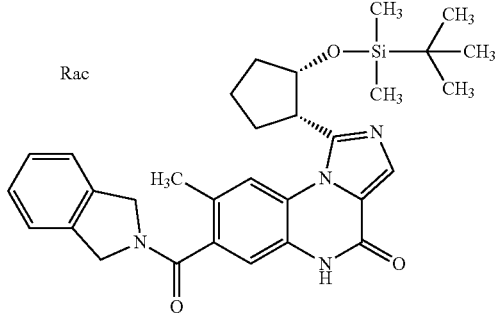 [SMILES: Cc1cc2c(cc1C(=O)N1Cc3ccccc3C1)[nH]c(=O)c1cnc([C@@H]3CCC[C@@H]3O[Si](C)(C)C(C)(C)C)n12] | ESI+: 543 |

TABLE 34-continued

| Pr | Structure | Data |
|---|---|---|
| 46-1 | 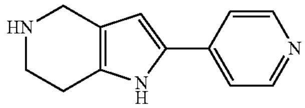 [SMILES: c1cc(-c2cc3c([nH]2)CCNC3)ccn1] | ESI+: 200 |
| 46-2 | 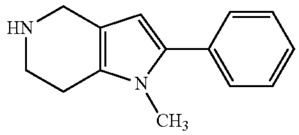 [SMILES: Cn1c(-c2ccccc2)cc2c1CCNC2] | ESI+: 213 |
| 47 | 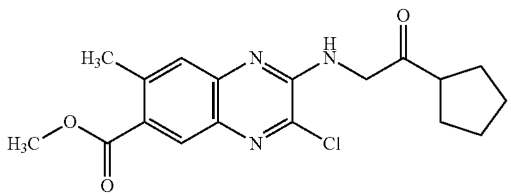 [SMILES: COC(=O)c1cc2nc(Cl)c(NCC(=O)C3CCCC3)nc2cc1C] | ESI+: 362, 364 |
| 48 | 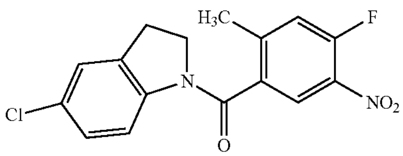 [SMILES: Cc1cc(F)c([N+](=O)[O-])cc1C(=O)N1CCc2cc(Cl)ccc21] | ESI+: 335, 337 |

TABLE 35

| Ex | Structure |
|---|---|
| 1 | 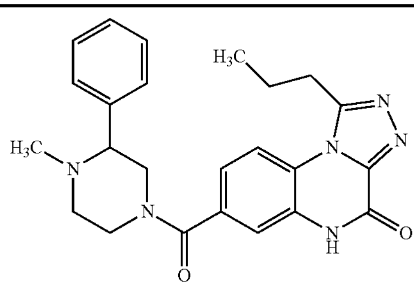 |
| 2 | 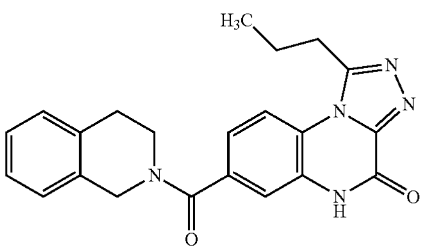 [SMILES: CCCc1nnc2c(=O)[nH]c3cc(C(=O)N4CCc5ccccc5C4)ccc3n12] |
| 3 | 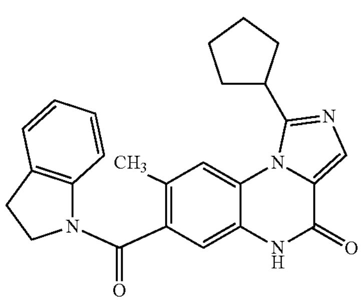 [SMILES: Cc1cc2c(cc1C(=O)N1CCc3ccccc31)[nH]c(=O)c1cnc(C3CCCC3)n12] |
| 4 | |
| 5 | |

TABLE 36

| Ex | Structure |
|---|---|
| 6 | (structure) |
| 7 | (structure) |
| 8 | (structure) |
| 9 | (structure) |
| 10 | (structure) |

TABLE 36-continued

| Ex | Structure |
|---|---|
| 11 | (structure) |

TABLE 37

| Ex | Structure |
|---|---|
| 12 | (structure) |
| 13 | (structure) |
| 14 (a) | (structure) |
| 14 (b) | (structure) |

TABLE 37-continued
| Ex | Structure |
|---|---|
| 15 | 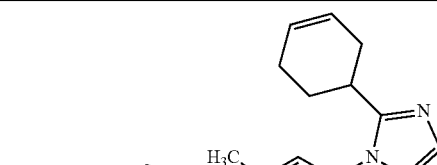 |
TABLE 38
| Ex | Structure |
|---|---|
| 16 | 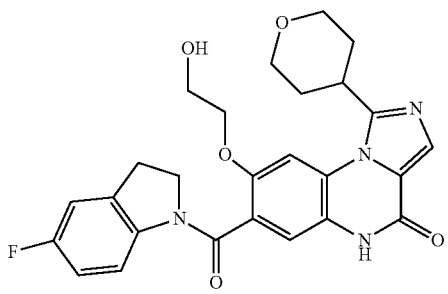 |
| 17 | 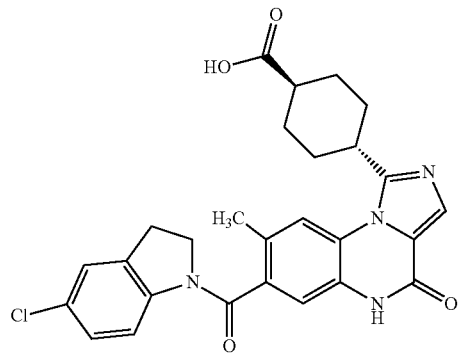 [SMILES: Cc1cc2c(cc1C(=O)N1CCc3cc(Cl)ccc31)[nH]c(=O)c1cnc([C@H]3CC[C@H](C(=O)O)CC3)n12] |
| 18 | 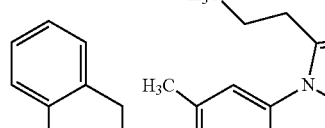 |
TABLE 38-continued
| Ex | Structure |
|---|---|
| 19 | 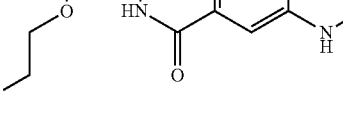 |
| 20 | 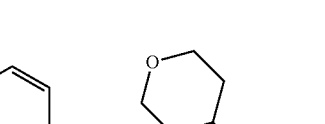 |
| 21 | 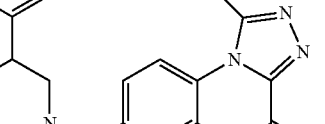 |
TABLE 39
| Ex | Structure |
|---|---|
| 22 | 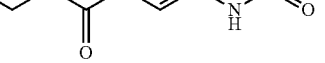 |
| 23 | 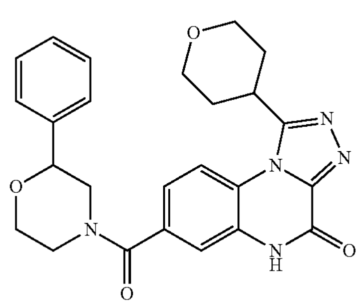 [SMILES: O=C(c1ccc2c(c1)[nH]c(=O)c1nnc(C3CCOCC3)n12)N1CCOC(c2ccccc2)C1] |

TABLE 39-continued

| Ex | Structure |
|---|---|
| 24 | 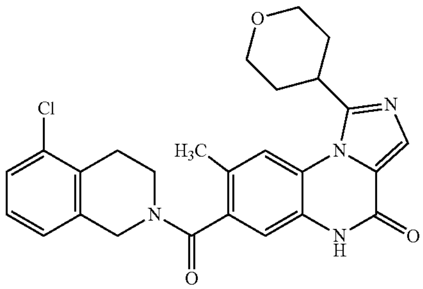 [SMILES: Cc1cc2c(cc1C(=O)N1CCc3c(Cl)cccc3C1)[nH]c(=O)c1cnc(C3CCOCC3)n12] |
| 25 | 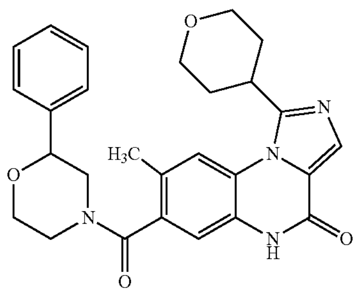 [SMILES: Cc1cc2c(cc1C(=O)N1CCOC(c3ccccc3)C1)[nH]c(=O)c1cnc(C3CCOCC3)n12] |
| 26 | 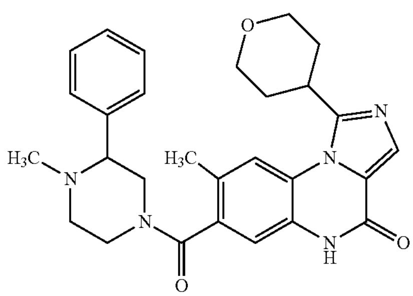 [SMILES: Cc1cc2c(cc1C(=O)N1CCN(C)C(c3ccccc3)C1)[nH]c(=O)c1cnc(C3CCOCC3)n12] |
| 27 | 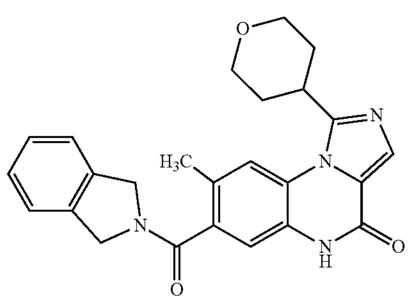 [SMILES: Cc1cc2c(cc1C(=O)N1Cc3ccccc3C1)[nH]c(=O)c1cnc(C3CCOCC3)n12] |

TABLE 40

| Ex | Structure |
|---|---|
| 28 | |
| 29 | 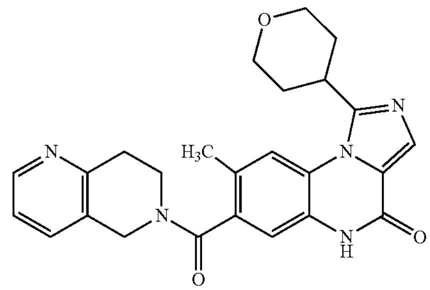 |
| 30 | 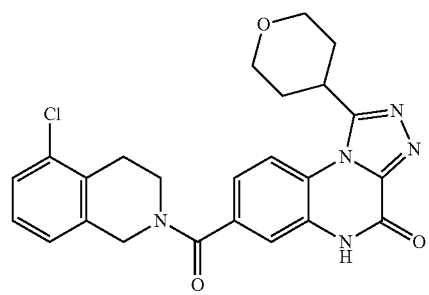 [SMILES: O=C(c1ccc2c(c1)[nH]c(=O)c1nnc(C3CCOCC3)n12)N1CCc2c(Cl)cccc2C1] |
| 31 | 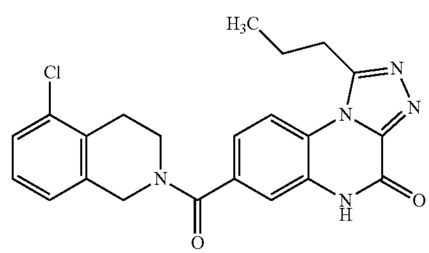 |
| 32 | 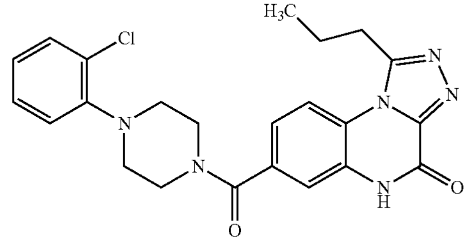 |
| 33 | 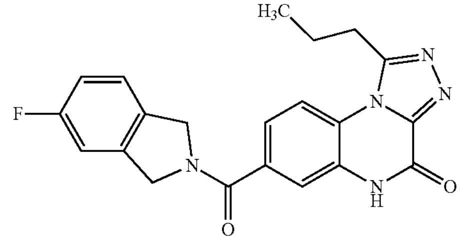 [SMILES: CCCc1nnc2c(=O)[nH]c3cc(C(=O)N4Cc5ccc(F)cc5C4)ccc3n12] |

TABLE 41
| Ex | Structure |
|---|---|
| 34 | 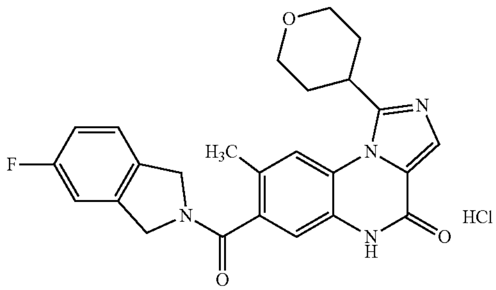 [SMILES: Cc1cc2c(cc1C(=O)N1Cc3ccc(F)cc3C1)[nH]c(=O)c1cnc(C3CCOCC3)n12 ; Cl] |
| 35 | 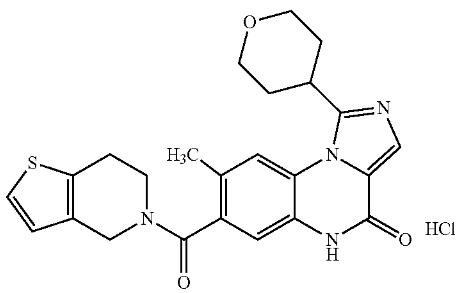 [SMILES: Cc1cc2c(cc1C(=O)N1CCc3sccc3C1)[nH]c(=O)c1cnc(C3CCOCC3)n12 ; Cl] |
| 36 | 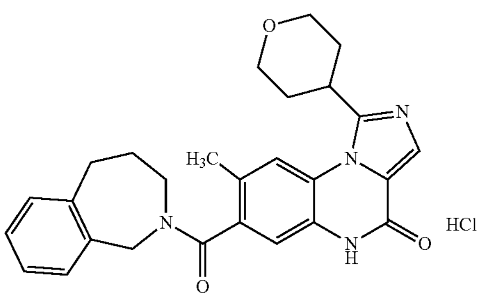 [SMILES: Cc1cc2c(cc1C(=O)N1CCCc3ccccc3C1)[nH]c(=O)c1cnc(C3CCOCC3)n12 ; Cl] |
| 37 | 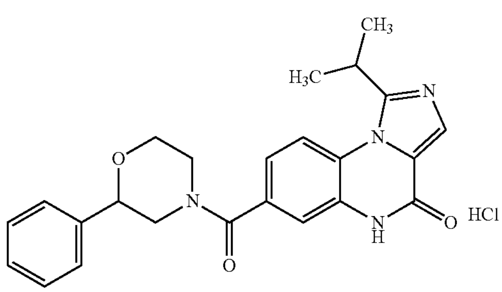 [SMILES: CC(C)c1ncc2c(=O)[nH]c3cc(C(=O)N4CCOC(c5ccccc5)C4)ccc3n12 ; Cl] |
| 38 | 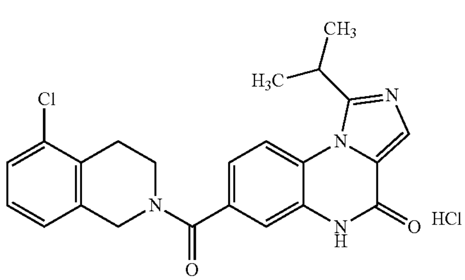 [SMILES: CC(C)c1ncc2c(=O)[nH]c3cc(C(=O)N4CCc5c(Cl)cccc5C4)ccc3n12 ; Cl] |
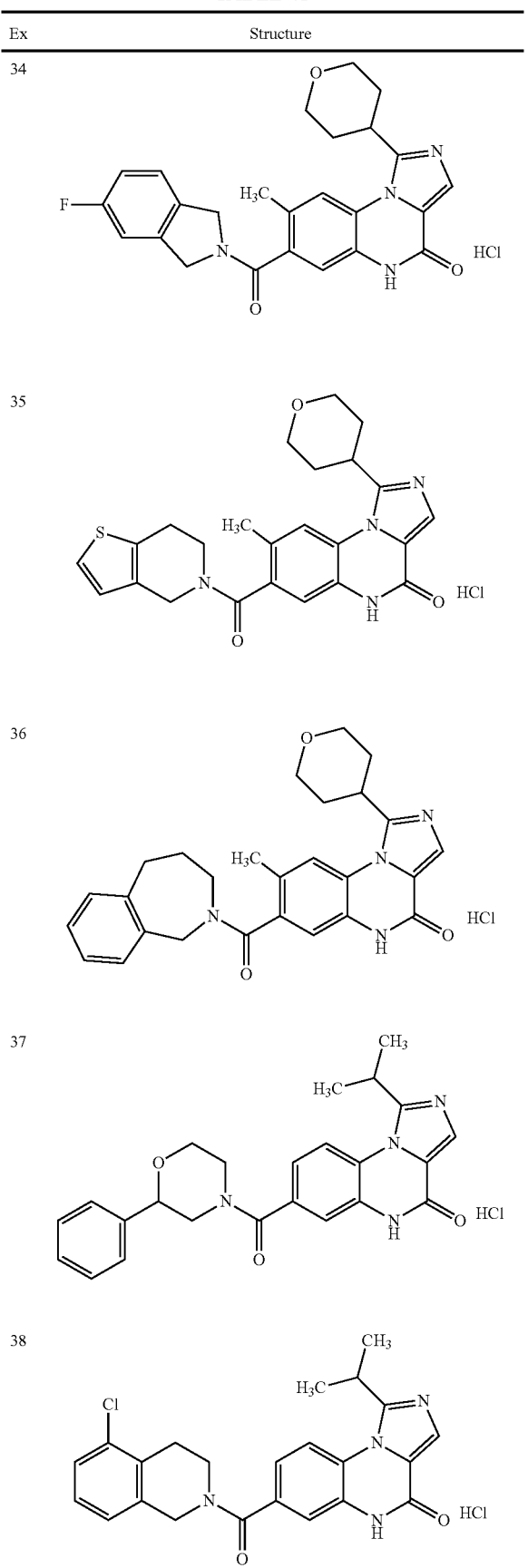
TABLE 41-continued
| Ex | Structure |
|---|---|
| 39 | 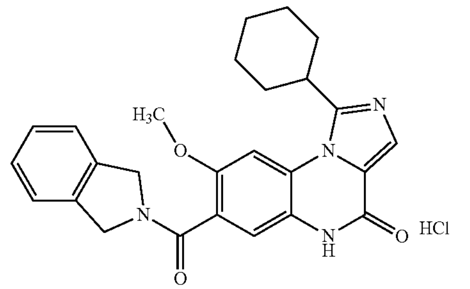 [SMILES: COc1cc2c(cc1C(=O)N1Cc3ccccc3C1)[nH]c(=O)c1cnc(C3CCCCC3)n12 ; Cl] |
TABLE 42
| Ex | Structure |
|---|---|
| 40 | 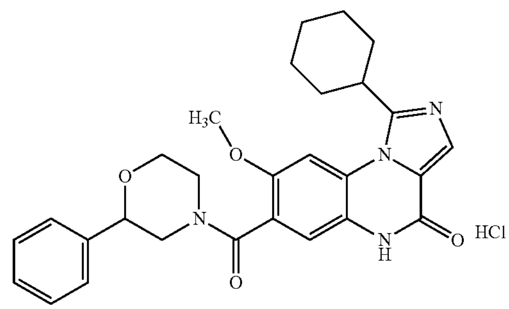 [SMILES: COc1cc2c(cc1C(=O)N1CCOC(c3ccccc3)C1)[nH]c(=O)c1cnc(C3CCCCC3)n12 ; Cl] |
| 41 | 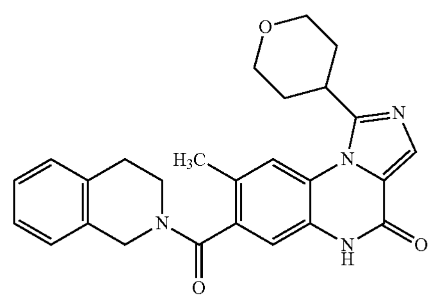 [SMILES: Cc1cc2c(cc1C(=O)N1CCc3ccccc3C1)[nH]c(=O)c1cnc(C3CCOCC3)n12] |
| 42 | 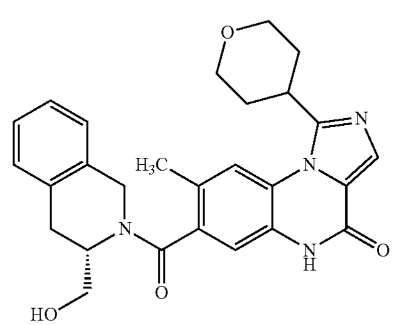 [SMILES: Cc1cc2c(cc1C(=O)N1Cc3ccccc3C[C@H]1CO)[nH]c(=O)c1cnc(C3CCOCC3)n12] |
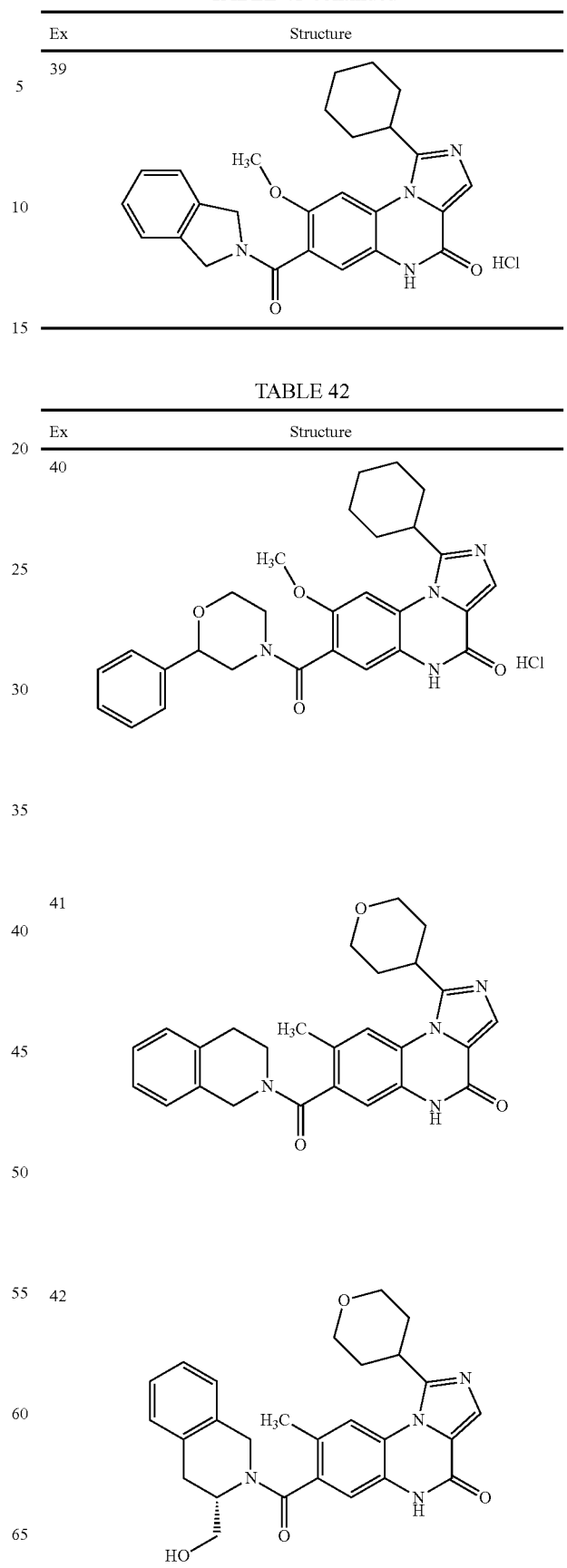

TABLE 42-continued

| Ex | Structure |
|---|---|
| 43 | 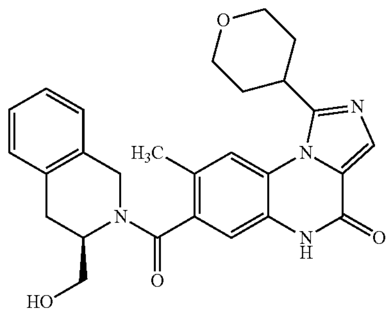 [SMILES: Cc1cc2c(cc1C(=O)N1Cc3ccccc3C[C@@H]1CO)[nH]c(=O)c1cnc(C3CCOCC3)n12] |
| 44 | 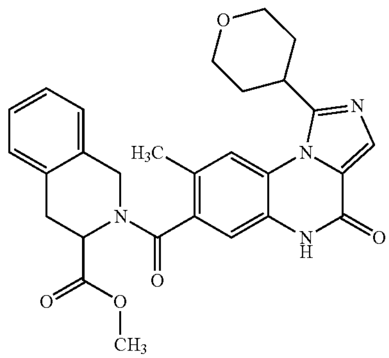 [SMILES: COC(=O)C1Cc2ccccc2CN1C(=O)c1cc2[nH]c(=O)c3cnc(C4CCOCC4)n3c2cc1C] |

TABLE 43

| Ex | Structure |
|---|---|
| 45 | 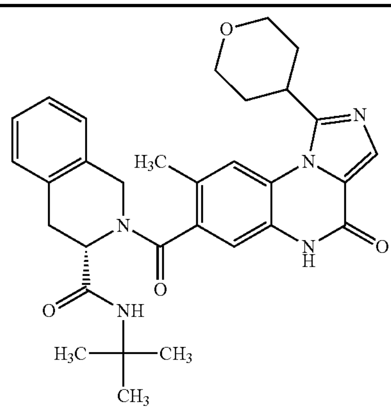 |
| 46 | 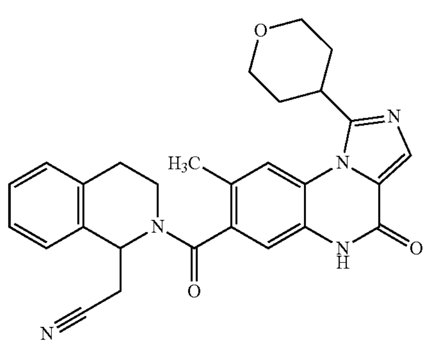 [SMILES: Cc1cc2c(cc1C(=O)N1CCc3ccccc3C1CC#N)[nH]c(=O)c1cnc(C3CCOCC3)n12] |

TABLE 43-continued

| Ex | Structure |
|---|---|
| 47 | 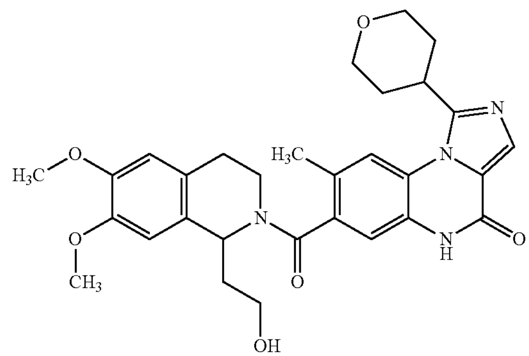 [SMILES: COc1cc2c(cc1OC)C(CCO)N(C(=O)c1cc3[nH]c(=O)c4cnc(C5CCOCC5)n4c3cc1C)CC2] |
| 48 | 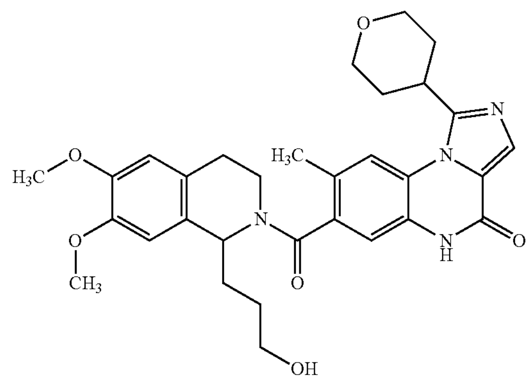 [SMILES: COc1cc2c(cc1OC)C(CCCO)N(C(=O)c1cc3[nH]c(=O)c4cnc(C5CCOCC5)n4c3cc1C)CC2] |
| 49 | 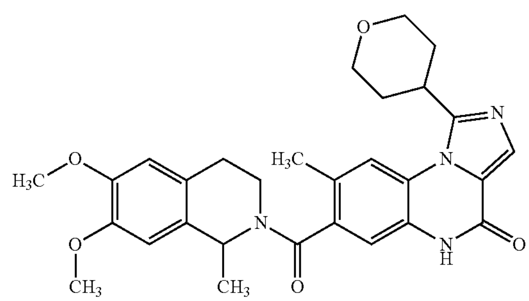 [SMILES: COc1cc2c(cc1OC)C(C)N(C(=O)c1cc3[nH]c(=O)c4cnc(C5CCOCC5)n4c3cc1C)CC2] |

TABLE 44

| Ex | Structure |
|---|---|
| 50 | 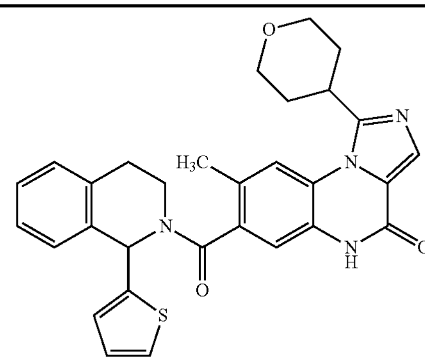 |

TABLE 44-continued

| Ex | Structure |
|---|---|
| 51 | 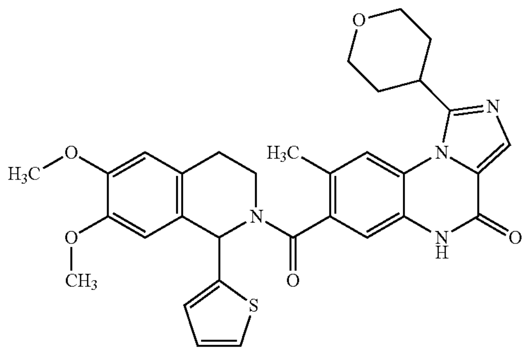 [SMILES: COc1cc2c(cc1OC)C(c1cccs1)N(C(=O)c1cc3[nH]c(=O)c4cnc(C5CCOCC5)n4c3cc1C)CC2] |
| 52 | 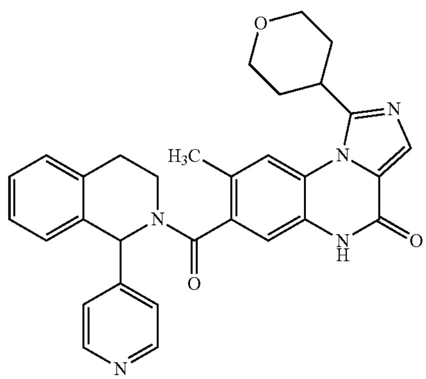 [SMILES: Cc1cc2c(cc1C(=O)N1CCc3ccccc3C1c1ccncc1)[nH]c(=O)c1cnc(C3CCOCC3)n12] |
| 53 | 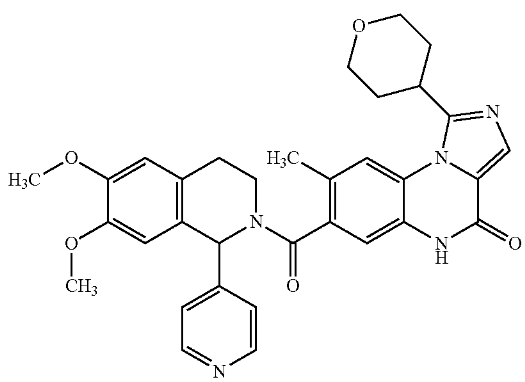 [SMILES: COc1cc2c(cc1OC)C(c1ccncc1)N(C(=O)c1cc3[nH]c(=O)c4cnc(C5CCOCC5)n4c3cc1C)CC2] |
| 54 | 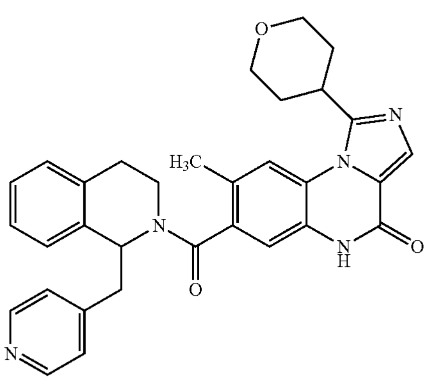 [SMILES: Cc1cc2c(cc1C(=O)N1CCc3ccccc3C1Cc1ccncc1)[nH]c(=O)c1cnc(C3CCOCC3)n12] |

TABLE 45

| Ex | Structure |
|---|---|
| 55 | 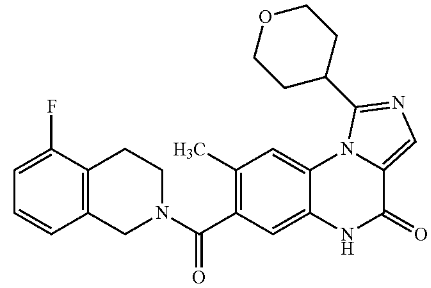 [SMILES: Cc1cc2c(cc1C(=O)N1CCc3c(F)cccc3C1)[nH]c(=O)c1cnc(C3CCOCC3)n12] |
| 56 | 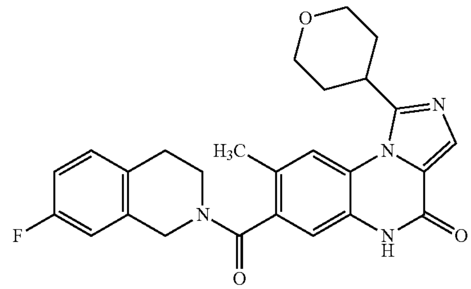 [SMILES: Cc1cc2c(cc1C(=O)N1CCc3ccc(F)cc3C1)[nH]c(=O)c1cnc(C3CCOCC3)n12] |
| 57 | 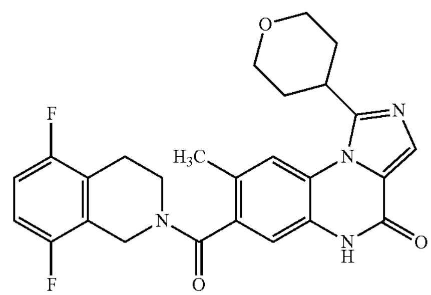 [SMILES: Cc1cc2c(cc1C(=O)N1CCc3c(F)ccc(F)c3C1)[nH]c(=O)c1cnc(C3CCOCC3)n12] |
| 58 | 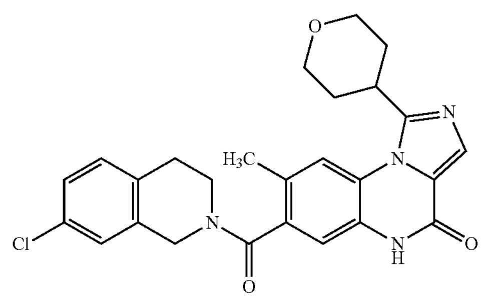 [SMILES: Cc1cc2c(cc1C(=O)N1CCc3ccc(Cl)cc3C1)[nH]c(=O)c1cnc(C3CCOCC3)n12] |
| 59 | 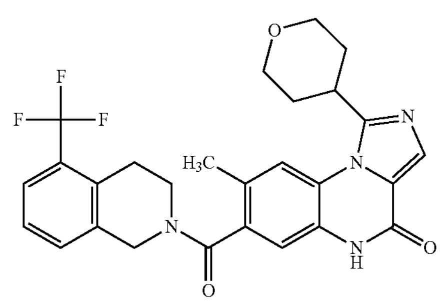 [SMILES: Cc1cc2c(cc1C(=O)N1CCc3c(cccc3C(F)(F)F)C1)[nH]c(=O)c1cnc(C3CCOCC3)n12] |

TABLE 45-continued
| Ex | Structure |
|---|---|
| 60 | 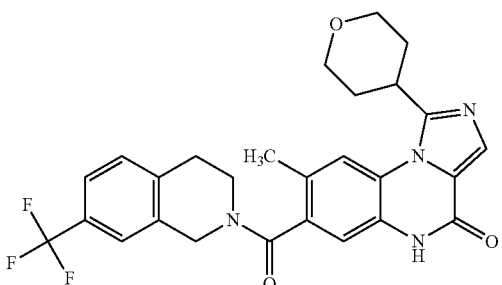 |
TABLE 46
| Ex | Structure |
|---|---|
| 61 | 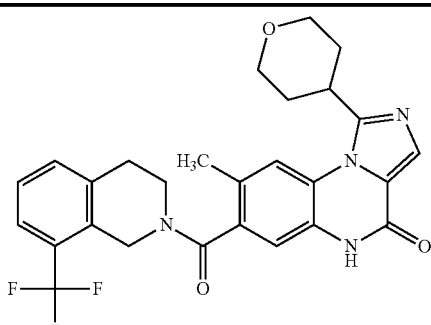 |
| 62 | 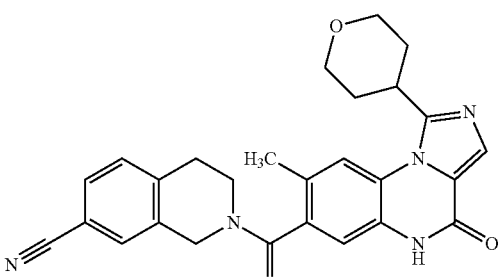 |
| 63 | 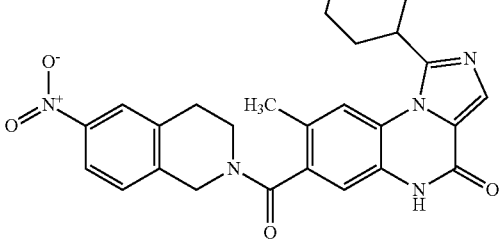 |
TABLE 46-continued
| Ex | Structure |
|---|---|
| 64 | 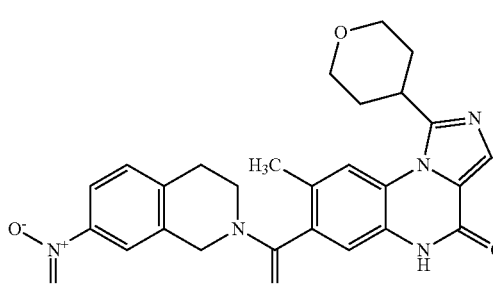 |
| 65 | 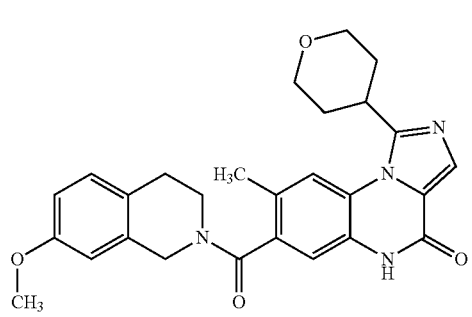 [SMILES: COc1ccc2c(c1)CN(C(=O)c1cc3[nH]c(=O)c4cnc(C5CCOCC5)n4c3cc1C)CC2] |
TABLE 47
| Ex | Structure |
|---|---|
| 66 | 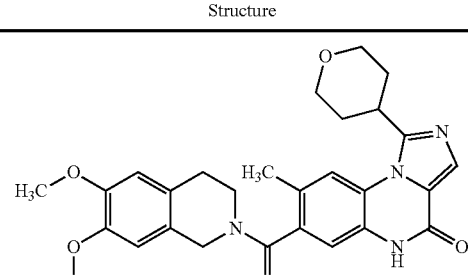 |
| 67 | 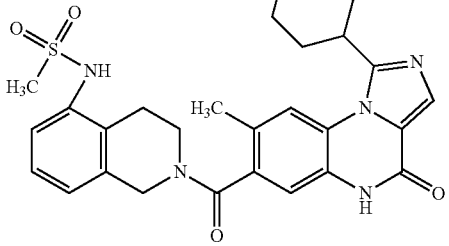 |

TABLE 47-continued

| Ex | Structure |
|---|---|
| 68 | (structure with HCl) |
| 69 | (structure) |
| 70 | (structure) |

TABLE 48

| Ex | Structure |
|---|---|
| 71 | (structure) |
| 72 | (structure) |
| 73 | (structure) |
| 74 | (structure) |
| 75 | (structure with HCl) |
| 76 | (structure with HCl) |

TABLE 49

| Ex | Structure |
|---|---|
| 77 | (structure) HCl |
| 78 | (structure) HCl |
| 79 | (structure) HCl |
| 80 | (structure) HCl |
| 81 | (structure) |

TABLE 50

| Ex | Structure |
|---|---|
| 82 | (structure) |
| 83 | (structure) |
| 84 | (structure) |
| 85 | (structure) |
| 86 | (structure) |

TABLE 51

| Ex | Structure |
|---|---|
| 87 | (structure) |
| 88 | (structure) |
| 89 | (structure) HCl |
| 90 | (structure) |
| 91 | (structure) |

TABLE 51-continued

| Ex | Structure |
|---|---|
| 92 | (structure) |

TABLE 52

| Ex | Structure |
|---|---|
| 93 | (structure) |
| 94 | (structure) |
| 95 | (structure) |
| 96 | (structure) |

TABLE 52-continued
| Ex | Structure |
|---|---|
| 97 | 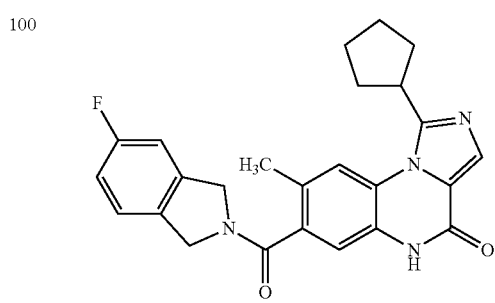 |
| 98 | 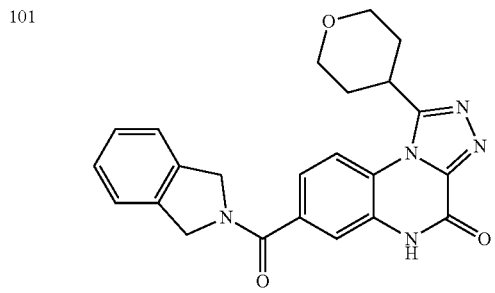 |
TABLE 53
| Ex | Structure |
|---|---|
| 99 | 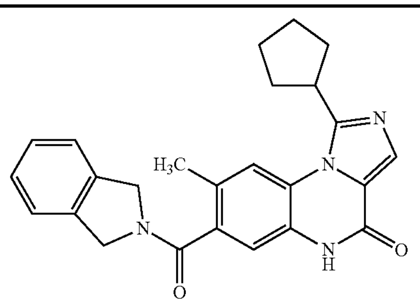 |
| 100 | 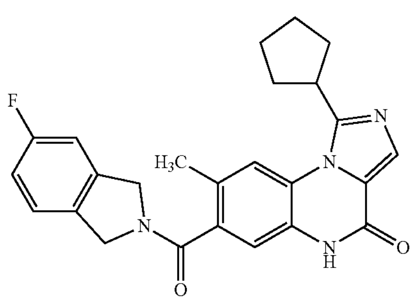 [SMILES: Cc1cc2c(cc1C(=O)N1Cc3ccccc3C1)[nH]c(=O)c1cnc(C3CCCC3)n12] |
| 101 | 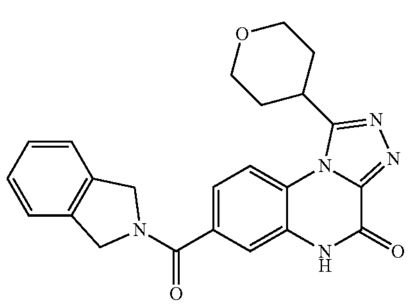 [SMILES: O=C(c1ccc2c(c1)[nH]c(=O)c1nnc(C3CCOCC3)n12)N1Cc2ccccc2C1] |
TABLE 53-continued
| Ex | Structure |
|---|---|
| 102 | 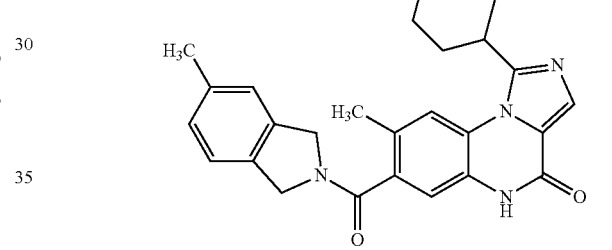 |
| 103 | 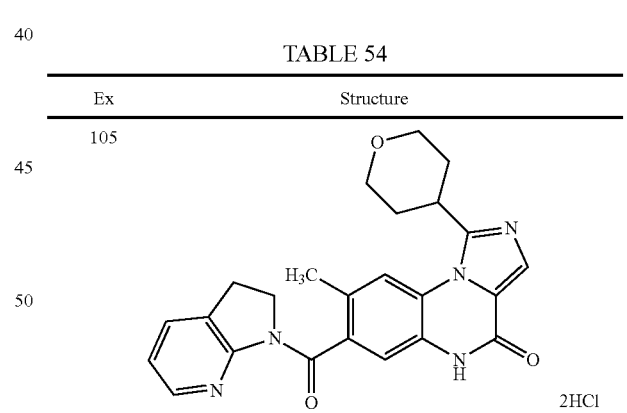 |
| 104 | 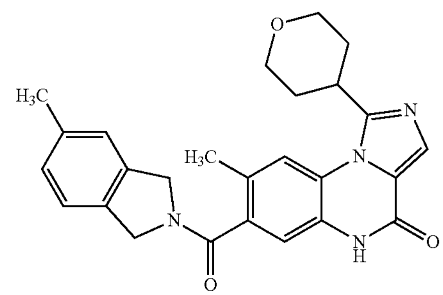 [SMILES: Cc1ccc2c(c1)CN(C(=O)c1cc3[nH]c(=O)c4cnc(C5CCOCC5)n4c3cc1C)C2] |
TABLE 54
| Ex | Structure |
|---|---|
| 105 | 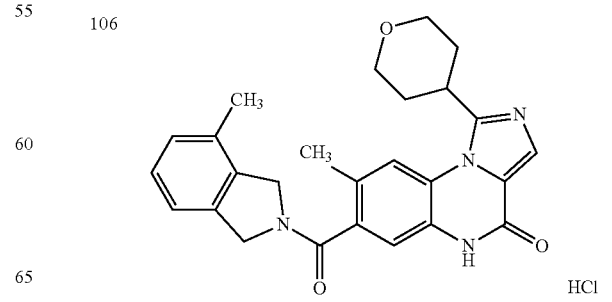 |
| 106 | 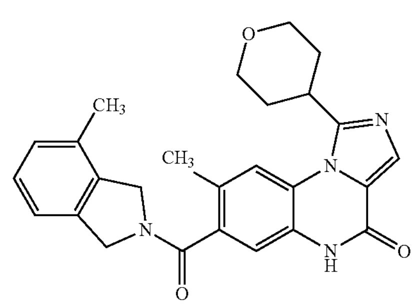 |

TABLE 54-continued
| Ex | Structure |
|---|---|
| 107 | 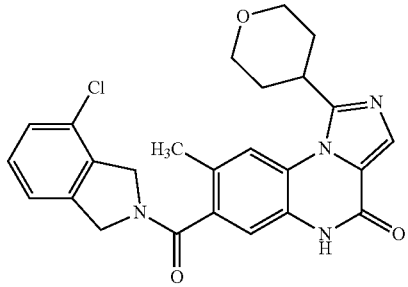 HCl |
| 108 | 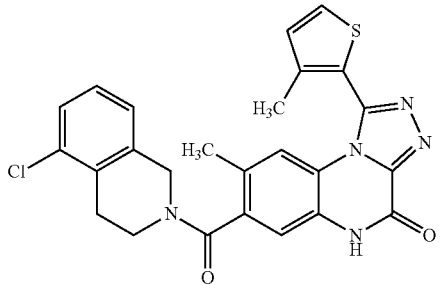 [SMILES: Cc1cc2c(cc1C(=O)N1CCc3c(Cl)cccc3C1)[nH]c(=O)c1nnc(-c3sccc3C)n12] |
| 109 | 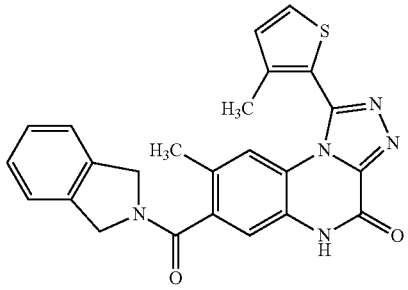 [SMILES: Cc1cc2c(cc1C(=O)N1Cc3ccccc3C1)[nH]c(=O)c1nnc(-c3sccc3C)n12] |
| 110 | 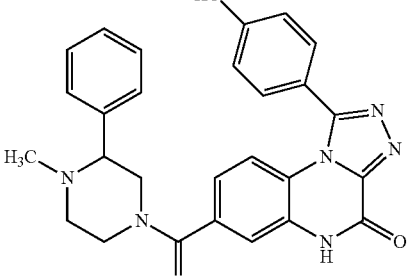 |
TABLE 55
| Ex | Structure |
|---|---|
| 111 | 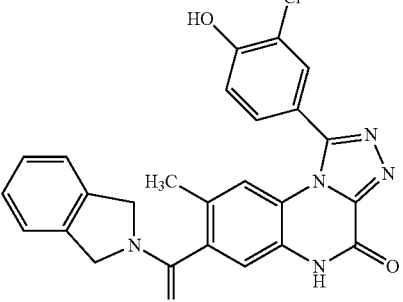 |
| 112 | 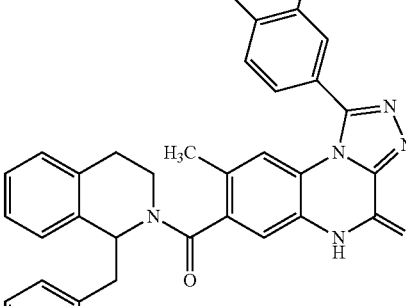 |
| 113 | 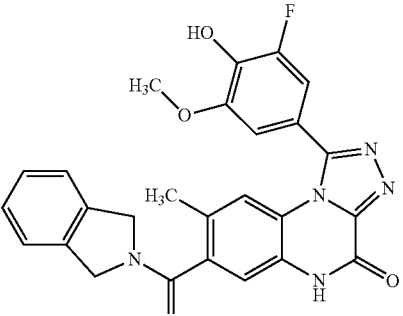 |
| 114 | 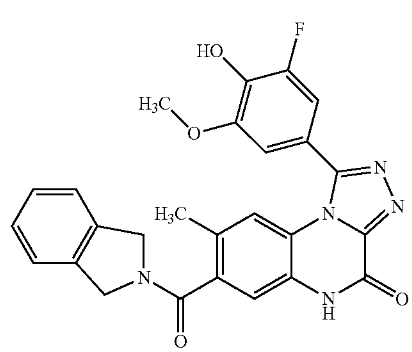 [SMILES: COc1cc(-c2nnc3c(=O)[nH]c4cc(C(=O)N5Cc6ccccc6C5)c(C)cc4n23)cc(F)c1O] |

TABLE 55-continued

| Ex | Structure |
|---|---|
| 115 | (structure) |

TABLE 56

| Ex | Structure |
|---|---|
| 116 | (structure) |
| 117 | (structure) |

TABLE 56-continued

| Ex | Structure |
|---|---|
| 118 | (structure) |
| 119 | (structure) |
| 120 | (structure) |

TABLE 57

| Ex | Structure |
|---|---|
| 121 | (structure) |

TABLE 57-continued

| Ex | Structure |
|---|---|
| 122 | 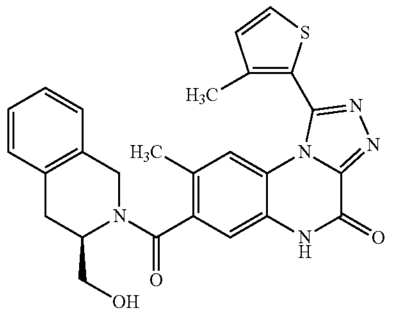 [SMILES: Cc1cc2c(cc1C(=O)N1Cc3ccccc3C[C@@H]1CO)[nH]c(=O)c1nnc(-c3sccc3C)n12] |
| 123 | 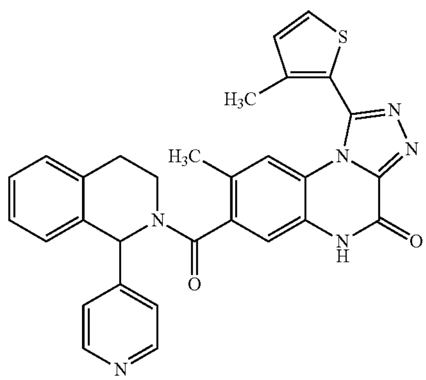 [SMILES: Cc1cc2c(cc1C(=O)N1CCc3ccccc3C1c1ccncc1)[nH]c(=O)c1nnc(-c3sccc3C)n12] |
| 124 | 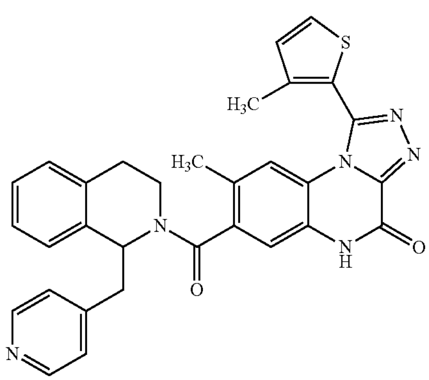 [SMILES: Cc1cc2c(cc1C(=O)N1CCc3ccccc3C1Cc1ccncc1)[nH]c(=O)c1nnc(-c3sccc3C)n12] |
| 125 | 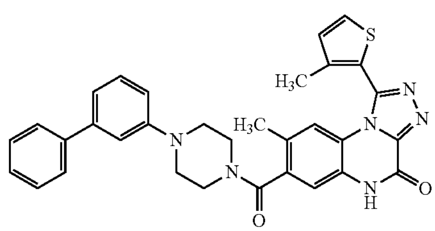 [SMILES: Cc1cc2c(cc1C(=O)N1CCN(c3cccc(-c4ccccc4)c3)CC1)[nH]c(=O)c1nnc(-c3sccc3C)n12] |

TABLE 58

| Ex | Structure |
|---|---|
| 126 | 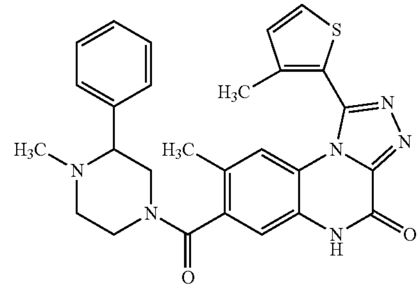 [SMILES: Cc1cc2c(cc1C(=O)N1CCN(C)C(c3ccccc3)C1)[nH]c(=O)c1nnc(-c3sccc3C)n12] |
| 127 | 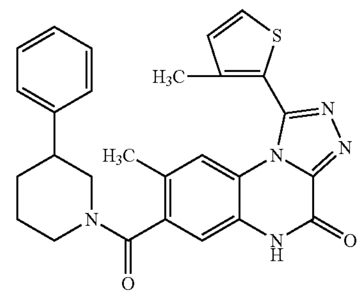 [SMILES: Cc1cc2c(cc1C(=O)N1CCCC(c3ccccc3)C1)[nH]c(=O)c1nnc(-c3sccc3C)n12] |
| 128 | 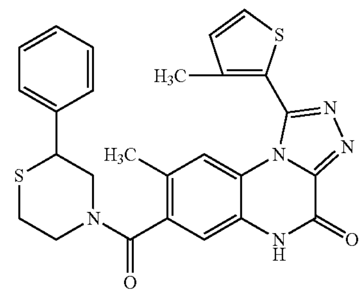 [SMILES: Cc1cc2c(cc1C(=O)N1CCSC(c3ccccc3)C1)[nH]c(=O)c1nnc(-c3sccc3C)n12] |
| 129 | 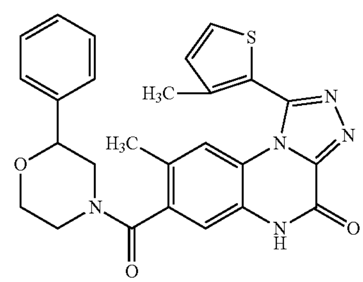 [SMILES: Cc1cc2c(cc1C(=O)N1CCOC(c3ccccc3)C1)[nH]c(=O)c1nnc(-c3sccc3C)n12] |
| 130 | 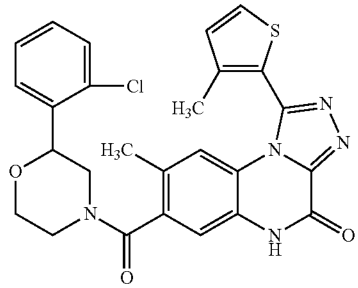 [SMILES: Cc1cc2c(cc1C(=O)N1CCOC(c3ccccc3Cl)C1)[nH]c(=O)c1nnc(-c3sccc3C)n12] |

TABLE 58-continued

| Ex | Structure |
|---|---|
| 131 | (structure) |

TABLE 59

| Ex | Structure |
|---|---|
| 132 | (structure) |
| 133 | (structure) |
| 134 | (structure) |
| 135 | (structure) |

TABLE 59-continued

| Ex | Structure |
|---|---|
| 136 | (structure) |
| 137 | (structure) |

TABLE 60

| Ex | Structure |
|---|---|
| 138 | (structure) |
| 139 | (structure) |
| 140 | (structure) |
| 141 | (structure) |

TABLE 60-continued

| Ex | Structure |
|---|---|
| 142 | 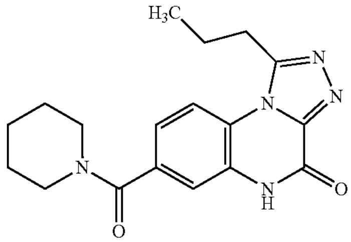 [SMILES: CCCc1nnc2c(=O)[nH]c3cc(C(=O)N4CCCCC4)ccc3n12] |
| 143 | 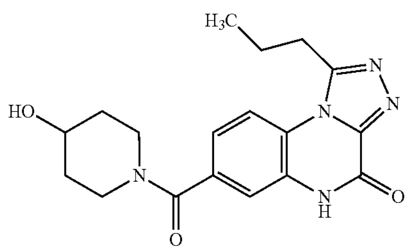 [SMILES: CCCc1nnc2c(=O)[nH]c3cc(C(=O)N4CCC(O)CC4)ccc3n12] |

TABLE 61

| Ex | Structure |
|---|---|
| 144 | 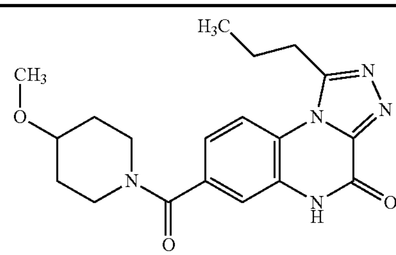 |
| 145 | 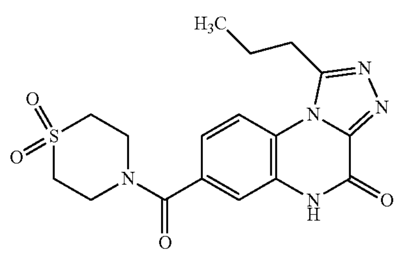 [SMILES: CCCc1nnc2c(=O)[nH]c3cc(C(=O)N4CCS(=O)(=O)CC4)ccc3n12] |
| 146 | 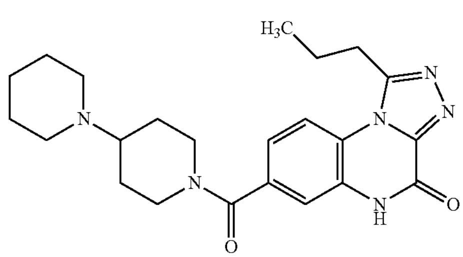 [SMILES: CCCc1nnc2c(=O)[nH]c3cc(C(=O)N4CCC(N5CCCCC5)CC4)ccc3n12] |

TABLE 61-continued

| Ex | Structure |
|---|---|
| 147 | 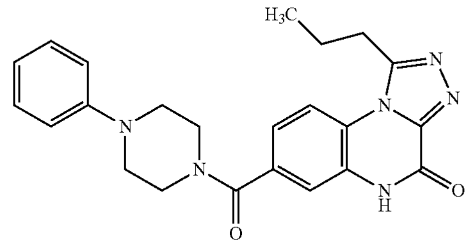 [SMILES: CCCc1nnc2c(=O)[nH]c3cc(C(=O)N4CCN(c5ccccc5)CC4)ccc3n12] |
| 148 | 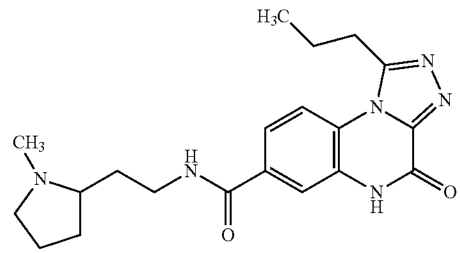 [SMILES: CCCc1nnc2c(=O)[nH]c3cc(C(=O)NCCC4CCCN4C)ccc3n12] |
| 149 | 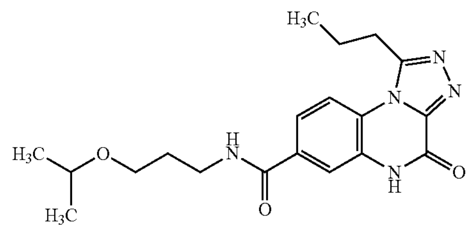 [SMILES: CCCc1nnc2c(=O)[nH]c3cc(C(=O)NCCCOC(C)C)ccc3n12] |

TABLE 62

| Ex | Structure |
|---|---|
| 150 | 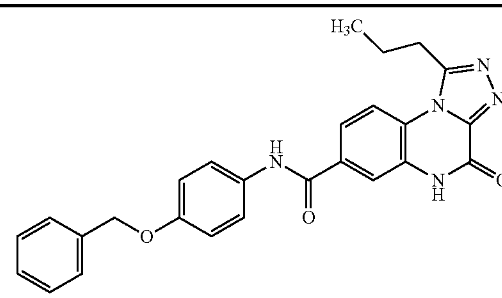 |
| 151 | 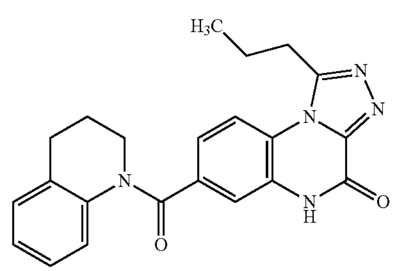 [SMILES: CCCc1nnc2c(=O)[nH]c3cc(C(=O)N4CCCc5ccccc54)ccc3n12] |

TABLE 62-continued
| Ex | Structure |
|---|---|
| 152 | 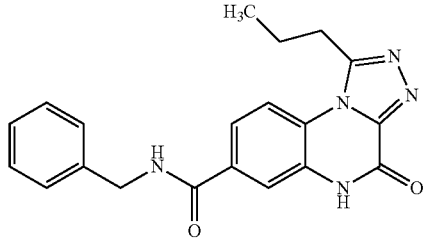 [SMILES: CCCc1nnc2c(=O)[nH]c3cc(C(=O)NCc4ccccc4)ccc3n12] |
| 153 | 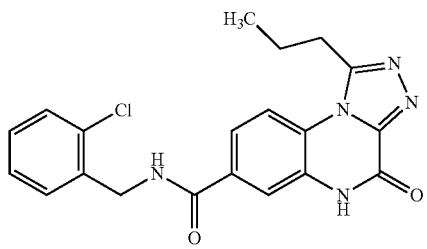 [SMILES: CCCc1nnc2c(=O)[nH]c3cc(C(=O)NCc4ccccc4Cl)ccc3n12] |
| 154 | 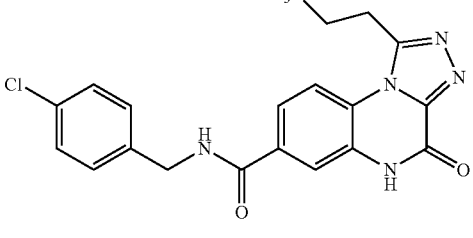 |
| 155 | 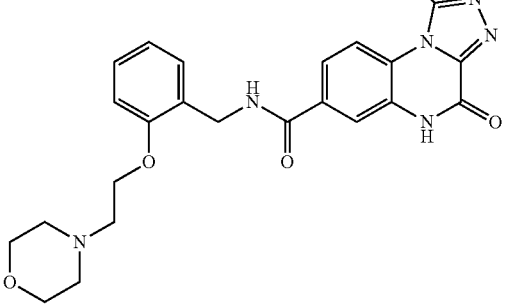 |
TABLE 63
| Ex | Structure |
|---|---|
| 156 | 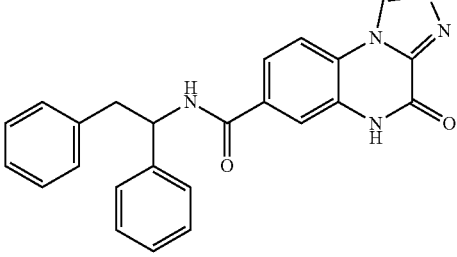 |
TABLE 63-continued
| Ex | Structure |
|---|---|
| 157 | 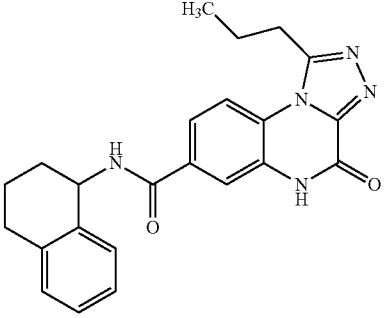 [SMILES: CCCc1nnc2c(=O)[nH]c3cc(C(=O)NC4CCCc5ccccc54)ccc3n12] |
| 158 | 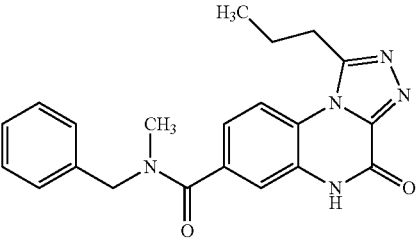 [SMILES: CCCc1nnc2c(=O)[nH]c3cc(C(=O)N(C)Cc4ccccc4)ccc3n12] |
| 159 | 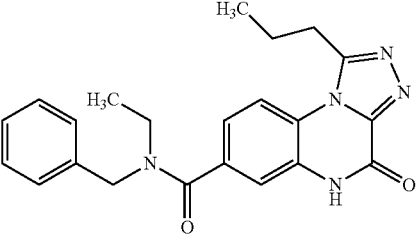 [SMILES: CCCc1nnc2c(=O)[nH]c3cc(C(=O)N(CC)Cc4ccccc4)ccc3n12] |
| 160 | 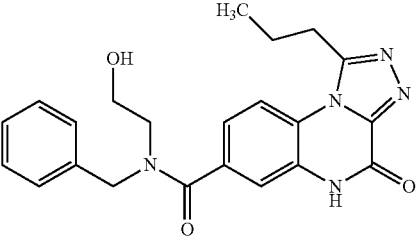 [SMILES: CCCc1nnc2c(=O)[nH]c3cc(C(=O)N(CCO)Cc4ccccc4)ccc3n12] |
| 161 | 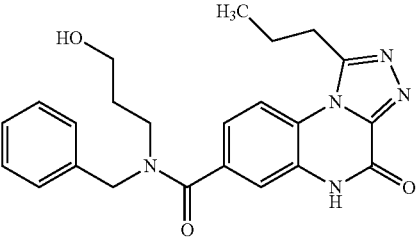 [SMILES: CCCc1nnc2c(=O)[nH]c3cc(C(=O)N(CCCO)Cc4ccccc4)ccc3n12] |

TABLE 64

| Ex | Structure |
|---|---|
| 162 | (structure) |
| 163 | (structure) |
| 164 | (structure) |
| 165 | (structure) |
| 166 | (structure) |
| 167 | (structure) |

TABLE 65

| Ex | Structure |
|---|---|
| 168 | (structure) |
| 169 | (structure) |
| 170 | (structure) |
| 171 | (structure) |
| 172 | (structure) |
| 173 | (structure) |

TABLE 66

| Ex | Structure |
|---|---|
| 174 | (structure) |
| 175 | (structure) |
| 176 | (structure) |
| 177 | (structure) |
| 178 | (structure) |

TABLE 66-continued

| Ex | Structure |
|---|---|
| 179 | (structure) |

TABLE 67

| Ex | Structure |
|---|---|
| 180 | (structure) |
| 181 | (structure) |
| 182 | (structure) |
| 183 | (structure) |

TABLE 67-continued

| Ex | Structure |
|---|---|
| 184 | 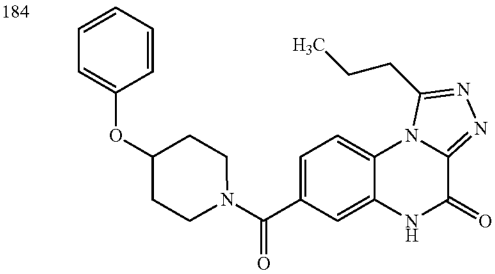 |
| 185 | 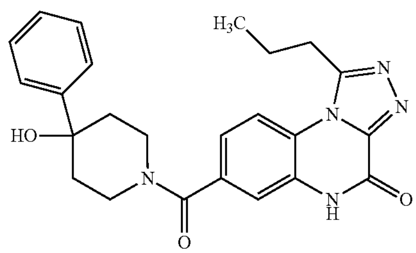 [SMILES: CCCc1nnc2c(=O)[nH]c3cc(C(=O)N4CCC(O)(c5ccccc5)CC4)ccc3n12] |

TABLE 68

| Ex | Structure |
|---|---|
| 186 | 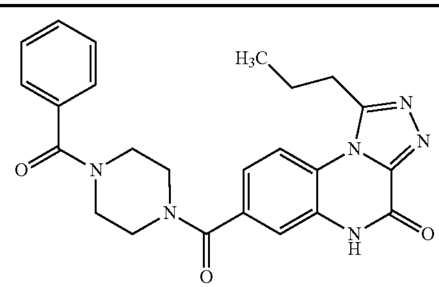 |
| 187 | 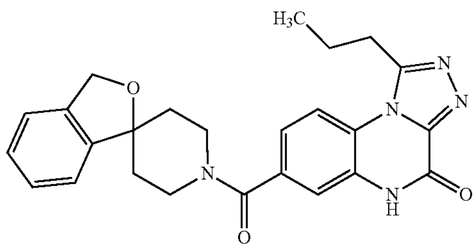 [SMILES: CCCc1nnc2c(=O)[nH]c3cc(C(=O)N4CCC5(CC4)OCc4ccccc45)ccc3n12] |
| 188 | 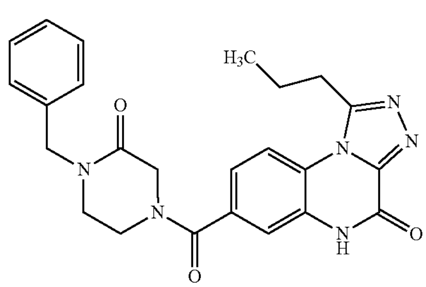 [SMILES: CCCc1nnc2c(=O)[nH]c3cc(C(=O)N4CCN(Cc5ccccc5)C(=O)C4)ccc3n12] |

TABLE 68-continued

| Ex | Structure |
|---|---|
| 189 | 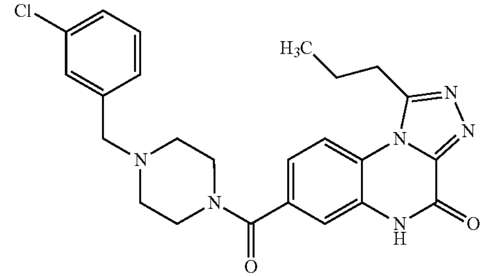 [SMILES: CCCc1nnc2c(=O)[nH]c3cc(C(=O)N4CCN(Cc5cccc(Cl)c5)CC4)ccc3n12] |
| 190 | 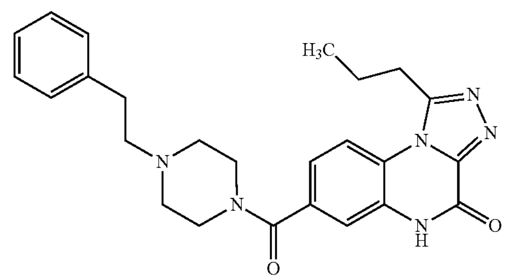 [SMILES: CCCc1nnc2c(=O)[nH]c3cc(C(=O)N4CCN(CCc5ccccc5)CC4)ccc3n12] |
| 191 | 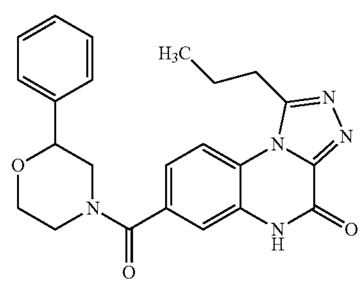 [SMILES: CCCc1nnc2c(=O)[nH]c3cc(C(=O)N4CCOC(c5ccccc5)C4)ccc3n12] |

TABLE 69

| Ex | Structure |
|---|---|
| 192 | 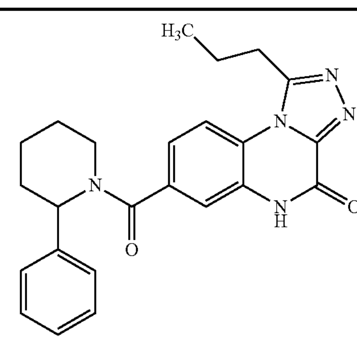 |

TABLE 69-continued

| Ex | Structure |
|---|---|
| 193 | 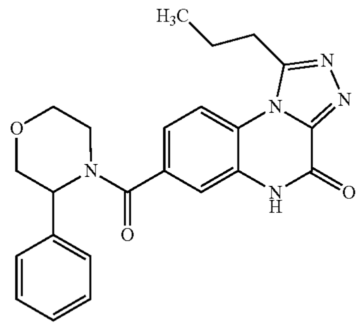 [SMILES: CCCc1nnc2c(=O)[nH]c3cc(C(=O)N4CCOCC4c4ccccc4)ccc3n12] |
| 194 | 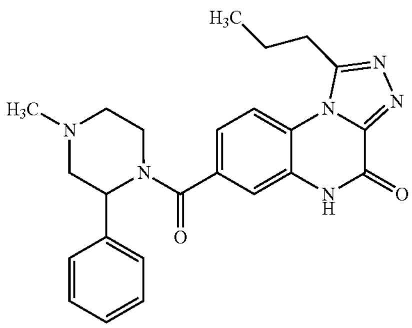 [SMILES: CCCc1nnc2c(=O)[nH]c3cc(C(=O)N4CCN(C)CC4c4ccccc4)ccc3n12] |
| 195 | 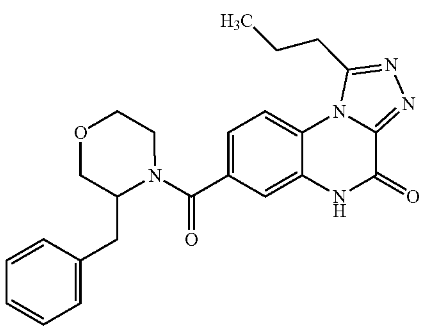 [SMILES: CCCc1nnc2c(=O)[nH]c3cc(C(=O)N4CCOCC4Cc4ccccc4)ccc3n12] |
| 196 | 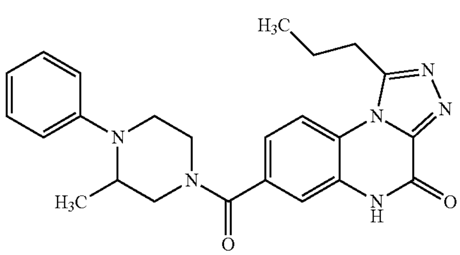 [SMILES: CCCc1nnc2c(=O)[nH]c3cc(C(=O)N4CCN(c5ccccc5)C(C)C4)ccc3n12] |
| 197 | 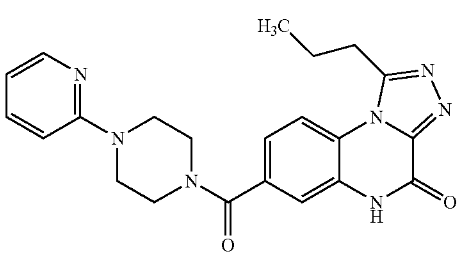 [SMILES: CCCc1nnc2c(=O)[nH]c3cc(C(=O)N4CCN(c5ccccn5)CC4)ccc3n12] |

TABLE 70

| Ex | Structure |
|---|---|
| 198 | 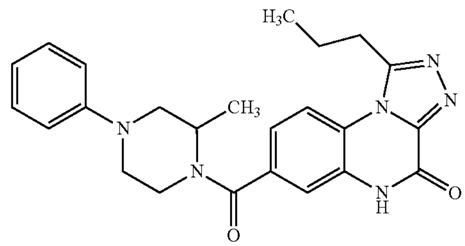 [SMILES: CCCc1nnc2c(=O)[nH]c3cc(C(=O)N4CCN(c5ccccc5)CC4C)ccc3n12] |
| 199 | 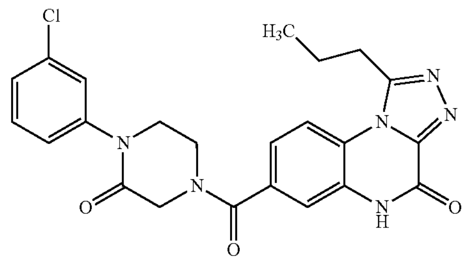 [SMILES: CCCc1nnc2c(=O)[nH]c3cc(C(=O)N4CCN(c5cccc(Cl)c5)C(=O)C4)ccc3n12] |
| 200 | 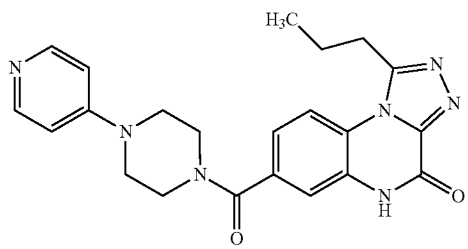 [SMILES: CCCc1nnc2c(=O)[nH]c3cc(C(=O)N4CCN(c5ccncc5)CC4)ccc3n12] |
| 201 | 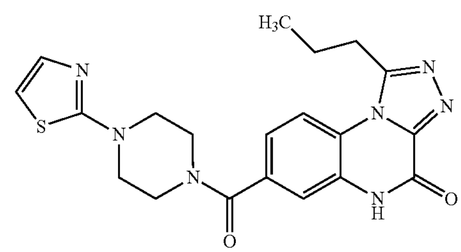 [SMILES: CCCc1nnc2c(=O)[nH]c3cc(C(=O)N4CCN(c5nccs5)CC4)ccc3n12] |
| 202 | 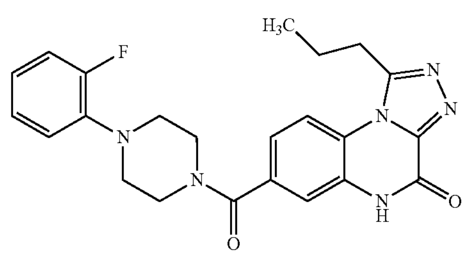 [SMILES: CCCc1nnc2c(=O)[nH]c3cc(C(=O)N4CCN(c5ccccc5F)CC4)ccc3n12] |
| 203 | 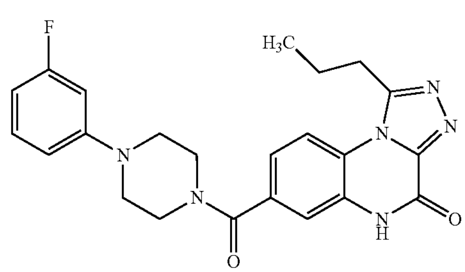 [SMILES: CCCc1nnc2c(=O)[nH]c3cc(C(=O)N4CCN(c5cccc(F)c5)CC4)ccc3n12] |

TABLE 70-continued

| Ex | Structure |
|---|---|
| 204 | (4-fluorophenyl-piperazinyl-carbonyl triazoloquinoxalinone with propyl) |

TABLE 71

| Ex | Structure |
|---|---|
| 205 | (2-methoxyphenyl-piperazinyl-carbonyl triazoloquinoxalinone with propyl) |
| 206 | (3-methoxyphenyl-piperazinyl-carbonyl triazoloquinoxalinone with propyl) |
| 207 | (4-chlorophenyl-piperazinyl-carbonyl triazoloquinoxalinone with propyl) |
| 208 | (3,4-dichlorophenyl-piperazinyl-carbonyl triazoloquinoxalinone with propyl) |
| 209 | (3-biphenyl-piperazinyl-carbonyl triazoloquinoxalinone with propyl) |

TABLE 71-continued

| Ex | Structure |
|---|---|
| 210 | (2-phenylpyrrolidinyl-carbonyl triazoloquinoxalinone with propyl) |

TABLE 72

| Ex | Structure |
|---|---|
| 211 | (3-phenylpyrrolidinyl-carbonyl triazoloquinoxalinone with propyl) |
| 212 | (4-benzyl-1,4-diazepan-1-yl-carbonyl triazoloquinoxalinone with propyl) |
| 213 | (4,7-difluoroisoindolinyl-carbonyl imidazoquinoxalinone with tetrahydropyranyl and methyl) HCl |
| 214 | (4-cyanoisoindolinyl-carbonyl imidazoquinoxalinone with tetrahydropyranyl and methyl) HCl |

TABLE 72-continued

| Ex | Structure |
|---|---|
| 215 | (structure) HCl |
| 216 | (structure) HCl |

TABLE 73

| Ex | Structure |
|---|---|
| 217 | (structure) HCl |
| 218 | (structure) HCl |

TABLE 73-continued

| Ex | Structure |
|---|---|
| 219 | (structure) HCl |
| 220 | (structure) HCl |

TABLE 74

| Ex | Structure |
|---|---|
| 221 | (structure) HCl |
| 222 | (structure) HCl |

US 8,357,688 B2
153
TABLE 74-continued
| Ex | Structure |
|---|---|
| 223 | 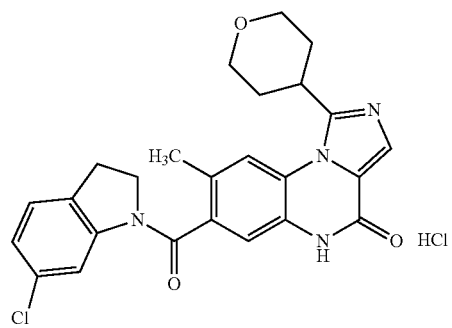 [SMILES: Cc1cc2c(cc1C(=O)N1CCc3ccc(Cl)cc31)[nH]c(=O)c1cnc(C3CCOCC3)n12 ; Cl] HCl |
| 224 | 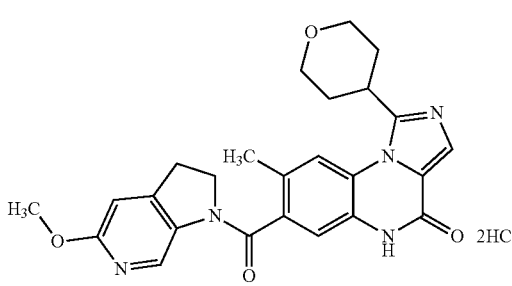 [SMILES: COc1cc2c(cn1)N(C(=O)c1cc3[nH]c(=O)c4cnc(C5CCOCC5)n4c3cc1C)CC2 ; "2HCl"] 2HCl |
| 225 | 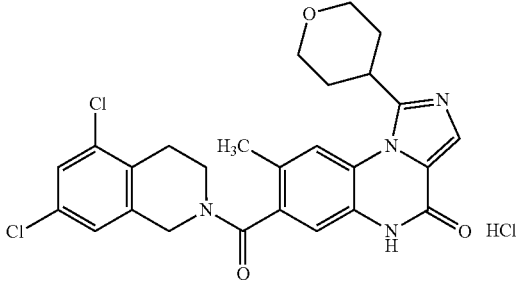 [SMILES: Cc1cc2c(cc1C(=O)N1CCc3c(Cl)cc(Cl)cc3C1)[nH]c(=O)c1cnc(C3CCOCC3)n12 ; Cl] HCl |
TABLE 75
| Ex | Structure |
|---|---|
| 226 | 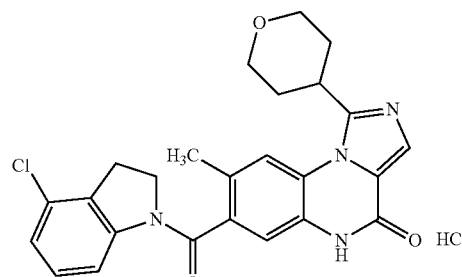 2HCl |
154
TABLE 75-continued
| Ex | Structure |
|---|---|
| 227 | 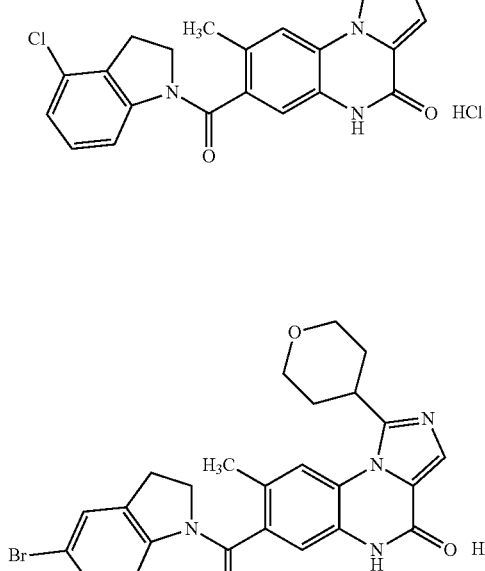 HCl |
| 228 | 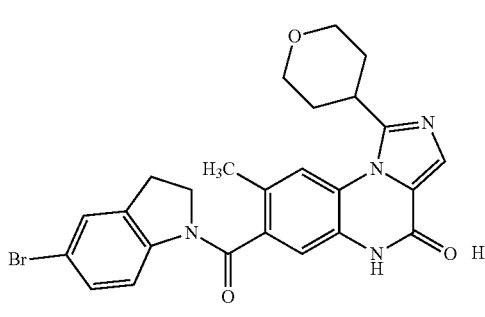 HCl |
| 229 | 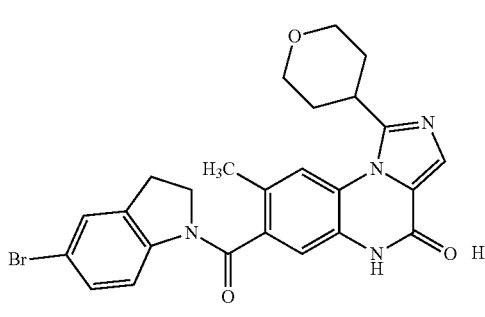 HCl |
| 230 | 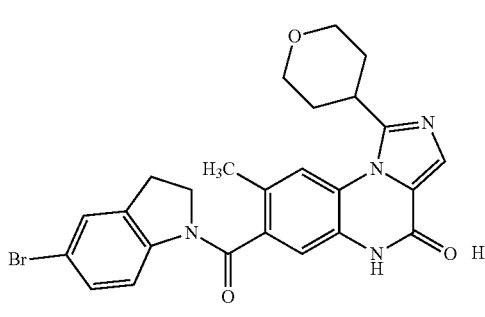 HCl |

TABLE 76

| Ex | Structure |
|---|---|
| 231 | (chloro-isoindoline / methyl / tetrahydropyran-imidazo-quinoxalinone) · HCl |
| 232 | (4,7-dimethyl-isoindoline / methyl / tetrahydropyran-imidazo-quinoxalinone) · HCl |
| 233 | (5-methyl-indoline / methyl / tetrahydropyran-imidazo-quinoxalinone) · HCl |
| 234 | (5-methyl-indoline / methyl / tetrahydrofuran-imidazo-quinoxalinone) · HCl |
| 235 | (5-chloro-isoindoline / methyl / tetrahydrofuran-imidazo-quinoxalinone) · HCl |

TABLE 77

| Ex | Structure |
|---|---|
| 236 | (4-methyl-isoindoline / methyl / tetrahydrofuran-imidazo-quinoxalinone) · HCl |
| 237 | (5-fluoro-indoline / methyl / tetrahydrofuran-imidazo-quinoxalinone) · HCl |
| 238 | (5-methyl-pyrrolopyridine / methyl / tetrahydropyran-imidazo-quinoxalinone) · 2HCl |
| 239 | (5-bromo-pyrrolopyridine / methyl / tetrahydropyran-imidazo-quinoxalinone) · 2HCl |
| 240 | (5-chloro-indoline / methyl / cyclopentyl-triazolo-quinoxalinone) · HCl |

TABLE 78

| Ex | Structure |
|---|---|
| 241 | (structure) HCl |
| 242 | (structure) HCl |
| 243 | (structure) HCl |
| 244 | (structure) HCl |
| 245 | (structure) |

TABLE 79

| Ex | Structure |
|---|---|
| 246 | (structure) 2HCl |
| 247 | (structure) HCl |
| 248 | (structure) HCl |
| 249 | (structure) HCl |
| 250 | (structure) HCl |

TABLE 80
| Ex | Structure |
|---|---|
| 251 | 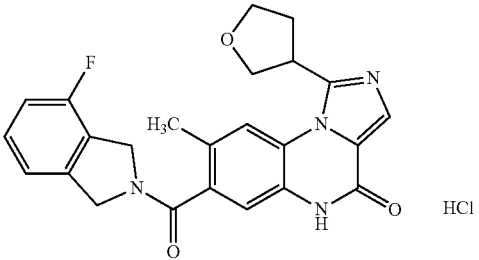 [SMILES: Cc1cc2c(cc1C(=O)N1Cc3cccc(F)c3C1)[nH]c(=O)c1cnc(C3CCOC3)n12 ; Cl] HCl |
| 252 | 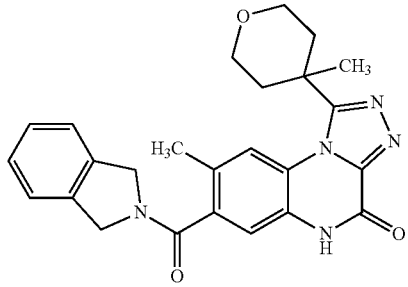 [SMILES: Cc1cc2c(cc1C(=O)N1Cc3ccccc3C1)[nH]c(=O)c1nnc(C3(C)CCOCC3)n12] |
| 253 | 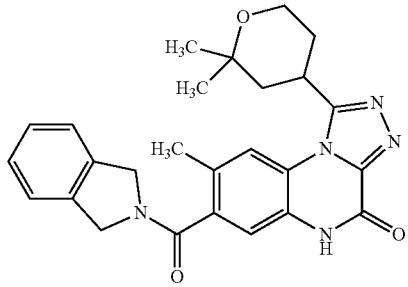 [SMILES: Cc1cc2c(cc1C(=O)N1Cc3ccccc3C1)[nH]c(=O)c1nnc(C3CCOC(C)(C)C3)n12] |
| 254 | 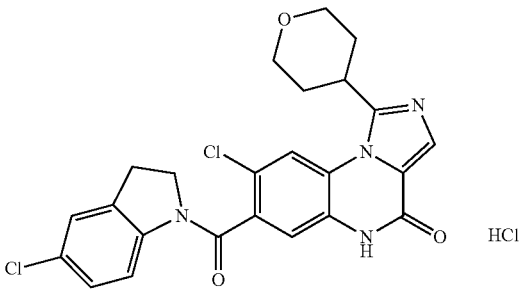 [SMILES: O=C(c1cc2[nH]c(=O)c3cnc(C4CCOCC4)n3c2cc1Cl)N1CCc2cc(Cl)ccc21 ; Cl] HCl |
| 255 | 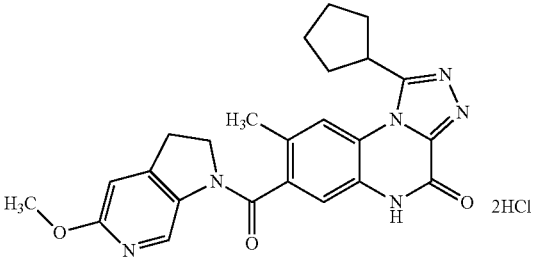 [SMILES: COc1cc2c(cn1)N(C(=O)c1cc3[nH]c(=O)c4nnc(C5CCCC5)n4c3cc1C)CC2 ; "2HCl"] 2HCl |
TABLE 81
| Ex | Structure |
|---|---|
| 256 | 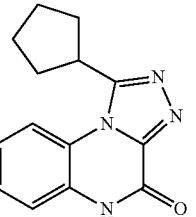 2HCl |
| 257 (a) (−)− | 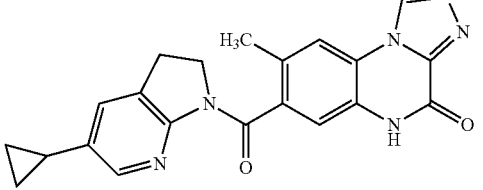 HCl |
| 257 (b) (+)− | 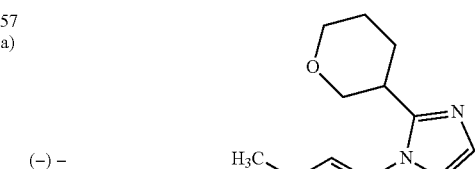 HCl |
| 258 (a) (−)− | 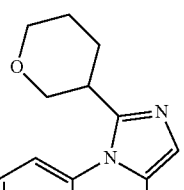 HCl |
| 258 (b) (+)− | 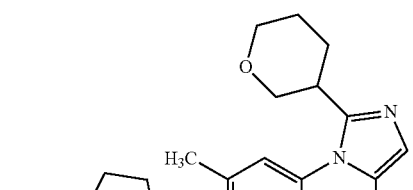 HCl |

TABLE 81-continued
| Ex | Structure |
|---|---|
| 259 (a) | 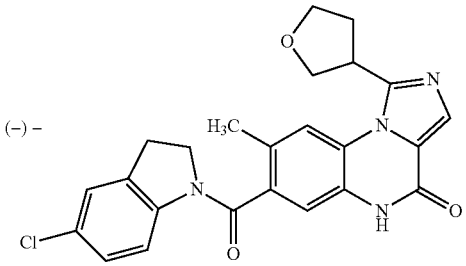 HCl |
TABLE 82
| Ex | Structure |
|---|---|
| 259 (b) | 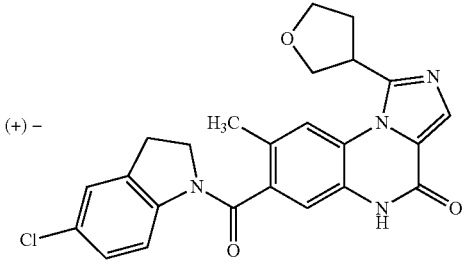 HCl |
| 260 | 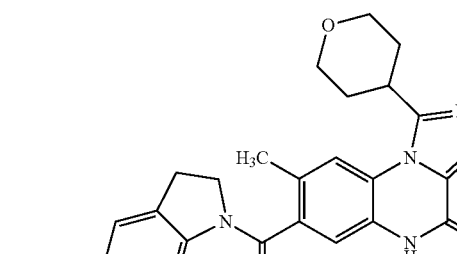 HCl |
| 261 | 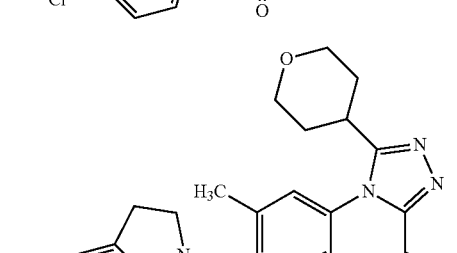 HCl |
| 262 | 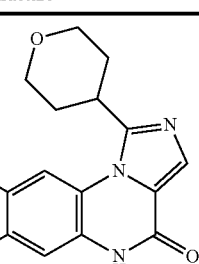 2HCl |
TABLE 82-continued
| Ex | Structure |
|---|---|
| 263 | 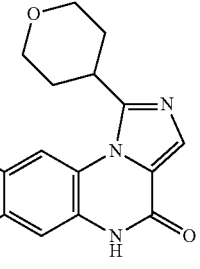 HCl |
TABLE 83
| Ex | Structure |
|---|---|
| 264 | 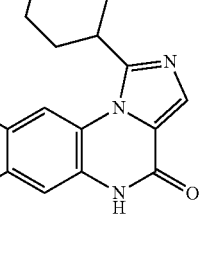 HCl |
| 265 | 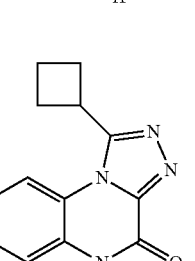 HCl |
| 266 | 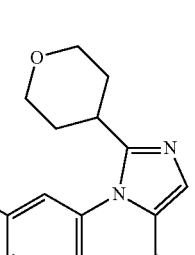 HCl |
| 267 | 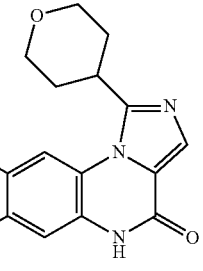 HCl |

TABLE 83-continued

| Ex | Structure |
|---|---|
| 268 | (structure) HCl |

TABLE 84

| Ex | Structure |
|---|---|
| 269 | (structure) HCl |
| 270 | (structure) |
| 271 | (structure) |
| 272 | (structure) |
| 273 | (structure) HCl |

TABLE 85

| Ex | Structure |
|---|---|
| 274 | (structure) |
| 275 | (structure) HCl |

TABLE 85-continued

| Ex | Structure |
|---|---|
| 276 | (structure; 2HCl) |
| 277 | (structure; 2HCl) |
| 278 | (structure; HCl) |

TABLE 86

| Ex | Structure |
|---|---|
| 279 | (structure; 2HCl) |
| 280 | (structure; HCl) |

TABLE 86-continued

| Ex | Structure |
|---|---|
| 281 | (structure; HCl) |
| 282 | (structure; HCl) |
| 283 | (structure; HCl) |

TABLE 87

| Ex | Structure |
|---|---|
| 284 | (structure; HCl) |

TABLE 87-continued

| Ex | Structure |
|---|---|
| 285 | (structure) 2HCl |
| 286 | (structure) 2HCl |
| 287 | (structure) HCl |
| 288 | (structure) HCl |

TABLE 88

| Ex | Structure |
|---|---|
| 289 | (structure) HCl |
| 290 | (structure) HCl |
| 291 | (structure) HCl |
| 292 | (structure) HCl |

TABLE 88-continued

| Ex | Structure |
|---|---|
| 293 | (structure) HCl |

TABLE 89

| Ex | Structure |
|---|---|
| 294 | (structure) 2HCl |
| 295 | (structure) HCl |
| 296 | (structure) |
| 297 | (structure) HCl |

TABLE 89-continued

| Ex | Structure |
|---|---|
| 298 | (structure) |

TABLE 90

| Ex | Structure |
|---|---|
| 299 | (structure) 2HCl |
| 300 | (structure) HCl |
| 301 | (structure) HCl |
| 302 | (structure) HCl |

TABLE 90-continued

| Ex | Structure |
|---|---|
| 303 | (structure) HCl |

TABLE 91

| Ex | Structure |
|---|---|
| 304 | (structure) HCl |
| 305 | (structure) |
| 306 | (structure) 2HCl |

TABLE 91-continued

| Ex | Structure |
|---|---|
| 307 | (structure) 2HCl |
| 308 | (structure) 2HCl |

TABLE 92

| Ex | Structure |
|---|---|
| 309 | (structure) 2HCl |
| 310 | (structure) HCl |

TABLE 92-continued

| Ex | Structure |
|---|---|
| 311 | (structure with 4,4-difluorocyclohexyl, triazoloquinoxalinone, bromopyridine-fused pyrrolidine carbonyl) 2HCl |
| 312 | (structure with tetrahydrofuran-3-yl, triazoloquinoxalinone, bromopyridine-fused pyrrolidine carbonyl) HCl |
| 313 | (structure with tetrahydropyran-4-yl, triazoloquinoxalinone, bromopyridine-fused pyrrolidine carbonyl) 2HCl |

TABLE 93

| Ex | Structure |
|---|---|
| 314 | (structure with tetrahydropyran-4-yl, triazoloquinoxalinone, cyclopropylpyridine-fused pyrrolidine carbonyl) 2HCl |
| 315 | (structure with cyclobutyl, triazoloquinoxalinone, chloroindoline carbonyl) HCl |

TABLE 93-continued

| Ex | Structure |
|---|---|
| 316 | (structure with cyclobutyl, triazoloquinoxalinone, fluoroindoline carbonyl) HCl |
| 317 | (structure with tetrahydrothiopyran-4-ylmethyl, triazoloquinoxalinone, indane-2-yl carbonyl) HCl |
| 318 | (structure with tetrahydropyran-4-yl, imidazoquinoxalinone, fluoroindoline carbonyl) HCl |
| 319 | (structure with tetrahydrofuran-3-yl, triazoloquinoxalinone, pyrrolopyridine carbonyl) HCl |

TABLE 94

| Ex | Structure |
|---|---|
| 320 | (structure with tetrahydropyran-4-yl, methoxymethyl-substituted imidazoquinoxalinone, bromopyrrolopyridine carbonyl) HCl |

TABLE 94-continued

| Ex | Structure |
|---|---|
| 321 | (structure) HCl |
| 322 | (structure) HCl |
| 323 | (structure) |
| 324 | (structure) |

TABLE 95

| Ex | Structure |
|---|---|
| 325 | (structure) |
| 326 | (structure) HCl |
| 327 | (structure) HCl |
| 328 | (structure) |
| 329 | (structure) HCl |

TABLE 96
| Ex | Structure |
|---|---|
| 330 | 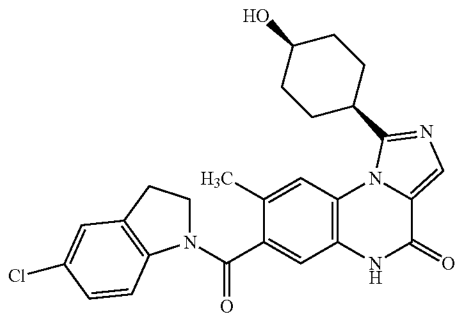 |
| 331 | 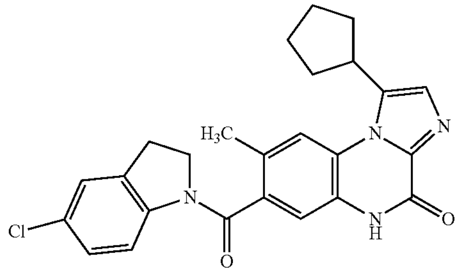 |
| 332 | 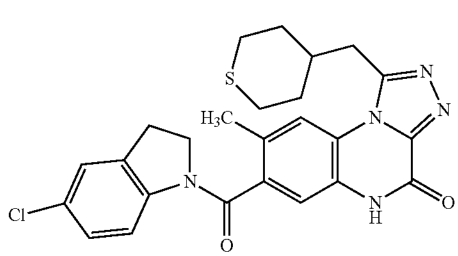 |
| 333 | 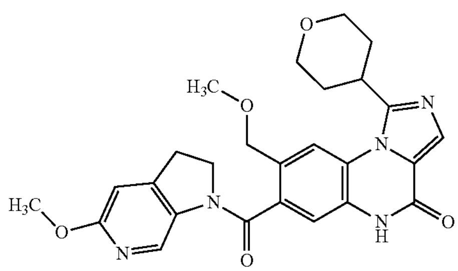 |
| 334 | 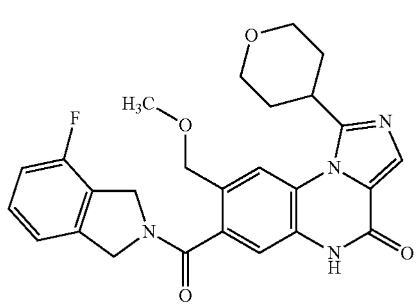 |
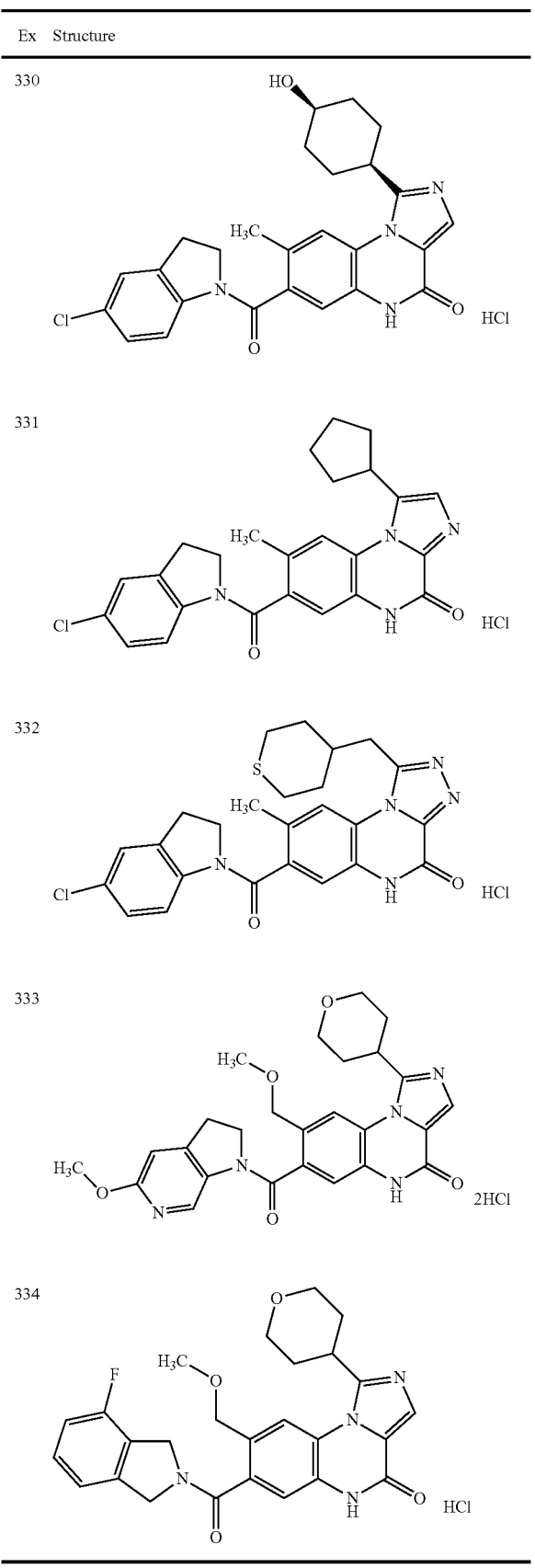
TABLE 97
| Ex | Structure |
|---|---|
| 335 | 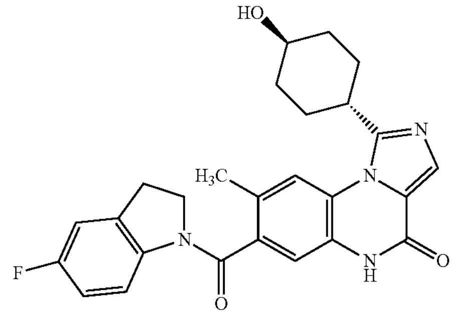 |
| 336 | 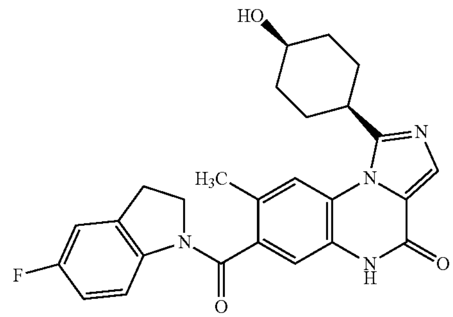 |
| 337 | 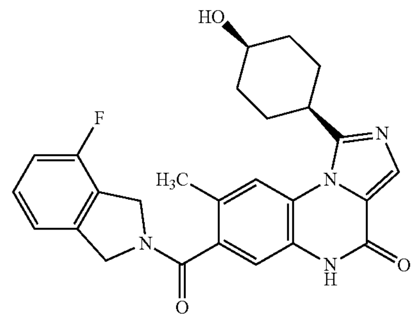 |
| 338 | 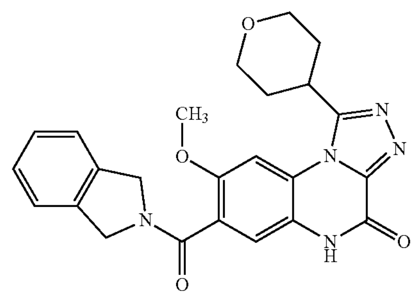 [SMILES: O=C(c1cc2[nH]c(=O)c3nnc(C4CCOCC4)n3c2cc1Br)N1Cc2ccccc2C1] |
| 339 | 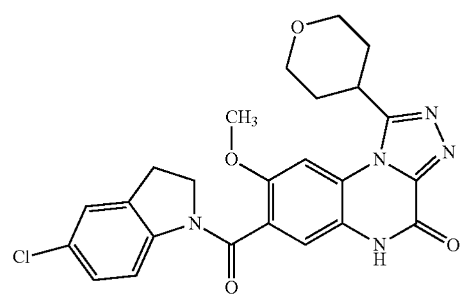 [SMILES: COCc1cc2c(cc1C(=O)N1CCc3cc(Cl)ccc31)[nH]c(=O)c1nnc(C3CCOCC3)n12] |
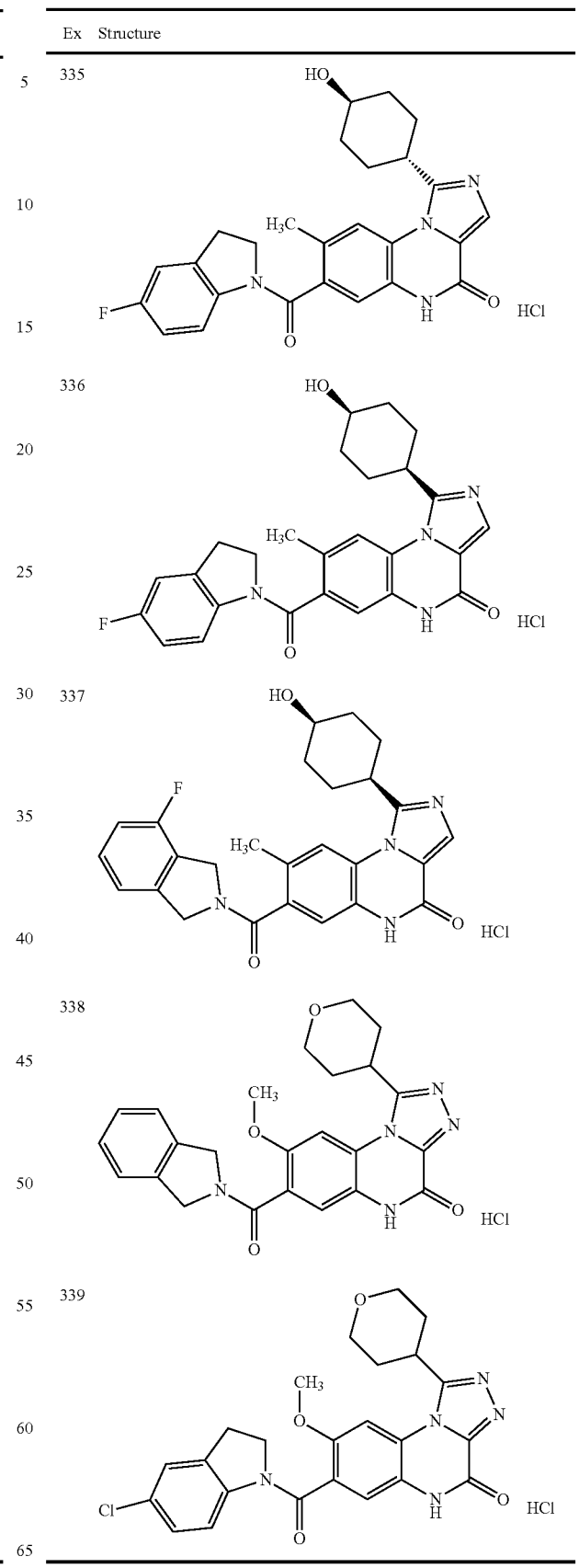

TABLE 98

| Ex | Structure |
|---|---|
| 340 | (structure) HCl |
| 341 | (structure) HCl |
| 342 | (structure) |
| 343 | (structure) Rac |
| 344 | (structure) HCl |

TABLE 99

| Ex | Structure |
|---|---|
| 345 | (structure) |
| 346 | (structure) 2HCl |
| 347 | (structure) |
| 348 | (structure) |
| 349 | (structure) |

TABLE 100
| Ex | Structure |
|---|---|
| 350 | 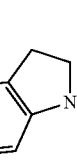 2HCl |
| 351 | HCl |
| 352 | HCl |
| 353 | 2HCl |
| 354 | 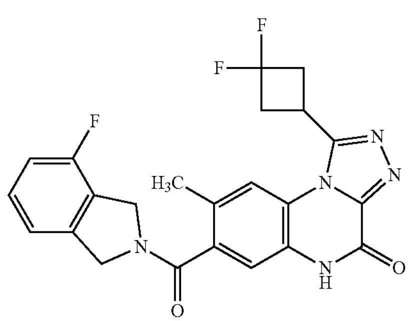 [SMILES: Cc1cc2c(cc1C(=O)N1Cc3cccc(F)c3C1)[nH]c(=O)c1nnc(C3CC(F)(F)C3)n12] |
TABLE 101
| Ex | Structure |
|---|---|
| 355 |  HCl |
| 356 | 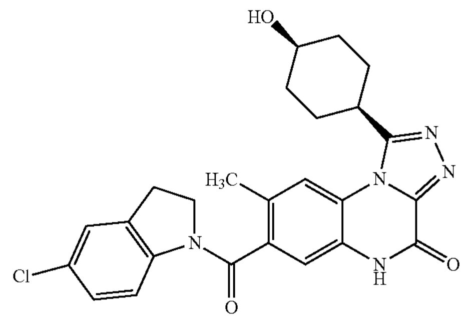 [SMILES: Cc1cc2c(cc1C(=O)N1CCc3cc(Cl)ccc31)[nH]c(=O)c1nnc([C@H]3CC[C@@H](O)CC3)n12] |
| 357 | 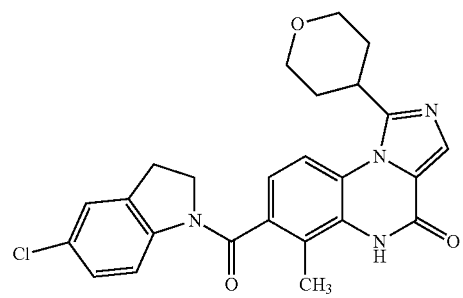 [SMILES: Cc1c(C(=O)N2CCc3cc(Cl)ccc32)ccc2c1[nH]c(=O)c1cnc(C3CCOCC3)n12] |
| 358 | 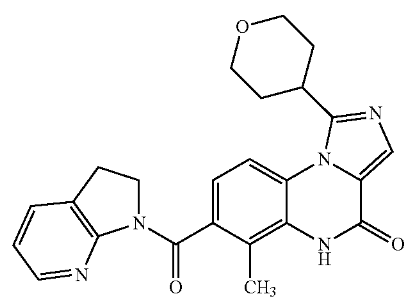 [SMILES: Cc1c(C(=O)N2CCc3cccnc32)ccc2c1[nH]c(=O)c1cnc(C3CCOCC3)n12] |
| 359 | 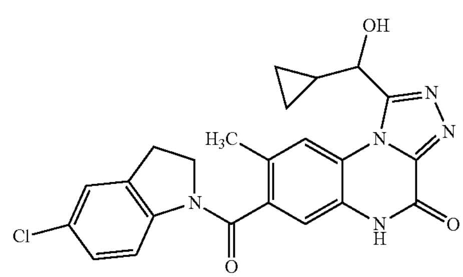 [SMILES: Cc1cc2c(cc1C(=O)N1CCc3cc(Cl)ccc31)[nH]c(=O)c1nnc(C(O)C3CC3)n12] |

TABLE 102

| Ex | Structure |
|---|---|
| 360 | (structure) |
| 361 | (structure) 2HCl |
| 362 | (structure) 2HCl |
| 363 | (structure) |
| 364 | (structure) HCl |

TABLE 103

| Ex | Structure |
|---|---|
| 365 | Rac (structure) |
| 366 | (structure) |
| 367 | (structure) |
| 368 | (structure) |
| 369 | (structure) |

TABLE 104

| Ex | Structure |
|---|---|
| 370 | 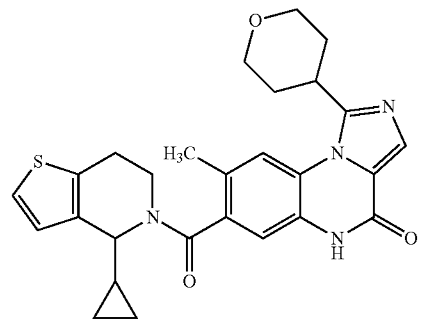 [SMILES: Cc1cc2c(cc1C(=O)N1CCc3sccc3C1C1CC1)[nH]c(=O)c1cnc(C3CCOCC3)n12] |
| 371 | 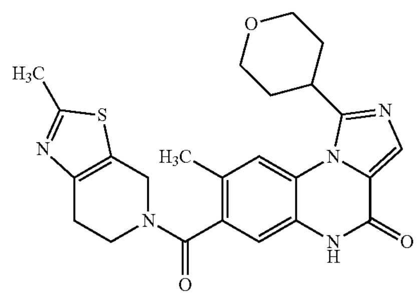 [SMILES: Cc1nc2c(s1)CN(C(=O)c1cc3[nH]c(=O)c4cnc(C5CCOCC5)n4c3cc1C)CC2] |
| 372 | 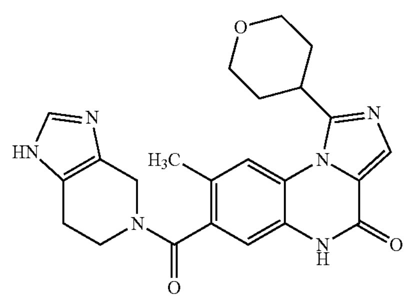 [SMILES: Cc1cc2c(cc1C(=O)N1CCc3[nH]cnc3C1)[nH]c(=O)c1cnc(C3CCOCC3)n12] |
| 373 | 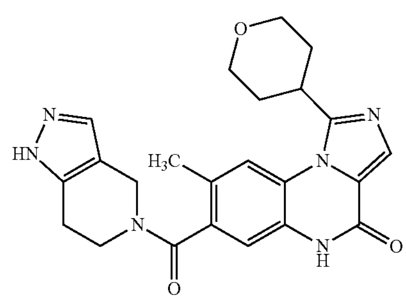 [SMILES: Cc1cc2c(cc1C(=O)N1CCc3[nH]ncc3C1)[nH]c(=O)c1cnc(C3CCOCC3)n12] |
| 374 | 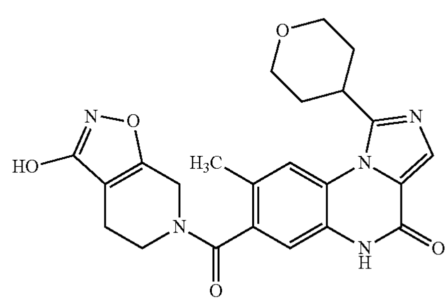 [SMILES: Cc1cc2c(cc1C(=O)N1CCc3c(O)noc3C1)[nH]c(=O)c1cnc(C3CCOCC3)n12] |

TABLE 105

| Ex | Structure |
|---|---|
| 375 | 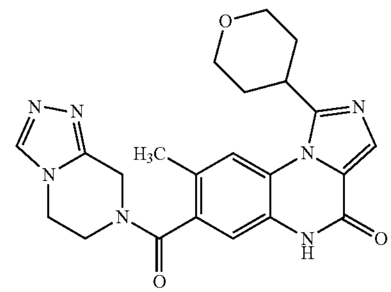 [SMILES: Cc1cc2c(cc1C(=O)N1CCn3cnnc3C1)[nH]c(=O)c1cnc(C3CCOCC3)n12] |
| 376 | 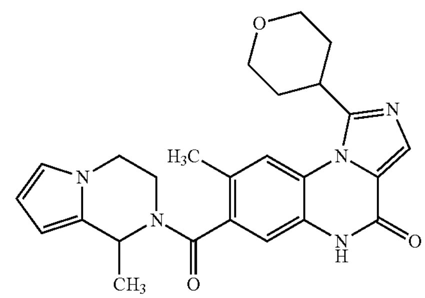 [SMILES: Cc1cc2c(cc1C(=O)N1CCn3cccc3C1C)[nH]c(=O)c1cnc(C3CCOCC3)n12] |
| 377 | 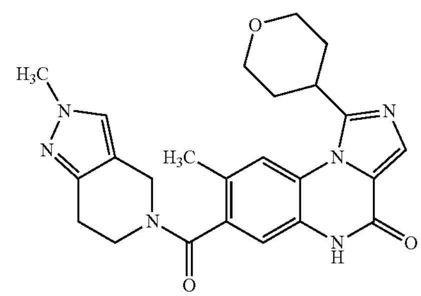 [SMILES: Cc1cc2c(cc1C(=O)N1CCc3nn(C)cc3C1)[nH]c(=O)c1cnc(C3CCOCC3)n12] |
| 378 | 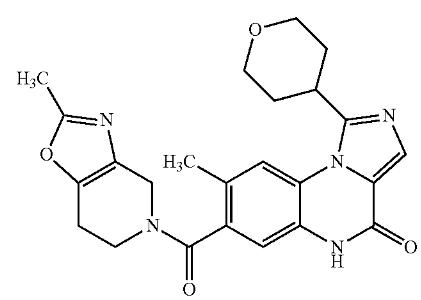 [SMILES: Cc1nc2c(o1)CCN(C(=O)c1cc3[nH]c(=O)c4cnc(C5CCOCC5)n4c3cc1C)C2] |
| 379 | 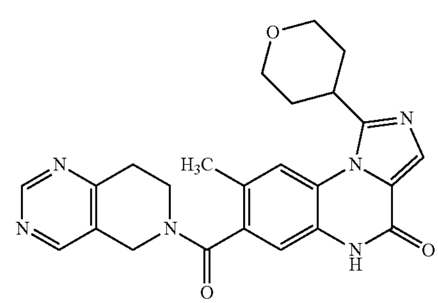 [SMILES: Cc1cc2c(cc1C(=O)N1CCc3ncncc3C1)[nH]c(=O)c1cnc(C3CCOCC3)n12] |

TABLE 106

| Ex | Structure |
|---|---|
| 380 | 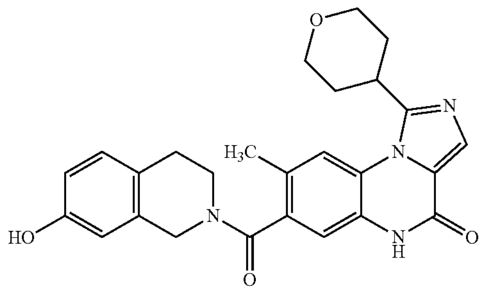 [SMILES: Cc1cc2c(cc1C(=O)N1CCc3ccc(O)cc3C1)[nH]c(=O)c1cnc(C3CCOCC3)n12] |
| 381 | 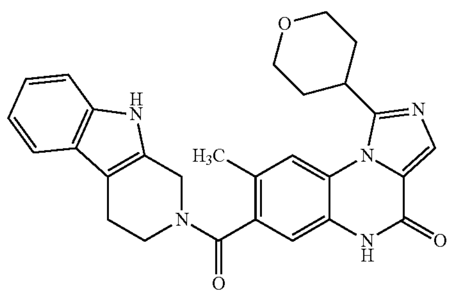 [SMILES: Cc1cc2c(cc1C(=O)N1CCc3c([nH]c4ccccc34)C1)[nH]c(=O)c1cnc(C3CCOCC3)n12] |
| 382 | 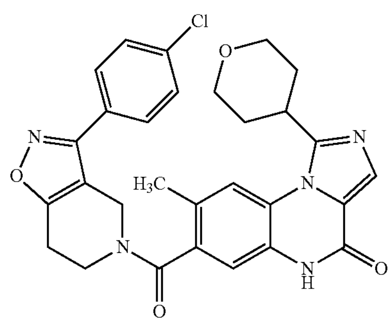 [SMILES: Cc1cc2c(cc1C(=O)N1CCc3onc(-c4ccc(Cl)cc4)c3C1)[nH]c(=O)c1cnc(C3CCOCC3)n12] |
| 383 | 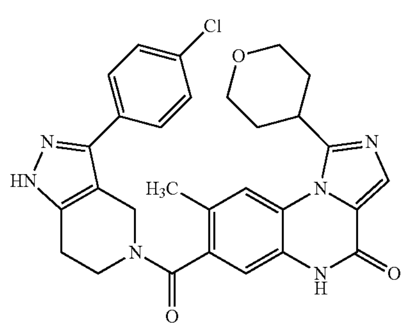 [SMILES: Cc1cc2c(cc1C(=O)N1CCc3[nH]nc(-c4ccc(Cl)cc4)c3C1)[nH]c(=O)c1cnc(C3CCOCC3)n12] |
| 384 | 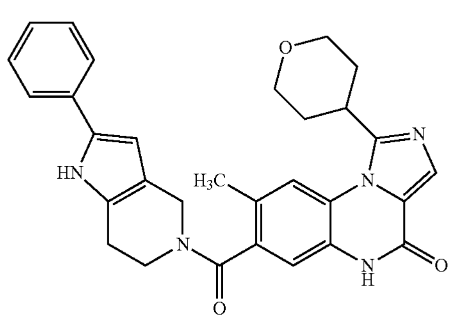 [SMILES: Cc1cc2c(cc1C(=O)N1CCc3[nH]c(-c4ccccc4)cc3C1)[nH]c(=O)c1cnc(C3CCOCC3)n12] |

TABLE 107

| Ex | Structure |
|---|---|
| 385 | 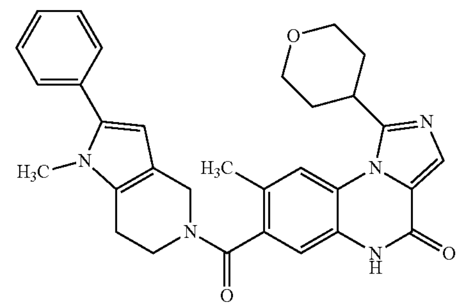 [SMILES: Cc1cc2c(cc1C(=O)N1CCc3c(cc(-c4ccccc4)n3C)C1)[nH]c(=O)c1cnc(C3CCOCC3)n12] |
| 386 | 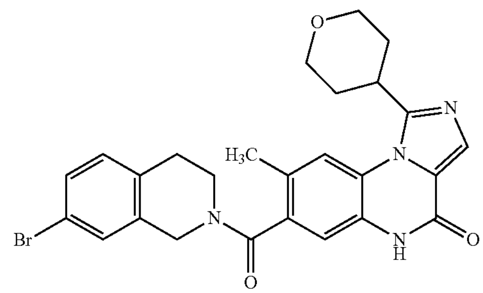 |
| 387 | 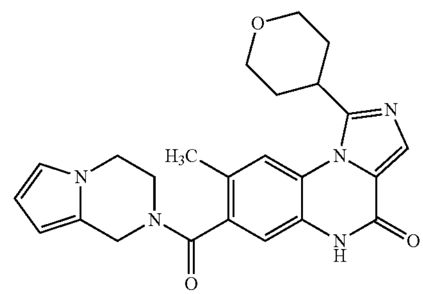 |
| 388 | 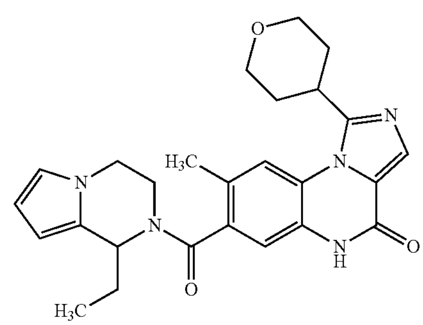 [SMILES: CCC1c2cccn2CCN1C(=O)c1cc2[nH]c(=O)c3cnc(C4CCOCC4)n3c2cc1C] |
| 389 | 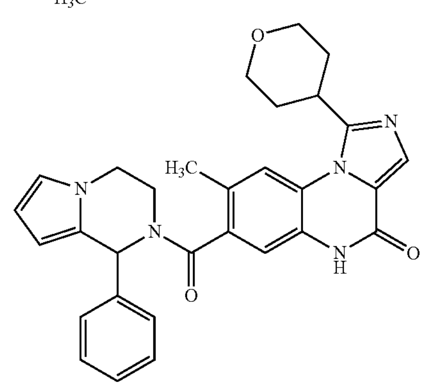 |

189
TABLE 108
| Ex | Structure |
|---|---|
| 390 | 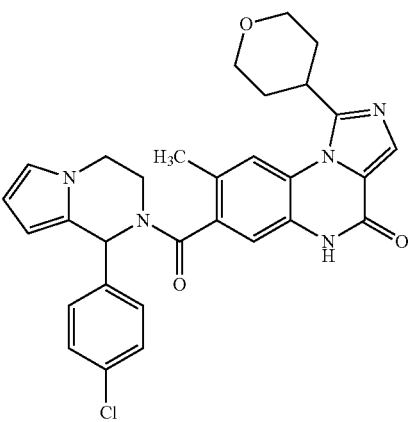 [SMILES: Cc1cc2c(cc1C(=O)N1CCn3cccc3C1c1ccc(Cl)cc1)[nH]c(=O)c1cnc(C3CCOCC3)n12] |
| 391 | 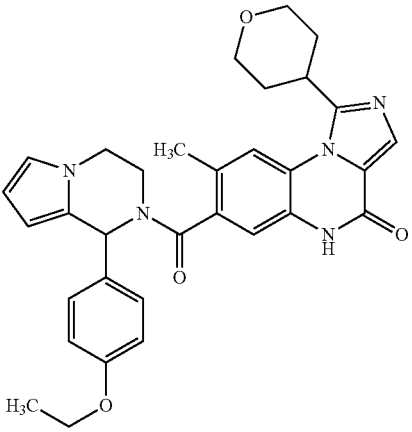 [SMILES: CCOc1ccc(C2c3cccn3CCN2C(=O)c2cc3[nH]c(=O)c4cnc(C5CCOCC5)n4c3cc2C)cc1] |
| 392 | 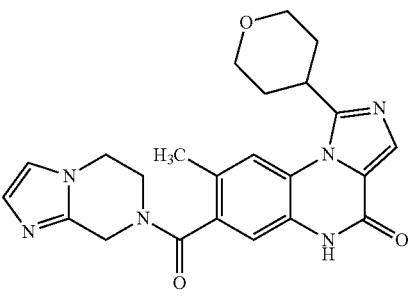 [SMILES: Cc1cc2c(cc1C(=O)N1CCn3ccnc3C1)[nH]c(=O)c1cnc(C3CCOCC3)n12] |
| 393 | 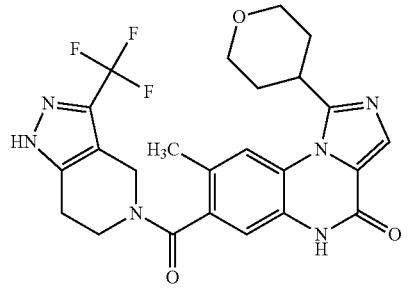 [SMILES: Cc1cc2c(cc1C(=O)N1CCc3[nH]nc(C(F)(F)F)c3C1)[nH]c(=O)c1cnc(C3CCOCC3)n12] |
190
TABLE 109
| Ex | Structure |
|---|---|
| 394 | 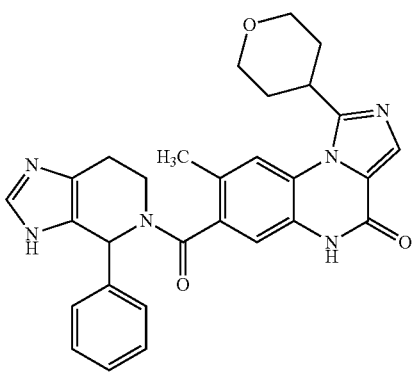 [SMILES: Cc1cc2c(cc1C(=O)N1CCc3nc[nH]c3C1c1ccccc1)[nH]c(=O)c1cnc(C3CCOCC3)n12] |
| 395 | 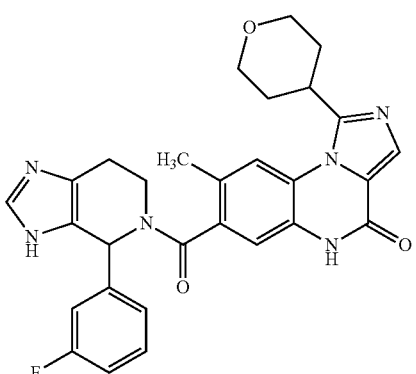 |
| 396 | 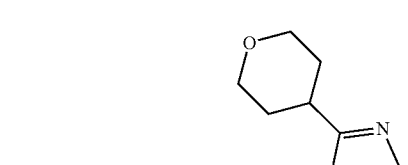 |
| 397 | 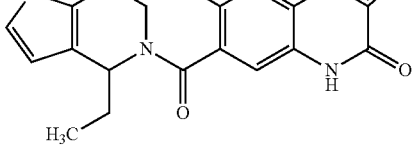 |

TABLE 110

| Ex | Structure |
|---|---|
| 398 | 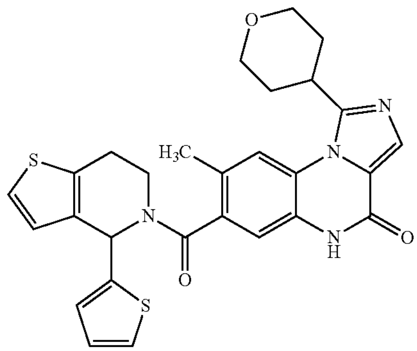 [SMILES: Cc1cc2c(cc1C(=O)N1CCc3sccc3C1c1cccs1)[nH]c(=O)c1cnc(C3CCOCC3)n12] |
| 399 | 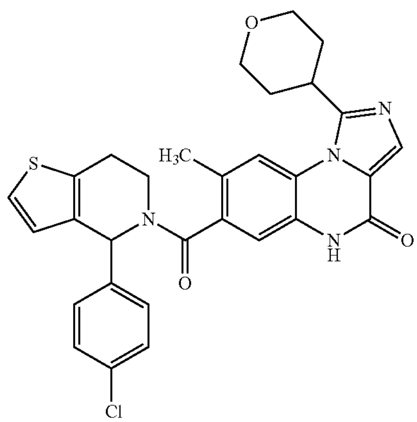 [SMILES: Cc1cc2c(cc1C(=O)N1CCc3sccc3C1c1ccc(Cl)cc1)[nH]c(=O)c1cnc(C3CCOCC3)n12] |
| 400 | 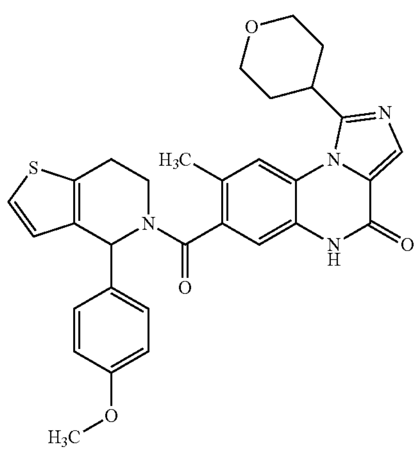 [SMILES: COc1ccc(C2c3ccsc3CCN2C(=O)c2cc3[nH]c(=O)c4cnc(C5CCOCC5)n4c3cc2C)cc1] |
| 401 | 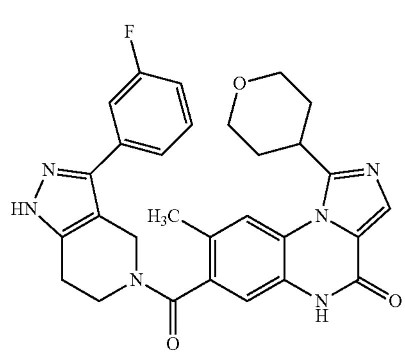 [SMILES: Cc1cc2c(cc1C(=O)N1CCc3[nH]nc(-c4cccc(F)c4)c3C1)[nH]c(=O)c1cnc(C3CCOCC3)n12] |

TABLE 111

| Ex | Structure |
|---|---|
| 402 | 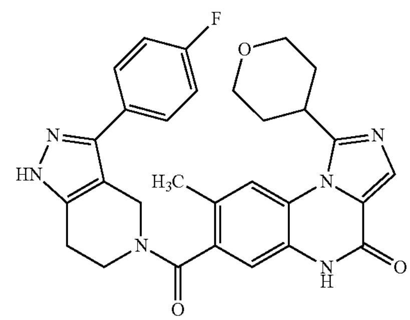 [SMILES: Cc1cc2c(cc1C(=O)N1CCc3[nH]nc(-c4ccc(F)cc4)c3C1)[nH]c(=O)c1cnc(C3CCOCC3)n12] |
| 403 | 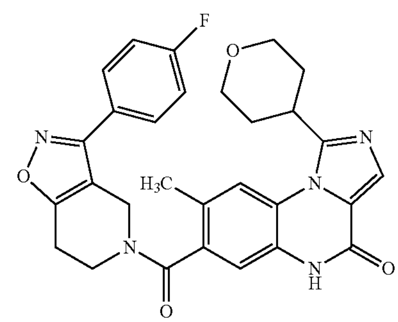 [SMILES: Cc1cc2c(cc1C(=O)N1CCc3onc(-c4ccc(F)cc4)c3C1)[nH]c(=O)c1cnc(C3CCOCC3)n12] |
| 404 | 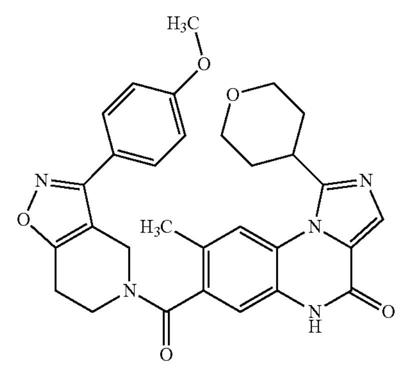 [SMILES: COc1ccc(-c2noc3c2CN(C(=O)c2cc4[nH]c(=O)c5cnc(C6CCOCC6)n5c4cc2C)CC3)cc1] |
| 405 | 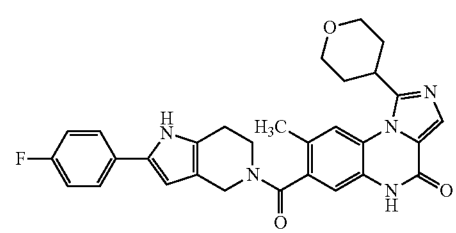 [SMILES: Cc1cc2c(cc1C(=O)N1CCc3[nH]c(-c4ccc(F)cc4)cc3C1)[nH]c(=O)c1cnc(C3CCOCC3)n12] |
| 406 | 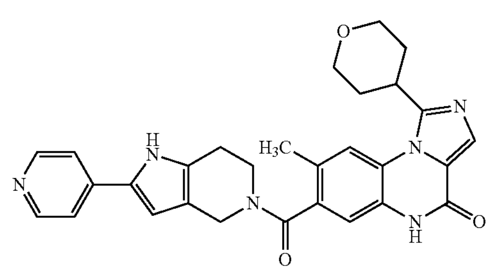 [SMILES: Cc1cc2c(cc1C(=O)N1CCc3[nH]c(-c4ccncc4)cc3C1)[nH]c(=O)c1cnc(C3CCOCC3)n12] |

TABLE 112

| Ex | Structure |
|---|---|
| 407 | 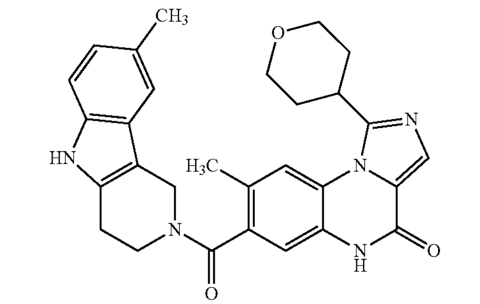 [SMILES: Cc1ccc2[nH]c3c(c2c1)CN(C(=O)c1cc2[nH]c(=O)c4cnc(C5CCOCC5)n4c2cc1C)CC3] |
| 408 | 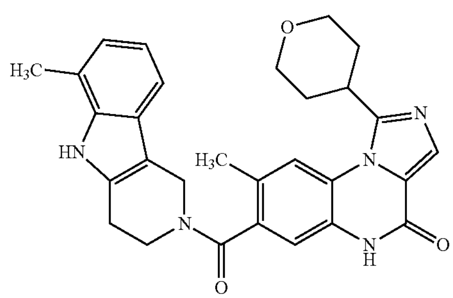 [SMILES: Cc1cc2c(cc1C(=O)N1CCc3[nH]c4c(C)cccc4c3C1)[nH]c(=O)c1cnc(C3CCOCC3)n12] |
| 409 | 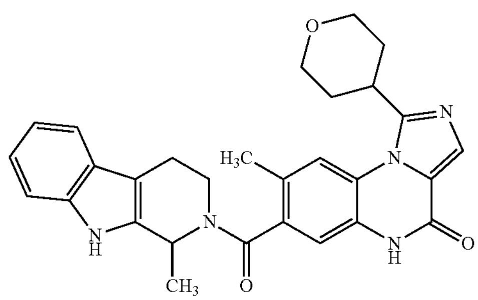 [SMILES: Cc1cc2c(cc1C(=O)N1CCc3c([nH]c4ccccc34)C1C)[nH]c(=O)c1cnc(C3CCOCC3)n12] |
| 410 | 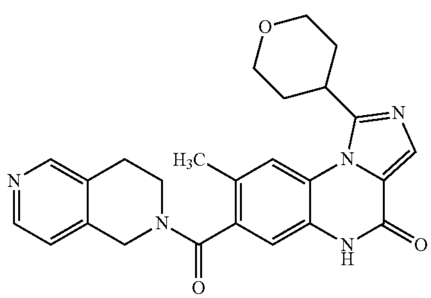 [SMILES: Cc1cc2c(cc1C(=O)N1CCc3cnccc3C1)[nH]c(=O)c1cnc(C3CCOCC3)n12] |
| 411 | 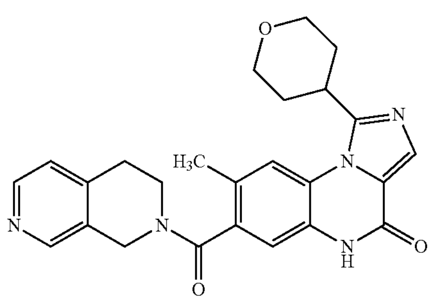 [SMILES: Cc1cc2c(cc1C(=O)N1CCc3ccncc3C1)[nH]c(=O)c1cnc(C3CCOCC3)n12] |

TABLE 113

| Ex | Structure |
|---|---|
| 412 | 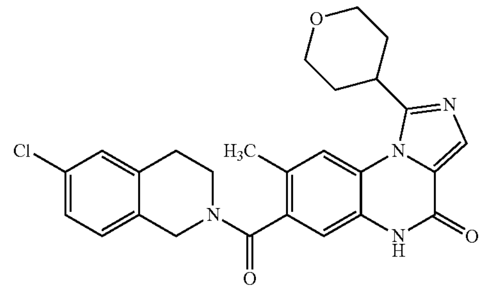 [SMILES: Cc1cc2c(cc1C(=O)N1CCc3cc(Cl)ccc3C1)[nH]c(=O)c1cnc(C3CCOCC3)n12] |
| 413 | 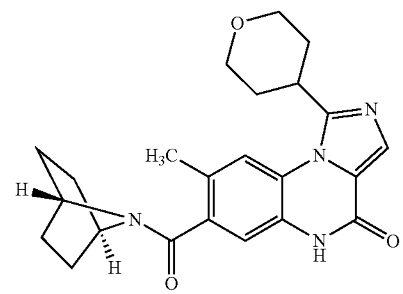 [SMILES: Cc1cc2c(cc1C(=O)N1[C@H]3CC[C@@H]1CC3)[nH]c(=O)c1cnc(C3CCOCC3)n12] |
| 414 | 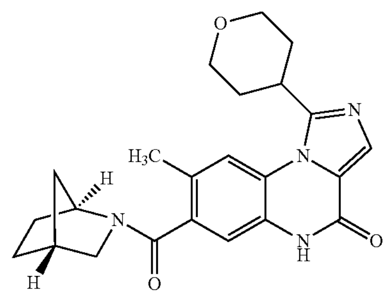 [SMILES: Cc1cc2c(cc1C(=O)N1C[C@@H]3CC[C@H]1C3)[nH]c(=O)c1cnc(C3CCOCC3)n12] |
| 415 | 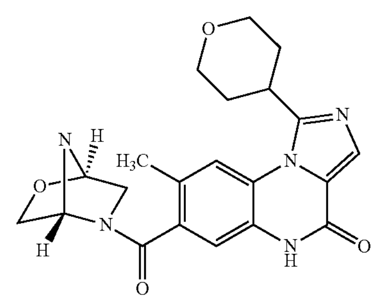 [SMILES: Cc1cc2c(cc1C(=O)N1C[C@@H]3N[C@H]1CO3)[nH]c(=O)c1cnc(C3CCOCC3)n12] |
| 416 | 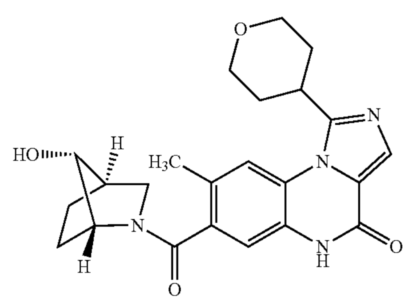 [SMILES: Cc1cc2c(cc1C(=O)N1C[C@H]3CC[C@@H]1[C@@H]3O)[nH]c(=O)c1cnc(C3CCOCC3)n12] |

TABLE 114

| Ex | Structure |
|---|---|
| 417 | 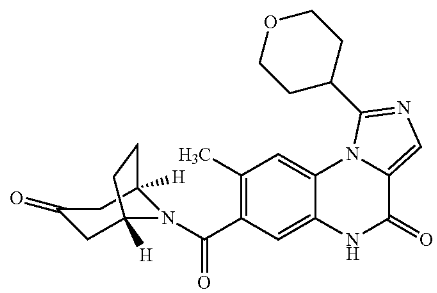 [SMILES: Cc1cc2c(cc1C(=O)N1[C@@H]3CC[C@H]1CC(=O)C3)[nH]c(=O)c1cnc(C3CCOCC3)n12] |
| 418 | 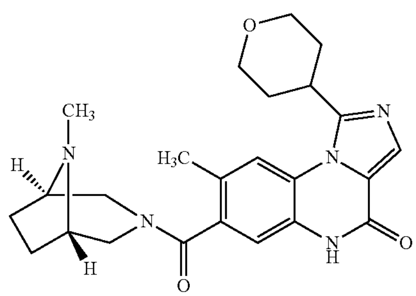 [SMILES: Cc1cc2c(cc1C(=O)N1C[C@H]3CC[C@@H](C1)N3C)[nH]c(=O)c1cnc(C3CCOCC3)n12] |
| 419 | 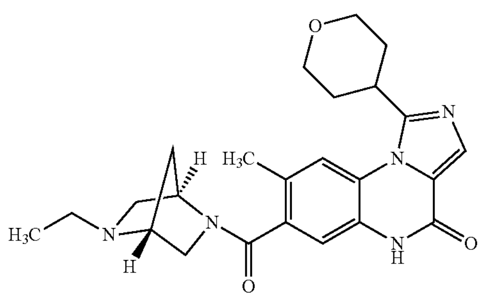 [SMILES: CCN1C[C@H]2C[C@@H]1CN2C(=O)c1cc2[nH]c(=O)c3cnc(C4CCOCC4)n3c2cc1C] |
| 420 | 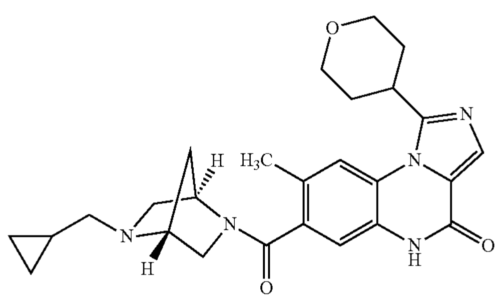 [SMILES: Cc1cc2c(cc1C(=O)N1C[C@H]3C[C@@H]1CN3CC1CC1)[nH]c(=O)c1cnc(C3CCOCC3)n12] |
| 421 | 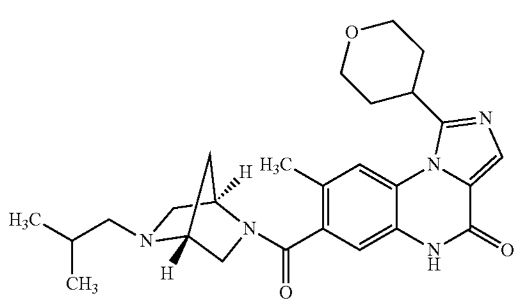 [SMILES: Cc1cc2c(cc1C(=O)N1C[C@H]3C[C@@H]1CN3CC(C)C)[nH]c(=O)c1cnc(C3CCOCC3)n12] |

TABLE 115

| Ex | Structure |
|---|---|
| 422 | 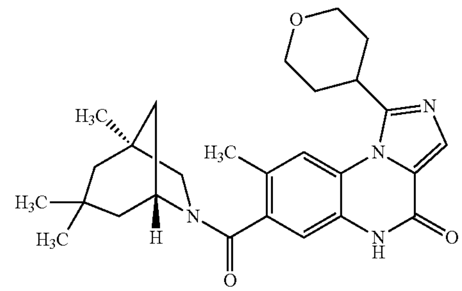 [SMILES: Cc1cc2c(cc1C(=O)N1C[C@]3(C)C[C@H]1CC(C)(C)C3)[nH]c(=O)c1cnc(C3CCOCC3)n12] |
| 423 | 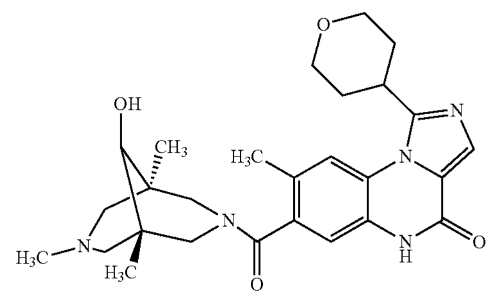 [SMILES: Cc1cc2c(cc1C(=O)N1C[C@]3(C)CN(C)C[C@](C)(C1)C3O)[nH]c(=O)c1cnc(C3CCOCC3)n12] |
| 424 | 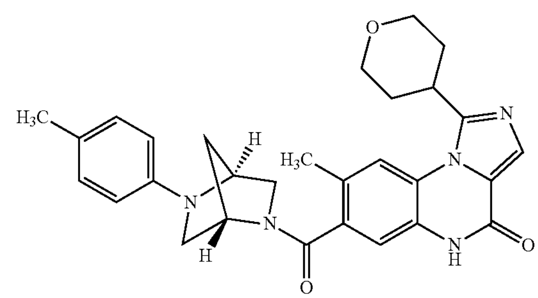 [SMILES: Cc1ccc(N2C[C@@H]3C[C@H]2CN3C(=O)c2cc3[nH]c(=O)c4cnc(C5CCOCC5)n4c3cc2C)cc1] |
| 425 | 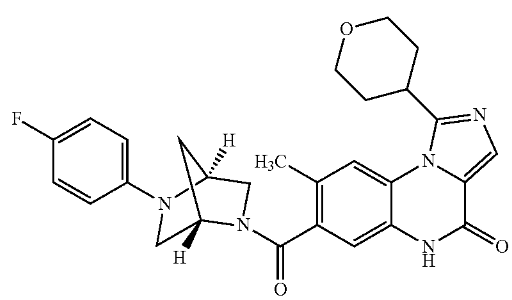 [SMILES: Cc1cc2c(cc1C(=O)N1C[C@@H]3C[C@H]1CN3c1ccc(F)cc1)[nH]c(=O)c1cnc(C3CCOCC3)n12] |
| 426 | 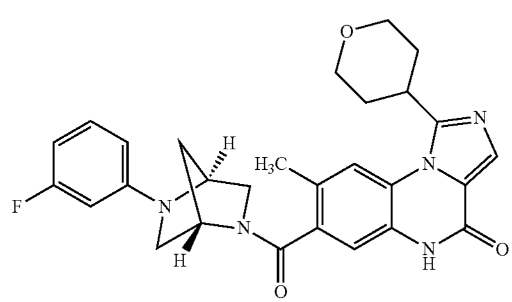 [SMILES: Cc1cc2c(cc1C(=O)N1C[C@@H]3C[C@H]1CN3c1cccc(F)c1)[nH]c(=O)c1cnc(C3CCOCC3)n12] |

TABLE 116

| Ex | Structure |
|---|---|
| 427 | 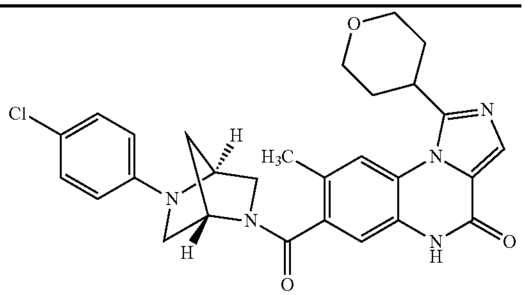 |
| 428 | 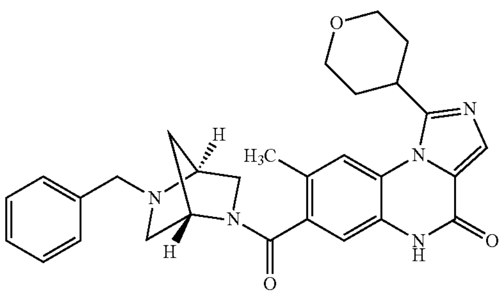 [SMILES: Cc1cc2c(cc1C(=O)N1C[C@@H]3C[C@H]1CN3Cc1ccccc1)[nH]c(=O)c1cnc(C3CCOCC3)n12] |
| 429 | 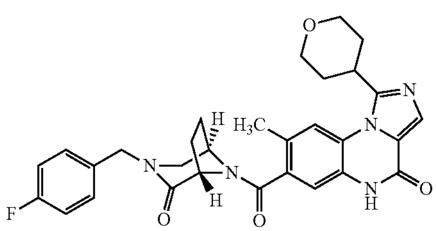 [SMILES: Cc1cc2c(cc1C(=O)N1[C@@H]3CC[C@H]1C(=O)N(Cc1ccc(F)cc1)C3)[nH]c(=O)c1cnc(C3CCOCC3)n12] |
| 430 | 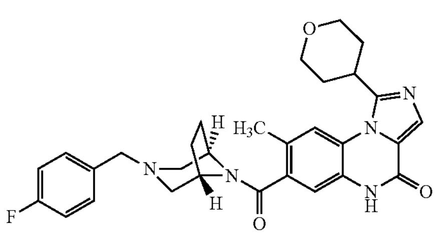 [SMILES: Cc1cc2c(cc1C(=O)N1[C@@H]3CC[C@H]1CN(Cc1ccc(F)cc1)C3)[nH]c(=O)c1cnc(C3CCOCC3)n12] |
| 431 | 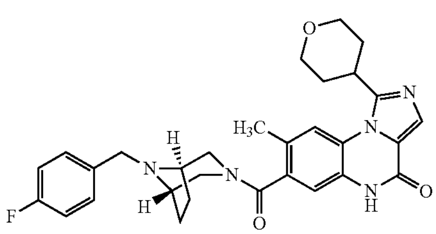 [SMILES: Cc1cc2c(cc1C(=O)N1C[C@H]3CC[C@@H](C1)N3Cc1ccc(F)cc1)[nH]c(=O)c1cnc(C3CCOCC3)n12] |

TABLE 117

| Ex | Structure |
|---|---|
| 432 | 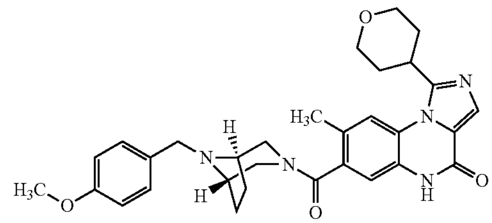 [SMILES: COc1ccc(CN2[C@@H]3CC[C@H]2CN(C(=O)c2cc4[nH]c(=O)c5cnc(C6CCOCC6)n5c4cc2C)C3)cc1] |
| 433 | 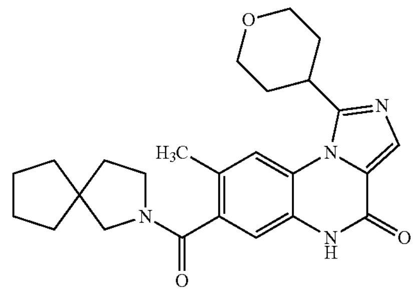 [SMILES: Cc1cc2c(cc1C(=O)N1CCC3(CCCC3)C1)[nH]c(=O)c1cnc(C3CCOCC3)n12] |
| 434 | 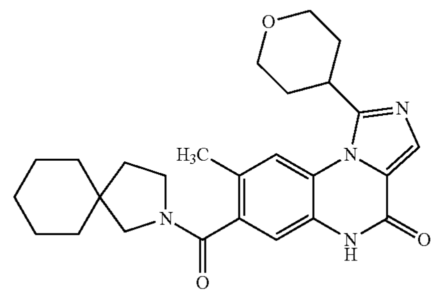 [SMILES: Cc1cc2c(cc1C(=O)N1CCC3(CCCCC3)C1)[nH]c(=O)c1cnc(C3CCOCC3)n12] |
| 435 | 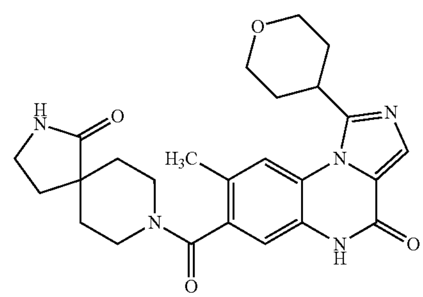 [SMILES: Cc1cc2c(cc1C(=O)N1CCC3(CCNC3=O)CC1)[nH]c(=O)c1cnc(C3CCOCC3)n12] |
| 436 | 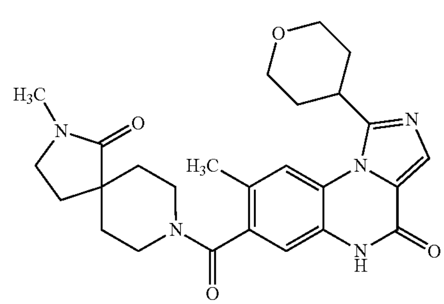 [SMILES: Cc1cc2c(cc1C(=O)N1CCC3(CCN(C)C3=O)CC1)[nH]c(=O)c1cnc(C3CCOCC3)n12] |

TABLE 118

| Ex | Structure |
|---|---|
| 437 | 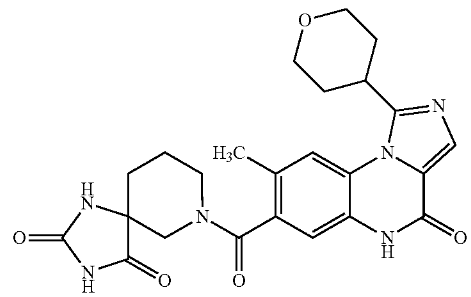 [SMILES: Cc1cc2c(cc1C(=O)N1CCCC3(C1)NC(=O)NC3=O)[nH]c(=O)c1cnc(C3CCOCC3)n12] |
| 438 | 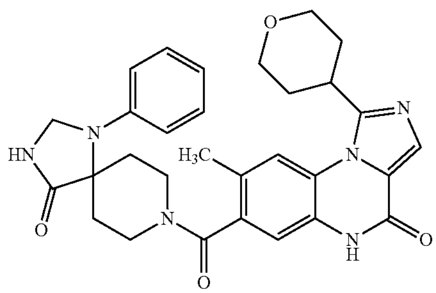 [SMILES: Cc1cc2c(cc1C(=O)N1CCC3(CC1)C(=O)NCN3c1ccccc1)[nH]c(=O)c1cnc(C3CCOCC3)n12] |
| 439 | 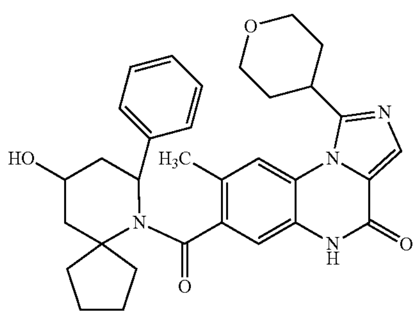 [SMILES: Cc1cc2c(cc1C(=O)N1C(c3ccccc3)CC(O)CC13CCCC3)[nH]c(=O)c1cnc(C3CCOCC3)n12] |
| 440 | 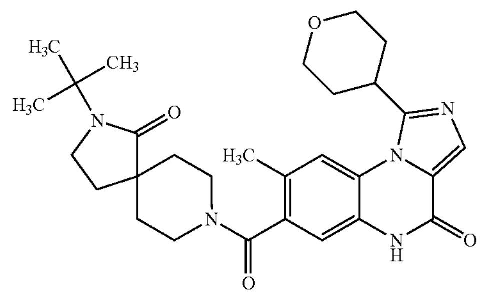 [SMILES: Cc1cc2c(cc1C(=O)N1CCC3(CC1)CCN(C(C)(C)C)C3=O)[nH]c(=O)c1cnc(C3CCOCC3)n12] |
| 441 | 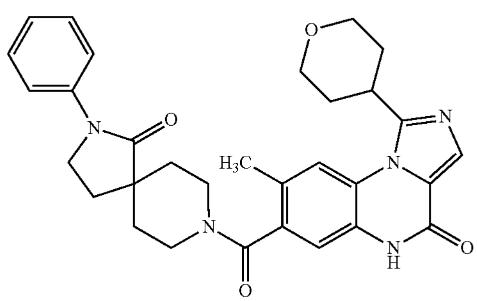 [SMILES: Cc1cc2c(cc1C(=O)N1CCC3(CC1)CCN(c1ccccc1)C3=O)[nH]c(=O)c1cnc(C3CCOCC3)n12] |

TABLE 119

| Ex | Structure |
|---|---|
| 442 | 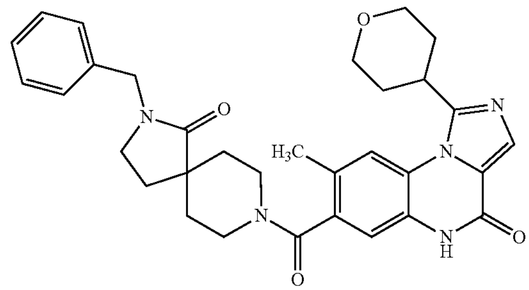 [SMILES: Cc1cc2c(cc1C(=O)N1CCC3(CC1)CCN(Cc1ccccc1)C3=O)[nH]c(=O)c1cnc(C3CCOCC3)n12] |
| 443 | 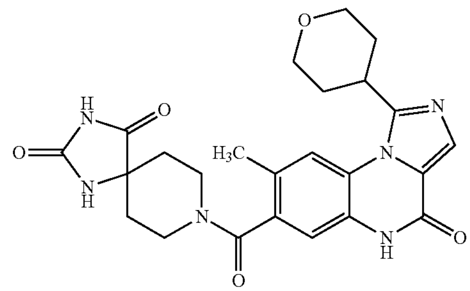 [SMILES: Cc1cc2c(cc1C(=O)N1CCC3(CC1)NC(=O)NC3=O)[nH]c(=O)c1cnc(C3CCOCC3)n12] |
| 444 | 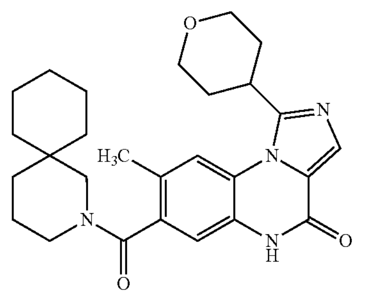 [SMILES: Cc1cc2c(cc1C(=O)N1CCCC3(CCCCC3)C1)[nH]c(=O)c1cnc(C3CCOCC3)n12] |
| 445 | 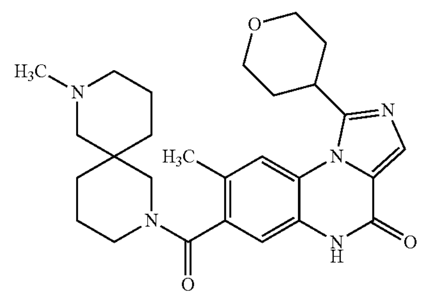 [SMILES: Cc1cc2c(cc1C(=O)N1CCCC3(CCCN(C)C3)C1)[nH]c(=O)c1cnc(C3CCOCC3)n12] |
| 446 | 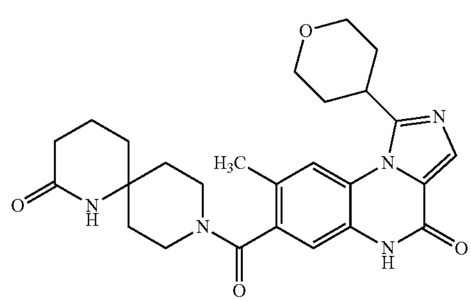 [SMILES: Cc1cc2c(cc1C(=O)N1CCC3(CCCC(=O)N3)CC1)[nH]c(=O)c1cnc(C3CCOCC3)n12] |

TABLE 120

| Ex | Structure |
|---|---|
| 447 | 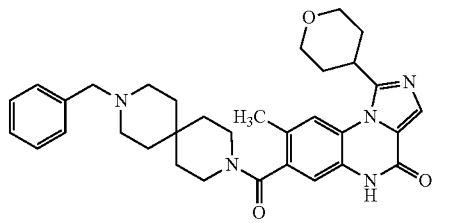 [SMILES: Cc1cc2c(cc1C(=O)N1CCC3(CCN(Cc4ccccc4)CC3)CC1)[nH]c(=O)c1cnc(C3CCOCC3)n12] |
| 448 | 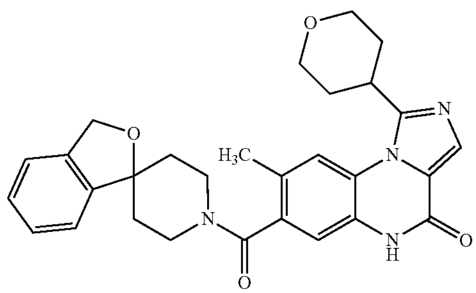 [SMILES: Cc1cc2c(cc1C(=O)N1CCC3(CC1)OCc1ccccc13)[nH]c(=O)c1cnc(C3CCOCC3)n12] |
| 449 | 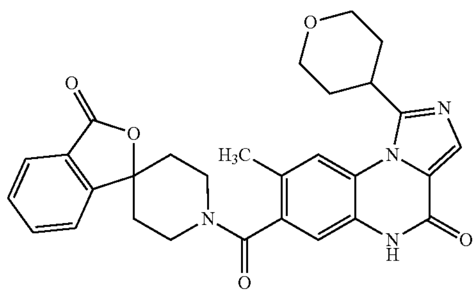 [SMILES: Cc1cc2c(cc1C(=O)N1CCC3(CC1)OC(=O)c1ccccc13)[nH]c(=O)c1cnc(C3CCOCC3)n12] |
| 450 | 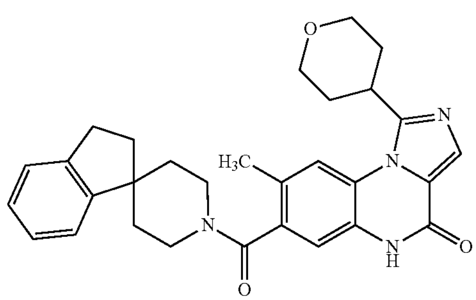 |
| 451 | 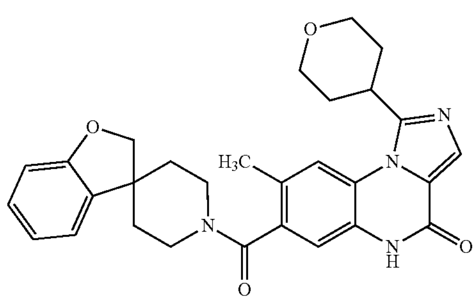 [SMILES: Cc1cc2c(cc1C(=O)N1CCC3(CC1)COc1ccccc13)[nH]c(=O)c1cnc(C3CCOCC3)n12] |

TABLE 121

| Ex | Structure |
|---|---|
| 452 | 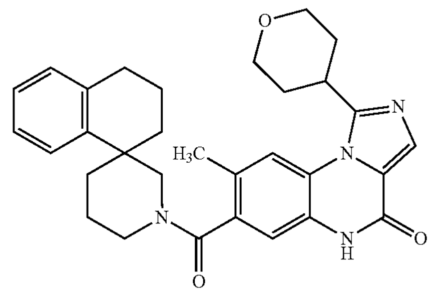 [SMILES: Cc1cc2c(cc1C(=O)N1CCCC3(CCCc4ccccc43)C1)[nH]c(=O)c1cnc(C3CCOCC3)n12] |
| 453 | 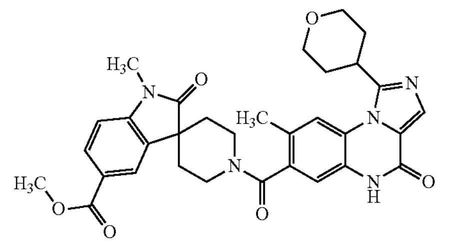 [SMILES: COC(=O)c1ccc2c(c1)C1(CCN(C(=O)c3cc4[nH]c(=O)c5cnc(C6CCOCC6)n5c4cc3C)CC1)C(=O)N2C] |
| 454 | 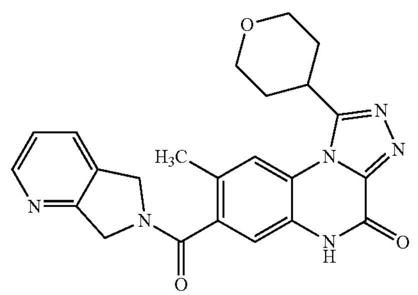 [SMILES: Cc1cc2c(cc1C(=O)N1Cc3cccnc3C1)[nH]c(=O)c1nnc(C3CCOCC3)n12] |
| 455 | 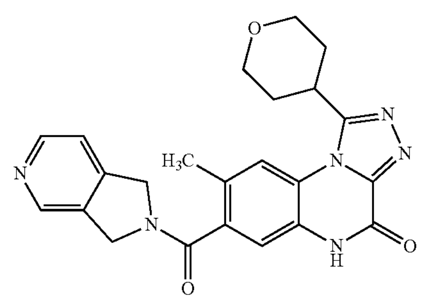 [SMILES: Cc1cc2c(cc1C(=O)N1Cc3ccncc3C1)[nH]c(=O)c1nnc(C3CCOCC3)n12] |
| 456 | 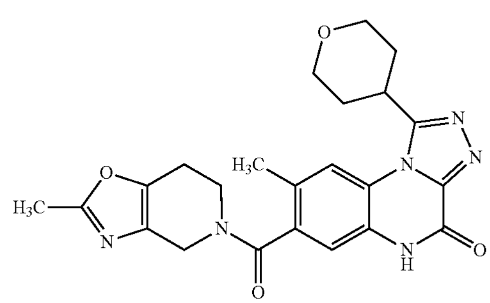 [SMILES: Cc1nc2c(o1)CCN(C(=O)c1cc3[nH]c(=O)c4nnc(C5CCOCC5)n4c3cc1C)C2] |

TABLE 122
| Ex | Structure |
|---|---|
| 457 | 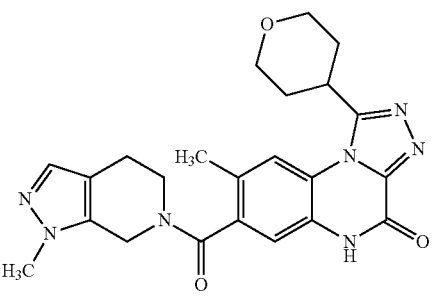 [SMILES: Cc1cc2c(cc1C(=O)N1CCc3cnn(C)c3C1)[nH]c(=O)c1nnc(C3CCOCC3)n12] |
| 458 | 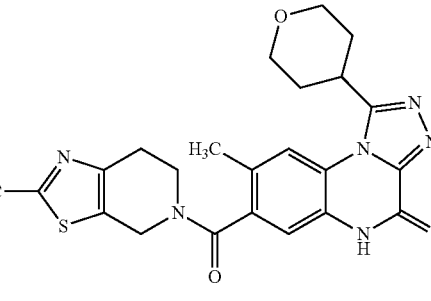 |
| 459 | 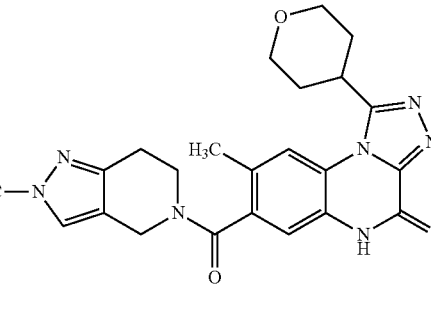 |
| 460 | 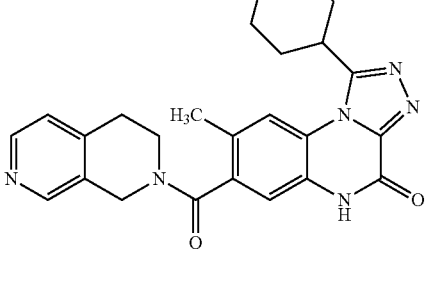 |
| 461 | 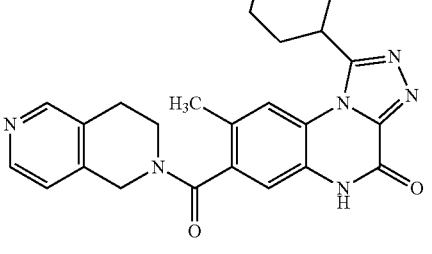 |
TABLE 123
| Ex | Structure |
|---|---|
| 462 | 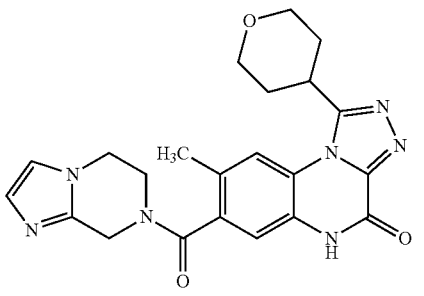 [SMILES: Cc1cc2c(cc1C(=O)N1CCn3ccnc3C1)[nH]c(=O)c1nnc(C3CCOCC3)n12] |
| 463 | 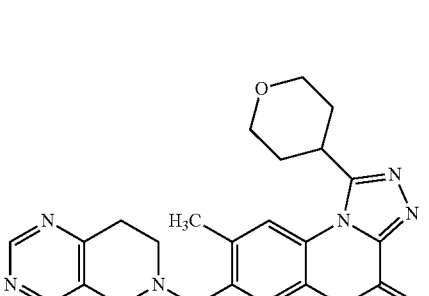 |
| 464 | 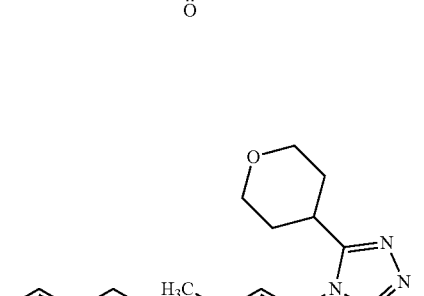 |
| 465 | 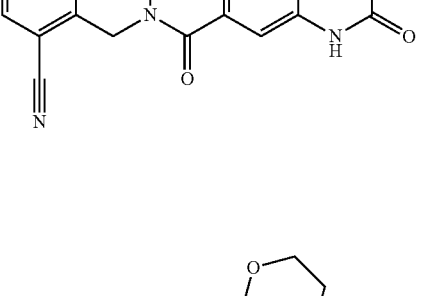 |

TABLE 123-continued
| Ex | Structure |
|---|---|
| 466 | 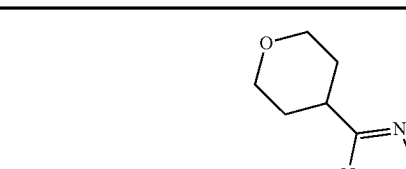 |
TABLE 124
| Ex | Structure |
|---|---|
| 467 | 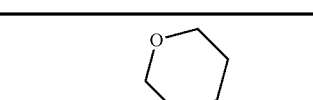 |
| 468 | 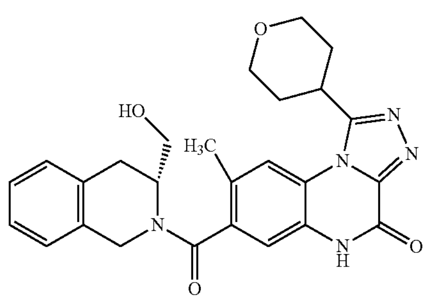 [SMILES: Cc1cc2c(cc1C(=O)N1Cc3ccccc3C[C@@H]1CO)[nH]c(=O)c1nnc(C3CCOCC3)n12] |
| 469 | 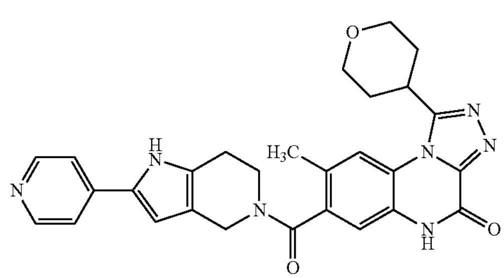 [SMILES: Cc1cc2c(cc1C(=O)N1CCc3[nH]c(-c4ccncc4)cc3C1)[nH]c(=O)c1nnc(C3CCOCC3)n12] |
TABLE 124-continued
| Ex | Structure |
|---|---|
| 470 | 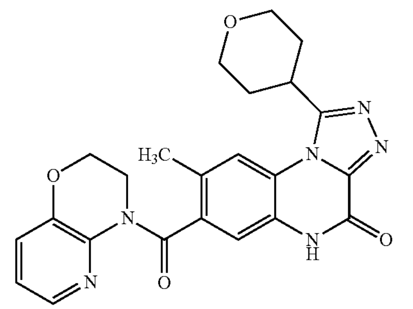 [SMILES: Cc1cc2c(cc1C(=O)N1CCOc3cccnc31)[nH]c(=O)c1nnc(C3CCOCC3)n12] |
| 471 | 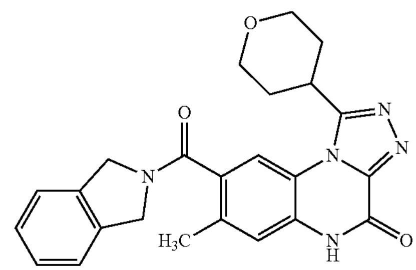 [SMILES: Cc1cc2[nH]c(=O)c3nnc(C4CCOCC4)n3c2cc1C(=O)N1Cc2ccccc2C1] |
TABLE 125
| Ex | Structure |
|---|---|
| 472 | 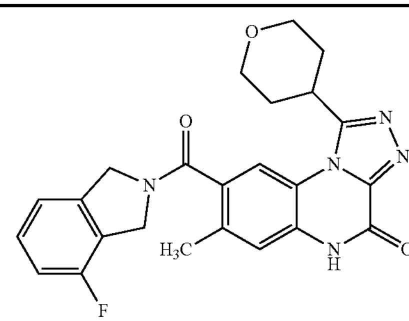 |
| 473 | 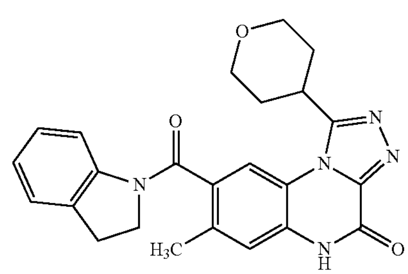 [SMILES: Cc1cc2[nH]c(=O)c3nnc(C4CCOCC4)n3c2cc1C(=O)N1CCc2ccccc21] |
| 474 | 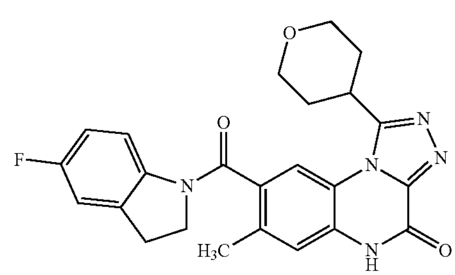 |

TABLE 125-continued
| Ex | Structure |
|---|---|
| 475 | 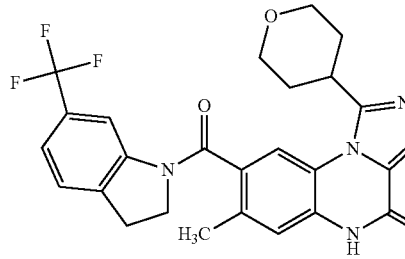 |
| 476 | 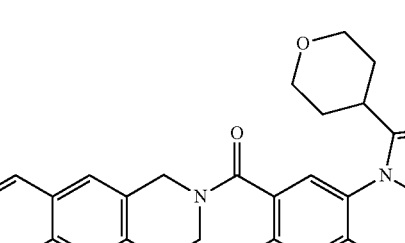 |
| 477 | 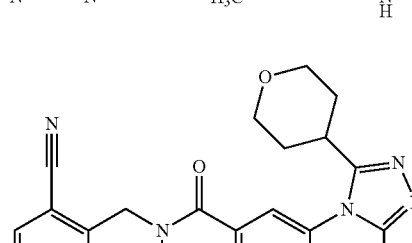 |
TABLE 126
| Ex | Structure |
|---|---|
| 478 | 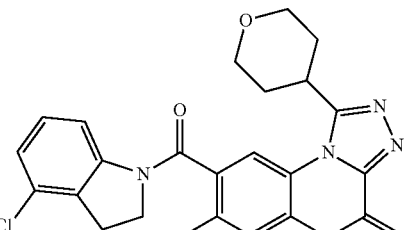 |
| 479 | 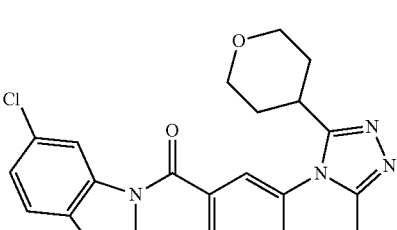 |
| 480 | 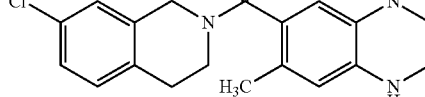 |
| 481 | 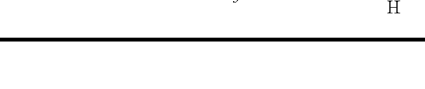 |
| 482 | 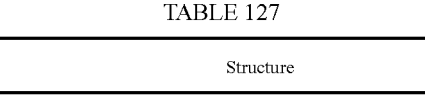 |
| 483 | 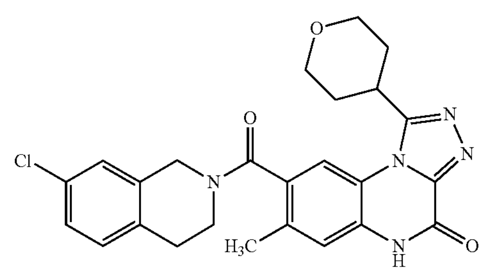 [SMILES: Cc1cc2[nH]c(=O)c3nnc(C4CCOCC4)n3c2cc1C(=O)N1CCc2ccc(Cl)cc2C1] |
TABLE 127
| Ex | Structure |
|---|---|
| 484 | 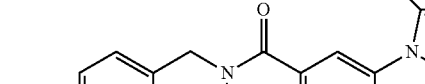 |

TABLE 127-continued
| Ex | Structure |
|---|---|
| 485 | 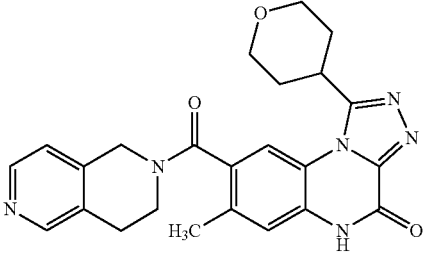 [SMILES: Cc1cc2[nH]c(=O)c3nnc(C4CCOCC4)n3c2cc1C(=O)N1CCc2cnccc2C1] |
| 486 | 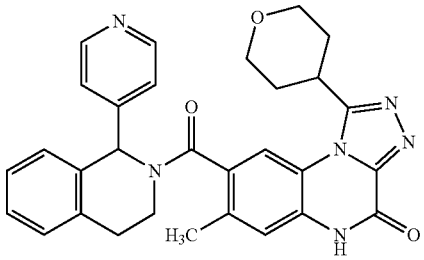 [SMILES: Cc1cc2[nH]c(=O)c3nnc(C4CCOCC4)n3c2cc1C(=O)N1CCc2ccccc2C1c1ccncc1] |
| 487 | 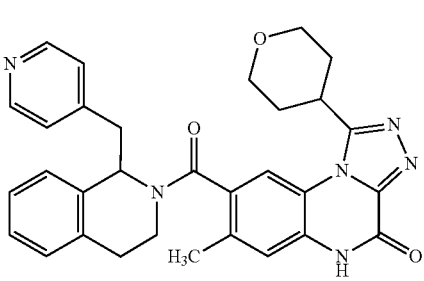 [SMILES: Cc1cc2[nH]c(=O)c3nnc(C4CCOCC4)n3c2cc1C(=O)N1CCc2ccccc2C1Cc1ccncc1] |
| 488 | 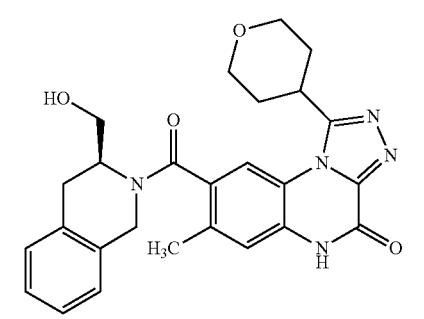 [SMILES: Cc1cc2[nH]c(=O)c3nnc(C4CCOCC4)n3c2cc1C(=O)N1Cc2ccccc2C[C@H]1CO] |
TABLE 128
| Ex | Structure |
|---|---|
| 489 | 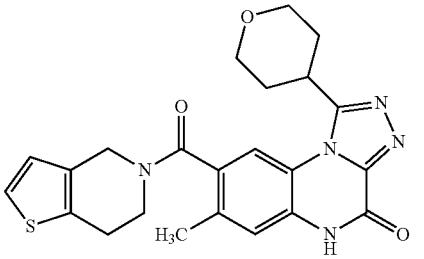 |
TABLE 128-continued
| Ex | Structure |
|---|---|
| 490 | 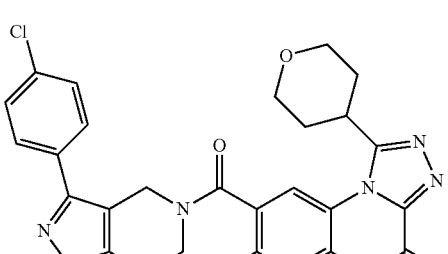 |
| 491 | 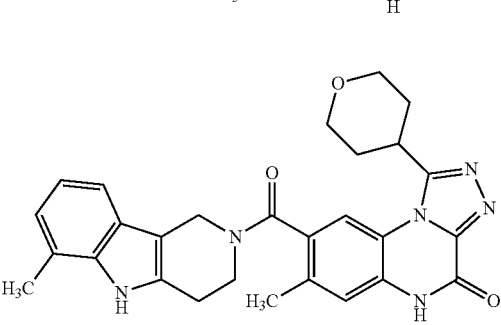 |
| 492 | 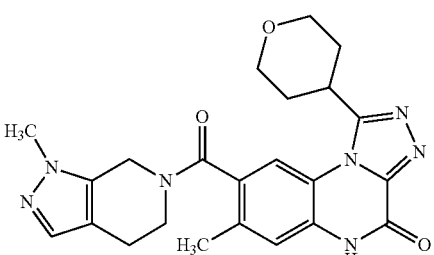 |
| 493 | 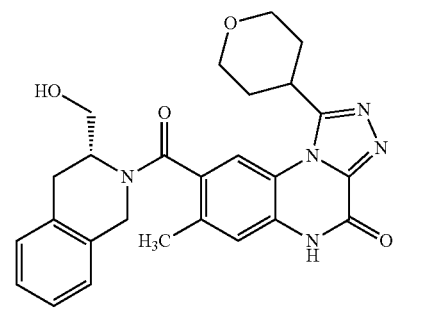 [SMILES: Cc1cc2[nH]c(=O)c3nnc(C4CCOCC4)n3c2cc1C(=O)N1Cc2ccccc2C[C@@H]1CO] |
TABLE 129
| Ex | Structure |
|---|---|
| 494 | 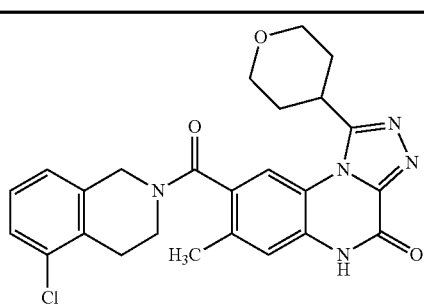 |

TABLE 129-continued

| Ex | Structure |
|---|---|
| 495 | 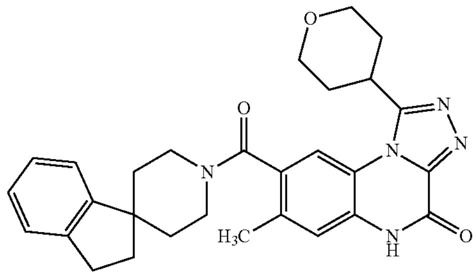 [SMILES: Cc1cc2[nH]c(=O)c3nnc(C4CCOCC4)n3c2cc1C(=O)N1CCC2(CCc3ccccc32)CC1] |
| 496 | 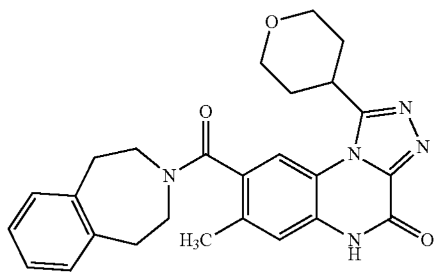 [SMILES: Cc1cc2[nH]c(=O)c3nnc(C4CCOCC4)n3c2cc1C(=O)N1CCc2ccccc2CC1] |
| 497 | 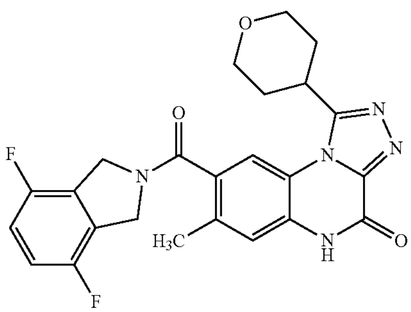 [SMILES: Cc1cc2[nH]c(=O)c3nnc(C4CCOCC4)n3c2cc1C(=O)N1Cc2c(F)ccc(F)c2C1] |
| 498 | 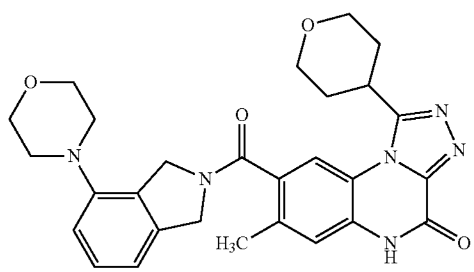 [SMILES: Cc1cc2[nH]c(=O)c3nnc(C4CCOCC4)n3c2cc1C(=O)N1Cc2cccc(N3CCOCC3)c2C1] |

TABLE 130

| Ex | Structure |
|---|---|
| 499 | 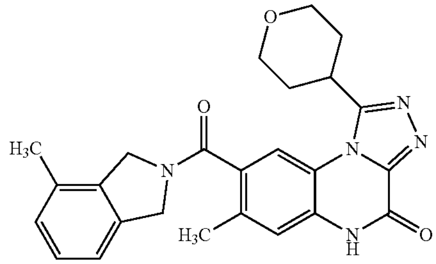 [SMILES: Cc1cc2[nH]c(=O)c3nnc(C4CCOCC4)n3c2cc1C(=O)N1Cc2cccc(C)c2C1] |

TABLE 130-continued

| Ex | Structure |
|---|---|
| 500 | 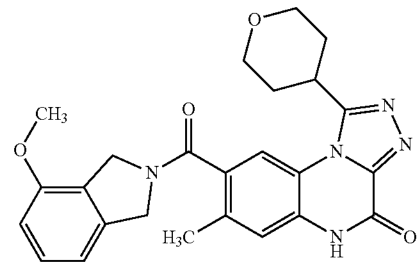 [SMILES: COc1cccc2c1CN(C(=O)c1cc3c(cc1C)[nH]c(=O)c1nnc(C4CCOCC4)n13)C2] |
| 501 | 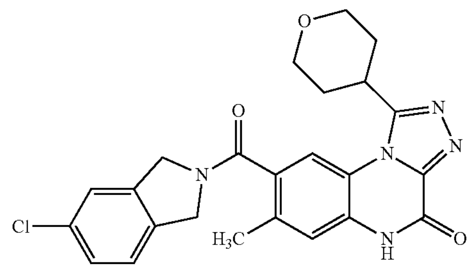 [SMILES: Cc1cc2[nH]c(=O)c3nnc(C4CCOCC4)n3c2cc1C(=O)N1Cc2ccc(Cl)cc2C1] |
| 502 | 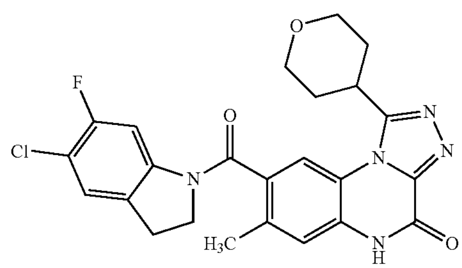 [SMILES: Cc1cc2[nH]c(=O)c3nnc(C4CCOCC4)n3c2cc1C(=O)N1CCc2cc(Cl)c(F)cc21] |
| 503 | 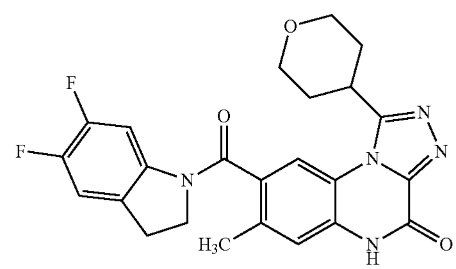 [SMILES: Cc1cc2[nH]c(=O)c3nnc(C4CCOCC4)n3c2cc1C(=O)N1CCc2cc(F)c(F)cc21] |
| 504 | 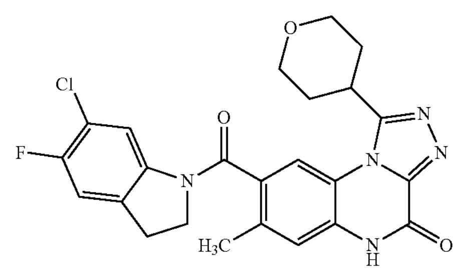 [SMILES: Cc1cc2[nH]c(=O)c3nnc(C4CCOCC4)n3c2cc1C(=O)N1CCc2cc(F)c(Cl)cc21] |

TABLE 131

| Ex | Structure |
|---|---|
| 505 | 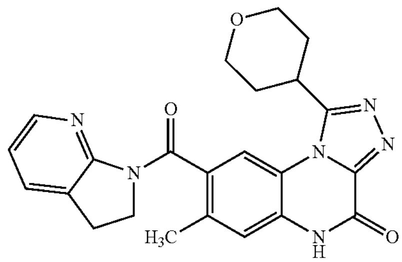 [SMILES: Cc1cc2[nH]c(=O)c3nnc(C4CCOCC4)n3c2cc1C(=O)N1CCc2cccnc21] |
| 506 | 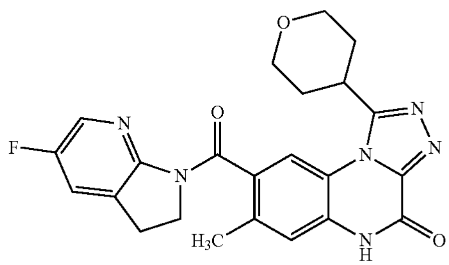 [SMILES: Cc1cc2[nH]c(=O)c3nnc(C4CCOCC4)n3c2cc1C(=O)N1CCc2cc(F)cnc21] |
| 507 | 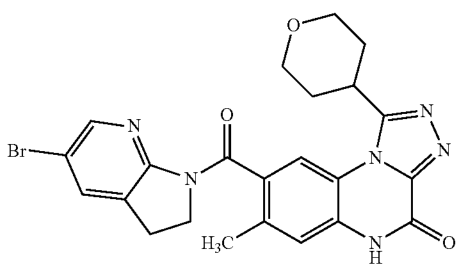 [SMILES: Cc1cc2[nH]c(=O)c3nnc(C4CCOCC4)n3c2cc1C(=O)N1CCc2cc(Br)cnc21] |
| 508 | 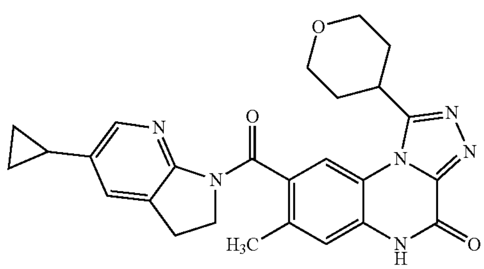 [SMILES: Cc1cc2[nH]c(=O)c3nnc(C4CCOCC4)n3c2cc1C(=O)N1CCc2cc(C3CC3)cnc21] |
| 509 | 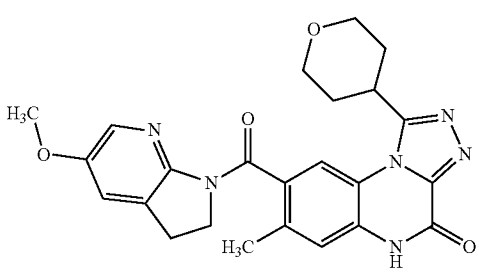 [SMILES: COc1cnc2c(c1)CCN2C(=O)c1cc2c(cc1C)[nH]c(=O)c1nnc(C3CCOCC3)n12] |
| 510 | 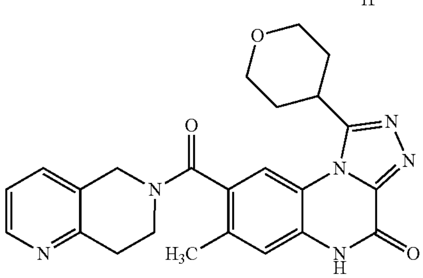 |

TABLE 132

| Ex | Structure |
|---|---|
| 511 | 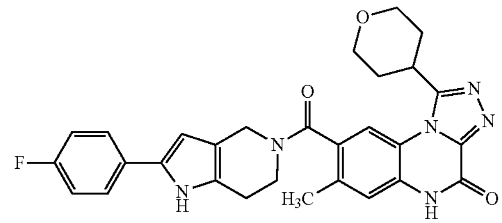 [SMILES: Cc1cc2[nH]c(=O)c3nnc(C4CCOCC4)n3c2cc1C(=O)N1CCc2[nH]c(-c3ccc(F)cc3)cc2C1] |
| 512 | 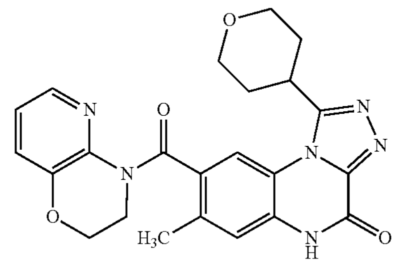 [SMILES: Cc1cc2[nH]c(=O)c3nnc(C4CCOCC4)n3c2cc1C(=O)N1CCOc2cccnc21] |
| 513 | 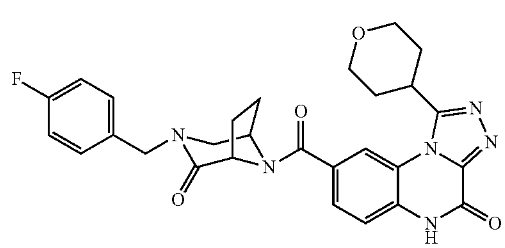 [SMILES: O=C1C2CCC(CN1Cc1ccc(F)cc1)N2C(=O)c1ccc2[nH]c(=O)c3nnc(C4CCOCC4)n3c2c1] |
| 514 | 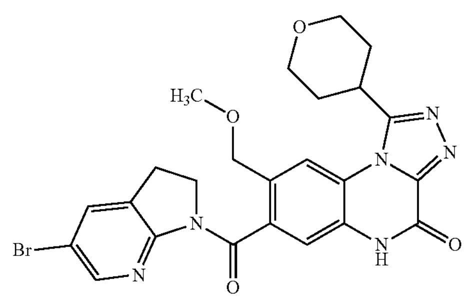 |
| 515 | 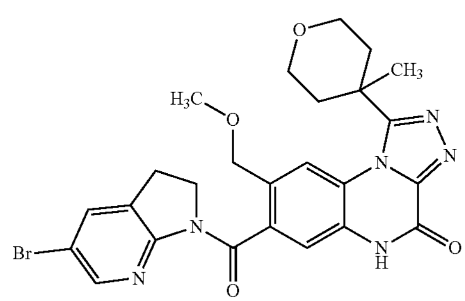 [SMILES: COCc1cc2c(cc1C(=O)N1CCc3cc(Br)cnc31)[nH]c(=O)c1nnc(C3(C)CCOCC3)n12] |

TABLE 133
| Ex | Structure |
|---|---|
| 516 | 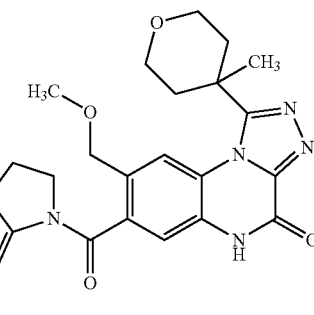 |
| 517 | 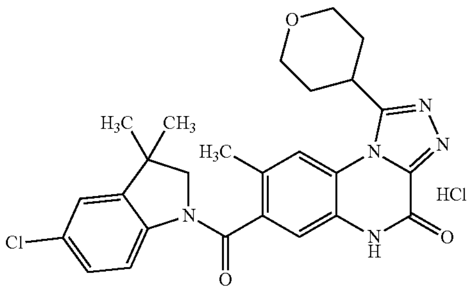 [SMILES: Cc1cc2c(cc1C(=O)N1CC(C)(C)c3cc(Cl)ccc31)[nH]c(=O)c1nnc(C3CCOCC3)n12 ; Cl] |
| 518 | 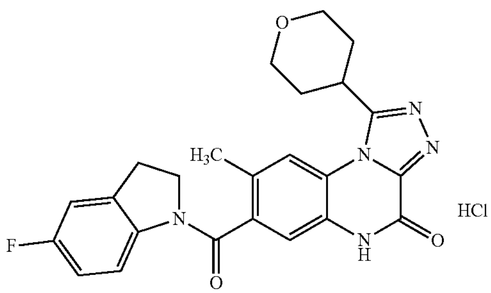 [SMILES: Cc1cc2c(cc1C(=O)N1CCc3cc(F)ccc31)[nH]c(=O)c1nnc(C3CCOCC3)n12 ; Cl] |
| 519 | 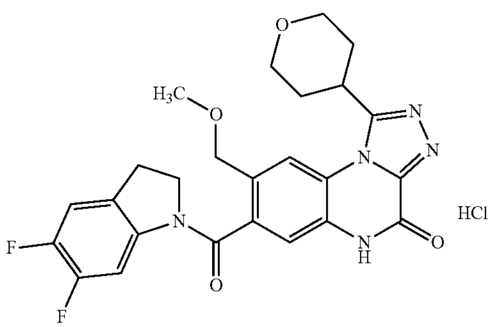 [SMILES: COCc1cc2c(cc1C(=O)N1CCc3cc(F)c(F)cc31)[nH]c(=O)c1nnc(C3CCOCC3)n12 ; Cl] |
| 520 | 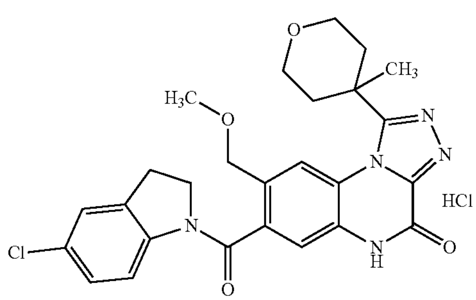 [SMILES: COCc1cc2c(cc1C(=O)N1CCc3cc(Cl)ccc31)[nH]c(=O)c1nnc(C3(C)CCOCC3)n12 ; Cl] |
TABLE 134
| Ex | Structure |
|---|---|
| 521 | 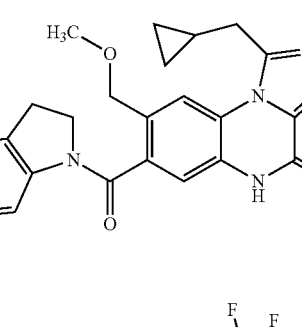 |
| 522 | 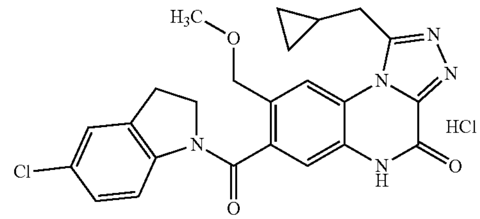 [SMILES: COCc1cc2c(cc1C(=O)N1CCc3cc(Cl)ccc31)[nH]c(=O)c1nnc(CC3CC3)n12 ; Cl] |
| 523 | 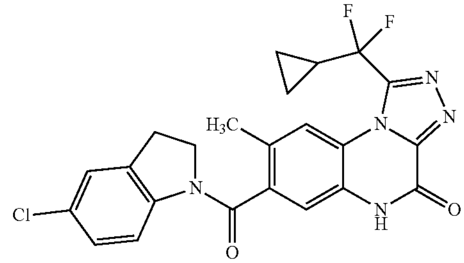 [SMILES: Cc1cc2c(cc1C(=O)N1CCc3cc(Cl)ccc31)[nH]c(=O)c1nnc(C(F)(F)C3CC3)n12] |
| 524 | 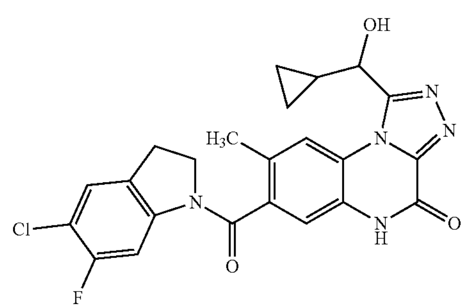 [SMILES: Cc1cc2c(cc1C(=O)N1CCc3cc(Cl)c(F)cc31)[nH]c(=O)c1nnc(C(O)C3CC3)n12] |
| 525 | 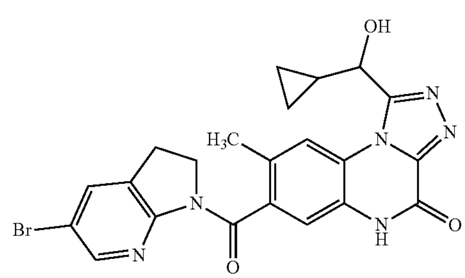 |

TABLE 135

| Ex | Structure |
|---|---|
| 526 | (structure) |
| 527 | (structure) |
| 528 | (structure) |
| 529 | (structure) |
| 530 | (structure) |

TABLE 136

| Ex | Structure |
|---|---|
| 531 | (structure) |

TABLE 137

| Ex | Data | Syn |
|---|---|---|
| 1 | ESI+: 431<br>NMR-DMSO-d6: 1.00-1.50 (3H, m), 1.80-2.30 (6H, m), 2.70-4.50 (8H, m), 7.20-7.50 (7H, m), 7.95-8.15 (1H, m), 12.09 (1H, br s) | 1 |
| 2 | ESI+: 388<br>NMR-DMSO-d6: 1.09 (3H, t, J = 8.0 Hz), 1.95 (2H, sex, J = 8.0 Hz), 2.89-4.78 (6H, m), 3.35 (2H, t, J = 8.0 Hz), 7.00-7.27 (4H, m), 7.40-7.46 (2H, m), 8.09 (1H, d, J = 8.0 Hz), 12.08 (1H, s) | 2 |
| 3 | ESI+: 413<br>NMR-DMSO-d6: 1.69-1.81 (4H, m), 2.04-2.38 (7H, m), 3.09-3.13 (2H, m), 3.75-4.19 (3H, m), 5.74 (0.2H, br), 6.88-7.30 (4H, m), 7.77-7.86 (1H, m), 7.97-8.01 (1H, m), 8.16-8.18 (0.8H, m), 11.38 (1H, s)<br>mp: 291° C. (dec.) | 3 |
| 4 | ESI+: 472, 474<br>NMR-DMSO-d6: 2.82-2.85 (2H, m), 3.58-3.82 (2H, m), 4.56-4.74 (2H, m), 6.98-7.52 (10H, m), 10.15 (1H, br), 12.13 (1H, br)<br>mp: 373° C. (dec.) | 4 |
| 5 | ESI+: 563, 565 | 5 |
| 6 | ESI+: 382, 384 | 6 |
| 7 | ESI+: 456<br>NMR-DMSO-d6: 0.71-0.83 (2H, m), 0.95-1.08 (2H, m), 1.87-2.16 (5H, m), 3.54-3.67 (2H, m), 3.80-3.95 (1H, m), 3.98-4.11 (2H, m), 4.56 (2H, s), 4.91 (2H, s), 7.21-7.38 (5H, m), 7.39-7.47 (1H, m), 12.01 (1H, brs) | 7 |
| 8 | ESI+: 492<br>NMR-DMSO-d6: 1.83-2.03 (2H, m), 2.17-2.31 (2H, m), 2.33-2.63 (4H, m), 3.03-3.15 (2H, m), 3.15-3.31 (2H, m), 3.38-3.51 (2H, m), 4.30-4.71 (2H, m), 4.89 (2H, s), 7.20-7.38 (4H, m), 7.42 (1H, d, J = 8.0 Hz), 7.92 (1H, s), 12.10 (1H, s)<br>mp: 253° C.(dec.) | 8 |

TABLE 138

| Ex | Data | Syn |
|---|---|---|
| 9 | ESI+: 476<br>NMR-DMSO-d6: 1.79-1.93 (2H, m), 2.00-2.16 (2H, m), 2.27-2.44 (4H, m), 2.62-2.78 (2H, m), 2.83-2.96 (2H, m), 3.38 (2H, d, J = 4.0 Hz), 4.50 (2H, s), 4.89 (2H, s), 7.20-7.38 (4H, m), 7.42 (1H, d, J = 8.0 Hz), 7.92 (1H, s), 12.05 (1H, s)<br>mp: 248° C.(dec.) | 9 |
| 10 | ESI+: 430<br>NMR-DMSO-d6: 1.65-2.00 (4H, m), 2.21-2.38 (5H, m), 3.80-3.90 (1H, m), 4.51 (2H, s), 4.50-4.61 (1H, m), 4.89 (2H, s), 5.24 (1H, d, J = 4.4 Hz), 7.25-7.41 (3H, m), 7.42 (1H, d, J = 7.6 Hz), 8.24 (1H, s), 12.08 (1H, s)<br>mp: 316° C. (dec.) | 10 |

TABLE 138-continued

| Ex | Data | Syn |
|---|---|---|
| 11 | ESI+: 452, 454<br>NMR-DMSO-d6: 0.54-0.60 (1H, m), 0.78-0.92 (3H, m), 2.05-2.14 (1H, m), 2.23-2.38 (3H, m), 3.09-3.14 (2H, m), 3.73-3.77 (1.6H, m), 4.22 (0.4H, br), 5.62-5.84 (1.2H, m), 6.83 (0.2H, br), 7.30-7.38 (2.8H, m), 7.93 (1H, s), 8.15-8.17 (0.8H, m), 12.23 (1H, s)<br>mp: 309-311° C. | 11 |
| 12 | ESI+: 448, 450<br>NMR-DMSO-d6: 1.29-1.35 (4H, m), 2.17 (0.6H, br s), 2.32 (2.4H, s), 3.10-3.14 (2H, m), 3.36-3.42 (1H, m), 3.73-3.77 (1.6H, m), 4.22 (0.4H, br), 5.61 (0.2H, br), 6.83 (0.2H, br), 7.30-7.38 (2.8H, m), 8.14-8.17 (0.8H, m), 8.52 (1H, s),<br>12.40 (1H, s)<br>mp: 288-290° C. | 12 |
| 13 | ESI+: 482<br>NMR-DMSO-d6: 1.91-2.02 (2H, m), 2.18-2.42 (9H, m), 3.10-3.14 (2H, m), 3.74-3.78 (1.6H, m), 3.88-4.06 (1H, m), 4.23 (0.4H, br), 5.64 (0.2H, br), 6.62 (0.2H, br), 7.06-7.33 (2.8H, m), 7.91 (1H, s), 8.15-8.19 (0.8H, m), 12.11 (1H, s)<br>mp: 220° C. (dec.) | 13 |

TABLE 139

| Ex | Data | Syn |
|---|---|---|
| 14 (a) | ESI+: 429<br>NMR-DMSO-d6: 1.70-1.94 (3H, m), 2.24-2.32 (1H, m), 2.37 (3H, s), 3.40-3.55 (1H, m), 3.69-3.82 (2H, m), 3.94-3.98 (1H, m), 4.17-4.21 (1H, m), 4.51 (2H, s), 4.89 (2H, s), 7.23-7.34 (4H, m), 7.42 (1H, d, J = 7.6 Hz), 7.84 (1H, s), 7.86 (1H, s), 11.46 (1H, s) | 14 |
| 14 (b) | ESI+: 429<br>NMR-DMSO-d6: 1.70-1.94 (3H, m), 2.24-2.32 (1H, m), 2.37 (3H, s), 3.40-3.55 (1H, m), 3.69-3.82 (2H, m), 3.94-3.98 (1H, m), 4.17-4.21 (1H, m), 4.51 (2H, s), 4.89 (2H, s), 7.23-7.34 (4H, m), 7.42 (1H, d, J = 7.6 Hz), 7.84 (1H, s), 7.86 (1H, s), 11.46 (1H, s) | 14 |
| 15 | ESI+: 429<br>NMR-DMSO-d6: 1.67-1.69 (2H, m), 1.80-2.20 (3H, m), 2.36 (3H, s), 3.95-4.10 (1H, m), 4.51 (2H, s), 4.55-4.69 (1H, m), 4.85-4.88 (3H, m), 7.22-7.32 (4H, m), 7.42 (1H, d, J = 7.6 Hz), 7.80 (1H, s), 8.02 (1H, s), 11.38 (1H, s)<br>mp: 301-302° C. (dec.) | 15 |
| 16 | ESI+: 459, 461<br>NMR-DMSO-d6: 1.69-1.83 (1H, m), 2.17-2.72 (8H, m), 3.10-3.14 (2H, m), 3.72-3.78 (2.6H, m), 4.21 (0.4H, br), 5.76 (0.2H, br), 5.79-5.85 (0.2H, m), 6.90 (0.2H, br), 7.25-7.37 (2.8H, m), 7.79 (1H, s), 7.84 (1H, s), 8.14-8.17 (0.8H, m), 11.46 (1H, s) | 16 |
| 17 | ESI+: 493<br>NMR-DMSO-d6: 1.9-2.15 (4H, m), 3.0-3.1 (2H, m), 7.05 (1H, t, J = 8.8 Hz), 7.16 (1H, t, J = 8.8 Hz), 7.28 (1H, s), 7.66 (1H, s), 7.87 (1H, s), 8.1-8.2 (1H, m), 11.45 (1H, s) | 17 |
| 18 | ESI+: 505, 507<br>NMR-DMSO-d6: 1.62-1.79 (4H, m), 2.01-2.09 (2H, m), 2.13-2.20 (2H, m), 2.24 (0.6H, s), 2.30-2.43 (3.4H, m), 3.07-3.17 (2H, m), 3.50-3.59 (1H, m), 3.72-3.82 (1.6H, m), 4.15-4.27 (0.4H, br), 5.62-5.72 (0.2H, m), 6.86-6.96 (0.2H, m), 7.24 (1H, s), 7.27-7.33 (0.8H, m), 7.36 (1H, s), 7.79 (1H, s), 7.84 (1H, s), 8.12-8.18 (0.8H, m), 11.4 (1H, s), 12.0-12.1 (1H, s) | 18 |

TABLE 140

| Ex | Data | Syn |
|---|---|---|
| 19 | ESI+: 436, 438<br>NMR-DMSO-d6: 1.00-1.15 (3H, m), 1.85-2.00 (2H, m), 2.15-5.00 (11H, m), 6.99-7.35 (4H, m), 7.69-7.73 (1H, m)<br>mp: 198-202° C. | 1 |

TABLE 140-continued

| Ex | Data | Syn |
|---|---|---|
| 20 | ESI+: 465, 467<br>NMR-DMSO-d6: 1.04-1.12 (3H, m), 1.91-2.00 (2H, m), 2.37 (3H, s), 2.93-3.86 (10H, m), 7.06-7.45 (5H, m), 7.84 (1H, s)<br>mp: 186-188° C. | 1 |
| 21 | ESI+: 432<br>NMR-DMSO-d6: 1.05-1.11 (3H, m), 1.90-2.00 (2H, m), 2.20-4.20 (10H, m), 4.40-4.65 (2H, m), 7.26-7.87 (7H, m), 12.00 (1H, br s) | 1 |
| 22 | ESI+: 505<br>NMR-DMSO-d6: 1.00-1.15 (3H, m), 1.90-2.00 (2H, m), 2.45 (3H, s), 1.85-2.00 (2H, m), 3.25-3.39 (6H, m), 3.55-3.60 (4H, m), 4.13-4.16 (2H, m), 4.45 (2H, d, J = 5.9 Hz), 6.93-7.28 (4H, m), 7.42 (1H, s), 7.82 (1H, s), 8.64-8.80 (1H, m), 11.99 (1H, br s) | 1 |
| 23 | ESI+: 460<br>mp: 275-276° C. | 2 |
| 24 | ESI+: 477, 479<br>NMR-DMSO-d6: 1.88-2.03 (4H, m), 2.19-2.34 (3H, m), 2.75-2.91 (2H, m), 3.48-3.97 (7H, m), 4.41-4.85 (2H, m), 6.99-7.37 (4H, m), 7.81-7.85 (2H, m), 11.34 (1H, br s)<br>mp: 267° C. (dec.) | 2 |
| 25 | ESI+: 473<br>NMR-DMSO-d6: 1.92-2.03 (4H, m), 2.29-4.14 (13H, m), 4.42-4.55 (2H, m), 7.16-7.47 (6H, m), 7.79-7.83 (2H, m), 11.39 (1H, s) | 2 |
| 26 | ESI+: 486<br>NMR-DMSO-d6: 1.86-2.52 (12H, m), 2.81-3.17 (4H, m), 3.59-4.00 (5H, m), 4.35-4.57 (1H, m), 7.20-7.44 (6H, m), 7.73-7.83 (2H, m), 11.40 (1H, s)<br>mp: 189-192° C. | 2 |

TABLE 141

| Ex | Data | Syn |
|---|---|---|
| 27 | ESI+: 429<br>NMR-DMSO-d6: 1.86-2.08 (4H, m), 2.38 (3H, s), 3.60-3.73 (2H, m), 3.81-3.92 (1H, m), 3.92-4.03 (2H, m), 4.51 (2H, s), 4.88 (2H, s), 7.19-7.37 (4H, m), 7.42 (1H, d, J = 7.4 Hz), 7.82 (1H, s), 7.86 (1H, s), 11.42 (1H, s)<br>mp: 312° C. (dec.) | 2 |
| 28 | ESI+: 447<br>NMR-DMSO-d6: 1.89-2.06 (4H, m), 2.38 (3H, s), 3.63-3.70 (2H, m), 3.83-3.91 (1H, m), 3.95-4.00 (2H, m), 4.56 (2H, br s), 4.93 (2H, br s), 7.09-7.42 (4H, m), 7.83-7.86 (2H, m), 11.39-11.42 (1H, m)<br>mp: 201-203° C. | 2 |
| 29 | ESI+: 444<br>NMR-DMSO-d6: 1.90-2.07 (4H, m), 2.25-2.37 (3H, s), 3.10-3.27 (2H, m), 3.60-5.03 (9H, m), 7.16-7.24 (1H, m), 7.72-7.89 (3H, m), 8.09-8.43 (1H, m), 8.68-8.72 (1H, m), 11.48-11.51 (1H, m)<br>mp: 236-239° C. | 2 |
| 30 | ESI+: 464, 466<br>NMR-DMSO-d6: 1.93-2.09 (4H, m), 2.89-4.78 (11H, m), 7.00-7.48 (5H, m), 8.11 (1H, d, J = 9.1 Hz), 12.11 (1H, s),<br>mp: 318° C. (dec.) | 2 |
| 31 | ESI+: 422, 424<br>NMR-DMSO-d6: 1.09 (3H, t, J = 8.0 Hz), 1.95 (2H, sex, J = 8.0 Hz), 2.89-4.80 (6H, m), 3.35 (2H, t, J = 8.0 Hz), 7.00-7.47 (5H, m), 8.10 (1H, d, J = 8.0 Hz), 12.08 (1H, s)<br>mp: 293-295° C. | 2 |
| 32 | ESI+: 451, 453<br>NMR-DMSO-d6: 1.09 (3H, t, J = 7.4 Hz), 1.94 (2H, sex, J = 7.4 Hz), 3.02 (4H, br s), 3.35 (2H, t, J = 7.4 Hz), 3.57-3.80 (4H, m), 7.08 (1H, dt, J = 1.6, 8.0 Hz), 7.18 (1H, dd, J = 1.6, 8.0 Hz), 7.30-7.34 (1H, m), 7.41 (1H, dd, J = 1.6, 8.0 Hz), 7.44 (1H, dd, J = 1.6, 8.0 Hz), 7.47 (1H, d, J = 1.6 Hz), 8.08 (1H, d, J = 8.0 Hz), 12.08 (1H, s)<br>mp: 278-281° C. | 2 |

TABLE 142

| Ex | Data | Syn |
|---|---|---|
| 33 | ESI+: 392<br>NMR-DMSO-d6: 1.10 (3H, t, J = 8.0 Hz), 1.95 (2H, sex, J = 8.0 Hz), 3.36 (2H, t, J = 8.0 Hz), 4.78-4.80 (2H, m), 4.86-4.90 (2H, m), 7.10-7.18 (1.5H, m), 7.27-7.33 (2H, m), 7.43-7.46 (0.5H, m), 7.58-7.60 (2H, m), 8.08-8.11 (1H, m), 12.10 (1H, s)<br>mp: 293° C. (dec.) | 2 |
| 34 | ESI+: 447<br>NMR-DMSO-d6: 1.90-2.04 (4H, m), 2.38 (3H, s), 3.65-3.70 (2H, m), 3.87-3.99 (3H, m), 4.47-4.50 (2H, m), 4.84-4.88 (2H, m), 7.09-7.18 (1.5H, m), 7.26-7.29 (2H, m), 7.43-7.46 (0.5H, m), 7.87 (1H, s), 7.91 (1H, s), 11.49 (1H, s)<br>mp: 200-203° C. | 2 |
| 35 | ESI+: 449<br>NMR-DMSO-d6: 1.89-2.03 (4H, m), 2.23 (1.2H, s), 2.35 (1.8H, s), 2.78 (1.2H, br s), 2.91-2.94 (0.8H, m), 3.44-4.92 (9H, m), 6.74 (0.4H, d, J = 5.0 Hz), 6.99 (0.6H, d, J = 5.0 Hz), 7.12 (0.4H, s), 7.16 (0.6H, s), 7.31 (0.4H, d, J = 5.0 Hz), 7.41 (0.6H, d, J = 5.0 Hz), 7.82-7.86 (2H, m), 11.39 (1H, s)<br>mp: 283-285° C. | 2 |
| 36 | ESI+: 457<br>NMR-DMSO-d6: 1.61-1.81 (2H, m), 1.76 (1.4H, s), 1.87-2.05 (4H, m), 2.21 (1.6H, s), 2.99 (2H, br s), 3.49-4.87 (9H, m), 6.16-6.18 (0.46H, m), 6.87-6.91 (0.46H, m), 6.98 (0.54H, s), 6.99 (0.46H, s), 7.13-7.23 (2.54H, m), 7.34-7.36 (0.54H, m), 7.77 (0.46H, s), 7.84 (0.54H, s), 7.86 (0.54H, s), 7.90 (0.46H, s), 11.25 (0.54H, s), 11.37 (0.46H, s)<br>mp: 170-172° C. | 2 |
| 37 | ESI+: 417<br>NMR-DMSO-d6: 1.43 (6H, d, J = 8.0 Hz), 2.93-3.97 (6H, m), 4.40-4.56 (2H, m), 7.32-7.45 (7H, m), 7.94 (1H, s), 8.12 (1H, d, J = 8.0 Hz), 11.59 (1H, s)<br>mp: 268-271° C. | 2 |

TABLE 143

| Ex | Data | Syn |
|---|---|---|
| 38 | ESI+: 421, 423<br>NMR-DMSO-d6: 1.44 (6H, d, J = 8.0 Hz), 2.89-4.78 (7H, m), 7.00-7.43 (5H, m), 7.92 (1H, s), 8.14 (1H, d, J = 8.0 Hz), 11.55 (1H, s)<br>mp: 328-329° C. | 2 |
| 39 | ESI+: 443<br>NMR-DMSO-d6: 1.28-1.39 (1H, m), 1.49-1.58 (2H, m), 1.68-1.78 (3H, m), 1.87-1.90 (2H, m), 2.18-2.21 (2H, m), 3.56-3.62 (1H, m), 3.97 (3H, s), 4.58 (2H, s), 4.84 (2H, s), 7.23-7.33 (4H, m), 7.40-7.41 (1H, m), 7.57 (1H, s), 7.90 (1H, s), 11.44 (1H, s)<br>mp: 299-303° C. | 2 |
| 40 | ESI+: 487<br>NMR-DMSO-d6: 1.28-1.37 (1H, m), 1.48-1.89 (7H, m), 2.14-2.20 (2H, m), 2.86-3.32 (3H, m), 3.57-3.70 (2H, m), 3.89-4.11 (1H, m), 4.42-4.52 (2H, m), 7.18-7.46 (7H, m), 7.52 (1H, s), 7.92-7.93 (1H, m), 11.45-11.47 (1H, m)<br>mp: 182-186° C. | 2 |
| 41 | ESI+: 443 | 2 |
| 42 | ESI+: 473 | 2 |
| 43 | ESI+: 473 | 2 |
| 44 | ESI+: 501 | 2 |
| 45 | ESI+: 542 | 2 |
| 46 | ESI+: 482 | 2 |
| 47 | ESI+: 547 | 2 |
| 48 | ESI+: 561 | 2 |
| 49 | ESI+: 517 | 2 |
| 50 | ESI+: 525 | 2 |
| 51 | ESI+: 585 | 2 |
| 52 | ESI+: 520 | 2 |
| 53 | ESI+: 580 | 2 |
| 54 | ESI+: 534 | 2 |

TABLE 144

| Ex | Data | Syn |
|---|---|---|
| 55 | ESI+: 461 | 2 |
| 56 | ESI+: 461 | 2 |
| 57 | ESI+: 479 | 2 |
| 58 | ESI+: 477, 479 | 2 |
| 59 | ESI+: 511 | 2 |
| 60 | ESI+: 511 | 2 |
| 61 | ESI+: 511 | 2 |
| 62 | ESI+: 468 | 2 |
| 63 | ESI+: 488 | 2 |
| 64 | ESI+: 488 | 2 |
| 65 | ESI+: 473 | 2 |
| 66 | ESI+: 503 | 2 |
| 67 | ESI+: 536 | 2 |
| 68 | ESI+: 501<br>NMR-DMSO-d6: 1.88-2.05 (4H, m), 2.19 (1.2H, s), 2.35 (1.8H, s), 2.87 (1.2H, br s), 3.01-3.04 (0.8H, m), 3.45-5.24 (12H, m), 7.13-7.21 (1H, m), 7.35-7.52 (2H, m), 7.75-7.87 (2H, m), 8.01 (1H, s), 11.54-11.56 (1H, m)<br>mp: 192-194° C. | 2 |
| 69 | ESI+: 501 | 2 |
| 70 | ESI+: 489 | 2 |
| 71 | ESI+: 495 | 2 |
| 72 | ESI+: 495 | 2 |
| 73 | ESI+: 443 | 2 |
| 74 | ESI+: 459 | 2 |

TABLE 145

| Ex | Data | Syn |
|---|---|---|
| 75 | ESI+: 443<br>NMR-DMSO-d6: 1.93-2.04 (4H, m), 2.15-2.39 (6H, m), 3.07-3.17 (2H, m), 3.64-4.19 (7H, m), 5.60 (0.3H, br), 6.63 (0.3H, br), 7.05-7.25 (2.7H, m), 7.88-7.89 (2H, m), 8.03-8.06 (0.7H, m), 11.48 (1H, s)<br>mp: 282-284° C. | 2 |
| 76 | ESI+: 447<br>NMR-DMSO-d6: 1.82-2.09 (4H, m), 2.18-2.46 (3H, m), 3.06-3.21 (2H, m), 3.39-4.04 (6.6H, m), 4.23 (0.4H, br), 5.67 (0.2H, br), 6.68 (0.2H, br), 7.01-7.31 (2.8H, m), 7.82-7.94 (2H, m), 8.10-8.22 (0.8H, m), 11.49 (1H, s)<br>mp: 297-298° C. | 2 |
| 77 | ESI+: 463, 465<br>NMR-DMSO-d6: 1.88-2.08 (4H, m), 2.18-2.48 (3H, m), 3.06-3.20 (2H, m), 3.62-3.71 (2H, m), 3.71-3.83 (1.6H, m), 3.83-3.93 (1H, m), 3.93-4.04 (2H, m), 4.22 (0.4H, br), 5.67 (0.2H, br), 6.90 (0.2H, br), 7.16-7.32 (1.8H, m), 7.37 (1H, s), 7.83 (1H, s), 7.88 (1H, s), 8.10-8.22 (0.8H, m), 11.45 (1H, s)<br>mp: 265-266° C. | 2 |
| 78 | ESI+: 474<br>NMR-DMSO-d6: 1.89-2.05 (4H, m), 2.33-2.40 (3H, m), 3.23-3.27 (2H, m), 3.49-4.25 (7H, m), 6.33 (0.1H, br), 7.31 (1H, s), 7.55-7.57 (1H, m), 7.88-8.02 (3H, m), 8.93 (0.9H, br s), 11.51 (1H, s)<br>mp: 301-304° C. | 2 |
| 79 | ESI+: 497<br>NMR-DMSO-d6: 1.90-2.05 (4H, m), 2.32-2.40 (3H, m), 3.19-3.22 (2H, m), 3.64-4.21 (7H, m), 5.71 (0.2H, br), 7.30 (1H, br s), 7.45-7.53 (2H, m), 7.90 (2H, br s), 8.46 (0.8H, br s), 11.52 (1H, s)<br>mp: 276-277° C. | 2 |
| 80 | ESI+: 536<br>NMR-DMSO-d6: 1.90-2.04 (4H, m), 2.33-2.38 (3H, m), 2.61-2.67 (6H, m), 3.16-3.23 (2H, m), 3.34-4.15 (7H, m), 5.87 (0.3H, br), 7.28 (1H, br s), 7.45-7.65 (2H, m), 7.88-7.89 (2H, m), 8.36 (0.7H, br), 11.50 (1H, s)<br>mp: 209-212° C. | 2 |

TABLE 146

| Ex | Data | Syn |
|---|---|---|
| 81 | ESI+: 498 | 2 |
| 82 | ESI+: 443 | 2 |
| 83 | ESI+: 457 | 2 |
| 84 | ESI+: 473 | 2 |
| 85 | ESI+: 472 | 2 |
| 86 | ESI+: 445 | 2 |
| 87 | ESI+: 446 | 2 |
| 88 | ESI+: 442<br>NMR-DMSO-d6: 0.98 (3H, d, J = 6.5 Hz), 1.26-1.36 (2H, m), 1.48-1.56 (1H, m), 1.71-1.86 (4H, m), 2.17-2.20 (2H, m), 2.39 (3H, s), 3.51-3.57 (1H, m), 4.51 (2H, s), 4.89 (2H, s), 7.23-7.34 (4H, m), 7.42 (1H, d, J = 8.0 Hz), 7.81 (1H, s), 12.02 (1H, br s)<br>mp: 318-321° C. | 2 |
| 89 | ESI+: 415<br>NMR-DMSO-d6: 2.38 (3H, s), 2.40-2.50 (2H, m), 3.91 (2H, t, J = 6.8 Hz), 4.16-4.23 (2H, m), 4.42-4.49 (1H, m), 4.52 (2H, s), 4.89 (2H, s), 7.23-7.34 (4H, m), 7.41 (1H, d, J = 8.0 Hz), 7.92 (1H, s), 7.96 (1H, s), 11.54 (1H, s)<br>mp: 270° C. (dec.) | 3 |
| 90 | ESI+: 414<br>NMR-DMSO-d6: 1.72-1.83 (4H, m), 2.13-2.27 (4H, m), 2.39 (3H, s), 4.05-4.12 (1H, m), 4.51 (2H, s), 4.89 (2H, s), 7.24-7.34 (4H, m), 7.41-7.43 (1H, m), 7.99 (1H, s), 12.01 (1H, s)<br>mp: 318° C. (dec.) | 3 |
| 91 | ESI+: 462, 464<br>NMR-DMSO-d6: 1.70-1.82 (4H, m), 2.11-2.36 (7H, m), 2.76-2.92 (2H, m), 3.49-3.52 (1H, m), 3.92-4.12 (2H, m), 4.40-4.95 (2H, m), 6.98-7.38 (4H, m), 7.94-7.98 (1H, m), 11.95 (1H, s)<br>mp: 236-237° C. | 3 |

TABLE 147

| Ex | Data | Syn |
|---|---|---|
| 92 | ESI+: 478, 480<br>NMR-DMSO-d6: 1.93-2.10 (4H, m), 2.22 (1.2H, s), 2.37 (1.8H, s), 2.75-2.92 (2H, m), 3.49-3.51 (1H, m), 3.67-3.74 (2H, m), 3.95-4.00 (4H, m), 4.40-4.96 (2H, m), 6.97-7.38 (4H, m), 7.82-7.86 (1H, m), 11.99 (1H, s)<br>mp: 269° C. (dec.) | 3 |
| 93 | ESI+: 430<br>NMR-DMSO-d6: 1.93-2.12 (4H, m), 2.39 (3H, s), 3.68-3.73 (2H, m), 3.94-4.02 (3H, m), 4.50 (2H, s), 4.89 (2H, s), 7.23-7.35 (4H, m), 7.41-7.43 (1H, m), 7.87 (1H, s), 12.05 (1H, s)<br>mp: 305° C. (dec.) | 3 |
| 94 | ESI+: 444<br>NMR-DMSO-d6: 1.93-2.12 (5.5H, m), 2.30 (1.5H, s), 2.39-2.41 (3H, m), 3.68-3.73 (2H, m), 3.94-4.00 (3H, m), 4.46-4.50 (2H, m), 4.84-4.90 (2H, m), 7.03-7.25 (3H, m), 7.31 (1H, br s), 7.87 (1H, s), 12.04 (1H, s)<br>mp: 262-263° C. | 3 |
| 95 | ESI+: 464, 466<br>NMR-DMSO-d6: 1.97-2.11 (4H, m), 2.40-2.41 (3H, m), 3.68-3.73 (2H, m), 3.96-4.00 (3H, m), 4.51-4.59 (2H, m), 4.89-4.97 (2H, m), 7.21-7.24 (0.5H, m), 7.32-7.40 (3.5H, m), 7.87 (1H, s), 12.03-12.07 (1H, m)<br>mp: 329° C. (dec.) | 3 |
| 96 | ESI+: 457<br>NMR-DMSO-d6: 1.73-1.75 (4H, m), 2.04-2.41 (6H, m), 2.49-2.51 (3H, m), 2.91-3.21 (1H, m), 3.53-3.73 (1H, m), 3.90-4.15 (2H, m), 4.42-4.55 (2H, m), 7.08-7.47 (6H, m), 7.93-7.97 (1H, m), 7.74-7.76 (1H, m), 11.34 (1H, s)<br>mp: 304-305° C. | 3 |
| 97 | ESI+: 470<br>NMR-DMSO-d6: 1.64-1.84 (4H, m), 1.90-3.52 (16H, m), 3.86-4.09 (1H, m), 4.30-4.63 (1H, m), 6.89-7.67 (6H, m), 8.22 (1H, m), 11.15-11.63 (1H, m)<br>mp: 246-248° C. | 3 |

TABLE 148

| Ex | Data | Syn |
|---|---|---|
| 98 | ESI+: 461, 463<br>NMR-DMSO-d6: 1.70-1.79 (4H, m), 2.06-2.34 (7H, s), 2.76-2.92 (2H, m), 3.50-3.53 (1H, m), 3.94-4.04 (2H, m), 4.41-4.87 (2H, m), 7.01-7.37 (4H, m), 7.76 (1H, s), 7.94-7.98 (1H, m), 11.31 (1H, s)<br>mp: 297-299° C. | 3 |
| 99 | ESI+: 413<br>NMR-DMSO-d6: 1.70-1.80 (4H, m), 2.05-2.22 (4H, m), 2.37 (3H, s), 3.96-4.04 (1H, m), 4.51 (2H, s), 4.88 (2H, s), 7.23-7.43 (5H, m), 7.77 (1H, s), 7.99 (1H, s), 11.36 (1H, m)<br>mp: 304° C. (dec.) | 3 |
| 100 | ESI+: 431<br>NMR-DMSO-d6: 1.73-1.79 (4H, m), 2.05-2.21 (4H, m), 2.37 (3H, s), 3.96-4.03 (1H, m), 4.47-4.50 (2H, m), 4.84-4.87 (2H, m), 7.09-7.29 (3.5H, m), 7.42-7.46 (0.5H, m), 7.77-7.99 (2H, m), 11.36 (1H, s)<br>mp: 228-231° C. | 3 |
| 101 | FAB−: 414<br>NMR-DMSO-d6: 1.94-2.11 (4H, m), 3.66-3.72 (2H, m), 3.87-4.02 (3H, m), 4.82 (2H, s), 4.91 (2H, s), 7.28-7.43 (4H, m), 7.59-7.62 (2H, m), 8.10-8.12 (1H, m), 12.11 (1H, s)<br>mp: 303° C. (dec.) | 3 |
| 102 | ESI+: 429<br>NMR-DMSO-d6: 1.95-2.11 (4H, m), 2.31-2.57 (3H, m), 3.16-4.25 (9H, m), 5.80 (0.2H, br), 6.90-7.37 (4H, m), 7.93-7.95 (2H, m), 8.23-8.25 (0.8H, m), 11.52 (1H, s)<br>mp: 216-219° C. | 3 |
| 103 | ESI+: 463, 465<br>NMR-DMSO-d6: 1.90-2.06 (4H, m), 2.37 (3H, s), 3.64-4.00 (5H, m), 4.48-4.50 (2H, m), 4.85-4.87 (2H, m), 7.26-7.52 (4H, m), 7.87-7.89 (2H, m), 11.47-11.48 (1H, m)<br>mp: 210-214° C. | 3 |

TABLE 149

| Ex | Data | Syn |
|---|---|---|
| 104 | ESI+: 443<br>NMR-DMSO-d6: 1.89-2.06 (4H, m), 2.28 (1.5H, s), 2.32 (1.5H, s), 2.37 (3H, s), 3.64-3.70 (2H, m), 3.84-4.00 (3H, m), 4.44-4.47 (2H, m), 4.83-4.84 (2H, m), 7.04-7.14 (2H, m), 7.23-7.30 (2H, m), 7.85-7.86 (2H, m), 11.42-11.43 (1H, m)<br>mp: 203-205° C. | 3 |
| 105 | ESI+: 430<br>NMR-DMSO-d6: 1.91-2.05 (4H, m), 2.27 (3H, s), 3.15-3.20 (2H, m), 3.64-4.20 (7H, m), 6.96-6.99 (1H, m), 7.22 (1H, s), 7.72-7.76 (2H, m), 7.82 (1H, s), 8.01 (1H, s), 11.53 (1H, s)<br>mp: 341° C. (dec.) | 3 |
| 106 | ESI+: 443<br>NMR-DMSO-d6: 1.93-2.09 (5.5H, m), 2.30 (1.5H, s), 2.38-2.39 (3H, m), 3.65-3.71 (2H, m), 3.91-4.18 (3H, m), 4.47-4.51 (2H, m), 4.84-4.90 (2H, m), 7.03-7.24 (3H, m), 7.30 (1H, s), 7.89 (1H, s), 8.00-8.01 (1H, m), 11.59 (1H, s)<br>mp: 206-208° C. | 3 |
| 107 | ESI+: 463, 465<br>NMR-DMSO-d6: 1.91-2.05 (4H, m), 2.39-3.40 (3H, m), 3.65-3.71 (2H, m), 3.88-4.00 (3H, m), 4.52-4.59 (2H, m), 4.87-4.97 (2H, m), 7.22-7.42 (4H, m), 7.88 (1H, s), 7.93-7.95 (1H, m), 11.51-11.52 (1H, m)<br>mp: 198-200° C. | 3 |
| 108 | ESI+: 490, 492<br>NMR-DMSO-d6: 1.89-2.09 (6H, m), 2.73-2.90 (2H, m), 3.44-3.47 (1.3H, m), 3.94 (0.7H, br s), 4.36-4.80 (2H, m), 6.81-6.83 (1H, m), 6.95-7.37 (5H, m), 7.96-7.99 (1H, m), 12.08 (1H, s)<br>mp: 310-312° C. | 3 |
| 109 | ESI+: 442<br>NMR-DMSO-d6: 2.06 (3H, s), 2.10 (3H, s), 4.63 (2H, s), 5.40 (2H, s), 6.83 (1H, s), 7.09-7.64 (6H, m), 7.97-7.99 (1H, m), 12.15 (1H, br s) | 3 |

TABLE 149-continued

| Ex | Data | Syn |
|---|---|---|
| 110 | ESI+: 481 | 4 |
| | mp: 286° C. (dec.) | |
| 111 | ESI+: 472, 474 | 5 |
| 112 | ESI+: 577, 579 | 5 |

TABLE 150

| Ex | Data | Syn |
|---|---|---|
| 113 | ESI+: 529, 531 | 5 |
| 114 | ESI+: 486 | 5 |
| 115 | ESI+: 530 | 5 |
| 116 | ESI+: 577 | 5 |
| 117 | ESI+: 591 | 5 |
| 118 | ESI+: 543 | 5 |
| 119 | ESI+: 528 | 5 |
| 120 | ESI+: 530 | 5 |
| 121 | ESI+: 564, 566 | 5 |
| 122 | ESI+: 486 | 5 |
| 123 | ESI+: 533 | 5 |
| 124 | ESI+: 547 | 5 |
| 125 | ESI+: 561 | 5 |
| 126 | ESI+: 499 | 5 |
| 127 | ESI+: 484 | 5 |
| 128 | ESI+: 502 | 5 |
| 129 | ESI+: 486 | 5 |
| 130 | ESI+: 520, 522 | 5 |
| 131 | ESI+: 520, 522 | 5 |
| 132 | ESI+: 396, 398 | 6 |
| 133 | ESI+: 396, 398 | 6 |
| 134 | ESI+: 410, 412 | 6 |
| 135 | ESI+: 363 | 6 |
| 136 | ESI+: 410, 412 | 6 |
| 137 | ESI+: 390 | 6 |
| 138 | ESI+: 392 | 6 |
| 139 | ESI+: 404 | 6 |

TABLE 151

| Ex | Data | Syn |
|---|---|---|
| 140 | ESI+: 445 | 6 |
| 141 | ESI+: 328 | 6 |
| 142 | ESI+: 340 | 6 |
| 143 | ESI+: 356 | 6 |
| 144 | ESI+: 370 | 6 |
| 145 | ESI+: 390 | 6 |
| 146 | ESI+: 423 | 6 |
| 147 | ESI+: 417 | 6 |
| 148 | ESI+: 383 | 6 |
| 149 | ESI+: 372 | 6 |
| 150 | ESI+: 454 | 6 |
| 151 | ESI+: 388 | 6 |
| 152 | ESI+: 362 | 6 |
| 153 | ESI+: 396, 398 | 6 |
| 154 | ESI+: 396, 398 | 6 |
| 155 | ESI+: 491 | 6 |
| 156 | ESI+: 452 | 6 |
| 157 | ESI+: 402 | 6 |
| 158 | ESI+: 376 | 6 |
| 159 | ESI+: 390 | 6 |
| 160 | ESI+: 406 | 6 |
| 161 | ESI+: 420 | 6 |
| 162 | ESI+: 420 | 6 |
| 163 | ESI+: 433 | 6 |
| 164 | ESI+: 452 | 6 |
| 165 | ESI+: 374 | 6 |
| 166 | ESI+: 406 | 6 |

TABLE 152

| Ex | Data | Syn |
|---|---|---|
| 167 | ESI+: 406 | 6 |
| 168 | ESI+: 422, 424 | 6 |
| 169 | ESI+: 456 | 6 |
| 170 | ESI+: 456 | 6 |
| 171 | ESI+: 456 | 6 |
| 172 | ESI+: 418 | 6 |
| 173 | ESI+: 448 | 6 |
| 174 | ESI+: 462 | 6 |
| 175 | ESI+: 492 | 6 |
| 176 | ESI+: 418 | 6 |
| 177 | ESI+: 418 | 6 |
| 178 | ESI+: 464 | 6 |
| 179 | ESI+: 465 | 6 |
| 180 | ESI+: 479 | 6 |
| 181 | ESI+: 416 | 6 |
| 182 | ESI+: 430 | 6 |
| 183 | ESI+: 412 | 6 |
| 184 | ESI+: 432 | 6 |
| 185 | ESI+: 432 | 6 |
| 186 | ESI+: 445 | 6 |
| 187 | ESI+: 444 | 6 |
| 188 | ESI+: 445 | 6 |
| 189 | ESI+: 465, 467 | 6 |
| 190 | ESI+: 445 | 6 |
| 191 | ESI+: 418 | 6 |
| 192 | ESI+: 416 | 6 |
| 193 | ESI+: 418 | 6 |

TABLE 153

| Ex | Data | Syn |
|---|---|---|
| 194 | ESI+: 431 | 6 |
| 195 | ESI+: 432 | 6 |
| 196 | ESI+: 431 | 6 |
| 197 | ESI+: 418 | 6 |
| 198 | ESI+: 431 | 6 |
| 199 | ESI+: 465, 467 | 6 |
| 200 | ESI+: 418 | 6 |
| 201 | ESI+: 424 | 6 |
| 202 | ESI+: 435 | 6 |
| 203 | ESI+: 435 | 6 |
| 204 | ESI+: 435 | 6 |
| 205 | ESI+: 447 | 6 |
| 206 | ESI+: 447 | 6 |
| 207 | ESI+: 451, 453 | 6 |
| 208 | ESI+: 485, 487 | 6 |
| 209 | ESI+: 493 | 6 |
| 210 | ESI+: 402 | 6 |
| 211 | ESI+: 402 | 6 |
| 212 | ESI+: 445 | 6 |
| 213 | ESI+: 465 | 2 |
| | NMR-DMSO-d6: 1.89-2.05 (4H, m), 2.39 (3H, s), 3.41-3.70 (2H, m), 3.85-3.99 (3H, m), 4.60 (2H, s), 4.96 (2H, s), 7.17-7.27 (3H, m), 7.86-7.87 (2H, m), 11.44 (1H, s) | |
| | mp: 199-201° C. (dec.) | |

TABLE 154

| Ex | Data | Syn |
|---|---|---|
| 214 | ESI+: 454<br>NMR-DMSO-d6: 1.92-2.06 (4H, m), 2.39-2.41 (3H, m),<br>3.65-3.71 (2H, m), 3.88-3.99 (3H, m), 4.60-4.71 (2H, m),<br>4.97-5.05 (2H, m), 7.30 (1H, d, J = 3.2 Hz), 7.48-7.61 (1.6H,<br>m), 7.76-7.82 (1.4H, m), 7.88 (1H, br s), 7.93-7.96 (1H, m),<br>11.54 (1H, s)<br>mp: 328° C. (dec.) | 2 |
| 215 | ESI+: 459<br>NMR-DMSO-d6: 1.91-2.05 (4H, m), 2.38 (3H, s),<br>3.64-3.71 (2.8H, m), 3.85-4.00 (5.2H, m), 4.39-4.50 (2H, m),<br>4.77-4.88 (2H, m), 6.81-7.01 (2H, m), 7.26-7.34 (2H, m), 7.87 (1H, s),<br>7.92-7.94 (1H, m), 11.48-11.90 (1H, m)<br>mp: 209° C. (dec.) | 2 |
| 216 | ESI+: 487<br>NMR-DMSO-d6: 1.89-2.04 (4H, m), 2.17 (1.3H, s),<br>2.35 (1.7H, s), 2.82-2.88 (1H, m), 3.00-3.03 (1H, m),<br>3.43-4.06 (7H, m), 4.76-5.29 (2H, m), 7.10-7.18 (1H, m),<br>7.31-7.48 (2H, m), 7.72-7.86 (2H, m), 7.91 (1H, s), 11.43-11.45 (1H,<br>m)<br>mp: 212-213° C. | Pr-3 |
| 217 | ESI+: 443<br>NMR-DMSO-d6: 1.90-2.05 (4H, m), 2.21 (3H, s), 2.99 (2H, t,<br>J = 7.3 Hz), 3.65-3.71 (2H, m), 3.80-4.00 (8H, m),<br>7.06-7.18 (3H, m), 7.39 (1H, s), 7.88 (1H, s), 7.90 (1H, s), 11.4 (1H, s) | 2 |
| 218 | ESI+: 514<br>NMR-DMSO-d6: 1.89-2.04 (4H, m), 2.21 (1H, s), 2.33 (2H,<br>s), 2.56-4.74 (17H, m), 7.03-7.30 (4H, m), 7.85 (1H, s),<br>7.91 (1H, s), 11.44-11.45 (1H, m) | 2 |
| 219 | ESI+: 469<br>NMR-DMSO-d6: 0.59-0.63 (1H, m), 0.68-0.72 (1H, m),<br>0.78-0.83 (1H, m), 0.95-0.99 (1H, m), 1.57-1.64 (0.5H, m),<br>1.87-2.05 (4.5H, m), 2.39-2.40 (3H, m), 3.57-4.01 (5.0H, m),<br>4.51 (1H, s), 4.60 (1H, s), 4.89 (1H, s), 4.96 (1H, s),<br>6.79 (0.5H, d, J = 8.4 Hz), 6.87 (0.5H, d, J = 8.4 Hz), 7.02 (0.5H,<br>d, J = 8.4 Hz), 7.17-7.29 (2.5H, m), 7.87-7.90 (2H, m),<br>11.46-11.48 (1H, m)<br>mp: 286° C. (dec.) | 2 |

TABLE 155

| Ex | Data | Syn |
|---|---|---|
| 220 | ESI+: 487<br>NMR-DMSO-d6: 1.29-1.38 (1H, m), 1.48-1.58 (2H, m),<br>1.69-1.78 (3H, m), 1.86-1.90 (2H, m), 2.18-2.21 (2H, m),<br>2.70-5.30 (11H, m), 6.94-7.55 (6H, m), 7.96 (1H, s),<br>11.39-11.51 (1H, m)<br>mp: 215° C. (dec.) | 2 |
| 221 | ESI+: 514<br>NMR-DMSO-d6: 1.90-2.05 (4H, m), 2.37-2.39 (3H, m),<br>2.81-2.84 (1.2H, m), 2.98-3.00 (2.8H, m), 3.55-4.00 (9H, m),<br>4.48-4.51 (2H, m), 4.86 (2H, s), 6.88-6.96 (1.7H, m),<br>7.09-7.10 (0.3H, m), 7.23-7.34 (2H, m), 7.87-7.88 (1H, m),<br>7.92-7.93 (1H, m), 111.46-11.48 (1H, m)<br>mp: 225° C. (dec.) | 2 |
| 222 | ESI+: 555<br>NMR-DMSO-d6: 1.90-2.05 (4H, m), 2.38 (1.5H, s),<br>2.40 (1.5H, s), 3.65-3.73 (2H, m), 3.87-3.87 (3H, m), 4.40 (1H, s),<br>4.65 (1H, s), 4.74 (1H, s), 5.02 (1H, s), 7.07 (0.5H, dd, J = 8.0,<br>8.0 Hz), 7.13 (0.5H, dd, J = 8.0, 8.0 Hz),<br>7.25-7.31 (1.5H, m), 7.45 (0.5H, d, J = 8.0 Hz), 7.68 (0.5H, d, J = 8.0 Hz),<br>7.71 (0.5H, d, J = 8.0 Hz), 7.87 (0.5H, s), 7.88 (0.5H, s),<br>7.91 (0.5H, s), 7.93 (0.5H, s), 11.49-11.50 (1H, m)<br>mp: 313° C. (dec.) | 2 |
| 223 | ESI+: 463, 465<br>NMR-DMSO-d6: 1.89-2.04 (4H, m), 2.29-2.40 (3H, m),<br>3.08-3.12 (2H, m), 3.65-3.71 (2H, m), 3.77-4.00 (5H, m),<br>5.58 (0.2H, br), 6.99-7.32 (3H, m), 7.89-7.94 (2H, m),<br>8.19 (0.8H, br s), 11.57 (1H, s)<br>mp: 188-189° C. | 2 |

TABLE 155-continued

| Ex | Data | Syn |
|---|---|---|
| 224 | ESI+: 460<br>NMR-DMSO-d6: 1.91-2.05 (4H, m), 2.29 (0.6H, s),<br>2.40 (2.4H, s), 3.12-3.17 (2H, m), 3.65-3.72 (2.6H, m),<br>3.75-3.79 (1.6H, m), 3.86 (2.4H, s), 3.97-4.00 (3H, m),<br>4.16-4.23 (0.4H, m), 6.36 (0.2H, br), 6.80-6.85 (1H, m), 7.27-7.32 (1H, m), 7.90-7.94 (1H, m), 8.02-8.05 (1H, m), 8.82 (0.8H, m),<br>11.65 (1H, s)<br>mp: 232-233° C. | 2 |

TABLE 156

| Ex | Data | Syn |
|---|---|---|
| 225 | ESI+: 511, 513<br>NMR-DMSO-d6: 1.89-2.04 (4H, m), 2.21 (1.2H, s),<br>2.35 (1.8H, s), 2.72-2.75 (1H, m), 2.85-2.88 (1H, m),<br>3.17-3.99 (7H, m), 4.42 (1H, s), 4.80 (1H, br),<br>7.10 (0.4H, s), 7.19-7.20 (1H, m), 7.49-7.54 (1.6H, m),<br>7.83-7.86 (1H, m),<br>7.90-7.92 (1H, m), 11.45 (1H, s)<br>mp: 188-190° C. (dec.) | 2 |
| 226 | ESI+: 447<br>NMR-DMSO-d6: 1.90-2.05 (4H, m), 2.24-2.35 (3H, m),<br>2.45-2.67 (2H, m), 3.38-4.99 (12H, m), 7.12 (0.3H, s),<br>7.17 (0.7H, s), 7.27 (1H, s), 7.84 (0.3H, s), 7.86 (0.7H, s),<br>7.94-7.96 (1H, m), 11.50-11.51 (1H, m)<br>mp: 192-194° C. (dec.) | 2 |
| 227 | ESI+: 463, 465<br>NMR-DMSO-d6: 1.88-2.05 (4H, m), 2.26-2.39 (3H, m),<br>3.11-3.15 (2H, m), 3.64-3.70 (2H, m), 3.80-4.22 (5H, m),<br>5.64 (0.3H, br), 6.92-8.13 (5.7H, m), 11.49 (1H, s)<br>mp: 272-273° C. | 2 |
| 228 | ESI+: 507, 509<br>NMR-DMSO-d6: 1.89-2.05 (4H, m), 2.24-2.39 (3H, m),<br>3.10-3.17 (2H, m), 3.64-3.99 (6.6H, m), 4.20 (0.4H, br),<br>5.61 (0.2H, br), 7.02 (0.2H, br), 7.22-7.27 (1H, m),<br>7.43-7.50 (1.8H, m), 7.88-7.91 (2.0H, m),<br>8.10-8.12 (0.8H, m), 11.53 (1H, s)<br>mp: 219-220° C. (dec.) | 2 |
| 229 | ESI+: 481, 483<br>NMR-DMSO-d6: 1.90-2.05 (4H, m), 2.40 (3H, br s),<br>3.11-3.15 (2H, m), 3.65-3.71 (2H, m), 3.78-4.05 (5H, m),<br>7.29 (1H, br s), 7.41 (0.5H, s), 7.43 (0.5H, s),<br>7.89 (1H, br s), 7.95 (1 H, s), 8.27-8.28 (1H, m),<br>11.58 (1 H, s)<br>mp: 315° C. (dec.) | 2 |

TABLE 157

| Ex | Data | Syn |
|---|---|---|
| 230 | ESI+: 463, 465<br>NMR-DMSO-d6: 1.71-1.93 (3H, m), 2.24-2.39 (4H, m),<br>3.11-3.17 (2H, m), 3.44-3.51 (1H, m), 3.70-3.84 (3.6H, m),<br>3.85-4.23 (2.4H, m), 5.68 (0.2H, br), 6.90 (0.2H, br),<br>7.23-7.37 (2.8H, m), 7.87 (1H, s), 7.88 (1H, s),<br>8.14-8.17 (0.8H, m), 11.54 (1H, s)<br>mp: 206-208° C. | 2 |
| 231 | ESI+: 463, 465<br>mp: 200-203° C. | 2 |
| 232 | ESI+: 443<br>NMR-DMSO-d6: 1.72-1.96 (3H, m), 2.09-2.39 (7H, m),<br>3.45-3.50 (1H, m), 3.57-3.79 (2H, m), 3.94-3.97 (1H, m),<br>4.17-4.21 (1H, m), 4.47-4.52 (2H, m), 4.84-4.90 (2H, m),<br>7.04-7.27 (4H, m), 7.86-7.87 (2H, m), 11.49 (1H, s)<br>mp: 283° C.(dec.) | 2 |
| 233 | ESI+: 443<br>NMR-DMSO-d6: 1.71-1.93 (3H, m), 2.16-2.38 (7H, m),<br>3.05-3.12 (2H, m), 3.44-4.22 (7H, m), 5.61-5.62 (0.2H, m),<br>6.62-6.64 (0.2H, m), 7.05-7.26 (2.8H, m), 7.87 (1H, s),<br>7.88 (1H, s), 8.04-8.06 (0.8H, m), 11.51 (1H, br s)<br>mp: 204-206° C. | 2 |

TABLE 157-continued

| Ex | Data | Syn |
|---|---|---|
| 234 | ESI+: 429<br>NMR-DMSO-d6: 2.15-2.48 (8H, m), 3.05-3.09 (2H, m),<br>3.70-3.75 (1.4H, m), 3.88-4.23 (4.6H, m),<br>4.41-4.49 (1H, m), 5.59-5.61 (0.3H, m), 6.62-6.64<br>(0.3H, m), 7.05-7.111 (1.7H, m), 7.20-7.25 (1H, m),<br>7.87 (1H, s), 7.96 (1H, s), 8.04-8.06 (0.7H, m),<br>11.5 (1H, s)<br>mp: 186-188° C. (dec.) | 3 |
| 235 | ESI+: 449, 451<br>NMR-DMSO-d6: 2.37-2.48 (5H, m), 3.91 (2H, t, J = 7.2 Hz), 4.15-4.23 (2H, m), 4.41-4.74 (3H, m),<br>4.86-4.88 (2H, m), 7.26-7.28 (1.5H, m), 7.33-7.41<br>(1.5H, m), 7.44-7.46 (0.5H, m), 7.49-7.52 (0.5H, m),<br>7.88-7.89 (1H, m), 7.96 (1H, br s), 11.5-11.5 (1H, m)<br>mp: 185-187° C. | 2 |

TABLE 158

| Ex | Data | Syn |
|---|---|---|
| 236 | ESI+: 429<br>NMR-DMSO-d6: 2.09 (1.5H, s), 2.29 (1.5H, s),<br>2.38-2.51 (5H, m), 3.89-3.93 (2H, m), 4.15-4.24 (2H, m),<br>4.40-4.47 (2H, m), 4.52 (1H, br s), 4.84 (1H, br s),<br>4.89 (1H, br s), 7.04-7.12 (1.5H, m), 7.17-7.24<br>(1.5H, m), 7.26 (1 H, br s), 7.86-7.87 (1H, m),<br>7.95 (1 H, br s), 11.49-11.50 (1H, m)<br>mp: 270-272° C. (dec.) | 2 |
| 237 | ESI+: 433<br>NMR-DMSO-d6: 2.23-2.55 (5H, m), 3.10-3.17 (2H, m),<br>3.75-3.80 (1.6H, m), 3.88-3.92 (2H, m), 4.15-4.23<br>(2.4H, m), 4.39-4.46 (1H, m), 5.65 (0.2H, br), 6.68<br>(0.2H, br), 7.05-7.27 (2.8H, m), 7.84 (1.0H, s), 7.96<br>(1.0H, s), 8.15-8.18 (0.8H,<br>m), 11.49 (1H, s)<br>mp: 186-188° C. | 3 |
| 238 | ESI+: 444<br>NMR-DMSO-d6: 1.91-2.05 (4H, m), 2.17 (3H, s),<br>2.27 (3H, s), 3.14 (2H, t, J = 8.0 Hz), 3.64-4.17<br>(7H, m), 7.21 (1H, s), 7.60 (2H, br s), 7.82 (1H, s),<br>7.99 (1H, s), 11.5 (1 H, s)<br>mp: 313-315° C. | 2 |
| 239 | ESI+: 508, 510<br>NMR-DMSO-d6: 1.90-2.04 (4H, m), 2.24 (3H, s),<br>3.15-3.19 (2H, m), 3.64-4.00 (5H, m), 4.20 (2H, t,<br>J = 8.0 Hz), 7.17 (1H, s), 7.79-7.80 (2H, m),<br>7.89-7.90 (1H, m), 7.94 (1H, s), 11.45 (1H, s) | 13 |
| 240 | ESI+: 448, 450<br>NMR-DMSO-d6: 1.73-1.82 (4H, m), 2.15-2.25 (7H, m),<br>3.10-3.17 (2H, m), 3.74-3.79 (1.6H, m), 4.06-4.22 (1.4H, m), 5.61 (0.2H, br), 6.84 (0.2H, br), 7.30-7.37 (2.8H, m),<br>8.01 (1.0H, s), 8.14-8.17 (0.8H, m), 12.10 (1.0H, s)<br>mp: 218-220° C. | 13 |
| 241 | ESI+: 430<br>NMR-DMSO-d6: 2.08 (1.5H, s), 2.30 (1.5H, s),<br>2.39-2.40 (3H, m), 2.46-2.52 (2H, m), 3.93 (2H, t, J = 7.2 Hz), 4.23-4.25 (2H, m), 4.47-4.52 (3H, m), 4.84 (1H, s), 4.90 (1H, s), 7.04-7.24 (3H, m), 7.31-7.32 (1 H, m),<br>7.94 (1H, s), 12.08-12.09 (1H, m)<br>mp: 311° C. (dec.) | 2 |

TABLE 159

| Ex | Data | Syn |
|---|---|---|
| 242 | ESI+: 450, 452<br>NMR-DMSO-d6: 2.24-2.40 (3H, m), 2.45-2.55 (2H, m), 3.11-3.17 (2H, m), 3.73-3.78 (1.6H, m), 3.92 (2H, t, J = 6.8 Hz), 4.22-4.24 (2.4H, m), 4.46-4.53 (1H, m), 5.61 (0.2H, br), 6.83 (0.2H, br), 7.31-7.38 (2.8H, m), 7.96 (1H, s), 8.15-8.17 (0.8H, m), 12.10 (1H, s) | 2 |
| 243 | ESI+: 430<br>NMR-DMSO-d6: 2.15-2.61 (8H, m), 3.05-3.10 (2H, m), 3.69-3.74 (1.4H, m), 3.90-3.94 (2H, m), 4.19-4.33 (2.6H, m), 4.46-4.53 (1H, m), 5.56-5.58 (0.3H, m), 6.58-6.60 (0.3H, m), 7.05-7.11 (1.7H, m), 7.25-7.30 (1H, m), 7.95 (1H, s), 8.04-8.06 (0.7H, m), 12.06-12.09 (1H, m) mp: 203-305° C. | 2 |
| 244 | ESI+: 531, 533<br>NMR-DMSO-d6: 2.31-2.38 (3H, m), 2.45-2.56 (2H, m), 2.82-2.99 (3H, m), 3.87-3.94 (2H, m), 4.12-4.24 (2H, m), 4.40-5.21 (4H, m), 7.18-7.28 (1H, m), 7.48-7.54 (1H, m), 7.63-7.73 (2H, m), 7.79-7.95 (2H, m), 12.00-12.02 (1H, m) mp: 219-221° C. | 2 |
| 245 | ESI+: 515<br>NMR-DMSO-d6: 2.23-2.54 (5H, m), 2.82-2.98 (2H, m), 3.55-3.58 (2H, m), 3.89-3.94 (2H, m), 4.17-4.24 (2H, m), 4.42-5.17 (3H, m), 7.18-7.55 (3.6H, m), 7.82-7.94 (2.4H, m), 11.96 (1H, s) mp: 282-284° C. (dec.) | 2 |
| 246 | ESI+: 415<br>NMR-DMSO-d6: 1.72-1.82 (4H, m), 2.10-2.26 (7H, m), 3.17 (2H, t, J = 8.0 Hz), 4.06-4.33 (3H, m), 6.95-6.98 (1H, m), 7.25 (1H, s), 7.71-7.74 (2H, m), 7.92 (1H, s), 12.00 (1H, s) mp: 207-209° C. | 2 |
| 247 | ESI+: 468, 470<br>NMR-DMSO-d6: 2.40 (3H, s), 2.46-2.54 (2H, m), 3.13 (2H, t, J = 8.0 Hz), 3.77-3.81 (2H, m), 3.90-3.94 (2H, m), 4.22-4.24 (2H, m), 4.46-4.53 (1H, m), 7.33 (1H, s), 7.41-7.43 (1H, m), 7.96 (1H, s), 8.27-8.29 (1H, m), 12.11 (1H, s) | 2 |

TABLE 160

| Ex | Data | Syn |
|---|---|---|
| 248 | ESI+: 466<br>NMR-DMSO-d6: 1.72-1.82 (4H, m), 2.10-2.27 (4H, m), 2.40 (3H, s), 3.13 (2H, t, J = 8.0 Hz), 3.73-4.23 (3H, m), 5.61 (0.2H, br), 7.33 (1H, m), 7.41-7.43 (1H, m), 8.01 (1H, s), 8.27-8.29 (0.8H, m), 12.09 (1H, s) mp: 276-278° C. | 13 |
| 249 | ESI+: 479<br>NMR-DMSO-d6: 1.88-2.14 (4H, m), 3.05-3.16 (2H, m), 3.55-4.05 (8H, m), 3.96 (3H, s), 7.27 (1H, s), 7.29 (1H, d, J = 8.2 Hz), 7.35 (1H, s), 7.56 (1H, s), 7.81 (1H, s), 8.11 (1H, d, J = 8.2 Hz) mp: 328-330° C. (dec.) | 13 |
| 250 | ESI+: 447<br>NMR-DMSO-d6: 1.71-1.95 (3H, m), 2.27-2.33 (1H, m), 2.38 (3H, s), 3.44-3.50 (1H, m), 3.69-3.85 (2H, m), 3.94-3.97 (1H, m), 4.17-4.20 (1H, m), 4.56 (2H, s), 4.93 (2H, s), 7.09-7.18 (1.5H, m), 7.27-7.29 (1.5H, m), 7.33-7.43 (1H, m), 7.86-7.87 (2H, m), 11.48-11.50 (1H, m) | 13 |
| 251 | ESI+: 433<br>NMR-DMSO-d6: 2.39-2.53 (5H, m), 3.89-3.92 (2H, m), 4.15-4.23 (2H, m), 4.40-4.47 (1H, m), 4.56 (2H, s), 493 (2H, s), 7.10-7.18 (1.5H, m), 7.27-7.43 (2.5H, m), 7.87-7.88 (1H, m), 7.95-7.96 (1H, m), 11.49-11.51 (1H, m) mp: 203-205° C. | 13 |
| 252 | ESI+: 444<br>NMR-DMSO-d6: 1.74 (3H, s), 1.84-2.00 (2H, m), 2.38 (3H, s), 2.56-2.66 (2H, m), 3.57-3.82 (4H, m), 4.53 (2H, s), 3.89 (2H, m), 7.20-7.38 (4H, m), 7.42 (1H, d, J = 7.2 Hz), 8.06 (1H, s), 12.13 (1H, s) mp: 232° C.(dec.) | 2 |

TABLE 160-continued

| Ex | Data | Syn |
|---|---|---|
| 253 | ESI+: 458<br>NMR-DMSO-d6: 1.20 (3H, s), 1.42-1.63 (4H, m), 1.96-2.20 (3H, m), 2.37 (3H, s), 3.77-3.93 (2H, m), 3.99-4.15 (1H, m), 4.43-4.61 (2H, m), 4.89 (2H, s), 7.18-7.37 (4H, m), 7.42 (1H, d, J = 7.6 Hz), 7.83 (1H, s), 12.07 (1H, s) mp: 287° C.(dec.) | 2 |

TABLE 161

| Ex | Data | Syn |
|---|---|---|
| 254 | ESI+: 483, 485<br>NMR-DMSO-d6: 1.84-2.07 (4H, m), 3.08-3.22 (2H, m), 3.58-3.69 (2H, m), 3.79-3.93 (3H, m), 3.93-4.04 (1.66H, m), 4.13-4.45 (0.34H, m), 5.76-5.86 (0.17H, m), 6.86-6.96 (0.17H, m), 7.27-7.35 (0.83H, m), 7.35-7.45 (2H, m), 7.92 (1H, s), 8.02 (1H, s), 8.08-8.18 (0.83H, m), 11.66-11.82 (1H, m) mp: 352° C.(dec.) | 2 |
| 255 | ESI+: 445<br>NMR-DMSO-d6: 1.74-1.82 (4H, m), 2.12-2.40 (7H, m), 3.03-3.17 (2H, m), 3.66 (0.6H, br), 3.74-3.78 (1.6H, m), 3.87 (2.4H, br), 4.06-4.20 (1.4H, m), 6.37 (0.2H, m), 6.80-6.85 (1H, m), 7.29-7.35 (1H, m), 8.01-8.04 (1H, m), 8.82 (0.8H, m), 12.08-12.11 (1H, m) mp: 263-265° C. | 2 |
| 256 | ESI+: 455<br>NMR-DMSO-d6: 0.60-0.64 (2H, m), 0.87-0.92 (2H, m), 1.72-1.86 (5H, m), 2.13-2.34 (7H, m), 3.12 (2H, t, J = 8.4 Hz), 4.06-4.17 (3H, m), 6.98 (0.1H, br), 7.24 (1H, s), 7.39 (0.9H, br), 7.59-7.74 (1H, m), 7.92 (1H, s), 12.01 (1H, s) mp: 208-209° C. | 2 |
| 257 (a) | ESI+: 447<br>NMR-DMSO-d6: 1.71-1.92 (3H, m), 2.18-2.39 (4H, m), 3.10-3.15 (2H, m), 3.44-3.50 (1H, m), 3.70-3.82 (3.6H, m), 3.94-3.97 (1H, m), 4.17-4.23 (1.4H, m), 5.68 (0.2H, br), 6.67-7.27 (3H, m), 7.86 (1H, s), 7.87 (1H, br s), 8.14-8.18 (0.8H, m), 11.51 (1H, s) mp: 185-188° C.<br>$[\alpha]_D^{25}$ − 50.9 (0.48 g/dL, methanol) | 14 |
| 257 (b) | ESI+: 447<br>NMR-DMSO-d6: 1.71-1.92 (3H, m), 2.18-2.39 (4H, m), 3.10-3.15 (2H, m), 3.44-3.50 (1H, m), 3.70-3.82 (3.6H, m), 3.94-3.97 (1H, m), 4.17-4.23 (1.4H, m), 5.68 (0.2H, br), 6.67-7.27 (3H, m), 7.86 (1H, s), 7.87 (1H, br s), 8.14-8.18 (0.8H, m), 11.51 (1H, s) mp: 180-182° C.<br>$[\alpha]_D^{25}$ + 52.3 (0.33 g/dL, methanol) | 14 |

TABLE 162

| Ex | Data | Syn |
|---|---|---|
| 258 (a) | ESI+: 415<br>NMR-DMSO-d6: 2.38 (3H, s), 2.39-2.51 (2H, m), 3.90 (2H, t, J = 6.8 Hz), 4.15-4.23 (2H, m), 4.39-4.46 (1H, m), 4.51 (2H, s), 4.88 (2H, s), 7.23-7.34 (4H, m), 7.42 (1H, d, J = 7.6 Hz), 7.85 (1H, s), 7.95 (1H, s), 11.48 (1H, s) mp: 180-182° C. | 14 |
| 258 (b) | ESI+: 415<br>NMR-DMSO-d6: 2.38 (3H, s), 2.39-2.51 (2H, m), 3.90 (2H, t, J = 6.8 Hz), 4.15-4.23 (2H, m), 4.39-4.46 (1H, m), 4.51 (2H, s), 4.88 (2H, s), 7.23-7.34 (4H, m), 7.42 (1H, d, J = 7.6 Hz), 7.85 (1H, s), 7.95 (1H, s), 11.48 (1H, s) mp: 183° C. (dec.) | 14 |
| 259 (a) | ESI+: 449, 451<br>NMR-DMSO-d6: 2.24-2.50 (5H, m), 3.10-3.15 (2H, m), 3.75-3.79 (1.6H, m), 3.86-3.94 (2H, m), 4.15-4.23 (2.4H, m), 4.39-4.46 (1H, m), 5.66 (0.2H, br), 6.87-7.37 (3H, m), 7.84 (1H, s), 7.96 (1H, s), 8.14-8.16 (0.8H, m), 11.49 (1H, s) mp: 184-186° C. | 14 |

TABLE 162-continued

| Ex | Data | Syn |
|---|---|---|
| 259 (b) | ESI+: 449, 451<br>NMR-DMSO-d6: 2.24-2.50 (5H, m), 3.10-3.15 (2H, m), 3.75-3.79 (1.6H, m), 3.86-3.94 (2H, m), 4.15-4.23 (2.4H, m), 4.39-4.46 (1H, m), 5.66 (0.2H, br), 6.87-7.37 (3H, m), 7.84 (1H, s), 7.96 (1H, s), 8.14-8.16 (0.8H, m), 11.49 (1H, s) mp: 183-185° C. | 14 |
| 260 | ESI+: 464, 466<br>NMR-DMSO-d6: 1.85-2.15 (4H, m), 2.20-2.45 (3H, m), 3.04-3.22 (2H, m), 3.63-3.84 (3.6H, m), 3.91-4.10 (3H, m), 4.13-4.33 (0.4H, m), 5.51-5.72 (0.2H, m), 6.72-6.94 (0.2H, m), 7.18-7.49 (2.8H, m), 7.89 (1H, s), 8.06-8.23 (0.8H, m), 12.09 (1H, s)<br>mp: 335-336° C. | 13 |
| 261 | ESI+: 482, 484<br>NMR-DMSO-d6: 1.83-2.20 (4H, m), 2.21-2.46 (3H, m), 3.02-3.23 (2H, m), 3.56-4.37 (7H, m), 5.47-5.72 (0.2H, m), 7.34 (1H, s), 7.38-7.56 (1H, m), 7.89 (1H, s), 8.18-8.36 (0.8H, m), 12.13 (1H, s)<br>mp: 316-319° C. | 1 |

TABLE 163

| Ex | Data | Syn |
|---|---|---|
| 262 | ESI+: 431<br>NMR-DMSO-d6: 1.89-2.16 (4H, m), 2.27 (3H, s), 3.17 (2H, t, J = 8.4 Hz), 3.57-3.82 (2H, m), 3.92-4.05 (3H, m), 4.18 (2H, t, J = 8.4 Hz), 6.88-7.01 (1H, m), 7.25 (1H, s), 7.63-7.76 (2H, m), 7.81 (1H, s), 12.03 (1H, s) mp: 370° C.(dec.) | 1 |
| 263 | ESI+: 489<br>NMR-DMSO-d6: 0.70-0.85 (2H, m), 0.95-1.07 (2H, m), 1.85-2.05 (4H, m), 3.08-3.19 (3H, m), 3.52-3.90 (7H, m), 7.15-7.50 (4H, m), 7.86 (1H, s), 8.17 (1H, d, J = 8.7 Hz), 11.52 (1H, s)<br>mp: 339-342° C. (dec.) | 13 |
| 264 | ESI+: 473<br>NMR-DMSO-d6: 0.71-0.85 (2H, m), 1.00-1.07 (2H, m), 1.85-2.05 (5H, m), 3.05-3.19 (2H, m), 3.52-3.65 (2H, m), 3.72-3.89 (2H, m), 4.00-4.07 (2H, m), 7.05-7.25 (3H, m), 7.39 (1H, s), 7.89 (1H, s), 8.15-8.25 (1H, m), 11.55 (1H, s)<br>mp: 318-321° C. (dec.) | 13 |
| 265 | ESI+: 400<br>NMR-DMSO-d6: 1.92-2.08 (1H, m), 2.08-2.27 (1H, m), 2.39 (3H, s), 2.54-2.69 (4H, m), 4.26-4.58 (3H, m), 4.89 (2H, s), 7.20-7.36 (4H, m), 7.42 (1H, d, J = 7.6 Hz), 7.72 (1H, s), 12.07 (1H, s)<br>mp: 236° C.(dec.) | 1 |
| 266 | ESI+: 463<br>NMR-DMSO-d6: 1.90-2.14 (4H, m), 3.06-3.18 (2H, m), 3.55-4.05 (7H, m), 3.97 (3H, s), 7.06 (1H, dt, J = 2.5, 8.8 Hz), 7.16 (1H, dd, J = 2.5, 8.8 Hz), 7.29 (1H, s), 7.56 (1H, s), 7.90 (1H, s), 8.12 (1H, dd, J = 4.6, 8.9 Hz), 11.49 (1H, s) mp: 321-324° C. (dec.) | 13 |
| 267 | ESI+: 445<br>NMR-DMSO-d6: 1.92-2.15 (4H, m), 3.57-3.67 (2H, m), 3.87-4.04 (3H, m), 3.96 (3H, s), 4.57 (2H, s), 4.84 (2H, s), 7.20-7.42 (5H, m), 7.57 (1H, s), 7.91 (1H, s), 11.47 (1H, s)<br>mp: 199-201° C. (dec.) | 13 |

TABLE 164

| Ex | Data | Syn |
|---|---|---|
| 268 | ESI+: 455<br>NMR-DMSO-d6: 0.73-0.85 (2H, m), 0.97-1.03 (2H, m), 1.90-2.05 (5H, m), 3.53-3.65 (2H, m), 3.73-3.85 (1H, m), 4.00-4.08 (2H, m), 4.56 (2H, s), 4.90 (2H, s), 7.21-7.45 (6H, m), 7.88 (1H, s), 11.51 (1H, s)<br>mp: 185-189° C. (dec.) | 13 |

TABLE 164-continued

| Ex | Data | Syn |
|---|---|---|
| 269 | ESI+: 489<br>NMR-DMSO-d6: 0.73-0.79 (2H, m), 0.96-1.04 (2H, m), 1.91-2.04 (2H, m), 3.52-3.65 (2H, m), 3.71-4.07 (3H, m), 4.54 (2H, d, J = 8.2 Hz), 4.88 (2H, d, J = 8.2 Hz), 7.22 (1H, s), 7.25-7.46 (3H, m), 7.52 (1H, s), 7.86 (1H, s), 11.50 (1H, s)<br>mp: 199-203° C. (dec.) | 13 |
| 270 | ESI+: 465<br>NMR-DMSO-d6: 1.70-1.93 (3H, m), 2.23-2.33 (1H, m), 2.39 (3H, s), 3.43-3.80 (3H, m), 3.94-3.98 (1H, m), 4.18-4.21 (1H, m), 4.60 (2H, s), 4.96 (2H, s), 7.18-7.28 (3H, m), 7.82 (1H, s), 7.85 (1H, s), 11.44 (1H, s)<br>mp: 223-225° C. | 13 |
| 271 | ESI+: 429<br>NMR-DMSO-d6: 1.74-1.81 (4H, m), 2.12-2.37 (7H, m), 2.54-5.09 (7H, m), 7.19-7.27 (1H, m), 7.55-7.67 (1H, m), 7.88-7.99 (1.4H, m), 8.19-8.21 (0.6H, m), 8.60-8.63 (1H, m), 12.04 (1H, s) | 2 |
| 272 | ESI+: 464<br>NMR-DMSO-d6: 1.94-2.04 (2H, m), 2.18-2.33 (6H, m), 2.41 (3H, s), 3.90-3.96 (1H, m), 4.50 (2H, s), 4.89 (2H, s), 7.24-7.34 (4H, m), 7.42 (1H, d, J = 7.4 Hz), 7.90 (1H, s), 12.07 (1H, s)<br>mp: 322° C. (dec.) | 13 |
| 273 | ESI+: 479, 481<br>NMR-DMSO-d6: 1.92-2.13 (4H, m), 3.57-3.67 (2H, m), 3.86-4.04 (3H, m), 3.96 (3H, s), 4.52-4.59 (2H, m), 4.80-4.86 (2H, m), 7.25-7.59 (4H, m), 7.56 (1H, s), 7.89 (1H, s), 11.46 (1H, s)<br>mp: 210-213° C. (dec.) | 13 |

TABLE 165

| Ex | Data | Syn |
|---|---|---|
| 274 | ESI+: 498, 500<br>mp: 230-233° C. | 13 |
| 275 | ESI+: 465<br>mp: 310° C. (dec.) | 13 |
| 276 | ESI+: 486<br>NMR-DMSO-d6: 0.52-0.55 (0.2H, m), 0.77-0.81 (1.8H, m), 0.93-1.07 (2H, m), 1.83-2.07 (4H, m), 3.12-3.18 (2H, m), 3.55-3.61 (2H, m), 3.66 (0.6H, br), 3.76-3.85 (5.4H, m), 4.02-4.05 (2H, m), 4.15-4.38 (1H, m), 6.38 (0.2H, br), 6.79-6.83 (1H, m), 7.19-7.26 (1H, m), 7.40-7.51 (1H, m), 7.90-7.92 (1H, m), 8.84 (0.8H, br), 11.54-11.57 (1H, m)<br>mp: 241° C. (dec.) | 13 |
| 277 | ESI+: 476<br>NMR-DMSO-d6: 1.88-2.11 (4H, m), 3.12 (2H, t, J = 8.0 Hz), 3.59-3.67 (2.5H, m), 3.82-4.51 (10.5H, m), 6.57 (0.2H, br), 6.78-6.82 (1H, m), 7.06-7.31 (1H, m), 7.57-7.62 (1H, m), 7.91-7.99 (1H, m), 8.79 (0.8H, br), 11.48-11.50 (1H, m)<br>mp: 237° C. (dec.) | 13 |
| 278 | ESI+: 450<br>NMR-DMSO-d6: 1.72-1.82 (4H, m), 2.11-2.26 (4H, m), 2.40 (3H, s), 4.05-4.12 (1H, m), 4.59 (2H, s), 4.97 (2H, s), 7.18-7.28 (2H, m), 7.31 (1H, s), 7.99 (1H, s), 12.03 (1H, s) | 13 |
| 279 | ESI+: 450, 452<br>NMR-DMSO-d6: 1.80-2.10 (4H, m), 3.18 (2H, t, J = 8.4 Hz), 3.55-3.70 (2H, m), 3.83-4.04 (3H, m), 4.19 (2H, t, J = 8.4 Hz), 6.88-7.02 (1H, m), 7.34 (1H, s), 7.60-7.79 (2H, m), 7.91-8.00 (2H, m), 11.71 (1H, s)<br>mp: 275° C.(dec.) | 2 |
| 280 | ESI+: 449, 451<br>NMR-DMSO-d6: 1.87-2.08 (4H, m), 3.55-3.92 (3H, m), 3.93-4.06 (2H, m), 4.57 (2H, s), 4.88 (2H, s), 7.21-7.36 (3H, m), 7.38 (1H, s), 7.42 (1H, d, J = 7.2 Hz), 7.91 (1H, s), 8.02 (1H, s), 11.72 (1H, s)<br>mp: 332° C.(dec.) | 2 |

TABLE 166

| Ex | Data | Syn |
|---|---|---|
| 281 | ESI+: 464, 466<br>NMR-DMSO-d6: 1.68-2.02 (3H, m), 2.18-2.46 (4H, m), 3.03-3.24 (2H, m), 3.41-3.58 (1H, m), 3.67-4.02 (4.6H, m), 4.15-4.30 (1.4H, m), 5.52-5.73 (0.2H, m), 6.71-6.94 (0.2H, m), 7.17-7.47 (2.8H, m), 7.88 (1H, s), 8.16 (0.8H, 8.8), 12.13 (1H, s)<br>mp: 298-301° C. | 13 |
| 282 | ESI+: 448<br>NMR-DMSO-d6: 1.64-2.05 (3H, m), 2.18-2.46 (4H, m), 3.00-3.26 (2H, m), 3.42-3.60 (1H, m), 3.65-4.03 (4.6H, m), 4.13-4.71 (1.4H, m), 5.48-5.76 (0.2H, m), 6.48-6.72 (0.2H, m), 6.98-7.44 (2.8H, m), 7.88 (1H, s), 8.08-8.29 (0.8H, m), 12.13 (1H, s)<br>mp: 235-237° C. | 13 |
| 283 | ESI+: 443<br>NMR-DMSO-d6: 1.87-2.02 (4H, m), 2.35 (3H, s), 2.56 (3H, s), 3.62-3.68 (2H, m), 3.77-3.85 (1H, m), 3.95-3.99 (2H, m), 4.51 (2H, s), 4.88 (2H, s), 7.19 (1H, s), 7.24-7.34 (3H, m), 7.41 (1H, d, J = 7.4 Hz), 7.78 (1H, s), 11.23 (1H, s)<br>mp: 335° C. (dec.) | 13 |
| 284 | ESI+: 477, 479<br>NMR-DMSO-d6: 1.89-2.02 (4H, m), 2.22-2.37 (3H, m), 2.58 (3H, s), 3.10-3.17 (2H, m), 3.63-3.69 (2H, m), 3.74-3.79 (1.6H, m), 3.82-3.91 (1H, m), 3.96-3.99 (2H, m), 4.21 (0.4H, br), 5.67 (0.2H, br), 6.90 (0.2H, br), 7.17-7.32 (1.8H, m), 7.37 (1H, s), 7.81 (1H, s), 8.14-8.16 (0.8H, m), 11.36 (1H, br s)<br>mp: 198° C. (dec.) | 13 |
| 285 | ESI+: 486<br>NMR-DMSO-d6: 0.61-0.62 (2H, m), 0.88-0.92 (2H, m), 1.83-2.10 (5H, m), 3.07-3.11 (2H, m), 3.58-4.14 (10H, m), 7.24 (1H, s), 7.33 (1H, br s), 7.48 (1H, s), 7.59 (1H, br s), 7.90 (1H, s), 11.41 (1H, s)<br>mp: 297° C. (dec.) | 13 |

TABLE 167

| Ex | Data | Syn |
|---|---|---|
| 286 | ESI+: 496<br>NMR-DMSO-d6: 0.63-0.91 (8H, m), 1.83-2.03 (6H, m), 3.13 (2H, t, J = 8.0 Hz), 3.55-3.61 (2H, m), 3.78-3.85 (1H, m), 4.01-4.43 (4H, m), 7.20-7.60 (4H, m), 7.96 (1H, s), 11.54 (1H, s)<br>mp: 310° C. (dec.) | 13 |
| 287 | ESI+: 416<br>NMR-DMSO-d6: 2.39 (3H, s), 2.44-2.54 (2H, m), 3.92 (2H, t, J = 6.8 Hz), 4.23-4.24 (2H, m), 4.46-4.52 (3H, m), 4.89 (2H, s), 7.24-7.35 (4H, m), 7.41-7.43 (1H, m), 7.95 (1H, s), 12.09 (1H, s)<br>mp: 223-224° C. | 13 |
| 288 | ESI+: 465<br>NMR-DMSO-d6: 1.89-2.05 (4H, m), 2.39 (3H, s), 3.08-3.12 (2H, m), 3.64-3.71 (2H, m), 3.78-4.27 (5H, m), 5.54 (0.1H, br), 7.28 (1H, s), 7.40-7.45 (1H, m), 7.89-7.93 (2H, m), 8.09-8.14 (0.9H, m), 11.55 (1H, s)<br>mp: 287-288° C. | 13 |
| 289 | ESI+: 450<br>NMR-DMSO-d6: 1.72-1.82 (4H, m), 2.12-2.40 (7H, m), 3.08-3.17 (2H, m), 3.77-3.81 (1.8H, m), 4.06-4.45 (1.2H, m), 5.54 (0.1H, br), 7.33 (1H, s), 7.40-7.45 (1H, m), 8.01 (1H, s), 8.09-8.14 (0.9H, m), 12.09 (1H, s)<br>mp: 210-212° C. (dec.) | 13 |
| 290 | ESI+: 481, 483<br>NMR-DMSO-d6: 1.90-2.04 (4H, m), 2.30-2.39 (3H, m), 3.11 (2H, t, J = 8.4 Hz), 3.64-3.70 (2H, m), 3.79-4.27 (5H, m), 5.54 (0.1H, br), 7.28 (1H, s), 7.51-7.53 (1H, m), 7.85-7.91 (2H, m), 8.07-8.09 (0.9H, m), 11.48-11.53 (1H, m) mp: 292-294° C. | 2 |

TABLE 167-continued

| Ex | Data | Syn |
|---|---|---|
| 291 | ESI+: 482, 484<br>NMR-DMSO-d6: 1.92-2.09 (4H, m), 2.33-2.40 (3H, m), 3.10 (2H, t, J = 8.0 Hz), 3.68-3.81 (3.6H, m), 3.97-4.24 (3.4H, m), 5.52 (0.2H, br), 7.33 (1H, s), 7.51-7.53 (1H, m), 7.89 (1H, m), 8.07-8.09 (0.8H, m), 12.09 (1H, s)<br>mp: 309-311° C. | 2 |

TABLE 168

| Ex | Data | Syn |
|---|---|---|
| 292 | ESI+: 473<br>NMR-DMSO-d6: 0.75-0.80 (2H, m), 0.99-1.03 (2H, m), 1.90-2.05 (5H, m), 3.54-3.80 (3H, m), 4.02-4.06 (2H, m), 4.62 (2H, s), 4.95 (2H, s), 7.10-7.18 (1.6H, m), 7.23 (1H, s), 7.27-7.29 (0.4H, m), 7.33-7.43 (2H, m), 7.85-7.86 (1H, m), 11.49-11.50 (1H, m)<br>mp: 205-207° C. | 13 |
| 293 | ESI+: 463<br>NMR-DMSO-d6: 1.93-2.11 (4H, m), 3.59-3.65 (2H, m), 3.83-4.03 (6H, m), 4.63 (2H, s), 4.89 (2H, s), 7.08-7.18 (1.5H, m), 7.25-7.27 (1.5H, m), 7.33-7.42 (1H, m), 7.58 (1H, s), 7.86-7.87 (1H, m), 11.43-11.44 (1H, m)<br>mp: 195-197° C. | 13 |
| 294 | ESI+: 431<br>NMR-DMSO-d6: 1.68-2.02 (3H, m), 2.22-2.40 (4H, m), 3.18 (2H, t, J = 8.4 Hz), 3.45-3.57 (1H, m), 3.71-3.83 (1H, m), 3.83-4.03 (2H, m), 4.17 (2H, t, J = 8.4 Hz), 4.21-4.28 (1H, m), 7.01 (1H, s), 7.29 (1H, s), 7.69-7.84 (3H, m), 12.08 (1H, s)<br>mp: 314° C. (dec.) | 13 |
| 295 | ESI+: 430<br>NMR-DMSO-d6: 1.68-2.03 (3H, m), 2.26-2.43 (4H, m), 3.43-3.60 (1H, m), 3.72-4.10 (3H, m), 4.19-4.29 (1H, m), 4.51 (2H, s), 4.89 (2H, s), 7.21-7.37 (4H, m), 7.42 (1H, d, J = 7.2 Hz), 7.87 (1H, s), 12.10 (1H, s)<br>mp: 303° C. (dec.) | 13 |
| 296 | ESI+: 494, 496<br>NMR-DMSO-d6: 1.90-2.13 (4H, m), 3.60-3.74 (2H, m), 3.89-4.07 (3H, m), 4.54 (2H, s), 4.88 (2H, s), 7.22-7.37 (3H, m), 7.40 (1H, s), 7.43 (1H, d, J = 7.2 Hz), 8.14 (1H, s), 12.28 (1H, s)<br>mp: 350° C. (dec.) | 13 |

TABLE 169

| Ex | Data | Syn |
|---|---|---|
| 297 | ESI+: 458<br>NMR-DMSO-d6: 1.88-2.15 (4H, m), 2.26 (3H, s), 2.67-2.90 (2H, m), 2.94-3.10 (2H, m), 3.25-3.45 (2H, m), 3.54-3.80 (3H, m), 3.84-4.10 (4H, m), 7.00-7.28 (5H, m), 7.83 (1H, s), 12.04 (1H, s)<br>mp: 212-215° C. | 1 |
| 298 | ESI+: 461<br>NMR-DMSO-d6: 1.87-2.00 (4H, m), 2.22-2.36 (3H, m), 2.55 (3H, s), 3.10-3.17 (2H, m), 3.62-3.68 (2H, m), 3.75-3.83 (2.6H, m), 3.95-3.98 (2H, m), 4.21 (0.4H, br), 5.66 (0.2H, br), 6.69 (0.2H, br), 7.05-7.18 (2.8H, m), 7.79 (1H, s), 8.14-8.17 (0.8H, m), 11.23 (1H, s)<br>mp: 177-180° C. | 13 |
| 299 | ESI+: 444<br>NMR-DMSO-d6: 1.97-2.04 (4H, m), 2.26 (3H, s), 2.66 (3H, s), 3.18 (2H, t, J = 8.4 Hz), 3.63-4.07 (5H, m), 4.17 (2H, t, J = 8.4 Hz), 6.97-7.00 (1H, m), 7.20 (1H, s), 7.72-7.75 (2H, m), 7.78 (1H, s), 11.55 (1H, s)<br>mp: 192° C. (dec.) | 2 |
| 300 | ESI+: 493, 495<br>NMR-DMSO-d6: 1.91-2.05 (4H, m), 3.05-3.15 (2H, m), 3.31 (2H, s), 3.55-3.85 (4H, m), 3.95-4.09 (4H, m), 4.53 (2H, s), 7.22-7.39 (3H, m), 7.90 (1H, s), 8.06-8.18 (2H, m), 11.57 (1H, s)<br>mp: 298-301° C. (dec.) | 13 |

TABLE 169-continued

| Ex | Data | Syn |
|---|---|---|
| 301 | ESI+: 477<br>NMR-DMSO-d6: 1.85-2.07 (4H, m), 3.05-3.15 (2H, m), 3.32 (2H, s), 3.55-3.65 (2H, m), 3.75-3.85 (2H, m), 3.90-4.15 (5H, m), 4.54 (2H, s), 7.00-7.36 (3H, m), 7.91 (1H, s), 8.08 (1H, s), 8.13 (1H, s), 11.59 (1H, s)<br>mp: 301-304° C. (dec.) | 13 |
| 302 | ESI+: 459<br>NMR-DMSO-d6: 1.85-2.07 (4H, m), 3.32 (3H, s), 3.55-3.65 (2H, m), 3.95-4.20 (3H, m), 4.53 (2H, s), 4.54 (2H, s), 4.87 (2H, s), 7.22-7.45 (5H, m), 7.88 (1H, s), 8.08 (1H, s), 11.53 (1H, s)<br>mp: 261-264° C. (dec.) | 13 |

TABLE 170

| Ex | Data | Syn |
|---|---|---|
| 303 | ESI+: 429<br>NMR-DMSO-d6: 1.83-2.12 (4H, m), 2.37 (3H, s), 3.55-3.75 (2H, m), 3.79-4.07 (3H, m), 4.48 (1H, s), 4.59-5.05 (2H, m), 7.17-7.38 (4H, m), 7.42 (1H, d, J = 7.6 Hz), 7.96-8.08 (2H, m), 10.68 (1H, s)<br>mp: 183-186° C. | 13 |
| 304 | ESI+: 450<br>NMR-DMSO-d6: 1.87-2.14 (4H, m), 2.24 (1.26H, s), 2.37 (1.74H, s), 2.72-2.87 (1H, m), 2.87-3.00 (1H, m), 3.44-3.55 (1H, m), 3.62-3.77 (2H, m), 3.88-5.10 (6H, m), 6.73 (0.42H, d, J = 5.2 Hz), 6.99 (0.58H, d, J = 5.2 Hz), 7.18 (0.42H, s), 7.24 (0.58H, s), 7.32 (0.42H, d, J = 5.2 Hz), 7.41 (0.58H, d, J = 5.2 Hz), 7.82 (0.42H, s), 7.86 (0.58H, s), 12.04 (1H, s)<br>mp: 216-219° C. | 2 |
| 305 | ESI+: 523<br>NMR-DMSO-d6: 1.82-2.17 (4H, m), 2.22-2.43 (3H, m), 2.56-2.88 (2H, m), 3.42-4.94 (12H, m), 5.81-6.11 (1H, m), 7.11-7.48 (6H, m), 7.77-7.94 (1H, m), 11.99 (1H, m)<br>mp: 223-225° C. | 2 |
| 306 | ESI+: 509, 511<br>NMR-DMSO-d6: 1.86-2.12 (4H, m), 2.24 (3H, s), 3.11-3.21 (2H, m), 3.64-3.74 (2H, m), 3.92-4.04 (3H, m), 4.12-4.51 (2H, m), 7.22 (1H, s), 7.73-7.80 (1H, m), 7.80 (1H, s), 7.87-7.90 (1H, m), 12.00 (1H, s)<br>mp: 222-223° C. | 13 |
| 307 | ESI+: 471<br>NMR-DMSO-d6: 0.59-0.63 (2H, m), 0.87-0.91 (2H, m), 1.81-2.11 (5H, m), 2.27 (3H, s), 3.10-3.14 (2H, m), 3.67-3.74 (2H, m), 3.96-4.24 (5H, m), 7.24 (1H, s), 7.37 (1H, brs), 7.56 (1H, brs), 7.80 (1H, s), 12.04 (1H, s)<br>mp: 210-212° C. | 2 |
| 308 | ESI+: 536, 538<br>NMR-DMSO-d6: 1.90-2.12 (4H, m), 2.72 (6H, s), 3.13 (2H, t, J = 8.4 Hz), 3.45-3.75 (4H, m), 3.84-4.17 (6H, m), 4.55-4.65 (1H, m), 7.25-7.40 (3H, m), 7.58 (1H, s), 7.87 (1H, s), 8.09 (1H, d, J = 8.8 Hz), 11.51 (1H, s) mp: 219-221° C. (dec.) | 13 |

TABLE 171

| Ex | Data | Syn |
|---|---|---|
| 309 | ESI+: 520<br>NMR-DMSO-d6: 1.9-2.25 (4H, m), 2.71 (6H, s), 3.1-3.2 (2H, m), 3.5-3.7 (4H, m), 3.8-4.2 (5H, m), 4.61 (2H, s), 7.06 (1H, t, J = 8.5 Hz), 7.18 (1H, d, J = 8.5 Hz), 7.33 (1H, s), 7.58 (1H, s), 7.88 (1H, s), 8.10 (1H, dd, J = 5.0, 9.0 Hz), 11.52 (1H, s)<br>mp: 216-219° C. (dec.) | 13 |
| 310 | ESI+: 464, 466<br>NMR-DMSO-d6: 1.89-2.05 (4H, m), 2.24 (3H, s), 3.15-3.19 (2H, m), 3.63-3.99 (5H, m), 4.20-4.24 (2H, m), 7.16 (1H, s), 7.73-7.74 (1H, m), 7.79-7.80 (2H, m), 7.89 (1H, s), 11.41 (1H, br s)<br>mp: 297° C. (dec.) | 13 |

TABLE 171-continued

| Ex | Data | Syn |
|---|---|---|
| 311 | ESI+: 543, 545<br>NMR-DMSO-d6: 1.94-2.07 (2H, m), 2.18-2.30 (9H, m), 3.15-3.19 (2H, m), 3.92-3.97 (1H, m), 4.19-4.23 (2H, m), 7.23 (1H, s), 7.76-7.77 (1H, m), 7.82 (1H, s), 7.90-7.91 (1H, m), 12.03 (1H, s)<br>mp: 343° C. (dec.) | 13 |
| 312 | ESI+: 495, 497<br>NMR-DMSO-d6: 2.26 (3H, s), 2.49-2.53 (2H, m), 3.16-3.21 (2H, m), 3.92-3.95 (2H, m), 4.20-4.25 (4H, m), 4.47-4.54 (1H, m), 7.23 (1H, s), 7.79-7.80 (1H, m), 7.87 (1H, s), 7.91-7.92 (1H, m), 12.01 (1H, s)<br>mp: 242-243° C. | 13 |
| 313 | ESI+: 509, 511<br>NMR-DMSO-d6: 1.73-2.00 (4H, m), 2.26 (3H, s), 3.15-3.20 (4H, m), 3.48-3.54 (1H, m), 3.75-4.25 (4H, m), 7.23 (1H, s), 7.78-7.79 (2H, m), 7.90-7.91 (1H, m), 12.01 (1H, s) mp: 218-220° C. (dec.) | 13 |
| 314 | ESI+: 471<br>NMR-DMSO-d6: 0.60-0.64 (2H, m), 0.87-0.92 (2H, m), 1.74-1.99 (4H, m), 2.27-2.34 (4H, m), 3.10-3.14 (2H, m), 3.48-3.54 (1H, m), 3.75-3.80 (1H, m), 3.85-3.97 (2H, m), 4.13-4.58 (3H, m), 7.25 (1H, s), 7.38 (1H, br s), 7.58 (1H, br s), 7.80 (1H, s), 12.04 (1H, s)<br>mp: 204-206° C. | 13 |

TABLE 172

| Ex | Data | Syn |
|---|---|---|
| 315 | ESI+: 434, 436<br>NMR-DMSO-d6: 1.94-2.08 (1H, m), 2.08-2.46 (4H, m), 2.47-2.72 (4H, m), 3.02-3.22 (2H, m), 3.65-3.89 (1.7H, m), 4.08-4.30 (0.3H, m), 4.30-4.48 (1H, m), 5.49-5.71 (0.15H, m), 6.71-7.47 (3H, m), 7.73 (1H, s), 8.15 (0.85H, d, J = 8.5 Hz), 12.13 (1H, s)<br>mp: 225-228° C. | 13 |
| 316 | ESI+: 418<br>NMR-DMSO-d6: 1.93-2.07 (1H, m), 2.09-2.46 (4H, m), 2.46-2.72 (4H, m), 3.03-3.23 (2H, m), 3.63-3.87 (1.7H, m), 4.12-4.45 (1.3H, m), 5.19-6.09 (0.15H, m), 6.50-6.70 (0.15H, m), 6.99-7.13 (0.85H, m), 7.13-7.23 (1H, m), 7.21-7.38 (1H, m), 7.72 (1H, s), 8.07-8.27 (0.85H, m), 12.09 (1H, s)<br>mp: 223-226° C. | 13 |
| 317 | ESI+: 460<br>NMR-DMSO-d6: 1.43-1.63 (2H, m), 2.04-2.21 (3H, m), 2.38 (3H, s), 2.56-2.72 (4H, m), 3.34 (2H, d, J = 4.0 Hz), 4.50 (2H, s), 4.89 (2H, s), 7.20-7.36 (4H, m), 7.42 (1H, d), 7.85 (1H, s), 12.07 (1H, s) | 13 |
| 318 | ESI+: 447<br>NMR-DMSO-d6: 1.71-1.92 (3H, m), 2.18-2.39 (4H, m), 3.10-3.15 (2H, m), 3.44-3.50 (1H, m), 3.70-3.82 (3.6H, m), 3.94-3.97 (1H, m), 4.17-4.23 (1.4H, m), 5.68 (0.2H, br), 6.67-7.27 (3H, m), 7.86 (1H, s), 7.87 (1H, br s), 8.14-8.18 (0.8H, m), 11.51 (1H, s) | 2 |
| 319 | ESI+: 417<br>NMR-DMSO-d6: 2.25 (3H, s), 3.16 (2H, t, J = 8.4 Hz), 3.83-3.93 (4H, m), 4.17-4.24 (4H, m), 4.47-4.53 (1H, m), 6.93 (1H, dd, J = 3.8, 4.8 Hz), 7.23 (1H, s), 7.67-7.71 (2H, m), 7.86 (1H, s), 12.00 (1H, s)<br>mp: 210-211° C. (dec.) | 13 |

TABLE 173

| Ex | Data | Syn |
|---|---|---|
| 320 | ESI+: 538, 540<br>NMR-DMSO-d6: 1.87-2.10 (4H, m), 3.10-3.21 (2H, m), 3.23 (3H, s), 3.55-3.65 (2H, m), 3.72-3.82 (1H, m), 3.97-4.05 (2H, m), 4.18 (2H, t, J = 8.0 Hz), 4.40 (2H, s), 7.21 (1H, s), 7.79-7.83 (1H, m), 7.84 (1H, s), 7.87-7.90 (1H, m), 8.00 (1H, s), 11.43 (1H, s)<br>mp: 310° C. (dec.) | 13 |

TABLE 173-continued

| Ex | Data | Syn |
|---|---|---|
| 321 | ESI+: 478, 480<br>NMR-DMSO-d6: 1.74 (3H, s), 1.81-1.98 (2H, m), 2.18-2.44 (3H, m), 2.53-2.66 (2H, m), 3.02-3.22 (2H, m), 3.39-4.00 (5.6H, m), 4.04-4.37 (0.4H, m), 5.55-5.78 (0.2H, m), 6.72-6.94 (0.2H, m), 7.21-7.47 (2.8H, m), 8.06 (1H, s), 8.15 (0.8H, d, J = 8.4 Hz), 12.19 (1H, s)<br>mp: 229-232° C. | 13 |
| 322 | ESI+: 462<br>NMR-DMSO-d6: 1.74 (3H, s), 1.83-1.97 (2H, m), 2.18-2.44 (3H, m), 2.54-2.69 (2H, m), 3.04-3.22 (2H, m), 3.52-4.30 (6H, m), 5.55-5.80 (0.2H, m), 6.51-6.74 (0.2H, m), 6.98-7.14 (0.8H, m), 7.14-7.24 (1H, m), 7.24-7.43 (1H, m), 8.07 (1H, s), 8.11-8.25 (0.8H, m), 12.17 (1H, s)<br>mp: 243-245° C. | 13 |
| 323 | ESI+: 460<br>NMR-DMSO-d6: 1.91-2.08 (4H, m), 2.12 (3H, s), 3.06-3.10 (2H, m), 3.56-3.62 (2H, m), 3.65 (3H, s), 3.82-3.92 (1H, m), 3.94-4.01 (2H, m), 4.07-4.14 (2H, m), 4.97 (0.1H, br), 7.19 (1H, s), 7.46-7.57 (2H, m), 7.53 (1H, s), 7.80 (0.9H, s), 11.31 (1H, br s)<br>mp: 288° C. (dec.) | 2 |
| 324 | ESI+: 466, 468<br>NMR-DMSO-d6: 1.72-1.82 (4H, m), 2.12-2.26 (4H, m), 2.33-2.40 (3H, m), 3.11 (2H, t, J = 8.0 Hz), 3.76-3.84 (1.6H, m), 4.06-4.13 (1H, m), 4.25 (0.4H, br), 5.49 (0.2H, br), 7.32 (1H, s), 7.51-7.53 (1H, m), 8.01 (1H, s), 8.07-8.10 (0.8H, m), 12.06 (1H, s) | 13 |

TABLE 174

| Ex | Data | Syn |
|---|---|---|
| 325 | ESI+: 440<br>NMR-DMSO-d6: 1.72-1.82 (4H, m), 2.10-2.26 (7H, m), 3.17-3.21 (2H, m), 4.06-4.13 (1H, m), 4.24 (2H, t, J = 8.4 Hz), 7.23 (1H, s), 7.92 (1H, s), 8.07-8.08 (1H, m), 8.16-8.17 (1H, m), 11.97 (1H, br s)<br>mp: 303-306° C. (dec.) | 13 |
| 326 | ESI+: 509, 511<br>NMR-DMSO-d6: 1.9-2.15 (4H, m), 3.05-3.15 (2H, m), 3.55-3.65 (2H, m), 3.7-4.05 (7H, m), 4.2-4.3 (2H, m), 7.25-7.3 (2H, m), 7.35 (1H, s), 7.65 (1H, s), 7.88 (1H, s), 8.13 (1H, d, J = 8.6 Hz), 11.46 (1H, s) | 17 |
| 327 | ESI+: 413<br>NMR-DMSO-d6: 1.67-1.89 (6H, m), 2.14-2.32 (2H, m), 2.40 (3H, s), 3.91-4.09 (1H, m), 4.23-4.71 (2H, m), 4.90 (2H, s), 7.21-7.36 (3H, m), 7.38 (1H, s), 7.40-7.45 (1H, m), 7.75 (1H, s), 8.10 (1H, s), 12.30 (1H, s) | 13 |
| 328 | ESI+: 441 | 13 |
| 329 | ESI+: 477, 479<br>NMR-DMSO-d6: 1.44-1.53 (2H, m), 1.67-1.76 (2H, m), 1.95-1.99 (2H, m), 2.08-2.12 (2H, m), 2.23-2.38 (3H, m), 3.09-3.13 (2H, m), 3.48-3.55 (2H, m), 3.74-3.78 (1.6H, m), 4.28 (0.4H, br), 5.66 (0.2H, br), 6.89 (0.2H, br), 7.26-7.36 (2.8H, m), 7.82 (1H, s), 7.92 (1H, s), 8.13-8.15 (0.8H, m), 11.55 (1H, s)<br>mp: 207-209° C. | 15 |
| 330 | ESI+: 477, 479<br>NMR-DMSO-d6: 1.70-1.85 (6H, m), 2.06-2.37 (5H, m), 3.10-3.14 (2H, m), 3.55-4.22 (4H, m), 5.67 (0.2H, br), 6.90 (0.2H, br), 7.25-7.37 (2.8H, m), 7.85-7.88 (2H, m), 8.14-8.16 (0.8H, m), 11.48 (1H, s)<br>mp: 204-206° C. | 15 |

TABLE 175

| Ex | Data | Syn |
|---|---|---|
| 331 | ESI+: 447, 449<br>NMR-DMSO-d6: 1.67-1.97 (6H, m), 2.11-2.46 (5H, m), 3.02-3.24 (2H, m), 3.60-4.53 (3H, m), 5.49-5.74 (0.2H, m), 6.70-6.97 (0.2H, m), 7.20-7.49 (2.8H, m), 7.66 (1H, s), 8.09 (1H, s), 8.16 (0.8H, d, J = 7.2 Hz), 12.05-12.33 (1H, m)<br>mp: 279° C.(dec.) | 13 |

TABLE 175-continued

| Ex | Data | Syn |
|---|---|---|
| 332 | ESI+: 494, 496<br>NMR-DMSO-d6: 1.42-1.62 (2H, m), 2.02-2.72 (10H, m), 2.98-3.23 (2H, m), 3.24-3.45 (2H, m), 3.64-3.90 (1.6H, m), 4.09-4.33 (0.4H, m), 5.51-5.70 (0.2H, m), 6.71-6.85 (0.2H, m), 7.18-7.47 (2.8H, m), 7.86 (1H, s), 8.16 (0.8H, d, J = 8.0 Hz), 12.10 (1H, s)<br>mp: 215-218° C. | 13 |
| 333 | ESI+: 490<br>NMR-DMSO-d6: 1.92-2.05 (4H, m), 3.10-3.14 (2H, m), 3.27-3.33 (3H, m), 3.57-3.65 (2.6H, m), 3.77-3.86 (5H, m), 4.00-4.26 (2.4H, m), 4.46-4.54 (2H, m), 6.41 (0.2H, br), 6.78-6.83 (1H, m), 7.27-7.35 (1H, m), 7.93 (1H, s), 8.08-8.12 (1H, m), 8.80 (0.8H, m), 11.57-11.61 (1H, m)<br>mp: 208° C. (dec.) | 13 |
| 334 | ESI+: 477<br>NMR-DMSO-d6: 1.90-2.05 (4H, m), 3.33 (3H, s), 3.57-3.63 (2H, m), 3.72-3.82 (1H, m), 4.00-4.04 (2H, m), 4.54 (2H, s), 4.60 (2H, s), 4.93 (2H, s), 7.10-7.43 (4H, m), 7.87 (1H, s), 8.08 (1H, s), 11.45-11.53 (1H, m)<br>mp: 277° C. (dec.) | 13 |
| 335 | ESI+: 461<br>NMR-DMSO-d6: 1.44-1.54 (2H, m), 1.67-1.77 (2H, m), 1.97-2.00 (2H, m), 2.09-2.13 (2H, m), 2.24 (0.6H, br s), 2.39 (2.4H, s), 3.10-3.20 (2H, m), 3.47-3.57 (2H, m), 3.76-4.22 (2H, m), 5.68 (0.2H, br), 6.68 (0.2H, br), 7.06-7.26 (2.8H, m), 7.83 (1H, s), 7.89 (1H, s), 8.15-8.18 (0.8H, m), 11.52 (1H, s)<br>mp: 199-201° C. | 15 |

TABLE 176

| Ex | Data | Syn |
|---|---|---|
| 336 | ESI+: 461<br>NMR-DMSO-d6: 1.70-1.85 (6H, m), 2.07-2.15 (2H, m), 2.24-2.38 (3H, m), 3.10-3.15 (2H, m), 3.58-4.22 (4H, m), 5.66 (0.2H, br), 6.68 (0.2H, br), 7.06-7.10 (0.8H, m), 7.17-7.26 (2H, m), 7.86 (1H, s), 7.94 (1H, s), 8.15-8.18 (0.8H, m), 11.54 (1H, s)<br>mp: 200-202° C. | 15 |
| 337 | ESI+: 461<br>NMR-DMSO-d6: 1.71-1.85 (6H, m), 2.06-2.16 (2H, m), 2.37-2.38 (3H, m), 3.56-3.93 (2H, m), 4.56 (2H, s), 4.93 (2H, s), 7.09-7.18 (1.5H, m), 7.26-7.44 (2.5H, m), 7.84 (1H, s), 7.91-7.92 (1H, m), 11.48-11.49 (1H, m) | 15 |
| 338 | ESI+: 446<br>NMR-DMSO-d6: 1.93-2..09 (2H, m), 2.10-2.24 (2H, m), 3.58-3.72 (2H, m), 3.92-4.09 (6H, m), 4.56 (2H, s), 4.85 (2H, s), 7.29-7.37 (4H, m), 7.41 (1H, d, J = 8.0 Hz), 7.53 (1H, s), 12.09 (1H, s)<br>mp: 228° C.(dec.) | 13 |
| 339 | ESI+: 480, 482<br>NMR-DMSO-d6: 2.90-2.24 (4H, m), 3.01-3.19 (2H, m), 3.59-3.73 (2H, m), 3.73-4.28 (8H, m), 5.75-5.89 (0.1H, m), 6.76-6.92 (0.1H, m), 7.22-7.42 (2.9H, m), 7.53 (1H, s), 8.12 (0.9H, d, J = 8.8 Hz), 12.09 (1H, s)<br>mp: 284° C.(dec.) | 13 |
| 340 | ESI+: 495<br>NMR-DMSO-d6: 1.90-2.06 (4H, m), 3.33 (3H, s), 3.57-3.63 (2H, m), 3.74-3.82 (1H, m), 4.00-4.04 (2H, m), 4.54 (2H, s), 4.63 (2H, s), 4.96 (2H, s), 7.18-7.28 (2H, m), 7.34 (1H, s), 7.89 (1H, s), 8.08 (1H, s), 11.53 (1H, s)<br>mp: 172-174° C. | 13 |
| 341 | ESI+: 522, 524<br>NMR-DMSO-d6: 1.70-1.85 (6H, m), 2.06-2.16 (2H, m), 2.23-2.33 (3H, m), 3.14-3.19 (2H, m), 3.58-3.94 (2H, m), 4.18-4.22 (2H, m), 7.16 (1H, s), 7.77 (1H, s), 7.80-7.81 (1H, m), 7.89-7.90 (2H, m), 11.40 (1H, s)<br>mp: 305-307° C. | 15 |

TABLE 177

| Ex | Data | Syn |
|---|---|---|
| 342 | ESI+: 454<br>NMR-DMSO-d6: 2.25 (0.6H, br s), 2.41 (2.4H, s), 3.23-3.42 (6H, m), 3.74-3.78 (1.6H, m), 4.08-4.38 (1.4H, m), 5.59 (0.2H, br), 6.60 (0.2H, br), 7.06-7.30 (2.8H, m), 7.72 (1H, m), 8.15-8.18 (0.8H, m), 12.11 (1H, br)<br>mp: 234-235° C. | 13 |
| 343 | ESI+: 463, 465<br>NMR-DMSO-d6: 1.65-1.70 (2H, m), 1.85-2.20 (3H, m), 2.25-2.40 (3H, m), 3.11-3.15 (2H, m), 3.75-4.84 (5H, m), 5.63 (0.2H, br), 6.85 (0.2H, br), 7.20-7.37 (2.8H, m), 7.80 (1H, s), 8.03 (1H, s), 8.15-8.20 (0.8H, m), 11.40 (1H, s)<br>mp: 238-240° C. | 15 |
| 344 | ESI+: 448<br>NMR-DMSO-d6: 1.90-2.04 (4H, m), 2.24 (3H, s), 3.18 (2H, t, J = 8.4 Hz), 3.64-3.70 (2H, m), 3.87-3.99 (3H, m), 4.23 (2H, t, J = 8.4 Hz), 7.17 (1H, s), 7.65-7.69 (2H, m), 7.80 (1H, s), 7.92 (1H, s), 11.43 (1H, s)<br>mp: 340° C. (dec.) | 13 |
| 345 | ESI+: 470, 472<br>NMR-DMSO-d6: 2.25-2.40 (3H, m), 3.10-3.41 (6H, m), 3.73-3.77 (1.6H, m), 4.21 (0.4H, br), 4.32-4.40 (1H, m), 5.60 (0.2H, br), 6.82 (0.2H, br), 7.30-7.38 (2.8H, s), 7.72 (1H, s), 8.14-8.16 (0.8H, m), 12.12 (1H, m)<br>mp: 243-245° C. | 13 |
| 346 | ESI+: 515, 517<br>NMR-DMSO-d6: 2.27 (3H, s), 3.18 (2H, t, J = 8.4 Hz), 3.25-3.42 (4H, m), 4.22 (2H, t, J = 8.4 Hz), 4.32-4.42 (1H, m), 7.23 (1H, s), 7.64 (1H, s), 7.78-7.79 (1H, m), 7.91-7.92 (1H, m), 12.05 (1H, s) | 13 |
| 347 | ESI+: 494, 496<br>NMR-DMSO-d6: 1.85-2.19 (4H, m), 2.99-3.44 (5H, m), 3.53-3.72 (2H, m), 3.72-3.96 (2.8H, m), 3.96-4.11 (2H, m), 4.37-4.68 (2.2H, m), 5.49-5.81 (0.2H, m), 6.61-7.00 (0.2H, m), 7.16-7.51 (2.8H, m), 7.94-8.25 (1.8H, m), 12.15 (1H, s)<br>mp: 198-201° C. | 13 |

TABLE 178

| Ex | Data | Syn |
|---|---|---|
| 348 | ESI+: 422<br>NMR-DMSO-d6: 1.97 (3H, s), 4.45 (2H, s), 4.84 (2H, s), 6.88 (1H, s), 7.23-7.39 (5H, m), 7.70-7.68 (5H, m), 12.18 (1H, s)<br>mp: 316° C. (dec.) | 2 |
| 349 | ESI+: 456, 458<br>NMR-DMSO-d6: 1.80-1.95 (3H, m), 3.07-3.11 (2H, m), 3.65-3.78 (2H, m), 4.18 (0.2H, br), 4.60 (0.2H, br), 6.89 (1H, s), 7.28-7.35 (2.8H, m), 7.67-7.77 (5H, m), 8.15-8.20 (0.8H, m), 12.40 (1H, m)<br>mp: 248-249° C. | 2 |
| 350 | ESI+: 474<br>NMR-DMSO-d6: 1.91-2.05 (4H, m), 2.98-4.99 (16H, m), 7.22-7.36 (1H, m), 7.70-8.51 (4H, m), 8.67-8.76 (1H, m), 11.54-11.58 (1H, m)<br>mp: 172-175° C. | 2 |
| 351 | ESI+: 478, 480<br>NMR-DMSO-d6: 1.48-1.58 (2H, m), 1.71-1.80 (2H, m), 1.98-2.00 (2H, m), 2.14-2.18 (2H, m), 2.25 (0.6H, br), 2.40 (2.4H, s), 3.10-3.14 (2H, m), 3.53-3.76 (3.6H, m), 4.21 (0.4H, br), 5.62 (0.2H, br), 6.84 (0.2H, br), 7.30-7.38 (2.8H, m), 7.84 (1H, s), 8.15-8.17 (0.8H, m), 12.08 (1H, s)<br>mp: 235-237° C. | 13 |
| 352 | ESI+: 449<br>NMR-DMSO-d6: 1.91-2.10 (4H, m), 2.26 (3H, s), 3.18 (2H, t, J = 8.4 Hz), 3.67-3.73 (2H, m), 3.96-4.03 (3H, m), 4.21-4.33 (2H, m), 7.23 (1H, s), 7.66-7.69 (2H, m), 7.80 (1H, s), 12.03 (1H, s) | 13 |

TABLE 178-continued

| Ex | Data | Syn |
|---|---|---|
| 353 | ESI+: 461<br>NMR-DMSO-d6: 1.86-2.10 (4H, m), 2.29 (0.6H, s), 2.41 (2.4H, s), 3.12-3.18 (2H, m), 3.65-3.78 (4.2H, m), 3.86 (2.4H, s), 3.97-4.04 (3H, m), 4.20 (0.4H, br), 6.37 (0.2H, br), 6.79 (0.2H, br), 6.86 (0.8H, s), 7.30 (0.2H, s), 7.36 (0.8H, s), 7.89-7.92 (1H, m), 8.82 (0.8H, s), 12.11-12.15 (1H, s)<br>mp: 271° C. (dec.) | 13 |

TABLE 179

| Ex | Data | Syn |
|---|---|---|
| 354 | ESI+: 454<br>NMR-DMSO-d6: 2.40 (3H, s), 3.23-3.41 (4H, m), 4.31-4.40 (1H, m), 4.54 (2H, s), 4.94 (2H, s), 7.10-7.19 (1.5H, m), 7.27-7.43 (2.5H, m), 7.71 (1H, s), 12.08-12.11 (1H, m) | 13 |
| 355 | ESI+: 457<br>NMR-DMSO-d6: 1.95-2.25 (4H, m), 2.29 (3H, s), 2.37 (3H, s), 2.63 (3H, s), 3.0-3.2 (2H, m), 3.6-3.8 (5H, m), 3.9-4.1 (2H, m), 7.05 (1H, d, J = 8.3 Hz), 7.10 (1H, s), 7.24 (1H, s), 7.83 (1H, s), 8.04 (1H, d, J = 8.3 Hz), 11.54 (1H, s)<br>mp: 264-266° C. (dec.) | 13 |
| 356 | ESI+: 478, 480<br>NMR-DMSO-d6: 1.73-1.90 (6H, m), 2.00-2.38 (5H, m), 3.10-3.14 (2H, m), 3.42-3.92 (3.6H, m), 4.21 (0.4H, br), 5.62 (0.2H, br), 6.84 (0.2H, br), 7.31-7.38 (2.8H, m), 7.86 (1H, s), 8.14-8.16 (0.8H, m), 12.07 (1H, s)<br>mp: 277-279° C. | 13 |
| 357 | ESI+: 463, 465<br>NMR-DMSO-d6: 1.84-2.03 (4H, m), 2.21 (0.6H, s), 2.34 (2.4H, s), 3.05-3.18 (2H, m), 3.57-3.66 (2H, m), 3.69-3.81 (2.6H, m), 3.92-3.99 (2H, m), 4.17-4.24 (0.4H, m), 5.57-5.64 (0.2H, m), 6.83-6.92 (0.4H, m), 7.04 (0.8H, d, J = 8.9 Hz), 7.30 (0.8H, d, J = 8.9 Hz), 7.39 (1H, s), 7.52-7.58 (0.2H, m), 7.58 (1H, s), 7.88 (0.8H, s), 8.18 (0.8H, d, J = 8.9 Hz), 10.51 (1H, s)<br>mp: 290° C. (dec.) | 13 |
| 358 | ESI+: 430<br>NMR-DMSO-d6: 1.87-2.03 (4H, m), 2.24 (3H, s), 3.12-3.17 (2H, m), 3.58-3.64 (2H, m), 3.75-3.83 (1H, m), 3.90-3.98 (2H, m), 4.16-4.23 (2H, m), 6.88 (1H, dd, J = 5.0, 7.5 Hz), 7.14 (1H, d, J = 8.8 Hz), 7.63 (1H, m), 7.67 (1H, d, J = 5.0 Hz), 7.87 (1H, s), 7.91 (1H, d, J = 8.8 Hz), 10.5 (1H, s)<br>mp: 320° C. (dec.) | 13 |

TABLE 180

| Ex | Data | Syn |
|---|---|---|
| 359 | ESI+: 450, 452<br>NMR-DMSO-d6: 0.28-0.40 (1H, m), 0.54-0.85 (3H, m), 1.73-1.87 (1H, m), 2.22 (0.6H, br s), 2.36 (2.4H, s), 3.06-3.24 (2H, m), 3.69-3.88 (1.6H, m), 4.22 (0.4H, br s), 4.51-4.63 (1H, m), 5.64 (0.2H, br s), 6.28 (0.8H, s), 6.86 (0.2H, br s), 7.21-7.47 (2H, m), 8.09-8.23 (0.8H, m), 8.32 (1H, s), 12.13 (1H, s)<br>mp: 260-262° C. (dec.) | 13 |
| 360 | ESI+: 434, 436<br>NMR-DMSO-d6: 0.32-0.36 (2H, m), 0.58-0.63 (2H, m), 1.33-1.42 (1H, m), 2.23-2.38 (3H, m), 3.10-3.14 (2H, m), 3.35-3.41 (2H, m), 3.73-3.77 (1.6H, m), 4.21 (0.4H, br), 5.61 (0.2H, br), 6.82 (0.2H, br), 7.24-7.37 (2.8H, m), 7.96 (1H, s), 8.14-8.16 (0.8H, m), 12.06 (1H, s)<br>mp: 303-305° C. | 13 |
| 361 | APCI/ESI+: 562 | 13 |
| 362 | ESI+: 546 | 13 |

TABLE 180-continued

| Ex | Data | Syn |
|---|---|---|
| 363 | ESI+: 595, 597<br>NMR-CDCl3: 1.66-1.78 (2H, m), 1.82-2.00 (2H, m), 2.25-2.36 (4H, m), 2.53-2.63 (1H, m), 3.11-3.23 (2H, m), 3.26-3.35 (1H, m), 3.86-3.78 (1.6H, m), 4.42-4.31 (0.4H, m), 5.66-5.73 (0.2H, m), 6.75-6.81 (0.2H, m), 7.22 (1H, s), 7.28 (1H, s), 7.32-7.40 (5.8H, m), 7.73 (1H, s), 8.03 (1H, s), 8.29 (1H, d, J = 8.8 Hz), 10.43-10.55 (1H, s) | Pr-13 |
| 364 | ESI+: 429<br>NMR-DMSO-d6: 1.70-1.94 (3H, m), 2.24-2.32 (1H, m), 2.37 (3H, s), 3.40-3.55 (1H, m), 3.69-3.82 (2H, m), 3.94-3.98 (1H, m), 4.17-4.21 (1H, m), 4.51 (2H, s), 4.89 (2H, s), 7.23-7.34 (4H, m), 7.42 (1H, d, J = 7.6 Hz), 7.84 (1H, s), 7.86 (1H, s), 11.46 (1H, s) | 13 |
| 365 | ESI+: 520 | 2 |
| 366 | ESI+: 430 | 6 |
| 367 | ESI+: 430 | 6 |
| 368 | ESI+: 431 | 6 |
| 369 | ESI+: 463 | 6 |

TABLE 181

| Ex | Data | Syn |
|---|---|---|
| 370 | ESI+: 489 | 6 |
| 371 | ESI+: 464 | 6 |
| 372 | ESI+: 433 | 6 |
| 373 | ESI+: 433 | 6 |
| 374 | ESI+: 450 | 6 |
| 375 | ESI+: 434 | 6 |
| 376 | ESI+: 446 | 6 |
| 377 | ESI+: 447 | 6 |
| 378 | ESI+: 448 | 6 |
| 379 | ESI+: 445 | 6 |
| 380 | ESI+: 459 | 6 |
| 381 | ESI+: 482 | 6 |
| 382 | ESI+: 544, 546 | 6 |
| 383 | ESI+: 543, 545 | 6 |
| 384 | ESI+: 508 | 6 |
| 385 | ESI+: 522 | 6 |
| 386 | ESI+: 521, 523 | 6 |
| 387 | ESI+: 432 | 6 |
| 388 | ESI+: 460 | 6 |
| 389 | ESI+: 508 | 6 |
| 390 | ESI+: 542, 544 | 6 |
| 391 | ESI+: 552 | 6 |
| 392 | ESI+: 433 | 6 |
| 393 | ESI+: 501 | 6 |
| 394 | ESI+: 509 | 6 |
| 395 | ESI+: 527 | 6 |
| 396 | ESI+: 477 | 6 |

TABLE 182

| Ex | Data | Syn |
|---|---|---|
| 397 | ESI+: 525 | 6 |
| 398 | ESI+: 531 | 6 |
| 399 | ESI+: 559, 561 | 6 |
| 400 | ESI+: 555 | 6 |
| 401 | ESI+: 527 | 6 |
| 402 | ESI+: 527 | 6 |
| 403 | ESI+: 528 | 6 |
| 404 | ESI+: 540 | 6 |
| 405 | ESI+: 526 | 6 |
| 406 | ESI+: 509 | 6 |
| 407 | ESI+: 496 | 6 |
| 408 | ESI+: 496 | 6 |
| 409 | ESI+: 496 | 6 |
| 410 | ESI+: 444 | 6 |
| 411 | ESI+: 444 | 6 |
| 412 | ESI+: 477, 479 | 6 |
| 413 | ESI+: 407 | 6 |
| 414 | ESI+: 407 | 6 |
| 415 | ESI+: 409 | 6 |
| 416 | ESI+: 423 | 6 |
| 417 | ESI+: 435 | 6 |
| 418 | ESI+: 436 | 6 |
| 419 | ESI+: 436 | 6 |
| 420 | ESI+: 462 | 6 |
| 421 | ESI+: 464 | 6 |
| 422 | ESI+: 463 | 6 |
| 423 | ESI+: 494 | 6 |

TABLE 183

| Ex | Data | Syn |
|---|---|---|
| 424 | ESI+: 498 | 6 |
| 425 | ESI+: 502 | 6 |
| 426 | ESI+: 502 | 6 |
| 427 | ESI+: 518, 520 | 6 |
| 428 | ESI+: 498 | 6 |
| 429 | ESI+: 544 | 6 |
| 430 | ESI+: 530 | 6 |
| 431 | ESI+: 530 | 6 |
| 432 | ESI+: 542 | 6 |
| 433 | ESI+: 435 | 6 |
| 434 | ESI+: 449 | 6 |
| 435 | ESI+: 464 | 6 |
| 436 | ESI+: 478 | 6 |
| 437 | ESI+: 479 | 6 |
| 438 | ESI+: 541 | 6 |
| 439 | ESI+: 541 | 6 |
| 440 | ESI+: 520 | 6 |
| 441 | ESI+: 540 | 6 |
| 442 | ESI+: 554 | 6 |
| 443 | ESI+: 479 | 6 |
| 444 | ESI+: 463 | 6 |
| 445 | ESI+: 478 | 6 |
| 446 | ESI+: 478 | 6 |
| 447 | ESI+: 554 | 6 |
| 448 | ESI+: 499 | 6 |
| 449 | ESI+: 513 | 6 |
| 450 | ESI+: 497 | 6 |

TABLE 184

| Ex | Data | Syn |
|---|---|---|
| 451 | ESI+: 499 | 6 |
| 452 | ESI+: 511 | 6 |
| 453 | ESI+: 584 | 6 |
| 454 | ESI+: 431 | 6 |
| 455 | ESI+: 431 | 6 |
| 456 | ESI+: 449 | 6 |
| 457 | ESI+: 448 | 6 |
| 458 | ESI+: 465 | 6 |
| 459 | ESI+: 448 | 6 |
| 460 | ESI+: 445 | 6 |
| 461 | ESI+: 445 | 6 |
| 462 | ESI+: 434 | 6 |
| 463 | ESI+: 446 | 6 |
| 464 | ESI+: 469 | 6 |
| 465 | ESI+: 521 | 6 |
| 466 | ESI+: 535 | 6 |
| 467 | ESI+: 474 | 6 |
| 468 | ESI+: 474 | 6 |
| 469 | ESI+: 510 | 6 |
| 470 | ESI+: 447 | 6 |
| 471 | ESI+: 430 | 6 |
| 472 | ESI+: 448 | 6 |
| 473 | ESI+: 430 | 6 |
| 474 | ESI+: 448 | 6 |
| 475 | ESI+: 508, 510 | 6 |
| 476 | ESI+: 464, 466 | 6 |
| 477 | ESI+: 444 | 6 |

TABLE 185

| Ex | Data | Syn |
|---|---|---|
| 478 | ESI+: 464, 466 | 6 |
| 479 | ESI+: 464, 466 | 6 |
| 480 | ESI+: 498 | 6 |
| 481 | ESI+: 496 | 6 |
| 482 | ESI+: 469 | 6 |
| 483 | ESI+: 478, 480 | 6 |
| 484 | ESI+: 478, 480 | 6 |
| 485 | ESI+: 445 | 6 |
| 486 | ESI+: 521 | 6 |
| 487 | ESI+: 535 | 6 |
| 488 | ESI+: 474 | 6 |
| 489 | ESI+: 474 | 6 |
| 490 | ESI+: 450 | 6 |
| 491 | ESI+: 545, 547 | 6 |
| 492 | ESI+: 497 | 6 |
| 493 | ESI+: 448 | 6 |
| 494 | ESI+: 478, 480 | 6 |
| 495 | ESI+: 498 | 6 |
| 496 | ESI+: 458 | 6 |
| 497 | ESI+: 466 | 6 |
| 498 | ESI+: 515 | 6 |
| 499 | ESI+: 444 | 6 |
| 500 | ESI+: 460 | 6 |
| 501 | ESI+: 464, 466 | 6 |
| 502 | ESI+: 482, 484 | 6 |
| 503 | ESI+: 466 | 6 |
| 504 | ESI+: 482, 484 | 6 |

TABLE 186

| Ex | Data | Syn |
|---|---|---|
| 505 | ESI+: 431 | 6 |
| 506 | ESI+: 449 | 6 |
| 507 | ESI+: 509, 511 | 6 |
| 508 | ESI+: 471 | 6 |
| 509 | ESI+: 461 | 6 |
| 510 | ESI+: 445 | 6 |
| 511 | ESI+: 527 | 6 |
| 512 | ESI+: 447 | 6 |
| 513 | ESI+: 545 | 6 |
| 514 | ESI+: 539, 541 | 13 |
| 515 | ESI+: 553, 555 | 13 |
| 516 | ESI+: 491, 493<br>NMR-DMSO-d6: 1.13-1.51 (6H, m), 1.83-2.13 (4H, m), 2.17-2.62 (3H, m), 3.40-3.78 (3.6H, m), 3.84-4.10 (3.4H, m), 5.59-5.79 (0.2H, m), 6.79-7.03 (0.2H, m), 7.18-7.48 (2.8H, m), 7.90 (1H, s), 8.00 (1H, s), 8.05-8.22 (0.8H, m), 11.60 (1H, s)<br>mp: 340° C.(dec.) | 13 |
| 517 | ESI+: 492, 494<br>NMR-DMSO-d6: 1.13-1.46 (6H, m), 1.81-2.16 (4H, m), 2.19-2.62 (3H, m), 3.41-3.61 (1.6H, m), 3.63-3.79 (2H, m), 3.84-4.08 (3.4H, m), 5.50-5.76 (0.2H, m), 6.71-6.96 (0.2H, m), 7.23-7.46 (2.8H, m), 7.89 (1H, s), 8.06-8.21 (0.8H, m), 12.10 (1H, s)<br>mp: 227-230° C. | 13 |
| 518 | ESI+: 448<br>NMR-DMSO-d6: 1.84-2.15 (4H, m), 2.18-2.47 (3H, m), 3.03-3.23 (2H, m), 3.63-3.83 (3.6H, m), 3.89-4.08 (3H, m), 4.13-4.31 (0.4H, m), 5.45-6.24 (0.2H, m), 6.48-6.71 (0.2H, m), 6.97-7.42 (2.8H, m), 7.89 (1H, s), 8.06-8.27 (0.8H, m), 12.14 (1H, s)<br>mp: 221-223° C. | 13 |

TABLE 187

| Ex | Data | Syn |
|---|---|---|
| 519 | ESI+: 496<br>NMR-DMSO-d6: 1.87-2.18 (4H, m), 2.99-3.19 (2H, m), 3.43 (3H, s), 3.58-3.75 (2H, m), 3.75-4.46 (5H, m), 4.55 (2H, s), 5.40-5.82 (0.2H, m), 7.26-7.55 (2H, m), 7.88-8.24 (1.8H, m), 12.19 (1H, s)<br>mp: 266-269° C. | 13 |
| 520 | ESI+: 508, 510<br>NMR-DMSO-d6: 1.72 (3H, s), 1.84-2.04 (2H, m), 2.45-2.64 (2H, m), 3.02-3.19 (2H, m), 3.33 (3H, s), 3.50-3.68 (2H, m), 3.68-3.95 (3.6H, m), 3.98-4.39 (0.4H, m), 4.54 (2H, s), 4.83-5.99 (0.2H, m), 6.69-7.01 (0.2H, m), 7.17-7.55 (2.8H, m), 7.99-8.22 (0.8H, m), 8.29 (1H, s), 12.24 (1H, s)<br>mp: 198-201° C. | 13 |
| 521 | ESI+: 510<br>NMR-DMSO-d6: 1.72 (3H, s), 1.86-2.03 (2H, m), 2.41-2.65 (2H, m), 3.00-3.16 (2H, m), 3.33 (3H, s), 3.51-3.69 (2H, m), 3.69-3.96 (4H, m), 4.54 (2H, s), 5.26-5.78 (0.2H, m), 7.35-7.52 (2H, m), 7.98-8.17 (0.8H, m), 8.29 (1H, s), 12.27 (1H, s)<br>mp: 195-198° C. | 13 |
| 522 | ESI+: 464, 466<br>NMR-DMSO-d6: 0.20-0.44 (2H, m), 0.46-0.68 (2H, m), 1.24-1.46 (1H, m), 2.98-3.51 (7H, m), 3.65-3.94 (1.6H, m), 3.96-4.32 (0.4H, m), 4.34-4.68 (2H, m), 5.04-5.97 (0.2H, m), 6.63-6.95 (0.2H, m), 7.12-7.51 (2.8H, m), 7.91-8.37 (1.8H, m), 12.20 (1H, s)<br>mp: 257° C.(dec.) | 13 |
| 523 | ESI+: 470, 472 | 11 |
| 524 | ESI+: 468, 470 | 13 |
| 525 | ESI+: 495, 497 | 13 |
| 526 | ESI+: 476, 478 | 12 |
| 527 | ESI+: 479, 481 | 13 |

TABLE 188

| Ex | Data | Syn |
|---|---|---|
| 528 | ESI+: 504, 506<br>NMR-DMSO-d6: 1.62-1.76 (4H, m), 1.87-1.96 (2H, m), 2.12-2.89 (3.6H, m), 2.39 (2.4H, s), 3.08-3.17 (2H, m), 3.47-3.55 (1H, m), 3.73-3.82 (1.6H, m), 4.15-4.27 (0.4H, m), 5.62-5.72 (0.2H, m), 6.72 (1H, s), 6.86-6.92 (0.2H, m), 7.24 (1H, s), 7.27 (1H, s), 7.31 (0.8H, d, J = 8.1 Hz), 7.37 (1H, s), 7.80 (1H, s), 7.83 (1H, s), 8.16 (0.8H, d, J = 8.1 Hz), 11.42 (1H, s)<br>mp: 234-237° C. | 1 |
| 529 | ESI+: 457 | 2 |
| 530 | ESI+: 448 | 2 |
| 531 | ESI+: 449, 451<br>NMR-DMSO-d6: 2.24-2.50 (5H, m), 3.10-3.15 (2H, m), 3.75-3.79 (1.6H, m), 3.86-3.94 (2H, m), 4.15-4.23 (2.4H, m), 4.39-4.46 (1H, m), 5.66 (0.2H, br), 6.87-7.37 (3H, m), 7.84 (1H, s), 7.96 (1H, s), 8.14-8.16 (0.8H, m), 11.49 (1H, s) | 2 |

Industrial Applicability

The compound of the formula (I) or a salt thereof has a PDE9-inhibiting action, and can be used as a prophylactic and/or therapeutic agent, such as a pharmaceutical composition for treating diseases related to degradation of cGMP by PDE9, for example, underactive bladder, hypotonic bladder, acontractile bladder, neurogenic bladder, detrusor underactivity, overactive bladder, urinary frequency, nocturia, incontinence, benign prostatic hyperplasia, lower urinary tract symptoms, voiding dysfunction accompanying urethra relaxation failure or detrusor-external urethral sphincter dyssynergia, interstitial cystitis, chronic prostatitis, or urethra calculus.

What invention claimed is:
1. A compound of formula (I):

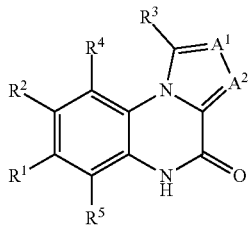

wherein
$A^1$ is N and $A^2$ is $CR^6$,
one of $R^1$ and $R^2$ is hydrogen; halogen; or lower alkyl, —O-lower alkyl, or cycloalkyl, each of which may be substituted with one or more substituents selected from the group consisting of —OH, —O-lower alkyl, —$NH_2$, —NH-lower alkyl, —N(lower alkyl)$_2$, and a monocyclic nitrogen-containing hetero ring which may be substituted with lower alkyl; and the other is a group of formula (II),

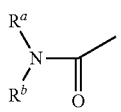

$R^3$ is lower alkyl, cycloalkyl, cycloalkenyl, aryl, heteroaryl, or a saturated hetero ring, each of which may be substituted with one or more substituents selected from the group consisting of halogen, lower alkyl, cycloalkyl, —OH, oxo, —O-lower alkyl, —COOH, —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—$NH_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, —CO—NH-lower alkylene-$CO_2H$, and a monocyclic sulfur-containing saturated hetero ring,
$R^4$ and $R^5$ are the same or different, and each is hydrogen or lower alkyl,
$R^6$ is hydrogen or lower alkyl, and
$R^a$ and $R^b$ are combined with the adjacent nitrogen atom to form a polycyclic nitrogen-containing hetero ring, which may be substituted with one or more substituents selected from the group consisting of halogen; —OH; oxo; —O-lower alkyl; cyano; nitro; halogeno-lower alkyl; cycloalkyl; aryl which may be further substituted with a group selected from a group $G_1$; a hetero ring which may be further substituted with a group selected from a group $G_2$; lower alkylene-(aryl which may be further substituted with a group selected from a group $G_1$); lower alkylene-$SO_2$—$NR^7R^8$; lower alkylene-hetero ring; lower alkyl which may be further substituted with —OH, —O-lower alkyl, cyano, or cycloalkyl; —COOH; —CO—O-lower alkyl; —CO—O-lower alkenyl; —CO—O-lower alkynyl; —CO—O-lower alkylene-O-lower alkyl; —CO—O-lower alkylene-aryl; —CO—O-lower alkylene-O-aryl; —CO—$NH_2$; —CO—NH-lower alkyl; —CO—N lower alkyl)$_2$, —CO—N(lower alkyl)-aryl; —CO—N(lower alkyl)-(lower alkylene-aryl); —CO—NH-lower alkylene-OH; —CO—NH-lower alkylene-$CO_2H$; —NH—$SO_2$—$R^9$; —$SO_2$—$NR^7R^8$; and a monocyclic nitrogen-containing hetero ring, wherein $R^7$ and $R^8$ are the same or different, and each is hydrogen or lower alkyl, $R^9$ is lower alkyl, or aryl which may be substituted with lower alkyl; group $G_1$ contains halogen, lower alkyl, halogeno-lower alkyl, —OH, —O-lower alkyl, —O-lower alkylene-aryl, —O-lower alkylene-hetero ring, —O-halogeno-lower alkyl, aryl, and a hetero ring, and group $G_2$ contains halogen, lower alkyl, halogeno-lower alkyl, —OH, —O-lower alkyl, —O-lower alkylene-aryl, —O-lower alkylene-hetero ring, —O-halogeno-lower alkyl, aryl, and a hetero ring,
or a pharmaceutically acceptable salt thereof.

2. A compound or pharmaceutically acceptable salt thereof according to claim 1, wherein
$R^1$ is a group of formula (II),
$R^2$ is halogen; cycloalkyl; or lower alkyl or —O-lower alkyl, each of which may be substituted with a substituent selected from the group consisting of —OH, —O-lower alkyl, —$NH_2$, —NH-lower alkyl, —N(lower alkyl)$_2$, and a monocyclic nitrogen-containing hetero ring which may be further substituted with lower alkyl; and
$R^4$, $R^5$, and $R^6$ are hydrogen atoms.

3. A compound or pharmaceutically acceptable salt thereof according to claim 2, wherein
$R^3$ is lower alkyl which is substituted with cycloalkyl and which may be further substituted with 1 to 3 substituents selected from the group consisting of —OH, oxo, and halogen; lower alkyl which may be substituted with a monocyclic sulfur-containing saturated hetero ring; or cycloalkyl or a monocyclic saturated hetero ring each of which may be substituted with 1 or 2 substituents selected from the group consisting of halogen, lower alkyl, —OH, oxo, —O-lower alkyl, —COOH, —CO—O-lower alkyl, —CO—O-lower alkenyl, —CO—O-lower alkynyl, —CO—O-lower alkylene-O-lower alkyl, —CO—O-lower alkylene-aryl, —CO—O-lower alkylene-O-aryl, —CO—$NH_2$, —CO—NH-lower alkyl, —CO—N(lower alkyl)$_2$, —CO—N(lower alkyl)-aryl, —CO—N(lower alkyl)-(lower alkylene-aryl), —CO—NH-lower alkylene-OH, and —CO—NH-lower alkylene-$CO_2$; and
$R^a$ and $R^b$ are combined with the adjacent nitrogen atom to form a polycyclic nitrogen-containing hetero ring, which may be substituted with 1 to 3 substituents selected from the group consisting of halogen, lower alkyl which may be further substituted with —OH, —O-lower alkyl, cycloalkyl, cyano, halogeno-lower alkyl, and a monocyclic nitrogen-containing hetero ring.

4. A compound or pharmaceutically acceptable salt thereof according to claim 3, wherein
$R^2$ is halogen, cyclopropyl, or lower alkyl which may be substituted with —O-lower alkyl,
$R^3$ is lower alkyl which is substituted with cyclopropyl and which may be further substituted with 1 to 3 substituents selected from the group consisting of —OH, oxo, and halogen; cycloalkyl which may be substituted with 1 or 2 substituents selected from the group consisting of —OH and halogen; tetrahydrofuranyl; or tetrahydropyranyl which may be substituted with lower alkyl, and
the polycyclic nitrogen-containing hetero ring which may be substituted, formed when $R^a$ and $R^b$ are combined with the adjacent nitrogen atom, is indolinyl, isoindolinyl, dihydropyrrolopyridyl, tetrahydroisoquinolyl, or tetrahydronaphthyridinyl, each of which may be substituted with 1 to 3 substituents selected from the group consisting of halogen, lower alkyl which may be further substituted with —OH, —O-lower alkyl, and cyano.

5. A compound or pharmaceutically acceptable salt thereof according to claim 3, wherein $R^2$ is halogen; cyclopropyl; lower alkyl which may be substituted with —O-lower alkyl; or —O-lower alkyl which may be substituted with —OH, —N(lower alkyl)$_2$, or pyrrolidinyl which may be further substituted with lower alkyl, $R^3$ is cyclopentyl or cyclohexyl, each of which may be substituted with —OH, —COOH or —CO—NH$_2$; tetrahydrofuranyl; or tetrahydropyranyl; and the polycyclic nitrogen-containing hetero ring which may be substituted, formed when $R^a$ and $R^b$ are combined with the adjacent nitrogen atom, is indolinyl, isoindolinyl, dihydropyrrolopyridyl, tetrahydroisoquinolyl, or tetrahydronaphthyridinyl, each of which may be substituted with 1 to 3 substituents selected from the group consisting of halogen, lower alkyl which may be further substituted with —OH, —O-lower alkyl, and cyano.

6. A compound or pharmaceutically acceptable salt thereof according to claim 1, wherein $R^1$ is hydrogen or lower alkyl and $R^2$ is a group of the formula (II), or $R^1$ is a group of formula (II) and $R^2$ is hydrogen; halogen; or lower alkyl, —O-lower alkyl, or cycloalkyl, each of which may be substituted, with one or more substituents selected from the group consisting of —OH, —O-lower alkyl, —NH$_2$, —NH-lower alkyl, —N(lower alkyl)$_2$, and a monocyclic nitrogen-containing hetero ring which may be further substituted with lower alkyl.

7. A compound or pharmaceutically acceptable salt thereof according to claim 1, wherein $R^1$ is lower alkyl,
$R^2$ is a group of formula (II), and
$R^4$, $R^5$, and $R^6$ are hydrogen atoms.

8. A pharmaceutical composition, comprising a compound or a pharmaceutically acceptable salt thereof according to claim 1, and a pharmaceutically acceptable excipient.

9. A compound or pharmaceutically acceptable salt thereof wherein the compound is:

7-[(5-chloro-2,3-dihydro-1H-indol-1-yl)carbonyl]-8-methyl-1-(tetrahydro-2H-pyran-4-yl)imidazo[1,5-a]quinoxalin-4(5H)-one.

* * * * *